United States Patent
Chu-Moyer et al.

(10) Patent No.: US 6,869,943 B2
(45) Date of Patent: Mar. 22, 2005

(54) SORBITOL DEHYDROGENASE INHIBITORS

(75) Inventors: Margaret Y. Chu-Moyer, Old Lyme, CT (US); Jerry A. Murry, Mystic, CT (US); Banavara L. Mylari, Waterford, CT (US); William J. Zembrowski, Oakdale, CT (US)

(73) Assignee: Pfizer Inc, New York, NY (US)

( * ) Notice: Subject to any disclaimer, the term of this patent is extended or adjusted under 35 U.S.C. 154(b) by 18 days.

(21) Appl. No.: 10/645,401

(22) Filed: Aug. 21, 2003

(65) Prior Publication Data

US 2004/0077671 A1 Apr. 22, 2004

Related U.S. Application Data

(62) Division of application No. 10/384,424, filed on Mar. 10, 2003, now Pat. No. 6,660,740, which is a division of application No. 10/087,869, filed on Feb. 28, 2002, now Pat. No. 6,602,875, which is a division of application No. 09/538,039, filed on Mar. 29, 2000, now Pat. No. 6,414,149.

(60) Provisional application No. 60/127,437, filed on Apr. 1, 1999.

(51) Int. Cl.$^7$ ................ A61K 31/33; A61K 31/495; C07D 239/00; C07D 295/00; C07D 241/00

(52) U.S. Cl. ............ 514/183; 514/241; 514/252.12; 514/252.13; 514/255.01; 544/242; 544/295; 544/326; 544/194

(58) Field of Search ............... 514/183, 241, 514/252.12, 252.13, 255.01; 544/242, 295, 326, 194

(56) References Cited

U.S. PATENT DOCUMENTS

| | | | |
|---|---|---|---|
| 5,138,058 A | 8/1992 | Geisen et al. | 544/295 |
| 5,215,990 A | 6/1993 | Geisen et al. | 514/255 |
| 5,728,704 A | 3/1998 | Mylari et al. | 514/256 |
| 5,866,578 A | 2/1999 | Mylari et al. | 514/256 |
| 6,414,149 B1 * | 7/2002 | Chu-Moyer et al. | 544/295 |
| 6,602,875 B2 * | 8/2003 | Chu-Moyer et al. | 514/253.04 |

FOREIGN PATENT DOCUMENTS

| | | | |
|---|---|---|---|
| DE | 3905364 | 8/1990 | ......... C07D/239/42 |
| EP | 0384370 | 8/1990 | ......... C07D/239/42 |
| EP | 470616 | * 2/1992 | |
| EP | 0470616 | 2/1992 | ......... C07D/239/42 |
| EP | 0794355 | 6/2002 | ............ F16H/1/20 |
| WO | WO9407867 | 4/1994 | ......... C07D/239/42 |

OTHER PUBLICATIONS

Chemical abstract DN 116:194353, also cited as E 470616.*
Ao, S., et al., Metabolism, 40, pp. 77–87, 1991.
Cameron, NE and Cotter, M.A., Diabetic Medicine, 8, Supp. 1, 35A–36A, 1991.
Geisen, K. et al., Arzneim Forsch, vol. 44, No. 9, 1994, pp. 1032–1043.
Schmidt, R.E., et al., Jrnl. Neur. Expt, Neur. 57 / 12, pp. 1175–1189.
Brown, D. J. The Pyrimidines, 1962.

* cited by examiner

*Primary Examiner*—Richard L. Raymond
*Assistant Examiner*—Sudhaker B. Patel
(74) *Attorney, Agent, or Firm*—Peter C. Richardson; Gregg C. Benson; Robert T. Ronau

(57) ABSTRACT

This invention is directed to sorbitol dehydrogenase inhibitory compounds of the formula I,

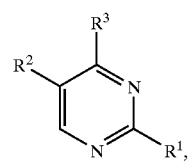

wherein $R^1$, $R^2$ and $R^3$ are as defined in the specification. This invention is also directed to pharmaceutical compositions containing those compounds and methods of treating or preventing diabetic complications, particularly diabetic neuropathy, diabetic nephropathy, diabetic microangiopathy, diabetic macroangiopathy and diabetic cardiomyopathy by administering such compounds to a mammal suffering from diabetes and therefore at risk for developing such complications. This invention is also directed to pharmaceutical compositions comprising a combination of compound of formula I of this invention with an aldose reductase inhibitor and to methods of treating or preventing diabetic complications therewith. This invention is also directed to pharmaceutical compositions comprising a combination of a compound of formula I of this invention with an NHE-1 inhibitor and to methods of treating cardiomyopathy and other heart-related problems therewith. This invention is also directed to certain intermediates used in the synthesis of the compounds of formula I and to processes for preparing those intermediates.

2 Claims, No Drawings

SORBITOL DEHYDROGENASE INHIBITORS

CROSS REFERENCE TO RELATED APPLICATIONS

This application is a division of U.S. application Ser. No. 10/384,424, filed Mar. 10, 2003, now U.S. Pat. No. 6,660,740, which is a division of U.S. application Ser. No. 10/087,869, filed Feb. 28, 2002, now U.S. Pat. No. 6,602,875 which is a division of U.S. application Ser. No. 09/538,039, filed Mar. 29, 2000, now U.S. Pat No. 6,414,149 which claims benefit of 60/127,437, filed Apr. 1, 1999.

BACKGROUND OF THE INVENTION

The present invention relates to novel pyrimidine derivatives and to the use of such derivatives and related compounds to inhibit sorbitol dehydrogenase (SDH), lower fructose levels, or treat or prevent diabetic complications such as diabetic neuropathy, diabetic retinopathy, diabetic nephropathy, diabetic cardiomyopathy, diabetic microangiopathy and diabetic macroangiopathy in mammals. This invention also relates to pharmaceutical compositions containing such pyrimidine derivatives and related compounds. This invention also relates to pharmaceutical compositions comprising a combination of a sorbitol dehydrogenase inhibitor of formula I and an aldose reductase inhibitor and to the use of such compositions to treat or prevent diabetic complications in mammals. This invention also relates to pharmaceutical compositions comprising a combination of a sorbitol dehydrogenase inhibitor of formula I and an NHE-1 inhibitor and to the use of such compositions to reduce tissue damage resulting from ischemia, and particularly to prevent perioperative myocardial ischemic injury.

S. Ao et al., *Metabolism*, 40, 77–87 (1991) have shown that significant functional improvement in the nerves of diabetic rats (based on nerve conduction velocity) occurs when nerve fructose levels are pharmacologically lowered, and that such improvement correlates more closely with the lowering of nerve fructose than the lowering of nerve sorbitol. Similar results were reported by N. E. Cameron and M. A. Cotter, *Diabetic Medicine*, 8, Suppl. 1, 35A–36A (1991). In both of these cases, lowering of nerve fructose was achieved using relatively high does of aldose reductase inhibitors, which inhibit the formation of sorbitol, a precursor of fructose, from glucose via the enzyme aldose reductase.

U.S. Pat. Nos. 5,138,058 and 5,215,990, which are hereby incorporated by reference, each disclose compounds of the formula

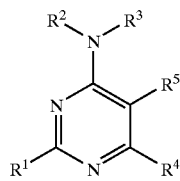

where $R^1$, $R^2$, $R^3$, $R^4$ and $R^5$ are as disclosed therein. Said compounds are disclosed as having utility as tools in screening for aldose reductase inhibitors due to the sorbitol accumulating activity of said compounds.

Commonly assigned U.S. Pat. Nos. 5,728,704 and 5,866,578, which are hereby incorporated by reference, each disclose compounds of the formula A,

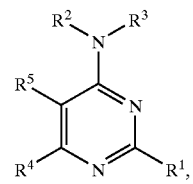

wherein $R^1$ through $R^5$ are defined as disclosed therein. Further, U.S. Pat. No. 5,728,704 discloses that sorbitol dehydrogenase compounds have utility in the treatment of diabetic complications.

Pyrimidine derivatives of the formula I, as defined below, and their pharmaceutically acceptable salts, lower fructose levels in the tissues of mammals affected by diabetes (e.g., nerve, kidney and retina tissue) and are useful in the treatment and prevention of the diabetic complications referred to above. These compounds, or their metabolites in vivo, are inhibitors of the enzyme sorbitol dehydrogenase, which catalyzes the oxidation of sorbitol to fructose.

SUMMARY OF THE INVENTION

The present invention is directed to a compound of the formula I

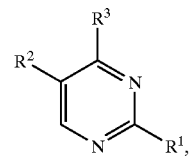

a prodrug thereof or a pharmaceutically acceptable salt of said compound or said prodrug, wherein:

$R^1$ is formyl, acetyl, propionyl, carbamoyl or —C(OH)$R^4R^5$;

$R^4$ and $R^5$ are each independently hydrogen, methyl, ethyl or hydroxy-($C_1$–$C_3$)alkyl;

$R^2$ is hydrogen, ($C_1$–$C_4$)alkyl or ($C_1$–$C_4$)alkoxy;

$R^3$ is a radical of the formula

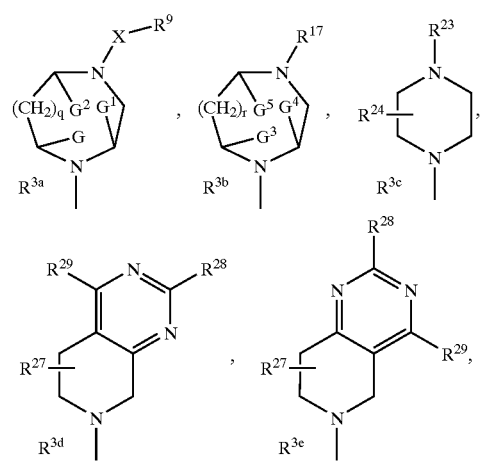

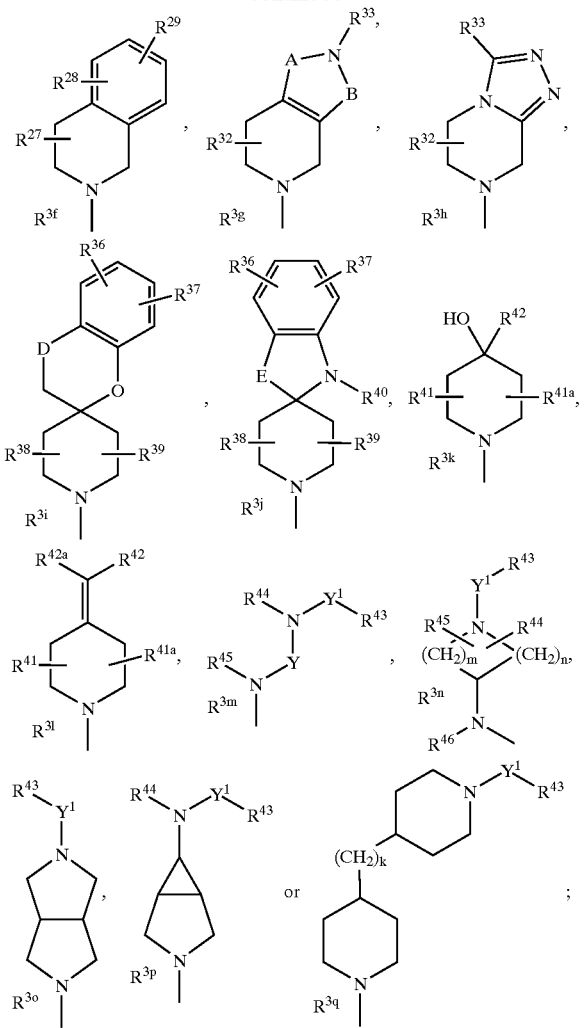

wherein said radical of formula R$^{3a}$ is additionally substituted on the ring by R$^6$, R$^7$ and R$^8$;

said radical of formula R$^{3b}$ is additionally substituted on the ring by R$^{18}$, R$^{19}$ and R$^{20}$;

G, G$^1$ and G$^2$ are taken separately and are each hydrogen and R$^6$ is hydrogen, (C$_1$–C$_4$)alkyl, (C$_1$–C$_4$)alkoxycarbonyl, (C$_1$–C$_4$)alkoxy-(C$_1$–C$_4$)alkyl, hydroxy-(C$_1$–C$_4$)alkyl or phenyl optionally independently substituted with up to three hydroxy, halo, hydroxy-(C$_1$–C$_4$)alkyl, (C$_1$–C$_4$)alkoxy-(C$_1$–C$_4$)alkyl, (C$_1$–C$_4$)alkyl or (C$_1$–C$_4$)alkoxy, wherein said (C$_1$–C$_4$)alkyl in the definition of R$^6$ and said (C$_1$–C$_4$)alkoxy in the definition of R$^6$ are optionally and independently substituted with up to five fluoro; R$^7$ and R$^8$ are each independently hydrogen or (C$_1$–C$_4$)alkyl; or G and G$^1$ are taken together and are (C$_1$–C$_3$)alkylene and R$^6$, R$^7$, R$^8$ and G$^2$ are hydrogen; or G$^1$ and G$^2$ are taken together and are (C$_1$–C$_3$)alkylene and R$^6$, R$^7$, R$^8$ and G are hydrogen;

q is 0 or 1;

X is a covalent bond, —(C=NR$^{10}$)—, oxycarbonyl, vinylenylcarbonyl, oxy(C$_1$–C$_4$)alkylenylcarbonyl, (C$_1$–C$_4$)alkylenylcarbonyl, (C$_3$–C$_4$)alkenylcarbonyl, thio(C$_1$–C$_4$)alkylenylcarbonyl, vinylenylsulfonyl, sulfinyl-(C$_1$–C$_4$)alkylenylcarbonyl, sulfonyl-(C$_1$–C$_4$)alkylenylcarbonyl or carbonyl(C$_0$–C$_4$)alkylenylcarbonyl; wherein said oxy(C$_1$–C$_4$)alkylenylcarbonyl, (C$_1$–C$_4$)alkylenylcarbonyl, (C$_3$–C$_4$)alkenylcarbonyl and thio(C$_1$–C$_4$)alkylenylcarbonyl in the definition of X are each optionally and independently substituted with up to two (C$_1$–C$_4$)alkyl, benzyl or Ar; said vinylenylsulfonyl and said vinylenylcarbonyl in the definition of X are optionally substituted independently on one or two vinylenyl carbons with (C$_1$–C$_4$)alkyl, benzyl or Ar; and said carbonyl(C$_0$–C$_4$)alkylenylcarbonyl in the definition of X is optionally substituted indepedently with up to three (C$_1$–C$_4$)alkyl, benzyl or Ar;

R$^{10}$ is hydrogen or (C$_1$–C$_4$)alkyl;

R$^9$ is (C$_3$–C$_7$)cycloalkyl, Ar$^1$—(C$_0$–C$_3$)alkylenyl or (C$_1$–C$_6$)alkyl optionally substituted with up to five fluoro; provided that when q=0 and X is a covalent bond, oxycarbonyl or (C$_1$–C$_4$)alkylenylcarbonyl, then R$^9$ is not (C$_1$–C$_6$)alkyl;

Ar and Ar$^1$ are independently a fully saturated, partially saturated or fully unsaturated five- to eight-membered ring optionally having up to four heteroatoms selected independently from oxygen, sulfur and nitrogen, or a bicyclic ring consisting of two fused independently partially saturated, fully saturated or fully unsaturated five- to seven-membered rings, taken independently, optionally having up to four heteroatoms selected independently from nitrogen, sulfur and oxygen, or a tricyclic ring consisting of three fused independently partially saturated, fully saturated or fully unsaturated five to seven membered rings, taken independently, optionally having up to four heteroatoms selected independently from nitrogen, sulfur and oxygen, said partially saturated, fully saturated ring or fully unsaturated monocyclic ring, bicyclic ring or tricyclic ring optionally having one or two oxo groups substituted on carbon or one or two oxo groups substituted on sulfur;

Ar and Ar$^1$ are optionally independently substituted on carbon or nitrogen, on one ring if the moiety is monocyclic, on one or both rings if the moiety is bicyclic, or on one, two or three rings if the moiety is tricyclic, with up to a total of four substituents independently selected from R$^{11}$, R$^{12}$, R$^{13}$ and R$^{14}$; wherein R$^{11}$, R$^{12}$, R$^{13}$ and R$^{14}$ are each taken separately and are each independently halo, formyl, (C$_1$–C$_6$)alkoxycarbonyl, (C$_1$–C$_6$)alkylenyloxycarbonyl, (C$_1$–C$_4$)alkoxy-(C$_1$–C$_4$)alkyl, C(OH)R$^{15}$R$^{16}$, naphthyl, phenyl, imidazolyl, pyridyl, triazolyl, morpholinyl, (C$_0$–C$_4$)alkylsulfamoyl, N—(C$_0$–C$_4$)alkylcarbamoyl, N,N-di-(C$_1$–C$_4$)alkylcarbamoyl, N-phenylcarbamoyl, N—(C$_1$–C$_4$)alkyl-N-phenylcarbamoyl, N,N-diphenyl carbamoyl, (C$_1$–C$_4$)alkylcarbonylamido, (C$_3$–C$_7$)cycloalkylcarbonylamido, phenylcarbonylamido, piperidinyl, pyrrolidinyl, piperazinyl, cyano, benzimidazolyl, amino, anilino, pyrimidyl, oxazolyl, isoxazolyl, tetrazolyl, thienyl, thiazolyl, benzothiazolyl, pyrrolyl, pyrazolyl, tetrahydroquinolyl, tetrahydroisoquinolyl, benzoxazolyl, pyridazinyl, pyridyloxy, pyridylsulfanyl, furanyl, 8-(C$_1$–C$_4$)alkyl-3, 8-diaza[3.2.1]bicyclooctyl, 3,5-dioxo-1,2,4-triazinyl, phenoxy, thiophenoxy, (C$_1$–C$_4$)alkylsulfanyl, (C$_1$–C$_4$)alkylsulfonyl, (C$_3$–C$_7$)cycloalkyl, (C$_1$–C$_4$)alkyl optionally substituted with up to five fluoro or (C$_1$–C$_4$)alkoxy optionally substituted with up to five fluoro; said naphthyl, phenyl, pyridyl, piperidinyl, benzimidazolyl, pyrimidyl, thienyl, benzothiazolyl, pyrrolyl, tetrahydroquinolyl, tetrahydroisoquinolyl, benzoxazolyl, pyridazinyl, pyridyloxy, pyridylsulfanyl, furanyl, thiophenoxy, anilino and phenoxy in the definition of $R^{11}$, $R^{12}$, $R^{13}$ and $R^{14}$ are optionally substituted with up to three substituents independently selected from hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said imidazolyl, oxazolyl, isoxazolyl, thiazolyl and pyrazolyl in the definition of $R^{11}$, $R^{12}$, $R^{13}$ and $R^{14}$ are optionally substituted with up to two substituents independently selected from hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said morpholinyl in the definition of $R^{11}$, $R^{12}$, $R^{13}$ and $R^{14}$ is optionally substituted with up to two substituents independently selected from $(C_1-C_4)$alkyl; said pyrrolidinyl in the definition of $R^{11}$, $R^{12}$, $R^{13}$ and $R^{14}$ is optionally substituted with up to two substituents independently selected from hydroxy, hydroxy-$(C_1-C_3)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said piperazinyl in the definition of $R^{11}$, $R^{12}$, $R^{13}$ and $R^{14}$ is optionally substituted with up to three substituents independently selected from $(C_1-C_4)$alkoxy-$(C_1-C_4)$alkyl, hydroxy-$(C_1-C_3)$alkyl, phenyl, pyridyl, $(C_0-C_4)$alkylsulfamoyl, $(C_1-C_4)$alkyl optionally substituted with up to five fluoro and $(C_1-C_4)$alkoxy optionally substituted with up to five fluoro; said triazolyl in the definition of $R^{11}$, $R^{12}$, $R^{13}$ and $R^{14}$ is optionally substituted with hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said tetrazolyl in the definition of $R^{11}$, $R^{12}$, $R^{13}$ and $R^{14}$ is optionally substituted with hydroxy-$(C_2-C_3)$alkyl or $(C_1-C_4)$alkyl optionally substituted with up to five fluoro; and said phenyl and pyridyl which are optionally substituted on piperazine in the definition of $R^{11}$, $R^{12}$, $R^{13}$ and $R^{14}$ are optionally substituted with up to three hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; or $R^{11}$ and $R^{12}$ are taken together on adjacent carbon atoms and are —CH$_2$OC(CH$_3$)$_2$OCH$_2$— or —O—(CH$_2$)$_p$—O—, and $R^{13}$ and $R^{14}$ are taken separately and are each independently hydrogen or $(C_1-C_4)$alkyl;

p is 1, 2 or 3;

$R^{15}$ and $R^{16}$ are taken separately and are each independently hydrogen, $(C_1-C_4)$alkyl optionally substituted with up to five fluoro; or $R^{15}$ and $R^{16}$ are taken separately and $R^{15}$ is hydrogen and $R^{16}$ is $(C_3-C_6)$cycloalkyl, hydroxy-$(C_1-C_3)$alkyl, phenyl, pyridyl, pyrimidyl, thienyl, furanyl, thiazolyl, oxazolyl, imidazolyl, benzothiazolyl or benzoxazolyl; or $R^{15}$ and $R^{16}$ are taken together and are $(C_3-C_6)$alkylene;

$G^3$, $G^4$ and $G^5$ are taken separately and are each hydrogen; r is 0; $R^{18}$ is hydrogen, $(C_1-C_4)$alkyl, $(C_1-C_4)$alkoxycarbonyl, $(C_1-C_4)$alkoxy-$(C_1-C_4)$alkyl, hydroxy-$(C_1-C_4)$alkyl, hydroxy-$(C_1-C_4)$alkyl or phenyl optionally independently substituted with up to three hydroxy, halo, hydroxy-$(C_1-C_4)$alkyl, $(C_1-C_4)$alkoxy-$(C_1-C_4)$alkyl, $(C_1-C_4)$alkyl or $(C_1-C_4)$alkoxy, wherein said $(C_1-C_4)$alkyl in the definition of $R^6$ and said $(C_1-C_4)$alkoxy in the definition of $R^6$ are optionally and independently substituted with up to five fluoro; and $R^{19}$ and $R^{20}$ are each independently $(C_1-C_4)$alkyl; or $G^3$, $G^4$ and $G^5$ are taken separately and are each hydrogen; r is 1; $R^{18}$ is hydrogen, $(C_1-C_4)$alkyl, $(C_1-C_4)$alkoxycarbonyl, $(C_1-C_4)$alkoxy-$(C_1-C_4)$alkyl, hydroxy-$(C_1-C_4)$alkyl or phenyl optionally independently substituted with up to three hydroxy, halo, hydroxy-$(C_1-C_4)$alkyl, $(C_1-C_4)$alkoxy-$(C_1-C_4)$alkyl, $(C_1-C_4)$alkyl or $(C_1-C_4)$alkoxy, wherein said $(C_1-C_4)$alkyl in the definition of $R^6$ and said $(C_1-C_4)$alkoxy in the definition of $R^6$ are optionally and independently substituted with up to five fluoro; and $R^{19}$ and $R^{20}$ are each independently hydrogen or $(C_1-C_4)$alkyl; or $G^3$ and $G^4$ are taken together and are $(C_1-C_3)$alkylene; r is 0 or 1; and $R^{18}$, $R^{19}$, $R^{20}$ and $G^5$ are hydrogen; or $G^4$ and $G^5$ are taken together and are $(C_1-C_3)$alkylene; r is 0 or 1; and $R^{18}$, $R^{19}$, $R^{20}$ and $G^3$ are hydrogen;

$R^{17}$ is $SO_2NR^{21}R^{22}$, $CONR^{21}R^{22}$, $(C_1-C_6)$alkoxycarbonyl, $(C_1-C_6)$alkylcarbonyl, $Ar^2$-carbonyl, $(C_1-C_6)$alkylsulfonyl, $(C_1-C_6)$alkylsulfinyl, $Ar^2$-sulfonyl, $Ar^2$-sufinyl and $(C_1-C_6)$alkyl;

$R^{21}$ and $R^{22}$ are taken separately and are each independently selected from hydrogen, $(C_1-C_6)$alkyl, $(C_3-C_7)$cycloalkyl and $Ar^2$—$(C_0-C_4)$alkylenyl; or $R^{21}$ and $R^{22}$ are taken together with the nitrogen atom to which they are attached to form azetidinyl, pyrrolidinyl, piperidinyl, piperazinyl, morpholinyl, azepinyl, azabicyclo[3.2.2]nonanyl, azabicyclo[2.2.1]heptyl, 6,7-dihydro-5H-dibenzo[c,e]azepinyl, 1,2,3,4-tetrahydro-isoquinolyl or 5,6,7,8-tetrahydropyrido[4,3-d]pyrimidyl; said azetidinyl in the definition of $R^{21}$ and $R^{22}$ is optionally substituted independently with one substituent selected from hydroxy, amino, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said pyrrolidinyl, piperidinyl, azepinyl in the definition of $R^{21}$ and $R^{22}$ are optionally substituted independently with up to two substituents independently selected from hydroxy, amino, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said morpholinyl in the definition of $R^{21}$ and $R^{22}$ is optionally substituted with up to two substituents independently selected from hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said piperazinyl in the definition of $R^{21}$ and $R^{22}$ is optionally substituted independently with up to three substituents independently selected from phenyl, pyridyl, pyrimidyl, $(C_1-C_4)$alkoxycarbonyl and $(C_1-C_4)$alkyl optionally substituted with up to five fluoro; said 1,2,3,4-tetrahydro-isoquinolyl and said 5,6,7,8-tetrahydropyrido[4,3-d]pyrimidyl in the definition of $R^{21}$ and $R^{22}$ are optionally substituted independently with up to three substituents independently selected from hydroxy, amino, halo, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; and said 6,7-dihydro-5H-dibenzo[c,e]azepinyl in the definition of $R^{21}$ and $R^{22}$ is optionally substituted with up to four substituents independently selected from hydroxy, amino, halo, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said pyrimidyl, pyridyl and phenyl which are optionally substituted on said piperazine in the definition of $R^{21}$ and $R^{22}$ is optionally substituted with up to three substituents selected from hydroxy, amino, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro;

$Ar^2$ is independently defined as set forth for Ar and $Ar^1$ above;

said $Ar^2$ is optionally independently substituted as set forth for Ar and $Ar^1$ above;

$R^{23}$ is $CONR^{25}R^{26}$ or $SO_2R^{25}R^{26}$, wherein $R^{25}$ is hydrogen $(C_1-C_4)$alkyl or $Ar^3-(C_0-C_4)$alkylenyl and $R^{25}$ is $Ar^3-(C_0-C_4)$alkylenyl; provided that when $Ar^3$ is phenyl, naphthyl or biphenyl, then $R^{23}$ cannot be $CONR^{26}R^{26}$ where $R^{25}$ is hydrogen or $Ar^3$ and $R^{26}$ is $Ar^3$;

$R^{24}$ is hydrogen, $(C_1-C_4)$alkyl, $(C_1-C_4)$alkoxycarbonyl, $(C_1-C_4)$alkoxy-$(C_1-C_4)$alkyl, hydroxy-$(C_1-C_4)$alkyl or phenyl optionally independently substituted with up to three hydroxy, halo, hydroxy-$(C_1-C_4)$alkyl, $(C_1-C_4)$alkoxy-$(C_1-C_4)$alkyl, $(C_1-C_4)$alkyl or $(C_1-C_4)$alkoxy, wherein said $(C_1-C_4)$alkyl in the definition of $R^6$ and said $(C_1-C_4)$alkoxy in the definition of $R^6$ are optionally and independently substituted with up to five fluoro;

$Ar^3$ is independently defined as set forth for Ar and $Ar^1$ above;

said $Ar^3$ is optionally independently substituted as set forth for Ar and $Ar^1$ above;

$R^{27}$ is hydrogen or $(C_1-C_4)$alkyl;

$R^{28}$ and $R^{29}$ are each independently hydrogen, hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro, $(C_1-C_4)$alkoxy optionally substituted with up to five fluoro, phenyl, pyridyl, pyrimidyl, thienyl, furanyl, thiazolyl, oxazolyl, phenoxy, thiophenoxy, $SO_2NR^{30}R^{31}$, $CONR^{30}R^{31}$ or $NR^{30}R^{31}$; said thienyl, pyrimidyl, furanyl, thiazolyl and oxazolyl in the definition of $R^{28}$ and $R^{29}$ are optionally substituted by up to two hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro; said phenyl, pyridyl, phenoxy and thiophenoxy in the definition of $R^{28}$ and $R^{29}$ are optionally substituted by up to three hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro;

$R^{30}$ and $R^{31}$ are each independently hydrogen, $(C_1-C_4)$alkyl, $(C_3-C_7)$cycloalkyl or phenyl, said phenyl is optionally substituted with up to three hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro; or $R^{30}$ and $R^{31}$ are taken together with the nitrogen to which they are attached to form indolinyl, pyrrolidinyl, piperidinyl, piperazinyl or morpholinyl; said pyrrolidinyl and piperidinyl in the definition of $R^{30}$ and $R^{31}$ are optionally substituted with up to two hydroxy, amino, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro; said indolinyl and piperazinyl in the definition of $R^{30}$ and $R^{31}$ are optionally substituted with up to three hydroxy, amino, hydroxy-$(C_1-C_4)$alkyl, $(C_1-C_4)$alkoxy-$(C_1-C_4)$alkyl, $(C_1-C_4)$alkoxycarbonyl, $(C_1-C_4)$alkyl optionally substituted with up to five fluoro or $(C_1-C_4)$alkoxy optionally substituted with up to five fluoro; said morpholinyl in the definition of $R^{30}$ and $R^{31}$ is optionally substituted with up to two substituents independently selected from hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro;

A is N optionally substituted with hydrogen or $(C_1-C_4)$alkyl and B is carbonyl; or A is carbonyl and B is N optionally substituted with hydrogen or $(C_1-C_4)$alkyl;

$R^{32}$ is hydrogen or $(C_1-C_4)$alkyl;

$R^{33}$ is phenyl, pyridyl, pyrimidyl, thiazolyl, oxazolyl, benzyl, quinolyl, isoquinolyl, phthalizinyl, quinoxanlyl, benzothiazoyl, benzoxazolyl, benzofuranyl or benzothienyl; said phenyl, pyridyl, pyrimidyl, thiazolyl, oxazolyl, benzyl, quinolyl, isoquinolyl, phthalizinyl, quinoxanlyl, benzothiazoyl, benzoxazolyl, benzofuranyl and benzothienyl in the definition of $R^{33}$ are optionally substituted with up to three phenyl, phenoxy, $NR^{34}R^{35}$, halo, hydroxy, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro;

$R^{34}$ and $R^{35}$ are each independently hydrogen, $(C_1-C_4$ alkyl), phenyl or phenylsulfonyl; said phenyl and phenylsulfonyl in the definition of $R^{34}$ and $R^{35}$ are optionally substituted with up to three halo, hydroxy, $(C_1-C_4)$alkyl optionally substituted with up to five fluoro or $(C_1-C_4)$alkoxy optionally substituted with up to five fluoro;

D is CO, CHOH or $CH_2$;

E is O, NH or S;

$R^{36}$ and $R^{37}$ are taken separately and are each independently hydrogen, halo, cyano, hydroxy, amino, $(C_1-C_6)$alkylamino, di-$(C_1-C_6)$alkylamino, pyrrolidino, piperidino, morpholino, $(C_1-C_4)$alkoxy-$(C_1-C_4)$alkyl, hydroxy-$(C_1-C_4)$alkyl, $Ar^4$, $(C_1-C_4)$alkyl optionally substituted with up to five fluoro or $(C_1-C_4)$alkoxy optionally substituted with up to five fluoro;

$R^{38}$, $R^{39}$ and $R^{40}$ are each independently hydrogen or $(C_1-C_4)$-alkyl;

$Ar^4$ is phenyl, furanyl, thienyl, pyridyl, pyrimidyl, pyrazinyl or pyridazinyl; said $Ar^4$ being optionally substituted with up to three hydroxy, $(C_1-C_4)$alkoxy-$(C_1-C_4)$alkyl, halo, hydroxy-$(C_1-C_4)$alkyl, $(C_1-C_4)$alkyl optionally substituted with up to five fluoro or $(C_1-C_4)$alkoxy optionally substituted with up to five fluoro; or $R^{36}$ and $R^{37}$ are taken together on adjacent carbon atoms and are —O—$(CH_2)_r$—O—;

t is 1, 2 or 3;

Y is $(C_2-C_6)$alkylene;

$R^{44}$, $R^{45}$ and $R^{46}$ are each independently hydrogen or $(C_1-C_4)$alkyl;

m and n are each independently 1, 2 or 3, provided that the sum of m and n is 2, 3 or 4;

k is 0, 1, 2, 3 or 4;

$Y^1$ is a covalent bond, carbonyl, sulfonyl or oxycarbonyl;

$R^{43}$ is $(C_3-C_7)$cycloalkyl, $Ar^5$—$(C_0-C_4)$alkylenyl, $NR^{47}R^{48}$ or $(C_1-C_6)$alkyl optionally substituted with one to five fluoro; provided that when $Y^1$ is a covalent bond or oxycarbonyl, then $R^{43}$ is not $NR^{47}R^{48}$;

$R^{47}$ and $R^{48}$ are taken separately and are each independently selected from hydrogen, $Ar^5$, $(C_1-C_6)$alkyl and $Ar^5$—$(C_0-C_4)$alkylenyl; or $R^{47}$ and $R^{48}$ are taken together with the nitrogen atom to which they are attached to form azetidinyl, pyrrolidinyl, piperidinyl, piperazinyl, morpholinyl, azepinyl, azabicyclo[3.2.2]nonanyl, azabicyclo[2.2.1] heptyl, 1,2,3,4-tetrahydroisoquinolyl, 6,7-dihydro-5H-dibenzo[c,e]azepinyl or 5,6,7,8-tetrahydropyrido[4,3-d]pyrimidyl; said azetidinyl in the definition of $R^{47}$ and $R^{48}$ are optionally substituted with one hydroxy, amino, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro; said pyrrolidinyl, piperidinyl and azepinyl in the definition of $R^{47}$ and $R^{48}$ are optionally substituted with up to two hydroxy, amino, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro; said morpholinyl in the definition of $R^{47}$ and $R^{48}$ is optionally substituted with up to two substituents independently selected from hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said piperazinyl, 1,2,3,4-tetrahydroisoquinolyl and 5,6,7,8-tetrahydro[4,3-d]pyrimidyl in the definition of $R^{47}$ and $R^{48}$ are optionally substituted with up to three hydroxy, amino, halo, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro; and said 6,7-dihydro-5H-dibenzo[c,e]azepinyl in the definition of $R^{47}$ and $R^{48}$ are optionally substituted with up to four hydroxy, amino, halo, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro;

$Ar^5$ is independently defined as set forth for Ar and $Ar^1$ above;

$Ar^5$ is optionally independently substituted as set forth for Ar and $Ar^1$ above;

$R^{42}$ and $R^{42a}$ are independently hydrogen, $(C_3-C_7)$cycloalkyl, $Ar^6$—$(C_0-C_3)$alkylenyl, $Ar^6$—$(C_2-C_4)$alkenyl, $Ar^6$-carbonyl or $(C_1-C_6)$alkyl optionally substituted with up to five fluoro;

$Ar^6$ is independently defined as set forth for Ar and $Ar^1$ above;

$Ar^8$ is optionally independently substituted as set forth for Ar and $Ar^1$ above; and $R^{41}$ and $R^{41a}$ are each independently hydrogen or $(C_1-C_4)$alkyl.

A preferred group of compounds of formula I, designated Group A, are those compounds of formula I, prodrugs thereof and pharmaceutically acceptable salts of said compounds or said prodrugs, wherein:

$R^3$ is

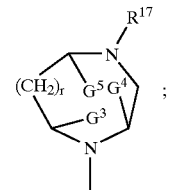

substituted by $R^{18}$, $R^{19}$ or $R^{20}$;

$G^3$, $G^4$ and $G^5$ are taken separately and are each hydrogen, r is 0 and $R^{18}$ is hydrogen, $(C_1-C_4)$alkyl, $(C_1-C_4)$alkoxycarbonyl or phenyl optionally substituted by up to three hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro; $R^{19}$ and $R^{20}$ are each independently $(C_1-C_4)$alkyl;

$G^3$, $G^4$ and $G^5$ are taken separately and are each hydrogen; r is 1; and $R^{18}$ is hydrogen, $(C_1-C_4)$alkyl, $(C_1-C_4)$alkoxycarbonyl or phenyl optionally substituted by up to three hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro; $R^{19}$ and $R^{20}$ are each independently hydrogen or $(C_1-C_4)$alkyl; or $G^3$ and $G^4$ are taken together and are $(C_1-C_3)$alkylene; r is 0 or 1; and $R^{18}$, $R^{19}$, $R^{20}$ and $G^5$ are hydrogen; or $G^4$ and $G^5$ are taken together and are $(C_1-C_3)$alkylene; r is 0 or 1; and $R^{18}$, $R^{19}$, $R^{20}$ and $G^3$ are hydrogen;

$R^{17}$ is $SO_2NR^{21}R^{22}$, $CONR^{21}R^{22}$, $(C_1-C_6)$alkoxycarbonyl, $(C_1-C_6)$alkylcarbonyl, $Ar^2$-carbonyl, $(C_1-C_6)$alkylsulfonyl, $(C_1-C_6)$alkylsulfinyl, $Ar^2$-sulfonyl, $Ar^2$-sufinyl and $(C_1-C_6)$alkyl;

$R^{21}$ and $R^{22}$ are taken separately and are each independently selected from hydrogen, $(C_1-C_6)$alkyl, $(C_3-C_7)$cycloalkyl and $A^2$—$(C_0-C_4)$alkylenyl; or $R^{21}$ and $R^{22}$ are taken together with the nitrogen atom to which they are attached to form azetidinyl, pyrrolidinyl, piperidinyl, piperazinyl, morpholinyl, azepinyl, azabicyclo[3.2.2]nonanyl, azabicyclo[2.2.1] heptyl, 6,7-dihydro-5H-dibenzo[c,e]azepinyl, 1,2,3,4-tetrahydro-isoquinolyl or 5,6,7,8-tetrahydropyrido[4,3-d]pyrimidyl; said azetidinyl in the definition of $R^{21}$ and $R^{22}$ is optionally substituted independently with one substituent selected from hydroxy, amino, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said pyrrolidinyl, piperidinyl, morpholinyl, azepinyl in the definition of $R^{21}$ and $R^{22}$ are optionally substituted independently with up to two substituents independently selected from hydroxy, amino, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said morpholinyl in the definition of $R^{21}$ and $R^{22}$ is optionally substituted with up to two substituents independently selected from hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said piperazinyl in the definition of $R^{21}$ and $R^{22}$ is optionally substituted independently with up to three substituents independently selected from phenyl, pyridyl, pyrimidyl, $(C_1-C_4)$alkoxycarbonyl and $(C_1-C_4)$alkyl optionally substituted with up to five fluoro; said 1,2,3,4-tetrahydro-isoquinolyl and said 5,6,7,8-tetrahydropyrido[4,3-d]pyrimidyl in the definition of $R^{21}$ and $R^{22}$ are optionally substituted independently with up to three substituents independently selected from hydroxy, amino, halo, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said pyrimidyl, pyridyl and phenyl which are optionally substituted on said piperazine in the definition of $R^{21}$ and $R^{22}$ is optionally substituted with up to three substituents selected from hydroxy, amino, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; and said 6,7-dihydro-5H-dibenzo[c,e]azepinyl in the definition of $R^{21}$ and $R^{22}$ is optionally substituted with up to four substituents independently selected from hydroxy, amino, halo, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro.

Another preferred group of compounds of formula I, designated Group B, are those compounds of formula I, prodrugs thereof and pharmaceutically acceptable salts of said compounds or said prodrugs, wherein:

$R^3$ is

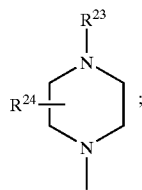

$R^{23}$ is $CONR^{25}R^{26}$, $SO_2R^{25}R^{26}$ wherein $R^{25}$ is hydrogen $(C_1-C_4)$alkyl or $Ar^3$—$(C_0-C_4)$alkylenyl and $R^{26}$ is $Ar^3$—$(C_0-C_4)$alkylenyl; provided that when $Ar^3$ is phenyl, naphthyl or biphenyl, then $R^{23}$ cannot be $CONR^{25}R^{26}$ where $R^{25}$ is hydrogen or $Ar^3$ and $R^{26}$ is $Ar^3$;

$R^{24}$ is hydrogen, $(C_1-C_4)$alkyl, $(C_1-C_4)$alkoxycarbonyl or phenyl optionally substituted by up to three $(C_1-C_4)$ alkyl optionally substituted with up to five fluoro, $(C_1-C_4)$alkoxy optionally substituted with up to five fluoro, hydroxy, halo or hydroxy-$(C_1-C_3)$alkyl.

Another preferred group of compounds of formula I, designated Group C, are those compounds of formula I, prodrugs thereof and pharmaceutically acceptable salts of said compounds or said prodrugs, wherein:

$R^3$ is

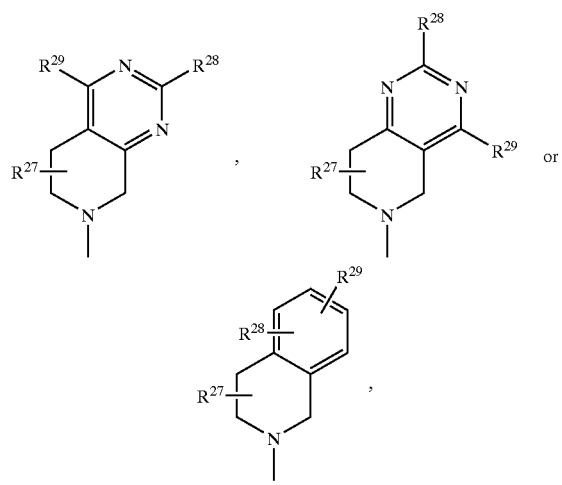

$R^{27}$ is hydrogen or $(C_1-C_4)$alkyl;

$R^{28}$ and $R^{29}$ are each independently hydrogen, hydroxy, halo, hydroxy-$(C_1-C_4)$alkyl, $(C_1-C_4)$alkoxy-$(C_1-C_4)$ alkyl, $(C_1-C_4)$alkyl optionally substituted with up to five fluoro, $(C_1-C_4)$alkoxy optionally substituted with up to five fluoro, phenyl, pyridyl, pyrimidyl, thienyl, furanyl, thiazolyl, oxazolyl, phenoxy, thiophenoxy, $SO_2NR^{30}R^{31}$, $CONR^{30}R^{31}$ or $NR^{30}R^{31}$; said thienyl, pyrimidyl, furanyl, thiazolyl and oxazolyl in the definition of $R^{28}$ and $R^{29}$ are optionally substituted by up to two hydroxy, halo, hydroxy-$(C_1-C_4)$alkyl, $(C_1-C_4)$ alkoxy-$(C_1-C_4)$alkyl, $(C_1-C_4)$alkyl optionally substituted with up to five fluoro or $(C_1-C_4)$alkoxy optionally substituted with up to five fluoro; said phenyl, pyridyl, phenoxy and thiophenoxy in the definition of $R^{28}$ and $R^{29}$ are optionally substituted by up to three hydroxy, halo, hydroxy-$(C_1-C_4)$alkyl, $(C_1-C_4)$alkoxy-$(C_1-C_4)$ alkyl, $(C_1-C_4)$alkyl optionally substituted with up to five fluoro or $(C_1-C_4)$alkoxy optionally substituted with up to five fluoro;

$R^{30}$ and $R^{31}$ are each independently hydrogen, $(C_1-C_4)$ alkyl, $(C_3-C_7)$cycloalkyl or phenyl, said phenyl is optionally substituted with up to three hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro; or $R^{30}$ and $R^{31}$ are taken together with the nitrogen to which they are attached to form indolinyl, pyrrolidinyl, piperidinyl, piperazinyl or morpholinyl; said pyrrolidinyl and piperidinyl in the definition of $R^{30}$ and $R^{31}$ are optionally substituted with up to two hydroxy, amino, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro; said indolinyl and piperazinyl in the definition of $R^{30}$ and $R^{31}$ are optionally substituted with up to three hydroxy, amino, or hydroxy-$(C_1-C_4)$alkyl, $(C_1-C_4)$alkoxy-$(C_1-C_4)$alkyl, $(C_1-C_4)$alkoxycarbonyl, $(C_1-C_4)$alkyl optionally substituted with up to five fluoro or $(C_1-C_4)$alkoxy optionally substituted with up to five fluoro; said morpholinyl in the definition of $R^{30}$ and $R^{31}$ is optionally substituted with up to two substituents independently selected from hydroxy-$(C_1-C_4)$ alkyl, $(C_1-C_4)$alkoxy-$(C_1-C_4)$alkyl, $(C_1-C_4)$alkyl optionally substituted with up to five fluoro and (C$_1$–C$_4$)alkoxy optionally substituted with up to five fluoro.

Yet another preferred group of compounds of formula I, designated Group D, are those compounds of formula I, prodrugs thereof and pharmaceutically acceptable salts of said compounds or said prodrugs, wherein:

R$^3$ is

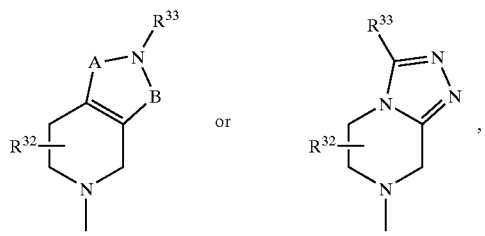

A is N optionally substituted with hydrogen or (C$_1$–C$_4$) alkyl and B is carbonyl; or
A is carbonyl and B is N optionally substituted with hydrogen or (C$_1$–C$_4$)alkyl;
R$^{32}$ is hydrogen or (C$_1$–C$_4$)alkyl;
R$^{33}$ is phenyl, pyridyl, pyrimidyl, thiazolyl, oxazolyl, benzyl, quinolyl, isoquinolyl, phthalizinyl, quinoxanlyl, benzothiazolyl, benzoxazolyl, benzofuranyl or benzothienyl; said phenyl, pyridyl, pyrimidyl, thiazolyl, oxazolyl, benzyl, quinolyl, isoquinolyl, phthalizinyl, quinoxanlyl, benzothiazoyl, benzoxazolyl, benzofuranyl and benzothienyl in the definition of R$^{33}$ are optionally substituted with up to three phenyl, phenoxy, NR$^{34}$R$^{35}$, halo, hydroxy, hydroxy-(C$_1$–C$_4$)alkyl, (C$_1$–C$_4$)alkoxy-(C$_1$–C$_4$)alkyl, (C$_1$–C$_4$)alkyl optionally substituted with up to five fluoro or (C$_1$–C$_4$)alkoxy optionally substituted with up to five fluoro;
R$^{34}$ and R$^{35}$ are each independently hydrogen, (C$_1$–C$_4$ alkyl), phenyl or phenylsulfonyl; said phenyl and phenylsulfonyl in the definition of R$^{34}$ and R$^{35}$ are optionally substituted with up to three halo, hydroxy, (C$_1$–C$_4$) alkyl optionally substituted with up to five fluoro or (C$_1$–C$_4$)alkoxy optionally substituted with up to five fluoro.

Still another preferred group of compounds of formula I, designated Group E, are those compounds of formula I, prodrugs thereof and pharmaceutically acceptable salts of said compounds or said prodrugs, wherein:

R$^3$ is

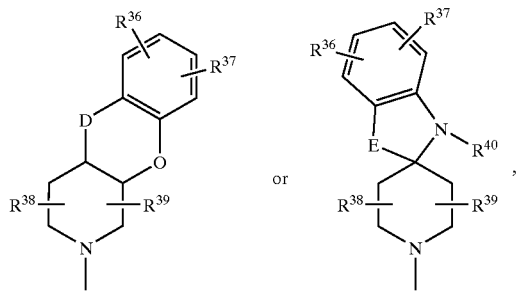

D is CO, CHOH or CH$_2$;
E is O, NH or S;
R$^{36}$ and R$^{37}$ are taken separately and are each independently hydrogen, halo, cyano, hydroxy, amino, (C$_1$–C$_6$) alkylamino, di-(C$_1$–C$_6$)alkylamino, pyrrolidino, piperidino, morpholino, (C$_1$–C$_4$)alkoxy-(C$_1$–C$_4$)alkyl, hydroxy-(C$_1$–C$_4$)alkyl, Ar$^4$, (C$_1$–C$_4$)alkyl optionally substituted with up to five fluoro or (C$_1$–C$_4$)alkoxy optionally substituted with up to five fluoro;
R$^{38}$, R$^{39}$ and R$^{40}$ are each independently hydrogen or (C$_1$–C$_4$)-alkyl;
Ar$^4$ is phenyl, furanyl, thienyl, pyridyl, pyrimidyl, pyrazinyl or pyridazinyl; said Ar$^4$ being optionally substituted with up to three hydroxy, (C$_1$–C$_4$)alkoxy-(C$_1$–C$_4$)alkyl, halo, hydroxy-(C$_1$–C$_4$)alkyl, (C$_1$–C$_4$)alkyl optionally substituted with up to five fluoro or (C$_1$–C$_4$)alkoxy optionally substituted with up to five fluoro; or
R$^{36}$ and R$^{37}$ are taken together on adjacent carbon atoms and are —O—(CH$_2$)$_t$—O—;
t is 1, 2 or 3.

Still another preferred group of compounds of formula I, designated Group F, are those compounds of formula I, prodrugs thereof and pharmaceutically acceptable salts of said compounds or said prodrugs, wherein:

R$^3$ is

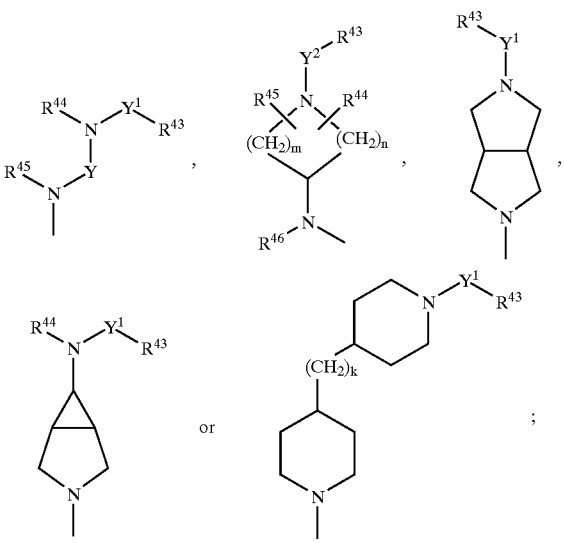

Y is (C$_2$–C$_6$)alkylene;
R$^{44}$, R$^{45}$ and R$^{46}$ are each independently hydrogen or (C$_1$–C$_4$)alkyl;
m and n are each independently 1, 2 or 3, provided that the sum of m and n is 2, 3 or 4;
k is 0 to 4;
Y$^1$ is a covalent bond, carbonyl, sulfonyl or oxycarbonyl;
R$^{43}$ is (C$_3$–C$_7$)cycloalkyl, Ar$^5$—(C$_0$–C$_4$)alkylenyl, NR$^{47}$R$^{48}$ or (C$_1$–C$_6$) substituted with one to five fluoro; provided that when Y$^1$ is a covalent bond or oxycarbonyl, then R$^{43}$ is not NR$^{47}$R$^{48}$;
R$^{47}$ and R$^{48}$ are taken separately and are each independently selected from hydrogen, Ar$^5$, (C$_1$–C$_6$)alkyl and Ar$^5$—(C$_0$–C$_4$)alkylenyl; or
R$^{47}$ and R$^{48}$ are taken together with the nitrogen atom to which they are attached to form azetidinyl, pyrrolidinyl, piperidinyl, piperazinyl, morpholinyl, azepinyl, azabicyclo[3.2.2]nonanyl, azabicyclo[2.2.1] heptyl, 1,2,3,4-tetrahydroisoquinolyl, 6,7-dihydro-5H-dibenzo[c,e]azepinyl or 5,6,7,8-tetrahydropyrido[4,3-d]pyrimidyl; said azetidinyl in the definition of R$^{47}$ and R[48] are optionally substituted with one hydroxy, amino, hydroxy-($C_1$–$C_4$)alkyl, ($C_1$–$C_4$)alkoxy-($C_1$–$C_4$)alkyl, ($C_1$–$C_4$)alkyl optionally substituted with up to five fluoro or ($C_1$–$C_4$)alkoxy optionally substituted with up to five fluoro; said pyrrolidinyl, piperidinyl and azepinyl in the definition of R[47] and R[48] are optionally substituted with up to two hydroxy, amino, hydroxy-$C_1$–$C_4$)alkyl, ($C_1$–$C_4$)alkoxy-($C_1$–$C_4$)alkyl, ($C_1$–$C_4$) alkyl optionally substituted with up to five fluoro or ($C_1$–$C_4$)alkoxy optionally substituted with up to five fluoro; said morpholinyl in the definition of R[47] and R[48] is optionally substituted with up to two substituents independently selected from hydroxy-($C_1$–$C_4$)alkyl, ($C_1$–$C_4$)alkoxy-($C_1$–$C_4$)alkyl, ($C_1$–$C_4$)alkyl optionally substituted with up to five fluoro and ($C_1$–$C_4$)alkoxy optionally substituted with up to five fluoro; said piperazinyl, 1,2,3,4-tetrahydroisoquinolyl and 5,6,7,8-tetrahydro[4,3-d]pyrimidyl in the definition of R[47] and R[48] are optionally substituted with up to three hydroxy, amino, halo, hydroxy-($C_1$–$C_4$)alkyl, ($C_1$–$C_4$)alkoxy-($C_1$–$C_4$)alkyl, ($C_1$–$C_4$)alkyl optionally substituted with up to five fluoro or ($C_1$–$C_4$)alkoxy optionally substituted with up to five fluoro; and said 6,7-dihydro-5H-dibenzo[c,e]azepinyl in the definition of R[47] and R[48] are optionally substituted with up to four hydroxy, amino, halo, hydroxy-($C_1$–$C_4$)alkyl, ($C_1$–$C_4$)alkoxy-($C_1$–$C_4$)alkyl, ($C_1$–$C_4$)alkyl optionally substituted with up to five fluoro or ($C_1$–$C_4$)alkoxy optionally substituted with up to five fluoro.

A preferred group of compounds within Group F, designated Group FA, are those compounds, prodrugs thereof and pharmaceutically acceptable salts of said compounds or said prodrugs wherein:

$R^1$ is (R)-1-hydroxy-ethyl;
$R^2$ is hydrogen;
$R^3$ is

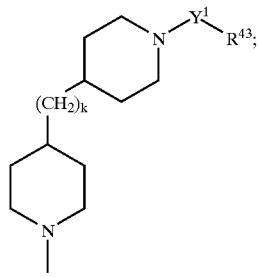

k is 0;
$Y^1$ is a covalent bond; and
$R^{43}$ is 4-pyrimidinyl substituted at the 2-position with 1-hydroxymethyl.

A preferred group of compounds within Group FA, designated Group FB, are those compounds, prodrugs thereof and pharmaceutically acceptable salts of said compounds or said prodrugs, which is 1R-(4-{1'-[2-(1R-hydroxy-ethyl)-pyrimidin-4-yl]-[4,4']bipiperidinyl-1-yl}-pyrimidin-2-yl)-ethanol.

Another preferred group of compounds of formula I, designated Group G, are those compounds of formula I, prodrugs thereof and pharmaceutically acceptable salts of said compounds or said prodrugs, wherein:

$R^3$ is

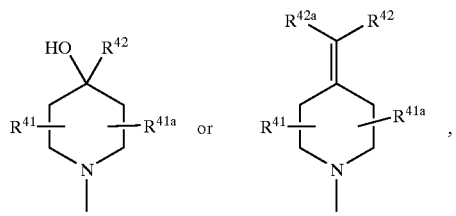

$R^{42}$ and $R^{42a}$ are independently hydrogen, ($C_3$–$C_7$) cycloalkyl, $Ar^6$—($C_0$–$C_3$)alkylenyl, $Ar^6$—($C_2$–$C_4$) alkenyl, $Ar^6$-carbonyl or ($C_1$–$C_6$)alkyl optionally substituted with up to five fluoro; and $R^{41}$ and $R^{41a}$ are independently hydrogen or ($C_1$–$C_4$) alkyl.

Still another preferred group of compounds of formula I, designated Group H, are those compounds of formula I, prodrugs thereof and pharmaceutically acceptable salts of said compounds or said prodrugs, wherein:

$R^1$ is $C(OH)R^4R^5$, where $R^4$ and $R^5$ are each independently hydrogen or methyl;

$R^2$ is hydrogen;

$R^3$ is

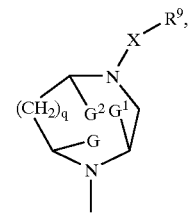

wherein said $R^3$ is substituted by $R^6$, $R^7$ or $R^8$;

G, $G^1$ and $G^2$ are taken separately and are each hydrogen and $R^6$ is hydrogen or ($C_1$–$C_4$)alkyl; $R^7$ and $R^8$ are each independently hydrogen or ($C_1$–$C_4$)alkyl; or G and $G^1$ are taken together and are ($C_1$–$C_3$)alkylene and $R^6$, $R^7$, $R^8$ and $G^2$ are hydrogen; or $G^1$ and $G^2$ are taken together and are ($C_1$–$C_3$)alkylene and $R^6$, $R^7$, $R^8$ and G are hydrogen;

q is 0 or 1;

X is a covalent bond, oxycarbonyl, vinylenylcarbonyl, oxy($C_1$–$C_4$)alkylenylcarbonyl, thio($C_1$–$C_4$) alkylenylcarbonyl or vinylenylsulfonyl; said vinylenylcarbonyl and said vinylenylsulfonyl in the definition of X are optionally substituted on one or two vinylenyl carbons with ($C_1$–$C_4$)alkyl, benzyl or Ar; said oxy ($C_1$–$C_4$)alkylenylcarbonyl and said thio($C_1$–$C_4$) alkylenylcarbonyl in the definition of X are optionally substituted with up to two ($C_1$–$C_4$)alkyl, benzyl or Ar;

$R^9$ is ($C_3$–$C_7$)cycloalkyl, $Ar^1$—($C_0$–$C_4$)alkylenyl or ($C_1$–$C_6$)alkyl optionally substite up to five fluoro;

$Ar^1$ is phenyl, naphthyl, pyridyl, pyrimidyl, pyrazinyl, pyridazinyl, triazinyl, quinolyl, isoquinolyl, quinazolyl, quinoxalyl, phthalazinyl, cinnolinyl, naphthyridinyl, pteridinyl, pyrazinopyrazinyl, pyrazinopyridazinyl, pyrimidopyridazinyl, pyrimidopyrimidyl, pyridopyrimidyl, pyridopyrazinyl, pyridopyridazinyl, pyrrolyl, furanyl, thienyl, imidazolyl, oxazolyl, thiazolyl, pyrazolyl, isoxazolyl, isothiazolyl, triazolyl, oxadiazolyl, thiadiazolyl, tetrazolyl, indolyl, benzofuranyl, benzothienyl, benzimidazolyl, benzoxazolyl, benzothiazolyl, indazolyl, benzisoxazolyl, benzisothiazolyl, pyrrolopyridyl, furopyridyl, thienopyridyl, imidazolopyridyl, oxazolopyridyl, thiazolopyridyl, pyrazolopyridyl, isoxazolopyridyl, isothiazolopyridyl, pyrrolopyrimidyl, furopyrimidyl, thienopyrimidyl, imidazolopyrimidyl, oxazolopyrimidyl, thiazolopyrimidyl, pyrazolopyrimidyl, isoxazolopyrimidyl, isothiazolopyrimidyl, pyrrolopyrazinyl, furopyrazinyl, thienopyrazinyl, imidazolopyrazinyl, oxazolopyrazinyl, thiazolopyrazinyl, pyrazolopyrazinyl, isoxazolopyrazinyl, isothiazolopyrazinyl, pyrrolopyridazinyl, furopyridazinyl, thienopyridazinyl, imidazolopyridazinyl, oxazolopyridazinyl, thiazolopyridazinyl, pyrazolopyridazinyl, isoxazolopyridazinyl or isothiazolopyridazinyl; and said $Ar^1$ is optionally substituted as set forth above.

A preferred group of compounds within Group H, designated Group HA, are those compounds, prodrugs thereof and pharmaceutically acceptable salts of said compounds or said prodrugs, wherein:

X is a covalent bond, oxycarbonyl or vinylenylcarbonyl optionally substituted on one or two vinylenyl carbons with $(C_1–C_4)$alkyl, benzyl or Ar;

$R^9$ is $Ar^1$—$(C_0–C_4)$alkylenyl;

$Ar^1$ is phenyl, naphthyl, pyridyl, pyrimidyl, pyrazinyl, triazinyl, quinolyl, isoquinolyl, quinazolyl, quinoxalyl, furanyl, thienyl, indolyl, benzofuranyl, benzothienyl, benzoxazolyl, benzothiazolyl, furopyridyl, oxazolopyridyl, thiazolopyridyl, thienopyridyl, furopyrimidyl, thienopyrimidyl, oxazolopyrimidyl or thiazolopyrimidyl; and said $Ar^1$ is optionally substituted as set forth in claim 1.

A preferred group of compounds within Group HA, designated Group HB, are those compounds, prodrugs thereof and pharmaceutically acceptable salts of said compounds or said prodrugs, wherein:

$R^2$ is hydrogen;

$R^4$ is hydrogen or methyl;

$R^5$ is methyl;

G, $G^1$ and $G^2$ are hydrogen;

$R^6$ and $R^7$ are each independently hydrogen or methyl;

$R^8$ is hydrogen.

A preferred group of compounds within Group HB, designated Group HC, are those compounds, prodrugs thereof and pharmaceutically acceptable salts of said compounds or said prodrugs wherein:

$R^1$ is (R)-1-hydroxy-ethyl; and $R^3$ is

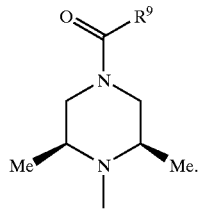

A preferred compound within Group HC is the compound wherein $R^9$ is 2-furo[3,2-c]pyridyl, a prodrug thereof or a pharmaceutically acceptable salt of said compound or said prodrug.

Another preferred compound within Group HC is the compound wherein $R^9$ is 2-(4-chloro-furo[3,2-c]pyridyl), a prodrug thereof or a pharmaceutically acceptable salt of said compound or said prodrug.

Another preferred compound within Group HC is the compound wherein $R^9$ is 2-(4-pyrrolidin-1-yl-furo[3,2-c]pyridyl), a prodrug thereof or a pharmaceutically acceptable salt of said compound or said prodrug.

Another preferred compound within Group HC is the compound wherein $R^9$ is 2-(4-morpholin-4-yl-furo[3,2-c]pyridyl), a prodrug thereof or a pharmaceutically acceptable salt of said compound or said prodrug.

Another preferred compound within Group HC is the compound wherein $R^9$ is 2-imidazo[1,2-a]pyridyl, a prodrug thereof or a pharmaceutically acceptable salt of said compound or said prodrug.

Preferred compounds within Group HC are furo[3,2-c]pyridin-2-yl-{4-[2-(1R-hydroxy-ethyl)-pyrimidin4-yl]-3R,5S-dimethyl-piperazin-1-yl}-methanone; (4-chloro-furo[3,2-c]pyridin-2-yl)-{4-[2-(1R-hydroxy-ethyl)-pyrimidin4-yl]-3R,5S-dimethyl-piperazin-1-yl}-methanone; {4-[2-(1R-hydroxy-ethyl)-pyrimidin4-yl]-3R,5S-dimethyl-piperazin-1-yl}-(4-pyrrolidin-1-yl-furo[3,2-c]pyridin-2-yl)-methanone; {4-[2-(1R-hydroxy-ethyl)-pyrimidin-4-yl]-3R,5S-dimethyl-piperazin-1-yl}-(4-morpholin4-yl-furo[3,2-c]pyridin-2-yl)-methanone; and {4-[2-(1R-hydroxy-ethyl)-pyrimidin4-yl]-3R,5S-dimethyl-piperazin-1-yl}-imidazo[1,2-a]pyridin-2-yl-methanone.

Another preferred group of compounds within Group HB, designated Group HD, are those compounds, prodrugs thereof and pharmaceutically acceptable salts of said compounds or said prodrugs wherein:

$R^1$ is (R)-1-hydroxy-ethyl; and $R^3$ is

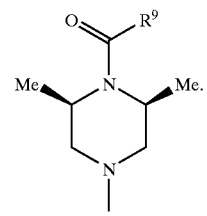

A preferred compound within Group HD is the compound wherein $R^9$ is 2-furo[3,2-c]pyridyl, a prodrug thereof or a pharmaceutically acceptable salt of said compound or said prodrug.

An especially preferred compound within Group HD is furo[3,2-c]pyridin-2-yl-{4-[2-(1R-hydroxy-ethyl)-pyrimidin4-yl]-2R,6S-dimethyl-piperazin-1-yl}-methanone.

Another preferred group of compounds within Group HB, designated Group HE, are those compounds, prodrugs thereof and pharmaceutically acceptable salts of said compounds or said prodrugs wherein:

$R^1$ is (R)-1-hydroxy-ethyl; and

R³ is

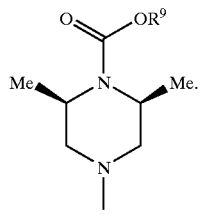

A preferred compound within Group HE is the compound wherein R⁹ is 3-pyridyl, a prodrug thereof or a pharmaceutically acceptable salt of said compound or said prodrug.

Another preferred compound within Group HE is the compound wherein R⁹ is 3-(2-methylpyridyl), a prodrug thereof or a pharmaceutically acceptable salt of said compound or said prodrug.

Another preferred compound within Group HE is the compound wherein R⁹ is 3-(5-chloropyridyl), a prodrug thereof or a pharmaceutically acceptable salt of said compound or said prodrug.

Another preferred compound within Group HE is the compound wherein R⁹ is 3-(6-methylpyridyl), a prodrug thereof or a pharmaceutically acceptable salt of said compound or said prodrug.

Preferred compounds within Group HE are 4-[2-(1R-hydroxy-ethyl)-pyrimidin-4-yl]-2R,6S-dimethyl-piperazine-1-carboxylic acid pyridin-3-yl ester; 4-[2-(1R-hydroxy-ethyl)-pyrimidin-4-yl]-2R,6S-dimethyl-piperazine-1-carboxylic acid 2-methyl-pyridin-3-yl ester; 4-[2-(1R-hydroxy-ethyl)-pyrimidin4-yl]-2R,6S-dimethyl-piperazine-1-carboxylic acid 5-chloro-pyridin-3-yl ester; and 4-[2-(1R-hydroxy-ethyl)-pyrimidin-4-yl]-2R,6S-dimethyl-piperazine-1-carboxylic acid 6-methyl-pyridin-3-yl ester.

Another preferred group of compounds within Group HB, designated Group HF, are those compounds, prodrugs thereof and pharmaceutically acceptable salts of said compounds or said prodrugs wherein:

R¹ is (R)-1-hydroxy-ethyl; and
R³ is

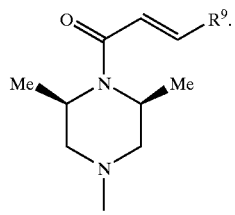

A preferred compound within the Group HF is the compound wherein R⁹ is 2-thienyl, a prodrug thereof or a pharmaceutically acceptable salt of said compound or said prodrug.

An especially preferred compound within Group HF is (E)-1-{4-[2-(1R-hydroxy-ethyl)-pyrimidin-4-yl]-2R,6S-dimethyl-piperazin-1-yl}-3-thiophen-2-yl-propenone.

Another preferred group of compounds within Group HB, designated Group HG, are those compounds, prodrugs thereof and pharmaceutically acceptable salts of said compounds or said prodrugs wherein:

R¹ is (R)-1-hydroxy-ethyl;

R³ is

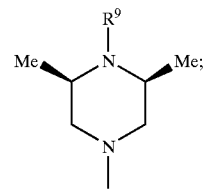

and

R⁹ is pyrimidyl or triazinyl; said pyrimidyl or triazinyl is optionally substituted with up to two hydroxy, $(C_1-C_4)$ alkyl, $(C_3-C_7)$cycloalkyl, $(C_1-C_4)$alkoxy, hydroxy-$(C_1-C_4)$alkyl, $(C_1-C_4)$alkoxy-$(C_1-C_4)$alkylenyl, phenyl, piperazinyl optionally substituted with $(C_1-C_4)$ alkyl, or imidazolyl optionally substituted with up to two $(C_1-C_4)$alkyl.

A preferred group of compounds within Group HG, designated Group HH, are those compounds, prodrugs thereof and pharmaceutically acceptable salts of said compounds or said prodrugs wherein: R⁹ is pyrimid-2-yl optionally substituted with up to two $(C_1-C_4)$alkyl, hydroxy-$(C_1-C_4)$alkyl or $(C_1-C_4)$alkoxy-$(C_1-C_4)$alkyl.

A preferred compound within the Group HH is the compound wherein R⁹ is 4,6-dimethylpyrimid-2-yl, a prodrug thereof or a pharmaceutically acceptable salt of said compound or said prodrug.

Another preferred compound within the Group HH is the compound wherein R⁹ is 4-methoxymethyl-6-methylpyrimid-2-yl, a prodrug thereof or a pharmaceutically acceptable salt of said compound or said prodrug.

Another preferred compound within the Group HH is the compound wherein R⁹ is 4-hydroxymethyl-6-methylpyrimid-2-yl, a prodrug thereof or a pharmaceutically acceptable salt of said compound or said prodrug.

A preferred group of compounds within the Group HH are 1R-{4-[4-(4,6-dimethyl-pyrimidin-2-yl)-3R,5S-dimethyl-piperazin-1-yl]-pyrimidin-2-yl}-ethanol; 1R-{4-[4-(4-methoxymethyl-6-methyl-pyrimidin-2-yl)-3R,5S-dimethyl-piperazin-1-yl]-pyrimidin-2-yl}-ethanol; and 1R-{4-[4-(4-hydroxymethyl-6-methyl-pyrimidin-2-yl)-3R,5S-dimethyl-piperazin-1-yl]-pyrimidin-2-yl}-ethanol.

Another preferred group of compounds within the Group HG, designated HI, are those compounds, prodrugs thereof and pharmaceutically acceptable salts of said compounds or said prodrugs wherein: R⁹ is pyrimid-4-yl optionally substituted with up to two $(C_1-C_4)$alkylpiperazin-1-yl or imidazolyl; and said imidazolyl is optionally substituted with up to two $(C_1-C_4)$alkyl.

A preferred compound within the Group HI is the compound wherein R⁹ is 2-(4-methylpiperazin-1-yl)-pyrimid-4-yl, a prodrug thereof or a pharmaceutically acceptable salt of said compound or said prodrug.

Another preferred compound within the Group HI is the compound wherein R⁹ is 2-(4-ethylpiperazin-1-yl)-pyrimid-4-yl, a prodrug thereof or a pharmaceutically acceptable salt of said compound or said prodrug.

Another preferred compound within the Group HI is the compound wherein R⁹ is 2-(4-methylimidazol-1-yl)-pyrimid-4-yl, a prodrug thereof or a pharmaceutically acceptable salt of said compound or said prodrug wherein.

Another preferred compound within the Group HI is the compound wherein R⁹ is 2-(2-methylimidazol-1-yl)-pyrimid-4-yl, a prodrug thereof or a pharmaceutically acceptable salt of said compound or said prodrug wherein.

Another preferred compound within the Group HI is the compound wherein R⁹ is 2-(2,4-dimethylimidazol-1-yl)- pyrimid-4-yl, a prodrug thereof or a pharmaceutically acceptable salt of said compound or said prodrug.

Another preferred compound within the Group HI is the compound wherein $R^9$ is 2-(4-isopropylpiperazin-1-yl)-pyrimid-4-yl, a prodrug thereof or a pharmaceutically acceptable salt of said compound or said prodrug.

Preferred compounds within Group HI are 1R-(4-{3R,5S-dimethyl-4-[2-(4-methyl-piperazin-1-yl)-pyrimidin-4-yl]-piperazin-1-yl}-pyrimidin-2-yl)-ethanol; 1R-(4-{4-[2-(4-ethyl-piperazin-1-yl)-pyrimidin-4-yl]-3R,5S-dimethyl-piperazin-1-yl}-pyrimidin-2-yl)-ethanol; 1R-(4-{3R,5S-dimethyl-4-[2-(4-methyl-imidazol-1-yl)-pyrimidin-4-yl]-piperazin-1-yl}-pyrimidin-2-yl)-ethanol; 1R-(4-{3R,5S-dimethyl-4-[2-(2-methyl-imidazol-1-yl)-pyrimidin-4-yl]-piperazin-1-yl}-pyrimidin-2-yl)-ethanol; 1R-(4-{4-[2-(2,4-dimethyl-imidazol-1-yl)-pyrimidin-4-yl]-3R,5S-dimethyl-piperazin-1-yl}-pyrimidin-2-yl)-ethanol; and 1R-(4-{4-[2-(4-isopropyl-piperazin-1-yl)-pyrimidin-4-yl]-3R,5S-dimethyl-piperazin-1-yl}-pyrimidin-2-yl)-ethanol.

Another preferred group of compounds within Group HG, designated Group HJ, are those compounds, prodrugs thereof and pharmaceutically acceptable salts of said compounds or said prodrugs wherein: $R^9$ is [1,3,5]-triazin-2-yl optionally substituted with up to two hydroxy, $(C_1–C_4)$alkyl, $(C_3–C_7)$cycloalkyl, $(C_1–C_4)$alkoxy, hydroxy-$(C_1–C_4)$alkyl, $(C_1–C_4)$alkylpiperazin-1-yl or phenyl.

A preferred compound within the Group HJ is the compound wherein $R^9$ is 4-methyl-6-(4-methylpiperazin-1-yl)-[1,3,5]-triazin-2-yl, a prodrug thereof or a pharmaceutically acceptable salt of said compound or said prodrug.

Another preferred compound within the Group HJ is the compound wherein $R^9$ is 4-methoxy-6-methyl-[1,3,5]-triazin-2-yl, a prodrug thereof or a pharmaceutically acceptable salt of said compound or said prodrug.

Another preferred compound within the Group HJ is the compound wherein $R^9$ is 4,6-dimethyoxy-[1,3,5]-triazin-2-yl, a prodrug thereof or a pharmaceutically acceptable salt of said compound or said prodrug.

Another preferred compound within the Group HJ is the compound wherein $R^9$ is 4-ethoxy-6-methyl-[1,3,5]-triazin-2-yl, a prodrug thereof or a pharmaceutically acceptable salt of said compound or said prodrug.

Another preferred compound within the Group HJ is the compound wherein $R^9$ is 4-isopropoxy-6-methyl-[1,3,5]-triazin-2-yl, a prodrug thereof or a pharmaceutically acceptable salt of said compound or said prodrug.

Another preferred compound within the Group HJ is the compound wherein $R^9$ is 4-phenyl-[1,3,5]-triazin-2-yl, a prodrug thereof or a pharmaceutically acceptable salt of said compound or said prodrug.

Another preferred compound within the Group HJ is the compound wherein $R^9$ is 4-hydroxymethyl-6-methoxy-[1,3,5]-triazin-2-yl, a prodrug thereof or a pharmaceutically acceptable salt of said compound or said prodrug.

Another preferred compound within the Group HJ is the compound wherein $R^9$ is 4-isopropoxy-6-methoxy-[1,3,5]-triazin-2-yl, a prodrug thereof or a pharmaceutically acceptable salt of said compound or said prodrug.

Another preferred compound within the Group HJ is the compound wherein $R^9$ is 4-isopropyl-[1,3,5]-triazin-2-yl, a prodrug thereof or a pharmaceutically acceptable salt of said compound or said prodrug.

Another preferred compound within the Group HJ is the compound wherein $R^9$ is 4-ethyl-6-methoxy-[1,3,5]-triazin-2-yl, a prodrug thereof or a pharmaceutically acceptable salt of said compound or said prodrug.

Another preferred compound within the Group HJ is the compound wherein $R^9$ is 4-cyclopropyl-[1,3,5]-triazin-2-yl, a prodrug thereof or a pharmaceutically acceptable salt of said compound or said prodrug.

Another preferred compound within the Group HJ is the compound wherein $R^9$ is 4,6-dimethyl-[1,3,5]-triazin-2-yl, a prodrug thereof or a pharmaceutically acceptable salt of said compound or said prodrug.

Another preferred compound within the Group HJ is the compound wherein $R^9$ is 4-methyl-6-phenyl-[1,3,5]-triazin-2-yl, a prodrug thereof or a pharmaceutically acceptable salt of said compound or said prodrug.

Preferred compounds within the Group HJ are 1R-(4-{3R,5S-dimethyl-4-[4-methyl-6-(4-methyl-piperazin-1-yl)-[1,3,5]triazin-2-yl]-piperazin-1-yl}-pyrimidin-2-yl)-ethanol; 1R-{4-[4-(4-methoxy-6-methyl-[1,3,5]triazin-2-yl)-3R,5S-dimethyl-piperazin-1-yl]-pyrimidin-2-yl}-ethanol; 1R-{4-[4-(4,6-dimethoxy-[1,3,5]triazin-2-yl)-3R,5S-dimethyl-piperazin-1-yl]-pyrimidin-2-yl}-ethanol; 1R-{4-[4-(4-ethoxy-6-methyl 1,3,5]triazin-2-yl)-3R,5S-dimethyl-piperazin-1-yl]-pyrimidin-2-yl}-ethanol; 1R-{4-[4-(4-isopropoxy-6-methyl-[1,3,5]triazin-2-yl]-3R,5S-dimethyl-piperazin-1-yl]-pyrimidin-2-yl}-ethanol; 1R-{4-[3R,5S-dimethyl-4-(4-phenyl-[1,3,5]triazin-2-yl)-piperazin-1-yl]-pyrimidin-2-yl}-ethanol; 1R-{4-[4-(4-hydroxymethyl-6-methoxy-[1,3,5]triazin-2-yl)-3R,5S-dimethyl-piperazin-1]-pyrimidin-2-yl}-ethanol; 1R-{4-[4-(4-isopropoxy-6-methoxy-[1,3,5]triazin-2-yl)-3R,5S-dimethyl-piperazin-1-yl]-pyrimidin-2-yl}-ethanol; 1R-{4-[4-(4-isopropyl-[1,3,5]triazin-2-yl)-3R,5S-dimethyl-piperazin-1-yl]-pyrimidin-2-yl}-ethanol; 1R-{4-[4-(4,6-dimethyl-[1,3,5]triazin-2-yl)-3R,5S-dimethyl-piperazin-1-yl]-pyrimidin-2-yl}-ethanol; 1R-{4-[3R,5S-dimethyl-4-(4-methyl-6-phenyl-[1,3,5]triazin-2-yl)-piperazin-1-yl]pyrimidin-2-yl}-ethanol; 1R-{4-[4-(4-cyclopropyl-[1,3,5]triazin-2-yl)-3R,5S-dimethyl-piperazin-1-yl]-pyrimidin-2-yl}-ethanol; and 1R-{4-[4-(4-ethyl-6-methoxy-[1,3,5]triazin-2-yl)-3R,5S-dimethyl-piperazin-1-yl]-pyrimidin-2-yl}-ethanol.

Another group of preferred compounds within the Group HB, designated Group HK, are those compounds, prodrugs thereof and pharmaceutically acceptable salts of said compounds or said prodrugs wherein:

$R^1$ is (R)-1-hydroxy-ethyl;

$R^3$ is

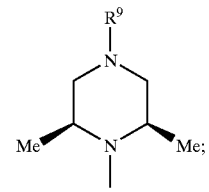

and $R^9$ is pyrimidyl or triazinyl, said pyrimidyl and triazinyl optionally substituted with up to two hydroxy, $(C_1–C_4)$ alkyl, $(C_3–C_7)$cycloalkyl, $(C_1–C_4)$alkoxy, hydroxy-$(C_1–C_4)$alkyl, $(C_1–C_4)$alkoxy-$(C_1–C_4)$alkyl, triazolyl, acetyl, morpholinyl, $(C_1–C_4)$alkylpiperazinyl, phenyl or imidazolyl optionally substituted with up to two $(C_1–C_4)$alkyl.

A preferred group of compounds within the Group HK, designated HL, are those compounds, prodrugs thereof and pharmaceutically acceptable salts of said compounds or said prodrugs wherein: $R^9$ is pyrimid-2-yl optionally substituted with up to two $(C_1–C_4)$alkyl, hydroxy-$(C_1–C_4)$alkyl or triazolyl.

A preferred compound within the Group HL is the compound wherein $R^9$ is 4,6-dimethyl-pyrimid-2-yl, a prodrug thereof or a pharmaceutically acceptable salt of said compound or said prodrug.

Another preferred compound within the Group HL is the compound wherein $R^9$ is 4-hydroxymethyl-6-methylpyrimid-2-yl, a prodrug thereof or a pharmaceutically acceptable salt of said compound or said prodrug.

Another preferred compound within the Group HL is the compound wherein $R^9$ is 4-[1,2,4]-triazol-1-yl-pyrimid-2-yl, a prodrug thereof or a pharmaceutically acceptable salt of said compound or said prodrug.

Preferred compounds within the Group HL are 1R-{4-[4-(4,6-dimethyl-pyrimidin-2-yl)-2R,6S-dimethyl-piperazin-1-yl]-pyrimidin-2-yl}-ethanol; 1R-{4-[4-(4-hydroxymethyl-6-methyl-pyrimidin-2-yl)-2R,6S-dimethyl-piperazin-1-yl]-pyrimidin-2-yl}-ethanol; and 1R-{4-[2R,6S-dimethyl-4-(4-[1,2,4]triazol-1-yl-pyrimidin-2-yl)-piperazin-1-yl]-pyrimidin-2-yl}-ethanol.

Another preferred group of compounds within the Group HK, designated Group HM, are those compounds, prodrugs thereof and pharmaceutically acceptable salts of said compounds or said prodrugs wherein: $R^9$ is pyrimid-4-yl optionally substituted with up to two $(C_1-C_4)$alkyl, hydroxy-$(C_1-C_4)$alkyl, acetyl, morpholinyl, $(C_1-C_4)$alkylpiperazinyl, triazolyl or imidazolyl optionally substituted with up to two $(C_1-C_4)$alkyl.

A preferred compound within the Group HM is the compound wherein $R^9$ is 2,6-dimethyl-pyrimid-4-yl, a prodrug thereof or a pharmaceutically acceptable salt of said compound or said prodrug.

Another preferred compound within the Group HM is the compound wherein $R^9$ is 2-hydroxymethyl-6-methyl-pyrimid-4-yl, a prodrug thereof or a pharmaceutically acceptable salt of said compound or said prodrug.

Another preferred compound within the Group HM is the compound wherein $R^9$ is 2-acetyl-pyrimid-4-yl, a prodrug thereof or a pharmaceutically acceptable salt of said compound or said prodrug.

Another preferred compound within the Group HM is the compound wherein $R^9$ is 2-morpholin-4-yl-pyrimid-4-yl, a prodrug thereof or a pharmaceutically acceptable salt of said compound or said prodrug.

Another preferred compound within the Group HM is the compound wherein $R^9$ is 2-(4-methylpiperazin-1-yl)-pyrimid-4-yl, a prodrug thereof or a pharmaceutically acceptable salt of said compound or said prodrug.

Another preferred compound within the Group HM is the compound wherein $R^9$ is 2-[1,2,4]-triazol-1-yl-pyrimid-4-yl, a prodrug thereof or a pharmaceutically acceptable salt of said compound or said prodrug.

Another preferred compound within the Group HM is the compound wherein $R^9$ is 2-(1S-hydroxyethyl)-pyrimid-4-yl, a prodrug thereof or a pharmaceutically acceptable salt of said compound or said prodrug.

Another preferred compound within the Group HM is the compound wherein $R^9$ is 2-(1R-hydroxyethyl)-pyrimid-4-yl, a prodrug thereof or a pharmaceutically acceptable salt of said compound or said prodrug.

Another preferred compound within the Group HM is the compound wherein $R^9$ is 2-(4-ethylpiperazin-1-yl)-pyrimid-4-yl, a prodrug thereof or a pharmaceutically acceptable salt of said compound or said prodrug.

Another preferred compound within the Group HM is the compound wherein $R^9$ is 2-(4-methylimidazol-1-yl)-pyrimid-4-yl, a prodrug thereof or a pharmaceutically acceptable salt of said compound or said prodrug.

Another preferred compound within the Group HM is the compound wherein $R^9$ is 2-(2,4-dimethylimidazol-1-yl)-pyrimid-4-yl, a prodrug thereof or a pharmaceutically acceptable salt of said compound or said prodrug.

Preferred compounds within the HB Group are 1R-{4-[4-(2,6-dimethyl-pyrimidin-4-yl)-2R,6S-dimethyl-piperazin-1-yl]-pyrimidin-2-yl}-ethanol; 1R-(4-{4-[2-(1R-hydroxy-ethyl)-pyrimidin-4-yl]-2R,6S-dimethyl-piperazin-1-yl}-pyrimidin-2-yl)-ethanol; 1R-{4-[4-(2-hydroxymethyl-6-methyl-pyrimidin-4-yl)-2R,6S-dimethyl-piperazin-1-yl]-pyrimidin-2-yl}-ethanol; 1R-(4-{4-[2-(1 S-hydroxy-ethyl)-pyrimidin-4-yl]-2R,6S-dimethyl-piperazin-1-yl}-pyrimidin-2-yl)-ethanol; (4-{4-[2-(1R-hydroxy-ethyl)-pyrimidin-4-yl]-3R,5S-dimethyl-piperazin-1-yl}-pyrimidin-2-yl)-ethanone; 1R-{4-[2R,6S-dimethyl-4-(2-morpholin-4-yl-pyrimidin-4-yl)-piperazin-1-yl]-pyrimidin-2-yl}-ethanol; 1R-(4-{2R,6S-dimethyl-4-[2-(4-methyl-piperazin-1-yl)-pyrimidin-4-yl]-piperazin-1-yl}-pyrimidin-2-yl)-ethanol; 1R-4-[2R,6S-dimethyl-4-(2-[1,2,4]triazol-1-yl-pyrimidin-4-yl)-piperazin-1-yl]-pyrimidin-2-yl}-ethanol; 1R-(4-{4-[2-(1R-hydroxy-ethyl)-pyrimidin-4-yl]-2R,6R-dimethyl-piperazin-1-yl}-pyrimidin-2-yl)-ethanol; 1R-(4-{4-[2-(4-ethyl-piperazin-1-yl)-pyrimidin-4-yl]-2R,6S-dimethyl-piperazin-1-yl}-pyrimidin-2-yl)-ethanol; 1R-(4-{2R,6S-dimethyl-4-[2-(4-methyl-imidazol-1-yl)-pyrimidin-4-yl]-piperazin-1-yl}-pyrimidin-2-yl)-ethanol; and 1R-(4-{4-[2-(2,4-dimethyl-imidazol-1-yl)-pyrimidin-4-yl]-2R,6S-dimethyl-piperazin-1-yl}-pyrimidin-2-yl)-ethanol.

Another preferred compound within the Group HB is the compound wherein $R^1$ is (R)-1-hydroxyethyl; $R^3$ is

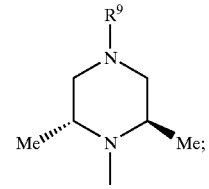

and $R^9$ is 2-(1R-hydroxyethyl-pyrimid-4-yl, a prodrug thereof or a pharmaceutically acceptable salt of said compound or said prodrug.

A preferred group of compounds within the Group HK, designated Group HN, are those compounds, prodrugs thereof and pharmaceutically acceptable salts of said compounds and said prodrugs, wherein $R^9$ is [1,3,5]-triazin-2-yl optionally substituted with up to two hydroxy, $(C_1-C_4)$alkyl, $(C_3-C_7)$cycloalkyl, hydroxy-$(C_1-C_4)$alkyl, $(C_1-C_4)$alkoxy-$(C_1-C_4)$alkyl, $(C_1-C_4)$alkoxy, morpholinyl or phenyl.

A preferred compound within the Group HN is the compound wherein $R^9$ is 4-morpholin-4-yl-[1,3,5]-triazin-2-yl, a prodrug thereof or a pharmaceutically acceptable salt of said compound or said prodrug.

Another preferred compound within the Group HN is the compound wherein $R^9$ is 4-methoxy-6-methyl-[1,3,5]-triazin-2-yl, a prodrug thereof or a pharmaceutically acceptable salt of said compound or said prodrug.

Another preferred compound within the Group HN is the compound wherein $R^9$ is 4,6-dimethoxy-[1,3,5]-triazin-2-yl, a prod rug thereof or a pharmaceutically acceptable salt of said compound or said prodrug.

Another preferred compound within the Group HN is the compound wherein $R^9$ is 4-phenyl-[1,3,5]-triazin-2-yl, a prodrug thereof or a pharmaceutically acceptable salt of said compound or said prodrug.

Another preferred compound within the Group HN is the compound wherein $R^9$ is 4-cyclopropyl-[1,3,5]-triazin-2-yl, a prodrug thereof or a pharmaceutically acceptable salt of said compound or said prodrug.

Another preferred compound within the Group HN is the compound wherein R⁹ is 4,6-dimethyl-[1,3,5]-triazin-2-yl, a prodrug thereof or a pharmaceutically acceptable salt of said compound or said prodrug.

Another preferred compound within the Group HN is the compound wherein R⁹ is 4-hydroxymethyl-6-phenyl-[1,3,5]-triazin-2-yl, a prodrug thereof or a pharmaceutically acceptable salt of said compound or said prodrug.

Another preferred compound within the Group HN is the compound wherein R⁹ is 4-methoxy-6-methoxymethyl-[1,3,5]-triazin-2-yl, a prodrug thereof or a pharmaceutically acceptable salt of said compound or said prodrug.

Another preferred compound within the Group HN is the compound wherein R⁹ is 4-methyl-[1,3,5]-triazin-2-yl, a prodrug thereof or a pharmaceutically acceptable salt of said compound or said prodrug.

Another preferred compound within the Group HN is the compound wherein R⁹ is 4-methoxymethyl-6-phenyl-[1,3,5]triazin-2-yl, a prod rug thereof or a pharmaceutically acceptable salt of said compound or said prodrug.

Preferred compounds within the Group HN are 1R-{4-[2R,6S-dimethyl-4-(4-morpholin-4-yl-[1,3,5]triazin-2-yl)-piperazin-1-yl]-pyrimidin-2-yl}-ethanol; 1R-{4-[4-(4-methoxy-6-methyl-[1,3,5]triazin-2-yl)-2R,6S-dimethyl-piperazin-1-yl]-pyrimidin-2-yl}-ethanol; 1R-{4-[4-(4,6-dimethoxy-[1,3,5]triazin-2-yl)-2R,6S-dimethyl-piperazin-1-yl]-pyrimidin-2-yl}-ethanol; 1R-{4-[4-(4-cyclopropyl-[1,3,5]triazin-2-yl)-2R,6S-dimethyl-piperazin-1-yl]-pyrimidin-2-yl}-ethanol; 1R-{4-[4-(4,6-dimethyl-[1,3,5]triazin-2-yl)-2R,6S-dimethyl-piperazin-1-yl]-pyrimidin-2-yl}-ethanol; 1R-{4-[4-(4-hydroxymethyl-6-phenyl-[1,3,5]triazin-2-yl)-2R,6S-dimethyl-piperazin-1-yl]-pyrimidin-2-yl}-ethanol; 1R-{4-[4-(4-methoxy-6-methoxymethyl-[1,3,5]triazin-2-yl)-2R,6S-dimethyl-piperazin-1-yl]-pyrimidin-2-yl}-ethanol; 1R-{4-[2R,6S-dimethyl-4-(4-methyl-[1,3,5]triazin-2-yl)-piperazin-1-yl]-pyrimidin-2-yl}-ethanol; 1R-{4-[4-(4-methoxymethyl-6-phenyl-[1,3,5]triazin-2-yl)-2R,6S-dimethyl-piperazin-1-yl]-pyrimidin-2-yl}-ethanol; and 1R-{4-[2R,6S-dimethyl-4-(4-phenyl-[1,3,5]triazin-2-yl)-piperazin-1-yl]-pyrimidin-2-yl}-ethanol.

Another preferred group of compounds within the Group HB, designated Group HO, are those compounds, prodrugs thereof and pharmaceutically acceptable salts of said compounds or said prodrugs wherein:

R¹ is (R)-1-hydroxy-ethyl;
R³ is

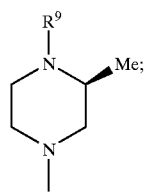

and

R⁹ is pyrimidyl, quinoxalyl or oxazolopyridyl optionally substituted with up to two (C₁–C₄)alkyl, (C₁–C₄)alkoxy or hydroxy-(C₁–C₄)alkyl.

A preferred compound within the Group HO is the compound wherein R⁹ is 4-hydroxymethyl-6-methyl-pyrimid-2-yl, a prodrug thereof or a pharmaceutically acceptable salt of said compound or said prodrug.

Another preferred compound within the Group HO is the compound wherein R⁹ is 2-hydroxymethyl-pyrimid-4-yl, a prodrug thereof or a pharmaceutically acceptable salt of said compound or said prodrug.

Another preferred compound within the Group HO is the compound wherein R⁹ is 2-hydroxymethyl-6-methyl-pyrimid-4-yl, a prodrug thereof or a pharmaceutically acceptable salt of said compound or said prodrug.

Another preferred compound within the Group HO is the compound wherein R⁹ is 2-(oxazolo[5,4-b]pyridyl), a prodrug thereof or a pharmaceutically acceptable salt of said compound or said prodrug.

Another preferred compound within the Group HO is the compound wherein R⁹ is 2-(oxazolo[4,5-b]pyridyl, a prodrug thereof or a pharmaceutically acceptable salt of said compound or said prodrug.

Another preferred compound within the Group HO is the compound wherein R⁹ is 2-quinoxalyl, a prodrug thereof or a pharmaceutically acceptable salt of said compound or said prodrug.

Preferred compounds within the Group HO are 1R-{4-[4-(4-hydroxymethyl-6-methyl-pyrimidin-2-yl)-3S-methyl-piperazin-1-yl]-pyrimidin-2-yl}-ethanol; 1R-{4-[4-(2-hydroxymethyl-pyrimidin-4-yl)-3S-methyl-piperazin-1-yl]-pyrimidin-2-yl}-ethanol; 1R-{4-[4-(2-hydroxymethyl-6-methyl-pyrimidin-4-yl)-3S-methyl-piperazin-1-yl]-pyrimidin-2-yl}-ethanol; 1R-[4-(3S-methyl-4-oxazolo[5,4-b]pyridin-2-yl-piperazin-1-yl)-pyrimidin-2-yl]-ethanol; 1R-[4-(3S-methyl-4-oxazolo[4,5-b]pyridin-2-yl-piperazin-1-yl)-pyrimidin-2-yl]-ethanol; and 1R-[4-(3S-methyl-4-quinoxalin-2-yl-piperazin-1-yl)-pyrimidin-2-yl]-ethanol.

Another preferred group of compounds within the Group HB, designated Group HP, are those compounds, prodrugs thereof and pharmaceutically acceptable salts of said compounds or said prodrugs wherein:

R¹ is (R)-1-hydroxy-ethyl;
R³ is

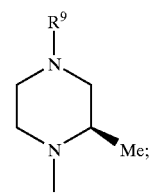

and

R⁹ is pyrimidyl optionally substituted with up to two (C₁–C₄)alkyl, (C₁–C₄)alkoxy, hydroxy-(C₁–C₄)alkyl.

A preferred compound within the Group HP is the compound wherein R⁹ is 2-(1R-hydroxyethyl)-pyrimid-4-yl, a prodrug thereof or a pharmaceutically acceptable salt of said compound or said prodrug.

A preferred compound within the Group HP is 1R-(4-{4-[2-(1R-hydroxy-ethyl)-pyrimidin-4-yl]-2R-methyl-piperazin-1-yl}-pyrimidin-2-yl)-ethanol.

Another preferred group of compounds within the Group HB, designated HQ, are those compounds, prodrugs thereof and pharmaceutically acceptable salts of said compounds or said prodrugs wherein:

R¹ is (R)-1-hydroxy-ethyl;

$R^3$ is

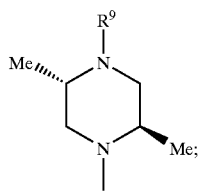

and $R^9$ is pyrimidyl optionally substituted with up to two $(C_1-C_4)$alkyl, $(C_1-C_4)$alkoxy, hydroxy-$(C_1-C_4)$alkyl.

A preferred compound within the Group HQ is the compound wherein $R^9$ is 2-(1R-hydroxyethyl)-pyrimid-4-yl, a prodrug thereof or a pharmaceutically acceptable salt of said compound or said prodrug.

An especially preferred compound within the Group HQ is (4-{4-[2-(1R-hydroxy-ethyl)-pyrimidin-4-yl]-2R,5S-dimethyl-piperazin-1-yl}-pyrimidin-2-yl)-ethanol.

Another preferred group of compounds within the Group HB, designated Group HR, are those compounds, prodrugs thereof and pharmaceutically acceptable salts of said compounds or said prodrugs wherein:

$R^1$ is (S)-1-hydroxy-ethyl;
$R^3$ is

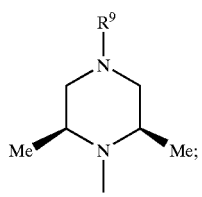

and $R^9$ is pyrimidyl optionally substituted with up to two $(C_1-C_4)$alkyl, $(C_1-C_4)$alkoxy or hydroxy-$(C_1-C_4)$alkyl.

A preferred compound within the Group HR is the compound wherein $R^9$ is 2-(1R-hydroxy-ethyl)-pyrimid-4-yl, a prodrug thereof or a pharmaceutically acceptable salt of said compound or said prodrug.

An especially preferred compound within the Group HR is 1S-(4-{4-[2-(1R-hydroxy-ethyl)-pyrimidin-4-yl]-2R,6S-dimethyl-piperazin-1-yl}-pyrimidin-2-yl)-ethanol.

Yet another preferred group of compounds within the Group HB, designated Group HS, are those compounds, prodrugs thereof and pharmaceutically acceptable salts of said compounds or said prodrugs wherein:

$R^1$ is acetyl;
$R^3$ is

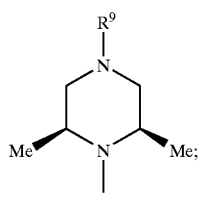

and $R^9$ is pyrimidyl optionally substituted with up to two $(C_1-C_4)$alkyl, $(C_1-C_4)$alkoxy, acetyl or hydroxy-$(C_1-C_4)$alkyl.

A preferred compound within the Group HS is the compound wherein $R^9$ is 2-acetyl-pyrimid-4-yl, a prodrug thereof or a pharmaceutically acceptable salt of said compound or said prodrug.

A preferred compound within the Group HS is the compound wherein $R^9$ is 2-(1R-hydroxyethyl)-pyrimid-4-yl, a prodrug thereof or a pharmaceutically acceptable salt of said compound or said prodrug.

Especially preferred compounds within the Group HS are 1-{4-[4-(2-acetyl-pyrimidin-4-yl)-2R*,6S*-dimethyl-piperazin-1-yl]-pyrimidin-2-yl}-ethanone or 1-(4-{4-[2-(1R-hydroxy-ethyl)-pyrimidin-4-yl]-2R,6S-dimethyl-piperazin-1-yl}-pyrimidin-2-yl)-ethanone.

A pharmaceutical composition, designated Composition A, comprising a compound of formula I, a prodrug thereof or a pharmaceutically acceptable salt of said compound or said prodrug and a pharmaceutically acceptable carrier or diluent.

A method of inhibiting sorbitol dehydrogenase in a mammal in need of such inhibition comprising administering to said mammal a sorbitol dehydrogenase inhibiting amount of a compound of formula I, a prodrug thereof or a pharmaceutically acceptable salt of said compound or said prodrug.

A method of treating diabetes in a mammal suffering from diabetes comprising administering to said mammal an effective amount of a compound of formula I, a prodrug thereof or a pharmaceutically acceptable salt of said compound or said prodrug.

A method, designated Method A, of treating or preventing diabetic complications in a mammal comprising administering to said mammal an effective amount of a compound of formula I, a prodrug thereof or a pharmaceutically acceptable salt of said compound or said prodrug.

A method of Method A wherein said mammal is suffering from diabetes.

A method of Method A wherein said diabetic complication is diabetic neuropathy.

A method of Method A wherein said diabetic complication is diabetic nephropathy.

A method of Method A wherein said diabetic complication is diabetic retinopathy.

A method of Method A wherein said diabetic complication is foot ulcers.

A method of Method A wherein said diabetic complication is a cardiovascular condition.

A pharmaceutical composition, designated Composition B, comprising a compound of formula I, a prodrug thereof or a pharmaceutically acceptable salt of said compound or said prodrug and an aldose reductase inhibitor, a prodrug thereof or a pharmaceutically acceptable salt of said aldose reductase inhibitor or said prodrug.

A composition of Composition B additionally comprising a pharmaceutically acceptable carrier or diluent.

A method of treating diabetes in a mammal suffering from diabetes comprising administering to said mammal an effective amount of a compound of formula I, a prodrug thereof or a pharmaceutically acceptable salt of said compound or said prodrug and an aldose reductase inhibitor, a prodrug of said aldose reductase inhibitor or a pharmaceutically acceptable salt of said aldose reductase inhibitor or said prodrug.

A method, designated Method B, of treating or preventing diabetic complications in a mammal comprising administering to said mammal an effective amount of a compound of formula I, a prodrug thereof or a pharmaceutically acceptable salt of said compound or said prodrug and an aldose reductase inhibitor, a prodrug of said aldose reductase inhibitor or a pharmaceutically acceptable salt of said aldose reductase inhibitor or said prodrug thereof.

A method of Method B wherein said mammal is suffering from diabetes.

A method of Method B wherein said diabetic complication is diabetic neuropathy.

A method of Method B wherein said diabetic complication is diabetic nephropathy.

A method of Method B wherein said diabetic complication is diabetic retinopathy.

A method of Method B wherein said diabetic complication is foot ulcers.

A method of Method B wherein said diabetic complication is a cardiovascular condition.

A pharmaceutical composition, designated Composition C, comprising a compound of formula I, a prodrug thereof or a pharmaceutically acceptable salt of said compound or said prodrug and a sodium hydrogen ion exchange (NHE-1) inhibitor, a prodrug of said NHE-1 inhibitor or a pharmaceutically acceptable salt of said NHE-1 inhibitor or said prodrug thereof.

A method, designated Method C, of treating ischemia in a mammal suffering from ischemia comprising administering to said mammal an effective amount of a compound of claim 1, a prodrug thereof or a pharmaceutically acceptable salt of said compound or said prodrug and a sodium hydrogen ion exchange (NHE-1) inhibitor, a prodrug of said NHE-1 inhibitor or a pharmaceutically acceptable salt of said NHE-1 inhibitor or said prodrug.

A method of Method C wherein said ischemia is perioperative myocardial ischemia.

A method of treating or preventing diabetic complications in a mammal, designated Method D, comprising administering to said mammal an effective amount of a compound of formula I, a prodrug thereof or a pharmaceutically acceptable salt of said compound or said prodrug and a sodium hydrogen ion exchange (NHE-1) inhibitor, a prodrug of said NHE-1 inhibitor or a pharmaceutically acceptable salt of said NHE-1 inhibitor or said prodrug.

A method of Method D wherein said mammal is suffering from diabetes.

A method of Method D wherein said diabetic complication is diabetic neuropathy.

A method of Method D wherein said diabetic complication is diabetic nephropathy.

A method of Method D wherein said diabetic complication is diabetic retinopathy.

A method of Method D wherein said diabetic complication is foot ulcers.

A method of Method D wherein said diabetic complication is a cardiovascular condition.

A method of treating diabetes in a mammal suffering from diabetes comprising administering to said mammal an effective amount of a compound of formula I, a prodrug thereof or a pharmaceutically acceptable salt of said compound or said prodrug, and a sodium hydrogen ion exchange (NHE-1) inhibitor, a prodrug of said NHE-1 inhibitor or a pharmaceutically acceptable salt of said NHE-1 inhibitor or said prodrug.

A kit comprising:
a. a compound of formula I, a prodrug thereof or a pharmaceutically acceptable salt of said compound or said prodrug in a first unit dosage form;
b. an aldose reductase inhibitor, a prodrug thereof or a pharmaceutically acceptable salt of said prodrug or said aldose reductase inhibitor in a second unit dosage form; and
c. a container.

A kit comprising:
a. a compound of formula I, a prodrug thereof or a pharmaceutically acceptable salt of said compound or said prodrug in a first unit dosage form;
b. a sodium hydrogen ion exchange (NHE-1) inhibitor, a prodrug thereof or a pharmaceutically acceptable salt of said prodrug or said NHE-1 inhibitor in a second unit dosage form; and
c. a container.

A method, designated Method E, of inhibiting sorbitol dehydrogenase in a mammal in need thereof comprising administering to said mammal Composition A.

A method of Method E wherein said ischemia is perioperative myocardial ischemia.

A method of treating ischemia in a mammal suffering from ischemia comprising administering to said mammal Composition C.

A method, designated Method F, of treating or preventing diabetic complications in a mammal comprising administering to said mammal Composition A.

A method of Method F wherein said mammal is suffering from diabetes.

A method, designated Method G, of treating or preventing diabetic complications in a mammal comprising administering to said mammal Composition B.

A method of Method G wherein said mammal is suffering from diabetes.

A method, designated Method H, of treating or preventing diabetic complications in a mammal comprising administering to said mammal Composition C.

A method of Method H wherein said mammal is suffering from diabetes.

A compound of formula I, a prodrug thereof or a pharmaceutically acceptable salt of said compound or said prodrug, wherein:

$R^1$ is $C(OH)R^4R^5$, where $R^4$ and $R^5$ are each independently hydrogen or methyl;

$R^2$ is hydrogen;

$R^3$ is wherein said piperazinyl $R^3$ is substituted by $R^6$, $R^7$ or $R^8$;

G, $G^1$ and $G^2$ are taken separately and are each hydrogen and $R^6$ is hydrogen or $(C_1-C_4)$alkyl; $R^7$ and $R^8$ are each independently hydrogen or $(C_1-C_4)$alkyl; or G and $G^1$ are taken together and are $(C_1-C_3)$alkylene and $R^6$, $R^7$, $R^8$ and $G^2$ are hydrogen; or $G^1$ and $G^2$ are taken together and are $(C_1-C_3)$alkylene and $R^6$, $R^7$, $R^8$ and G are hydrogen;

q is 0 or 1;

X is a covalent bond, oxycarbonyl, vinylenylcarbonyl, oxy$(C_1-C_4)$alkylenylcarbonyl, thio$(C_1-C_4)$alkylenylcarbonyl or vinylenylsulfonyl; said vinylenylcarbonyl and said vinylenylsulfonyl in the definition of X are optionally substituted on one or two vinylenyl carbons with (C₁–C₄)alkyl, benzyl or Ar; said oxy (C₁–C₄)alkylenylcarbonyl and said thio(C₁–C₄)alkylenylcarbonyl in the definition of X are optionally substituted with up to two (C₁–C₄)alkyl, benzyl or Ar;

R⁹ is (C₃–C₇)cycloalkyl, Ar¹—(C₀–C₄)alkylenyl or (C₁–C₆)alkyl optionally substite up to five fluoro;

Ar¹ is phenyl, naphthyl, pyridyl, pyrimidyl, pyrazinyl, pyridazinyl, triazinyl, quinolyl, isoquinolyl, quinazolyl, quinoxalyl, phthalazinyl, cinnolinyl, naphthyridinyl, pteridinyl, pyrazinopyrazinyl, pyrazinopyridazinyl, pyrimidopyridazinyl, pyrimidopyrimidyl, pyridopyrimidyl, pyridopyrazinyl, pyridopyridazinyl, pyrrolyl, furanyl, thienyl, imidazolyl, oxazolyl, thiazolyl, pyrazolyl, isoxazolyl, isothiazolyl, triazolyl, oxadiazolyl, thiadiazolyl, tetrazolyl, indolyl, benzofuranyl, benzothienyl, benzimidazolyl, benzoxazolyl, benzothiazolyl, indazolyl, benzisoxazolyl, benzisothiazolyl, pyrrolopyridyl, furopyridyl, thienopyridyl, imidazolopyridyl, oxazolopyridyl, thiazolopyridyl, pyrazolopyridyl, isoxazolopyridyl, isothiazolopyridyl, pyrrolopyrimidyl, furopyrimidyl, thienopyrimidyl, imidazolopyrimidyl, oxazolopyrimidyl, thiazolopyrimidyl, pyrazolopyrimidyl, isoxazolopyrimidyl, isothiazolopyrimidyl, pyrrolopyrazinyl, furopyrazinyl, thienopyrazinyl, imidazolopyrazinyl, oxazolopyrazinyl, thiazolopyrazinyl, pyrazolopyrazinyl, isoxazolopyrazinyl, isothiazolopyrazinyl, pyrrolopyridazinyl, furopyridazinyl, thienopyridazinyl, imidazolopyridazinyl, oxazolopyridazinyl, thiazolopyridazinyl, pyrazolopyridazinyl, isoxazolopyridazinyl or isothiazolopyridazinyl; and said Ar¹ is optionally substituted as set forth above;

k is 0, 1, 2, 3 or 4;

Y¹ is a covalent bond, carbonyl, sulfonyl or oxycarbonyl;

R⁴³ is (C₃–C₇)cycloalkyl, Ar⁵—(C₀–C₄)alkylenyl, NR⁴⁷R⁴⁸ or (C₁–C₆)alkyl optionally substituted with one to five fluoro; provided that when Y¹ is a covalent bond or oxycarbonyl, then R⁴³ is not NR⁴⁷R⁴⁸;

R⁴⁷ and R⁴⁸ are taken separately and are each independently selected from hydrogen, Ar⁵, (C₁–C₆)alkyl and Ar⁵—(C₀–C₄)alkylenyl; or R⁴⁷ and R⁴⁸ are taken together with the nitrogen atom to which they are attached to form azetidinyl, pyrrolidinyl, piperidinyl, piperazinyl, morpholinyl, azepinyl, azabicyclo[3.2.2]nonanyl, azabicyclo[2.2.1]heptyl, 1,2,3,4-tetrahydroisoquinolyl, 6,7-dihydro-5H-dibenzo[c,e]azepinyl or 5,6,7,8-tetrahydropyrido[4,3-d]pyrimidyl; said azetidinyl in the definition of R⁴⁷ and R⁴⁸ are optionally substituted with one hydroxy, amino, hydroxy-(C₁–C₄)alkyl, (C₁–C₄)alkoxy-(C₁–C₄)alkyl, (C₁–C₄)alkyl optionally substituted with up to five fluoro or (C₁–C₄)alkoxy optionally substituted with up to five fluoro; said pyrrolidinyl, piperidinyl and azepinyl in the definition of R⁴⁷ and R⁴⁸ are optionally substituted with up to two hydroxy, amino, hydroxy-(C₁–C₄)alkyl, (C₁–C₄)alkoxy-(C₁–C₄)alkyl, (C₁–C₄) alkyl optionally substituted with up to five fluoro or (C₁–C₄)alkoxy optionally substituted with up to five fluoro; said morpholinyl in the definition of R⁴⁷ and R⁴⁸ is optionally substituted with up to two substituents independently selected from hydroxy-(C₁–C₄)alkyl, (C₁–C₄)alkoxy-(C₁–C₄)alkyl, (C₁–C₄)alkyl optionally substituted with up to five fluoro and (C₁–C₄)alkoxy optionally substituted with up to five fluoro; said piperazinyl, 1,2,3,4-tetrahydroisoquinolyl and 5,6,7,8-tetrahydro[4,3-d]pyrimidyl in the definition of R⁴⁷ and R⁴⁸ are optionally substituted with up to three hydroxy, amino, halo, hydroxy-(C₁–C₄)alkyl, (C₁–C₄)alkoxy-(C₁–C₄)alkyl, (C₁–C₄)alkyl optionally substituted with up to five fluoro or (C₁–C₄)alkoxy optionally substituted with up to five fluoro; and said 6,7-dihydro-5H-dibenzo[c,e]azepinyl in the definition of R⁴⁷ and R⁴⁸ are optionally substituted with up to four hydroxy, amino, halo, hydroxy-(C₁–C₄)alkyl, (C₁–C₄)alkoxy-(C₁–C₄)alkyl, (C₁–C₄)alkyl optionally substituted with up to five fluoro or (C₁–C₄)alkoxy optionally substituted with up to five fluoro;

Ar⁵ is independently defined as set forth for Ar and Ar¹ above;

Ar⁵ is optionally independently substituted as set forth for Ar and Ar¹ above.

A compound selected from 1R-(4-{1'-[2-(1R-hydroxy-ethyl)-pyrimidin-4-yl]-[4,4]bipiperidinyl-1-yl}-pyrimidin-2-yl)-ethanol; furo[3,2-c]pyridin-2-yl-{4-[2-(1R-hydroxy-ethyl)-pyrimidin-4-yl]-3R,5S-dimethyl-piperazin-1-yl}-methanone; (4-chloro-furo[3,2-c]pyridin-2-yl)-{4-[2-(1R-hydroxy-ethyl)-pyrimidin-4-yl]-3R,5S-dimethyl-piperazin-1-yl}-methanone; {4-[2-(1R-hydroxy-ethyl)-pyrimidin-4-yl]-3R,5S-dimethyl-piperazin-1-yl}-(4-pyrrolidin-1-yl-furo[3,2-c]pyridin-2-yl)-methanone; {4-[2-(1R-hydroxy-ethyl)-pyrimidin-4-yl]-3R,5S-dimethyl-piperazin-1-yl}-(4-morpholin-4-yl-furo[3,2-c]pyridin-2-yl)-methanone; {4-[2-(1R-hydroxy-ethyl)-pyrimidin-4-yl]-3R,5S-dimethyl-piperazin-1-yl}-imidazo[1,2-a]pyridin-2-yl-methanone; furo[3,2-c]pyridin-2-yl-{4-[2-(1R-hydroxy-ethyl)-pyrimidin-4-yl]-2R,6S-dimethyl-piperazin-1-yl}-methanone; 4-[2-(1R-hydroxy-ethyl)-pyrimidin-4-yl]-2R,6S-dimethyl-piperazine-1-carboxylic acid pyridin-3-yl ester; 4-[2-(1R-hydroxy-ethyl)-pyrimidin-4-yl]-2R,6S-dimethyl-piperazine-1-carboxylic acid 2-methyl-pyridin-3-yl ester; 4-[2-(1R-hydroxy-ethyl)-pyrimidin-4-yl]-2R,6S-dimethyl-piperazine-1-carboxylic acid 5-chloro-pyridin-3-yl ester; 4-[2-(1R-hydroxy-ethyl)-pyrimidin-4-yl]-2R,6S-dimethyl-piperazine-1-carboxylic acid 6-methyl-pyridin-3-yl ester; (E)-1-{4-[2-(1R-hydroxy-ethyl)-pyrimidin-4-yl]-2R,6S-dimethyl-piperazin-1-yl}-3-thiophen-2-yl-propenone; 1R-{4-[4-(4,6-dimethyl-pyrimidin-2-yl)-3R,5S-dimethyl-piperazin-1-yl]-pyrimidin-2-yl}-ethanol; 1R-{4-[4-(4-methoxymethyl-6-methyl-pyrimidin-2-yl)-3R,5S-dimethyl-piperazin-1-yl]-pyrimidin-2-yl}-ethanol; 1R-{4-[4-(4-hydroxymethyl-6-methyl-pyrimidin-2-yl)-3R,5S-dimethyl-piperazin-1-yl]-pyrimidin-2-yl}-ethanol; 1R-(4-{3R,5S-dimethyl-4-[2-(4-methyl-piperazin-1-yl)-pyrimidin-4-yl]-piperazin-1-yl}-pyrimidin-2-yl)-ethanol; 1R-(4-{4-[2-(4-ethyl-piperazin-1-yl)-pyrimidin-4-yl]-3R,5S-dimethyl-piperazin-1-yl}-pyrimidin-2-yl)-ethanol; 1R-(4-{3R,5S-dimethyl-4-[2-(4-methyl-imidazol-1-yl)-pyrimidin-4-yl]-piperazin-1-yl}-pyrimidin-2-yl)-ethanol; 1R-(4-{3R,5S-dimethyl-4-[2-(2-methyl-imidazol-1-yl)-pyrimidin-4-yl]-piperazin-1-yl}-pyrimidin-2-yl)-ethanol; 1R-(4-{4-[2-(2,4-dimethyl-imidazol-1-yl)-pyrimidin-4-yl]-3R,5S-dimethyl-piperazin-1-yl}-pyrimidin-2-yl)-ethanol; 1R-(4-{4-[2-(4-isopropyl-piperazin-1-yl)-pyrimidin-4-yl]-3R,5S-dimethyl-piperazin-1-yl}-pyrimidin-2-yl)-ethanol; 1R-(4-{3R,5S-dimethyl-4-[4-methyl-6-(4-methyl-piperazin-1-yl)-[1,3,5]triazin-2-yl]-piperazin-1-yl}-pyrimidin-2-yl)-ethanol; 1R-{4-[4-(4-methoxy-6-methyl-[1,3,5]triazin-2-yl)-3R,5S-dimethyl-piperazin-1-yl]-pyrimidin-2-yl}-ethanol; 1R-{4-[4-(4,6-dimethoxy-[1,3,5]triazin-2-yl)-3R,5S-dimethyl-piperazin-1-yl]-pyrimidin-2-yl}-ethanol; 1R-{4-[4-(4-ethoxy-6-methyl-[1,3,5]triazin-2- yl)-3R,5S-dimethyl-piperazin-1-yl]-pyrimidin-2-yl}-ethanol; 1R-{4-[4-(4-isopropoxy-6-methyl-[1,3,5]triazin-2-yl)-3R,5S-dimethyl-piperazin-1-yl]-pyrimidin-2-yl}-ethanol; 1R-{4-[4-[3R,5S-dimethyl-4-(4-phenyl-[1,3,5]triazin-2-yl)-piperazin-1-yl]-pyrimidin-2-yl}-ethanol; 1R-{4-[4-(4-hydroxymethyl-6-methoxy-[1,3,5]triazin-2-yl)-3R,5S-dimethyl-piperazin-1-yl]-pyrimidin-2-yl}-ethanol; 1R-{4-[4-(4-isopropoxy-6-methoxy-[1,3,5]triazin-2-yl)-3R,5S-dimethyl-piperazin-1-yl]-pyrimidin-2-yl}-ethanol; 1R-{4-[4-(4-isopropyl-[1,3,5]triazin-2-yl)-3R,5S-dimethyl-piperazin-1-yl]-pyrimidin-2-yl}-ethanol; 1R-{4-[4-(4-ethyl-6-methoxy-[1,3,5]triazin-2-yl)-3R,5S-dimethyl-piperazin-1-yl]-pyrimidin-2-yl}-ethanol; 1R-{4-[4-(4,6-dimethyl-pyrimidin-2-yl)-2R,6S-dimethyl-piperazin-1-yl]-pyrimidin-2-yl}-ethanol; 1R-{4-[4-(4-hydroxymethyl-6-methyl-pyrimidin-2-yl)-2R,6S-dimethyl-piperazin-1-yl]-pyrimidin-2-yl}-ethanol; 1R-{4-[2R,6S-dimethyl-4-(4-[1,2,4]triazol-1-yl-pyrimidin-2-yl)-piperazin-1-yl]-pyrimidin-2-yl}-ethanol; 1R-{4-[4-(2,6-dimethyl-pyrimidin-4-yl)-2R,6S-dimethyl-piperazin-1-yl]-pyrimidin-2-yl}-ethanol; 1R-(4-{4-[2-(1R-hydroxy-ethyl)-pyrimidin-4-yl]-2R,6S-dimethyl-piperazin-1-yl}-pyrimidin-2-yl)-ethanol; 1R-{4-[4-(2-hydroxymethyl-6-methyl-pyrimidin-4-yl)-2R,6S-dimethyl-piperazin-1-yl]-pyrimidin-2-yl}-ethanol; 1R-4-{4-[2-(1S-hydroxy-ethyl)-pyrimidin-4-yl]-2R,6S-dimethyl-piperazin-1-yl}-pyrimidin-2-yl)-ethanol; 1S-(4-{4-[2-(1R-hydroxy-ethyl)-pyrimidin-4-yl]-2R,6S-dimethyl-piperazin-1-yl}-pyrimidin-2-yl)-ethanol; 1-{4-[4-(2-acetyl-pyrimidin-4-yl)-2R,6S-dimethyl-piperazin-1-yl]-pyrimidin-2-yl}-ethanone; 1RS-(4-{4-[2-(1RS-hydroxy-ethyl)-pyrimidin-4-yl]-2R,6S-dimethyl-piperazin-1-yl]-pyrimidin-2-yl)-ethanol; (4-{4-[2-(1R-hydroxy-ethyl)-pyrimidin-4-yl}-3R,5S-dimethyl-piperazin-1-yl]-pyrimidin-2-yl)-ethanone; 1R-{4-[2R,6S-dimethyl-4-(2-morpholin-4-yl-pyrimidin-4-yl)-piperazin-1-yl]-pyrimidin-2-yl)-ethanol; 1R-(4-{2R,6S-dimethyl-4-[2-(4-methyl-piperazin-1-yl)-pyrimidin-4-yl]-piperazin-1-yl}-pyrimidin-2-yl)-ethanol; 1R-{4-[2R,6S-dimethyl-4-(2-[1,2,4]triazol-1-yl-pyrimidin-4yl)-piperazin-1-yl]-pyrimidin-2-yl}-ethanol; 1R-(4-{4-[2-(1R-hydroxy-ethyl)-pyrimidin-4-yl]-2R,6R-dimethyl-piperazin-1-yl}-pyrimidin-2-yl)-ethanol; 1R-(4-{4-[2-(4-ethyl-piperazin-1-yl)-pyrimidin-4-yl]-2R,6S-dimethyl-piperazin-1-yl}-pyrimidin-2-yl)-ethanol; 1R-(4-{2R,6S-dimethyl-4-[2-(4-methyl-imidazol-1-yl)-pyrimidin-4-yl]-piperazin-1-yl}-pyrimidin-2-yl)-ethanol; 1R-(4-{4-[2-(2,4-dimethyl-imidazol-1-yl)-pyrimidin-4-yl]-2R,6S-dimethyl-piperazin-1-yl}-pyrimidin-2-yl)-ethanol; 1R-{4-[2R,6S-dimethyl-4-(4-morpholin-4-yl-[1,3,5]triazin-2-yl)-piperazin-1-yl]-pyrimidin-2-yl}-ethanol; 1R-{4-[4-(4-methoxy-6-methyl-[1,3,5]triazin-2-yl)-2R,6S-dimethyl-piperazin-1-yl]-pyrimidin-2-yl}-ethanol; 1R-{4-[4-(4,6-dimethoxy-[1,3,5]triazin-2-yl)-2R,6S-dimethyl-piperazin-1-yl]-pyrimidin-2-yl}-ethanol; 1R-{4-[2R,6S-dimethyl-4-(4-phenyl-[1,3,5]triazin-2-yl)-piperazin-1-yl]-pyrimidin-2-yl}-ethanol; 1R-{4-[4-(4-hydroxymethyl-6-methyl-pyrimidin-2-yl)-3S-methyl-piperazin-1-yl]-pyrimidin-2-yl}-ethanol; 1R-{4-[4-(2-hydroxymethyl-pyrimidin-4-yl)-3S-methyl-piperazin-1-yl]-pyrimidin-2-yl}-ethanol; 1R-{4-[4-(2-hydroxymethyl-6-methyl-pyrimidin-4-yl)-3S-methyl-piperazin-1-yl]-pyrimidin-2-yl}-ethanol; 1R-[4-(3S-methyl-4-oxazolo[5,4-b]pyridin-2-yl-piperazin-1-yl)-pyrimidin-2-yl)-ethanol; 1R-[4-(3S-methyl-4-oxazolo[4,5-b]pyridin-2-yl-piperazin-1-yl)-pyrimidin-2-yl]-ethanol; 1R-[4-(3S-methyl-4-quinoxalin-2-yl-piperazin-1-yl)-pyrimidin-2-yl]-ethanol; (4-{4-(2-((1R-hydroxy-ethyl)-pyrimidin-4-yl]-2R,5S-dimethyl-piperazin-1-yl]-pyrimidin-2-yl)-ethanol; 1R-{4-[4-(4,6-dimethyl-[1,3,5]triazin-2-yl)-3R,5S-dimethyl-piperazin-1-yl]-pyrimidin-2-yl}-ethanol; 1R-{4-[3R,5S-dimethyl-4-(4-methyl-6-phenyl-[1,3,5]triazin-2-yl)-piperazin-1-yl]pyrimidin-2-yl}-ethanol; 1R-{4-[4-(4-cyclopropyl-[1,3,5]triazin-2-yl)-3R,5S-dimethyl-piperazin-1-yl]-pyrimidin-2-yl}-ethanol; 1R-{4-[4-(4-cyclopropyl-[1,3,5]triazin-2-yl)-2R,6S-dimethyl-piperazin-1-yl]-pyrimidin-2-yl}-ethanol; 1R{4-[4-(4,6-dimethyl-[1,3,5]triazin-2-yl)-2R,6S-dimethyl-piperazin-1-yl]-pyrimidin-2-yl}-ethanol; 1R-{4-[4-(4-hydroxymethyl-6-phenyl-[1,3,5]triazin-2-yl)-2R,6S-dimethyl-piperazin-1-yl]-pyrimidin-2-yl}-ethanol; 1R-{4-[4-(4-methoxy-6-methoxymethyl-[1,3,5]triazin-2-yl)-2R,6S-dimethyl-piperazin-1-yl]-pyrimidin-2-yl}-ethanol; 1R-{4-[2R,6S-dimethyl-4-(4-methyl-[1,3,5]triazin-2-yl)-piperazin-1-yl]-pyrimidin-2-yl-ethanol; 1-{4-[4-(2-acetyl-pyrimidin-4-yl)-2R*,6S*-dimethyl-piperazin-1-yl]-pyrimidin-2-yl}-ethanone; 1-{4-(4-[2-(1R-hydroxy-ethyl)-pyrimidin-4-yl]-2R,6S-dimethyl-piperazin-1-yl}-pyrimidin-2-yl)-ethanone; 1R-4-[4-(4-methoxymethyl-6-phenyl-[1,3,5]-triazin-2-yl)-2R,6S-dimethyl-piperazin-1-yl]-pyrimidin-2-yl]-ethanol; and 1S-(4-{4-[2-(1R-hydroxy-ethyl)-pyrimidin-4-yl]-2R,6S-dimethyl-piperazin-1-yl}-pyrimidin-2-yl)-ethanol.

A compound of the formula I$^A$

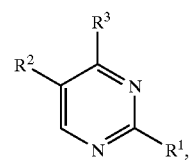

wherein:

R$^1$ is C—(OR$^{80}$)R$^4$R$^5$, where R$^{80}$ is independently (C$_1$–C$_4$)alkyl, benzyl, (C$_1$–C$_6$)alkylcarbonyl or phenylcarbonyl, where said benzyl and said phenyl are optionally substituted with up to three (C$_1$–C$_4$)alkyl, (C$_1$–C$_4$)alkoxy, halo or nitro;

R$^4$ and R$^5$ are each independently hydrogen, methyl, ethyl or hydroxy-(C$_1$–C$_3$)alkyl;

R$^2$ is hydrogen, (C$_1$–C$_4$)alkyl or (C$_1$–C$_4$)alkoxy;

R$^3$ is a radical of the formula

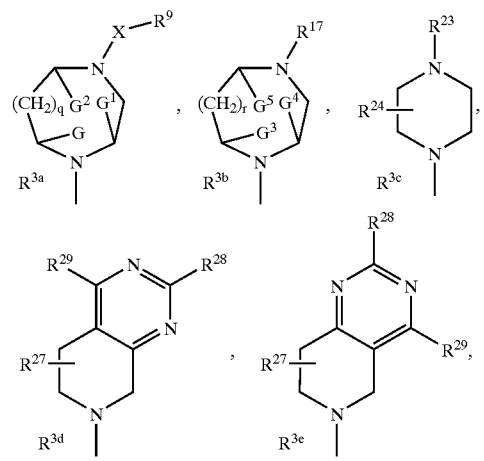

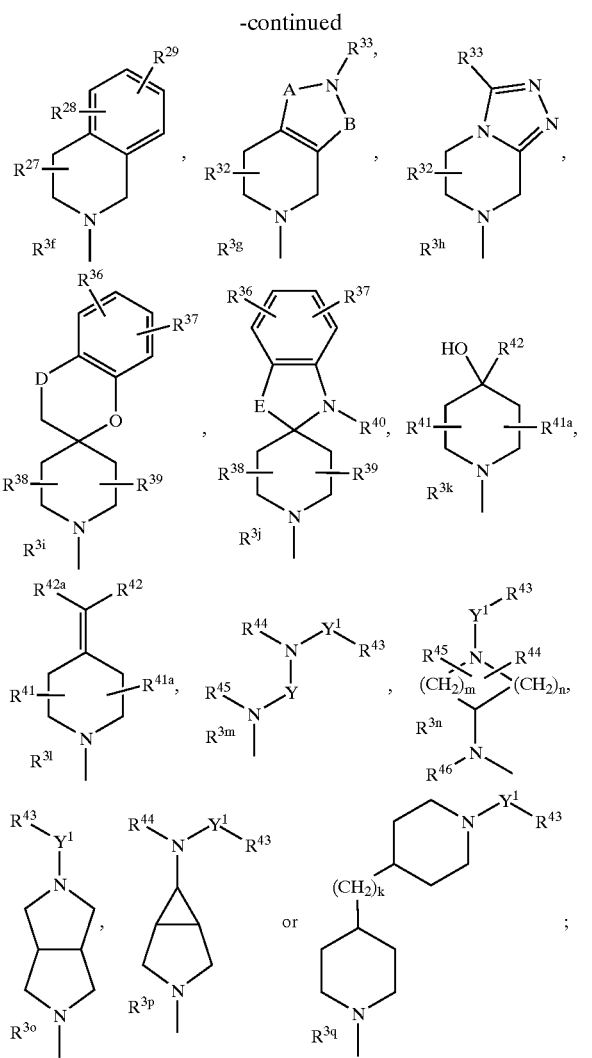

wherein said radical of formula $R^{3a}$ is substituted by $R^6$, $R^7$ and $R^8$;

said radical of formula $R^{3b}$ is substituted by $R^{18}$, $R^{19}$ and $R^{20}$;

G, $G^1$ and $G^2$ are taken separately and are each hydrogen and $R^8$ is hydrogen, $(C_1-C_4)$alkyl, $(C_1-C_4)$alkoxycarbonyl, $(C_1-C_4)$alkoxy-$(C_1-C_4)$alkyl, hydroxy-$(C_1-C_4)$alkyl or phenyl optionally independently substituted with up to three hydroxy, halo, hydroxy-$(C_1-C_4)$alkyl, $(C_1-C_4)$alkoxy-$(C_1-C_4)$alkyl, $(C_1-C_4)$alkyl or $(C_1-C_4)$alkoxy, wherein said $(C_1-C_4)$alkyl in the definition of $R^6$ and said $(C_1-C_4)$alkoxy in the definition of $R^6$ are optionally and independently substituted with up to five fluoro; $R^7$ and $R^8$ are each independently hydrogen or $(C_1-C_4)$alkyl; or G and $G^1$ are taken together and are $(C_1-C_3)$alkylene and $R^6$, $R^7$, $R^8$ and $G^2$ are hydrogen; or $G^1$ and $G^2$ are taken together and are $(C_1-C_3)$alkylene and $R^6$, $R^7$, $R^8$ and G are hydrogen;

q is 0 or 1;

X is a covalent bond, —(C=NR$^{10}$)—, oxycarbonyl, vinylenylcarbonyl, oxy$(C_1-C_4)$alkylenylcarbonyl, $(C_1-C_4)$alkylenylcarbonyl, $(C_3-C_4)$alkenylcarbonyl, thio$(C_1-C_4)$alkylenylcarbonyl, vinylenylsulfonyl, sulfinyl-$(C_1-C_4)$alkylenylcarbonyl, sulfonyl-$(C_1-C_4)$alkylenylcarbonyl or carbonyl$(C_0-C_4)$alkylenylcarbonyl; wherein said oxy$(C_1-C_4)$alkylenylcarbonyl, $(C_1-C_4)$alkylenylcarbonyl, $(C_3-C_4)$alkenylcarbonyl and thio$(C_1-C_4)$alkylenylcarbonyl in the definition of X are each optionally and independently substituted with up to two $(C_1-C_4)$alkyl, benzyl or Ar; said vinylenylsulfonyl and said vinylenylcarbonyl in the definition of X are optionally substituted independently on one or two vinylenyl carbons with $(C_1-C_4)$alkyl, benzyl or Ar; and said carbonyl$(C_0-C_4)$alkylenylcarbonyl in the definition of X is optionally substituted indepedently with up to three $(C_1-C_4)$alkyl, benzyl or Ar;

$R^{10}$ is hydrogen or $(C_1-C_4)$alkyl;

$R^9$ is $(C_3-C_7)$cycloalkyl, $Ar^1$—$(C_0-C_3)$alkylenyl or $(C_1-C_6)$alkyl optionally substituted with up to five fluoro; provided that when q=0 and X is a covalent bond, oxycarbonyl or $(C_1-C_4)$alkylenylcarbonyl, then $R^9$ is not $(C_1-C_6)$alkyl;

Ar and $Ar^1$ are independently a fully saturated, partially saturated or fully unsaturated five- to eight-membered ring optionally having up to four heteroatoms selected independently from oxygen, sulfur and nitrogen, or a bicyclic ring consisting of two fused independently partially saturated, fully saturated or fully unsaturated five- to seven-membered rings, taken independently, optionally having up to four heteroatoms selected independently from nitrogen, sulfur and oxygen, or a tricyclic ring consisting of three fused independently partially saturated, fully saturated or fully unsaturated five to seven membered rings, taken independently, optionally having up to four heteroatoms selected independently from nitrogen, sulfur and oxygen, said partially saturated, fully saturated ring or fully unsaturated monocyclic ring, bicyclic ring or tricyclic ring optionally having one or two oxo groups substituted on carbon or one or two oxo groups substituted on sulfur;

Ar and $Ar^1$ are optionally independently substituted on carbon or nitrogen, on one ring if the moiety is monocyclic, on one or both rings if the moiety is bicyclic, or on one, two or three rings if the moiety is tricyclic, with up to a total of four substituents independently selected from $R^{11}$, $R^{12}$, $R^{13}$ and $R^{14}$; wherein $R^{11}$, $R^{12}$, $R^{13}$ and $R^{14}$ are each taken separately and are each independently halo, formyl, $(C_1-C_6)$alkoxycarbonyl, $(C_1-C_6)$alkylenyloxycarbonyl, $(C_1-C_4)$alkoxy-$(C_1-C_4)$alkyl, C(OH)$R^{15}R^{16}$, naphthyl, phenyl, imidazolyl, pyridyl, triazolyl, morpholinyl, $(C_0-C_4)$alkylsulfamoyl, N—$(C_0-C_4)$alkylcarbamoyl, N,N-di-$(C_1-C_4)$alkylcarbamoyl, N-phenylcarbamoyl, N—$(C_1-C_4)$alkyl-N-phenylcarbamoyl, N,N-diphenyl carbamoyl, $(C_1-C_4)$alkylcarbonylamido, $(C_3-C_7)$cycloalkylcarbonylamido, phenylcarbonylamido, piperidinyl, pyrrolidinyl, piperazinyl, cyano, benzimidazolyl, amino, anilino, pyrimidyl, oxazolyl, isoxazolyl, tetrazolyl, thienyl, thiazolyl, benzothiazolyl, pyrrolyl, pyrazolyl, tetrahydroquinolyl, tetrahydroisoquinolyl, benzoxazolyl, pyridazinyl, pyridyloxy, pyridylsulfanyl, furanyl, 8-$(C_1-C_4)$alkyl-3,8-diaza[3.2.1]bicyclooctyl, 3,5-dioxo-1,2,4-triazinyl, phenoxy, thiophenoxy, $(C_1-C_4)$alkylsulfanyl, $(C_1-C_4)$alkylsulfonyl, $(C_3-C_7)$cycloalkyl, $(C_1-C_4)$alkyl optionally substituted with up to five fluoro or $(C_1-C_4)$alkoxy optionally substituted with up to five fluoro; said naphthyl, phenyl, pyridyl, piperidinyl, benzimidazolyl, pyrimidyl, thienyl, benzothiazolyl, pyrrolyl, tetrahydroquinolyl, tetrahydroisoquinolyl, benzoxazolyl, pyridazinyl, pyridyloxy, pyridylsulfanyl, furanyl, thiophenoxy, anilino and phenoxy in the definition of $R^{11}$, $R^{12}$, $R^{13}$ and $R^{14}$ are optionally substituted with up to three substituents independently selected from hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said imidazolyl, oxazolyl, isoxazolyl, thiazolyl and pyrazolyl in the definition of $R^{11}$, $R^{12}$, $R^{13}$ and $R^{14}$ are optionally substituted with up to two substituents independently selected from hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said morpholinyl in the definition of $R^{11}$, $R^{12}$, $R^{13}$ and $R^{14}$ is optionally substituted with up to two substituents independently selected from $(C_1-C_4)$alkyl; said pyrrolidinyl in the definition of $R^{11}$, $R^{12}$, $R^{13}$ and $R^{14}$ is optionally substituted with up to two substituents independently selected from hydroxy, hydroxy-$(C_1-C_3)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said piperazinyl in the definition of $R^{11}$, $R^{12}$, $R^{13}$ and $R^{14}$ is optionally substituted with up to three substituents independently selected from $(C_1-C_4)$alkoxy-$(C_1-C_4)$alkyl, hydroxy-$(C_1-C_3)$alkyl, phenyl, pyridyl, $(C_0-C_4)$alkylsulfamoyl, $(C_1-C_4)$alkyl optionally substituted with up to five fluoro and $(C_1-C_4)$alkoxy optionally substituted with up to five fluoro; said triazolyl in the definition of $R^{11}$, $R^{12}$, $R^{13}$ and $R^{14}$ is optionally substituted with hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said tetrazolyl in the definition of $R^{11}$, $R^{12}$, $R^{13}$ and $R^{14}$ is optionally substituted with hydroxy-$(C_2-C_3)$alkyl or $(C_1-C_4)$alkyl optionally substituted with up to five fluoro; and said phenyl and pyridyl which are optionally substituted on piperazine in the definition of $R^{11}$, $R^{12}$, $R^{13}$ and $R^{14}$ are optionally substituted with up to three hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; or $R^{11}$ and $R^{12}$ are taken together on adjacent carbon atoms and are —$CH_2OC(CH_3)_2OCH_2$— or —O—$(CH_2)_p$—O—, and $R^{13}$ and $R^{14}$ are taken separately and are each independently hydrogen or $(C_1-C_4)$alkyl;

p is 1, 2 or 3;

$R^{15}$ and $R^{16}$ are taken separately and are each independently hydrogen, $(C_1-C_4)$alkyl optionally substituted with up to five fluoro; or $R^{15}$ and $R^{16}$ are taken separately and $R^{15}$ is hydrogen and $R^{16}$ is $(C_3-C_6)$cycloalkyl, hydroxy-$(C_1-C_3)$alkyl, phenyl, pyridyl, pyrimidyl, thienyl, furanyl, thiazolyl, oxazolyl, imidazolyl, benzothiazolyl or benzoxazolyl; or $R^{15}$ and $R^{16}$ are taken together and are $(C_3-C_6)$alkylene; $G^3$, $G^4$ and $G^5$ are taken separately and are each hydrogen; r is 0; $R^{18}$ is hydrogen, $(C_1-C_4)$alkyl, $(C_1-C_4)$alkoxycarbonyl, $(C_1-C_4)$alkoxy-$(C_1-C_4)$alkyl, hydroxy-$(C_1-C_4)$ or phenyl optionally independently substituted with up to three hydroxy, halo, hydroxy-$(C_1-C_4)$alkyl, $(C_1-C_4)$alkoxy-$(C_1-C_4)$alkyl, $(C_1-C_4)$alkyl or $(C_1-C_4)$alkoxy, wherein said $(C_1-C_4)$alkyl in the definition of $R^6$ and said $(C_1-C_4)$alkoxy in the definition of $R^6$ are optionally and independently substituted with up to five fluoro; and $R^{19}$ and $R^{20}$ are each independently $(C_1-C_4)$alkyl; or $G^3$, $G^4$ and $G^5$ are taken separately and are each hydrogen; r is 1; $R^{18}$ is hydrogen, $(C_1-C_4)$alkyl, $(C_1-C_4)$alkoxycarbonyl, $(C_1-C_4)$alkoxy-$(C_1-C_4)$alkyl, hydroxy-$(C_1-C_4)$alkyl or phenyl optionally independently substituted with up to three hydroxy, halo, hydroxy-$(C_1-C_4)$alkyl, $(C_1-C_4)$alkoxy-$(C_1-C_4)$alkyl, $(C_1-C_4)$alkyl or $(C_1-C_4)$alkoxy, wherein said $(C_1-C_4)$alkyl in the definition of $R^6$ and said $(C_1-C_4)$alkoxy in the definition of $R^6$ are optionally and independently substituted with up to five fluoro; and $R^{19}$ and $R^{20}$ are each independently hydrogen or $(C_1-C_4)$alkyl; or $G^3$ and $G^4$ are taken together and are $(C_1-C_3)$alkylene; r is 0 or 1; and $R^{18}$, $R^{19}$, $R^{20}$ and $G^5$ are hydrogen; or $G^4$ and $G^5$ are taken together and are $(C_1-C_3)$alkylene; r is 0 or 1; and $R^{18}$, $R^{19}$, $R^{20}$ and $G^3$ are hydrogen;

$R^{17}$ is $SO_2NR^{21}R^{22}$, $CONR^{21}R^{22}$, $(C_1-C_6)$alkoxycarbonyl, $(C_1-C_6)$alkylcarbonyl, $Ar^2$-carbonyl, $(C_1-C_6)$alkylsulfonyl, $(C_1-C_6)$alkylsulfinyl, $Ar^2$-sulfonyl, $Ar^2$-sufinyl and $(C_1-C_6)$alkyl;

$R^{21}$ and $R^{22}$ are taken separately and are each independently selected from hydrogen, $(C_1-C_6)$alkyl, $(C_3-C_7)$cycloalkyl and $Ar^2$—$(C_0-C_4)$alkylenyl; or $R^{21}$ and $R^{22}$ are taken together with the nitrogen atom to which they are attached to form azetidinyl, pyrrolidinyl, piperidinyl, piperazinyl, morpholinyl, azepinyl, azabicyclo[3.2.2]nonanyl, azabicyclo[2.2.1]heptyl, 6,7-dihydro-5H-dibenzo[c,e]azepinyl, 1,2,3,4-tetrahydro-isoquinolyl or 5,6,7,8-tetrahydropyrido[4,3-d]pyrimidyl; said azetidinyl in the definition of $R^{21}$ and $R^{22}$ is optionally substituted independently with one substituent selected from hydroxy, amino, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said pyrrolidinyl, piperidinyl, azepinyl in the definition of $R^{21}$ and $R^{22}$ are optionally substituted independently with up to two substituents independently selected from hydroxy, amino, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said morpholinyl in the definition of $R^{21}$ and $R^{22}$ is optionally substituted with up to two substituents independently selected from hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said piperazinyl in the definition of $R^{21}$ and $R^{22}$ is optionally substituted independently with up to three substituents independently selected from phenyl, pyridyl, pyrimidyl, $(C_1-C_4)$alkoxycarbonyl and $(C_1-C_4)$alkyl optionally substituted with up to five fluoro; said 1,2,3,4-tetrahydro-isoquinolyl and said 5,6,7,8-tetrahydropyrido[4,3-d]pyrimidyl in the definition of $R^{21}$ and $R^{22}$ are optionally substituted independently with up to three substituents independently selected from hydroxy, amino, halo, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; and said 6,7-dihydro-5H-dibenzo[c,e]azepinyl in the definition of $R^{21}$ and $R^{22}$ is optionally substituted with up to four substituents independently selected from hydroxy, amino, halo, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said pyrimidyl, pyridyl and phenyl which are optionally substituted on said piperazine in the definition of $R^{21}$ and $R^{22}$ is optionally substituted with up to three substituents selected from hydroxy, amino, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro;

$Ar^2$ is independently defined as set forth for Ar and $Ar^1$ above;

said $Ar^2$ is optionally independently substituted as set forth for Ar and $Ar^1$ above;

$R^{23}$ is $CONR^{25}R^{26}$ or $SO_2R^{25}R^{26}$, wherein $R^{25}$ is hydrogen $(C_1-C_4)$alkyl or $Ar^3$—$(C_0-C_4)$alkylenyl and $R^{26}$ is $Ar^3$—$(C_0-C_4)$alkylenyl; provided that when $Ar^3$ is phenyl, naphthyl or biphenyl, then $R^{23}$ cannot be $CONR^{25}R^{26}$ where $R^{25}$ is hydrogen or $Ar^3$ and $R^{26}$ is $Ar^3$;

$R^{24}$ is hydrogen, $(C_1-C_4)$alkyl, $(C_1-C_4)$alkoxycarbonyl, $(C_1-C_4)$alkoxy-$(C_1-C_4)$alkyl, hydroxy-$(C_1-C_4)$alkyl or phenyl optionally independently substituted with up to three hydroxy, halo, hydroxy-$(C_1-C_4)$alkyl, $(C_1-C_4)$alkoxy-$(C_1-C_4)$alkyl, $(C_1-C_4)$alkyl or $(C_1-C_4)$alkoxy, wherein said $(C_1-C_4)$alkyl in the definition of $R^6$ and said $(C_1-C_4)$alkoxy in the definition of $R^6$ are optionally and independently substituted with up to five fluoro;

$Ar^3$ is independently defined as set forth for Ar and $Ar^1$ above;

said $Ar^3$ is optionally independently substituted as set forth for Ar and $Ar^1$ above;

$R^{27}$ is hydrogen or $(C_1-C_4)$alkyl;

$R^{28}$ and $R^{29}$ are each independently hydrogen, hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro, $(C_1-C_4)$alkoxy optionally substituted with up to five fluoro, phenyl, pyridyl, pyrimidyl, thienyl, furanyl, thiazolyl, oxazolyl, phenoxy, thiophenoxy, $SO_2NR^{30}R^{31}$, $CONR^{30}R^{31}$ or $NR^{30}R^{31}$; said thienyl, pyrimidyl, furanyl, thiazolyl and oxazolyl in the definition of $R^{28}$ and $R^{29}$ are optionally substituted by up to two hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro; said phenyl, pyridyl, phenoxy and thiophenoxy in the definition of $R^{28}$ and $R^{29}$ are optionally substituted by up to three hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro;

$R^{30}$ and $R^{31}$ are each independently hydrogen, $(C_1-C_4)$alkyl, $(C_3-C_7)$cycloalkyl or phenyl, said phenyl is optionally substituted with up to three hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro; or $R^{30}$ and $R^{31}$ are taken together with the nitrogen to which they are attached to form indolinyl, pyrrolidinyl, piperidinyl, piperazinyl or morpholinyl; said pyrrolidinyl and piperidinyl in the definition of $R^{30}$ and $R^{31}$ are optionally substituted with up to two hydroxy, amino, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro; said indolinyl and piperazinyl in the definition of $R^{30}$ and $R^{31}$ are optionally substituted with up to three hydroxy, amino, hydroxy-$(C_1-C_4)$alkyl, $(C_1-C_4)$alkoxy-$(C_1-C_4)$alkyl, $(C_1-C_4)$alkoxycarbonyl, $(C_1-C_4)$alkyl optionally substituted with up to five fluoro or $(C_1-C_4)$alkoxy optionally substituted with up to five fluoro; said morpholinyl in the definition of $R^{30}$ and $R^{31}$ is optionally substituted with up to two substituents independently selected from hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro;

A is N optionally substituted with hydrogen or $(C_1-C_4)$alkyl and B is carbonyl; or A is carbonyl and B is N optionally substituted with hydrogen or $(C_1-C_4)$alkyl;

$R^{32}$ is hydrogen or $(C_1-C_4)$alkyl;

$R^{33}$ is phenyl, pyridyl, pyrimidyl, thiazolyl, oxazolyl, benzyl, quinolyl, isoquinolyl, phthalizinyl, quinoxanlyl, benzothiazoyl, benzoxazolyl, benzofuranyl or benzothienyl; said phenyl, pyridyl, pyrimidyl, thiazolyl, oxazolyl, benzyl, quinolyl, isoquinolyl, phthalizinyl, quinoxanlyl, benzothiazoyl, benzoxazolyl, benzofuranyl and benzothienyl in the definition of $R^{33}$ are optionally substituted with up to three phenyl, phenoxy, $NR^{34}R^{35}$, halo, hydroxy, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro;

$R^{34}$ and $R^{35}$ are each independently hydrogen, $(C_1-C_4$ alkyl), phenyl or phenylsulfonyl; said phenyl and phenylsulfonyl in the definition of $R^{34}$ and $R^{35}$ are optionally substituted with up to three halo, hydroxy, $(C_1-C_4)$alkyl optionally substituted with up to five fluoro or $(C_1-C_4)$alkoxy optionally substituted with up to five fluoro;

D is CO, CHOH or $CH_2$;

E is O, NH or S;

$R^{36}$ and $R^{37}$ are taken separately and are each independently hydrogen, halo, cyano, hydroxy, amino, $(C_1-C_6)$alkylamino, di-$(C_1-C_6)$alkylamino, pyrrolidino, piperidino, morpholino, $(C_1-C_4)$alkoxy-$(C_1-C_4)$alkyl, hydroxy-$(C_1-C_4)$alkyl, $Ar^4$, $(C_1-C_4)$alkyl optionally substituted with up to five fluoro or $(C_1-C_4)$alkoxy optionally substituted with up to five fluoro;

$R^{38}$, $R^{39}$ and $R^{40}$ are each independently hydrogen or $(C_1-C_4)$-alkyl; $Ar^4$ is phenyl, furanyl, thienyl, pyridyl, pyrimidyl, pyrazinyl or pyridazinyl; said $Ar^4$ being optionally substituted with up to three hydroxy, $(C_1-C_4)$alkoxy-$(C_1-C_4)$alkyl, halo, hydroxy-$(C_1-C_4)$alkyl, $(C_1-C_4)$alkyl optionally substituted with up to five fluoro or $(C_1-C_4)$alkoxy optionally substituted with up to five fluoro; or $R^{36}$ and $R^{37}$ are taken together on adjacent carbon atoms and are —O—$(CH_2)_t$—O—;

t is 1, 2 or 3;

Y is $(C_2-C_6)$alkylene;

$R^{44}$, $R^{45}$ and $R^{46}$ are each independently hydrogen or $(C_1-C_4)$alkyl;

m and n are each independently 1, 2 or 3, provided that the sum of m and n is 2, 3 or 4;

k is 0, 1, 2, 3 or 4;

$Y^1$ is a covalent bond, carbonyl, sulfonyl or oxycarbonyl;

$R^{43}$ is $(C_3-C_7)$cycloalkyl, $Ar^5-(C_0-C_4)$alkylenyl, $NR^{47}R^{48}$ or $(C_1-C_6)$ substituted with one to five fluoro; provided that when $Y^1$ is a covalent bond or oxycarbonyl, then $R^{43}$ is not $NR^{47}R^{48}$;

$R^{47}$ and $R^{48}$ are taken separately and are each independently selected from hydrogen, $Ar^5$, $(C_1-C_6)$alkyl and $Ar^5-(C_0-C_4)$alkylenyl; or $R^{47}$ and $R^{48}$ are taken together with the nitrogen atom to which they are attached to form azetidinyl, pyrrolidinyl, piperidinyl, piperazinyl, morpholinyl, azepinyl, azabicyclo[3.2.2]nonanyl, azabicyclo[2.2.1]heptyl, 1,2,3,4-tetrahydroisoquinolyl, 6,7-dihydro-5H-dibenzo[c,e]azepinyl or 5,6,7,8-tetrahydropyrido[4,3-d]pyrimidyl; said azetidinyl in the definition of $R^{47}$ and $R^{48}$ are optionally substituted with one hydroxy, amino, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro; said pyrrolidinyl, piperidinyl and azepinyl in the definition of $R^{47}$ and $R^{48}$ are optionally substituted with up to two hydroxy, amino, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro; said morpholinyl in the definition of $R^{47}$ and $R^{48}$ is optionally substituted with up to two substituents independently selected from hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said piperazinyl, 1,2,3,4-tetrahydroisoquinolyl and 5,6,7,8-tetrahydro[4,3-d]pyrimidyl in the definition of $R^{47}$ and $R^{48}$ are optionally substituted with up to three hydroxy, amino, halo, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro; and said 6,7-dihydro-5H-dibenzo[c,e]azepinyl in the definition of $R^{47}$ and $R^{48}$ are optionally substituted with up to four hydroxy, amino, halo, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro;

$Ar^5$ is independently defined as set forth for Ar and $Ar^1$ above;

$Ar^5$ is optionally independently substituted as set forth for Ar and $Ar^1$ above;

$R^{42}$ and $R^{42a}$ are independently hydrogen, $(C_3-C_7)$ cycloalkyl, $Ar^6-(C_0-C_3)$alkylenyl, $Ar^6-(C_2-C_4)$alkenyl, $Ar^6$-carbonyl or $(C_1-C_6)$alkyl optionally substituted with up to five fluoro;

$Ar^6$ is independently defined as set forth for Ar and $Ar^1$ above;

$Ar^6$ is optionally independently substituted as set forth for Ar and $Ar^1$ above; and $R^{41}$ and $R^{41a}$ are each independently hydrogen or $(C_1-C_4)$ alkyl.

A compound of formula $1^A$ selected from 1R-(4-{4-[2-(1R-butyryloxy-ethyl)-pyrimidin-4-yl]-2R,6S-dimethyl-piperazin-1-yl}-pyrimidin-2-yl)-ethyl butyrate; 1R-(4-{4-[2-(1S-butyryloxy-ethyl)-pyrimidin-4-yl]-2R,6S-dimethyl-piperazin-1-yl}-pyrimidin-2-yl)-ethyl butyrate; 1S-(4-{4-[2-(1R-butyryloxy-ethyl)-pyrimidin-4-yl]-2R,6S-dimethyl-piperazin-1-yl}-pyrimidin-2-yl)-ethyl butyrate; (E)-1R-{4-[4-(2-methyl-32-phenyl-acryloyl)-piperazin-1-yl]-pyrimidin-2-yl}-ethyl acetate; (R)-1-[4-(4-quinoxalin-2-yl-piperazin-1-yl)-pyrimidin-2-yl]-ethyl acetate; 1R-(4-{4-[2-(1RS-hydroxy-ethyl)-pyrimidin-4-yl]-2R,6S-dimethyl-piperazin-1-yl}-pyrimidin-2-yl)-ethyl butyrate; 1RS-(4-{4-[2-(1R-hydroxy-ethyl)-pyrimidin-4-yl]-3R,5S-dimethyl-piperazin-1-yl}-pyrimidin-2-yl)-ethyl butyrate; 1R-[4-(3S-methyl-4-oxazolo[5,4-b]pyridin-2-yl-piperazin-1-yl)-pyrimidin-2-yl]-ethyl butyrate; 1R-{4-[3R,5S-dimethyl-4-(4-methyl-6-phenyl-[1,3,5]triazin-2-yl)-piperazin-1-yl]-pyrimidin-2-yl}-ethyl butyrate; 1R-{4-[4-(4-cyclopropyl-[1,3,5]triazin-2-yl)-3R,5S-dimethyl-piperazin-1-yl]-pyrimidin-2-yl}-ethyl butyrate; 1R-{4-[4-(4-cyclopropyl-[1,3,5]triazin-2-yl)-2R,6S-dimethyl-piperazin-1-yl]-pyrimidin-2-yl}-ethyl butyrate; 1R-{4-[4-(4,6-dimethyl-[1,3,5]triazin-2-yl)-2R,6S-dimethyl-piperazin-1-yl]-pyrimidin-2-yl}-ethyl butyrate; 1R-{4-[4-(4-hydroxymethyl-6-phenyl-[1,3,5]triazin-2-yl)-2R,6S-dimethyl-piperazin-1-yl]-pyrimidin-2-yl}-ethyl butyrate; 1R-{4-[4-(4-methoxy-6-methoxymethyl-[1,3,5]triazin-2-yl)-R,6S-dimethyl-piperazin-1-yl]-pyrimidin-2-yl}-ethyl butyrate; and 1R-{4-[2R,6S-dimethyl-4-(4-methyl-[1,3,5]triazin-2-yl)-piperazin-1-yl]-pyrimidin-2-yl}-ethyl butyrate.

This invention is also directed to a mutual prodrug of the formula $I^B$,

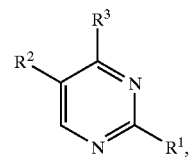

wherein:

$R^1$ is C—$(OR^8)R^4R^5$, where $R^{81}$ is independently an acyl radical of a carboxylic acid aldose reductase inhibitor;

$R^4$ and $R^5$ are each independently hydrogen, methyl, ethyl or hydroxy-$(C_1-C_3)$alkyl;

$R^2$ is hydrogen, $(C_1-C_4)$alkyl or $(C_1-C_4)$alkoxy;

$R^3$ is a radical of the formula

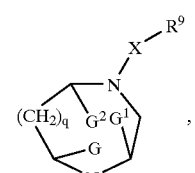

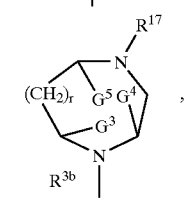

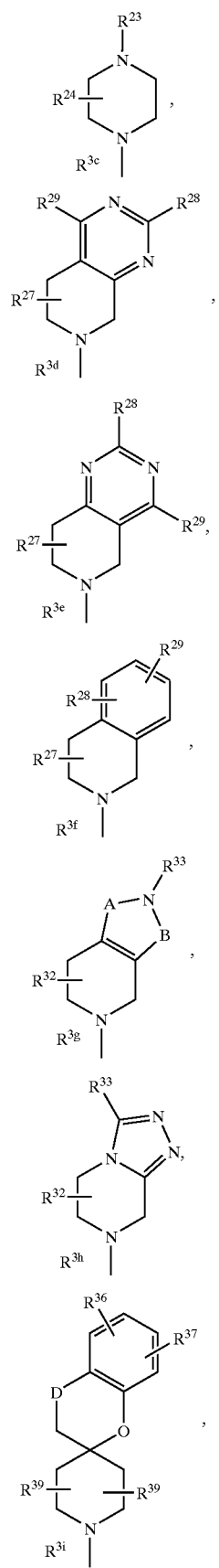
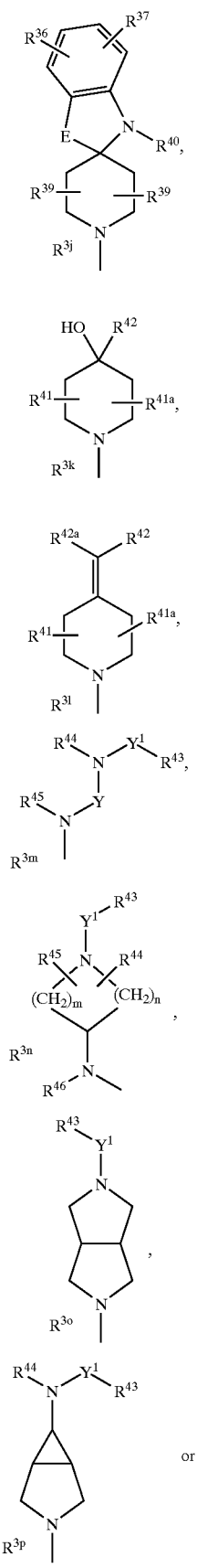

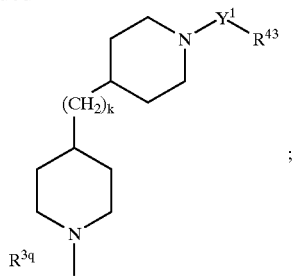

wherein said radical of formula $R^{3a}$ is substituted by $R^6$, $R^7$ and $R^8$;

said radical of formula $R^{3b}$ is substituted by $R^{18}$, $R^{19}$ and $R^{20}$;

G, $G^1$ and $G^2$ are taken separately and are each hydrogen and $R^6$ is hydrogen, $(C_1-C_4)$alkyl, $(C_1-C_4)$alkoxycarbonyl, $(C_1-C_4)$alkoxy-$(C_1-C_4)$alkyl, hydroxy-$(C_1-C_4)$alkyl or phenyl optionally independently substituted with up to three hydroxy, halo, hydroxy-$(C_1-C_4)$alkyl, $(C_1-C_4)$alkoxy-$(C_1-C_4)$alkyl, $(C_1-C_4)$alkyl or $(C_1-C_4)$alkoxy, wherein said $(C_1-C_4)$ alkyl in the definition of $R^6$ and said $(C_1-C_4)$alkoxy in the definition of $R^6$ are optionally and independently substituted with up to five fluoro; $R^7$ and $R^8$ are each independently hydrogen or $(C_1-C_4)$alkyl; or G and $G^1$ are taken together and are $(C_1-C_3)$alkylene and $R^6$, $R^7$, $R^8$ and $G^2$ are hydrogen; or $G^1$ and $G^2$ are taken together and are $(C_1-C_3)$alkylene and $R^6$, $R^7$, $R^8$ and G are hydrogen;

q is 0 or 1;

X is a covalent bond, $-(C=NR^{10})-$, oxycarbonyl, vinylenylcarbonyl, oxy$(C_1-C_4)$alkylenylcarbonyl, $(C_1-C_4)$alkylenylcarbonyl, $(C_3-C_4)$alkenylcarbonyl, thio$(C_1-C_4)$alkylenylcarbonyl, vinylenylsulfonyl, sulfinyl-$(C_1-C_4)$alkylenylcarbonyl, sulfonyl-$(C_1-C_4)$alkylenylcarbonyl or carbonyl$(C_0-C_4)$ alkylenylcarbonyl; wherein said oxy$(C_1-C_4)$ alkylenylcarbonyl, $(C_1-C_4)$alkylenylcarbonyl, $(C_3-C_4)$ alkenylcarbonyl and thio$(C_1-C_4)$alkylenylcarbonyl in the definition of X are each optionally and independently substituted with up to two $(C_1-C_4)$alkyl, benzyl or Ar; said vinylenylsulfonyl and said vinylenylcarbonyl in the definition of X are optionally substituted independently on one or two vinylenyl carbons with $(C_1-C_4)$alkyl, benzyl or Ar; and said carbonyl$(C_0-C_4)$ alkylenylcarbonyl in the definition of X is optionally substituted indepedently with up to three $(C_1-C_4)$alkyl, benzyl or Ar;

$R^{10}$ is hydrogen or $(C_1-C_4)$alkyl;

$R^9$ is $(C_3-C_7)$cycloalkyl, $Ar^1-(C_0-C_3)$alkylenyl or $(C_1-C_6)$alkyl optionally substituted with up to five fluoro; provided that when q=0 and X is a covalent bond, oxycarbonyl or $(C_1-C_4)$alkylenylcarbonyl, then $R^9$ is not $(C_1-C_6)$alkyl;

Ar and $Ar^1$ are independently a fully saturated, partially saturated or fully unsaturated five- to eight-membered ring optionally having up to four heteroatoms selected independently from oxygen, sulfur and nitrogen, or a bicyclic ring consisting of two fused independently partially saturated, fully saturated or fully unsaturated five- to seven-membered rings, taken independently, optionally having up to four heteroatoms selected independently from nitrogen, sulfur and oxygen, or a tricyclic ring consisting of three fused independently partially saturated, fully saturated or fully unsaturated five- to seven membered rings, taken independently, optionally having up to four heteroatoms selected independently from nitrogen, sulfur and oxygen, said partially saturated, fully saturated ring or fully unsaturated monocyclic ring, bicyclic ring or tricyclic ring optionally having one or two oxo groups substituted on carbon or one or two oxo groups substituted on sulfur;

Ar and $Ar^1$ are optionally independently substituted on carbon or nitrogen, on one ring if the moiety is monocyclic, on one or both rings if the moiety is bicyclic, or on one, two or three rings if the moiety is tricyclic, with up to a total of four substituents independently selected from $R^{11}$, $R^{12}$, $R^{13}$ and $R^{14}$; wherein $R^{11}$, $R^{12}$, $R^{13}$ and $R^{14}$ are each taken separately and are each independently halo, formyl, $(C_1-C_6)$ alkoxycarbonyl, $(C_1-C_6)$alkylenyloxycarbonyl, $(C_1-C_4)$alkoxy-$(C_1-C_4)$alkyl, C(OH)$R^{15}R^{16}$, naphthyl, phenyl, imidazolyl, pyridyl, triazolyl, morpholinyl, $(C_0-C_4)$alkylsulfamoyl, N—$(C_0-C_4)$alkylcarbamoyl, N,N-di-$(C_1-C_4)$alkylcarbamoyl, N-phenylcarbamoyl, N—$(C_1-C_4)$alkyl-N-phenylcarbamoyl, N,N-diphenyl carbamoyl, $(C_1-C_4)$alkylcarbonylamido, $(C_3-C_7)$ cycloalkylcarbonylamido, phenylcarbonylamido, piperidinyl, pyrrolidinyl, piperazinyl, cyano, benzimidazolyl, amino, anilino, pyrimidyl, oxazolyl, isoxazolyl, tetrazolyl, thienyl, thiazolyl, benzothiazolyl, pyrrolyl, pyrazolyl, tetrahydroquinolyl, tetrahydroisoquinolyl, benzoxazolyl, pyridazinyl, pyridyloxy, pyridylsulfanyl, furanyl, 8-$(C_1-C_4)$alkyl-3, 8-diaza[3.2.1]bicyclooctyl, 3,5-dioxo-1,2,4-triazinyl, phenoxy, thiophenoxy, $(C_1-C_4)$alkylsulfanyl, $(C_1-C_4)$ alkylsulfonyl, $(C_3-C_7)$cycloalkyl, $(C_1-C_4)$alkyl optionally substituted with up to five fluoro or $(C_1-C_4)$alkoxy optionally substituted with up to five fluoro; said naphthyl, phenyl, pyridyl, piperidinyl, benzimidazolyl, pyrimidyl, thienyl, benzothiazolyl, pyrrolyl, tetrahydroquinolyl, tetrahydroisoquinolyl, benzoxazolyl, pyridazinyl, pyridyloxy, pyridylsulfanyl, furanyl, thiophenoxy, anilino and phenoxy in the definition of $R^{11}$, $R^{12}$, $R^{13}$ and $R^{14}$ are optionally substituted with up to three substituents independently selected from hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said imidazolyl, oxazolyl, isoxazolyl, thiazolyl and pyrazolyl in the definition of $R^{11}$, $R^{12}$, $R^{13}$ and $R^{14}$ are optionally substituted with up to two substituents independently selected from hydroxy, halo, hydroxy-$(C_1-C_4)$alkyl, $(C_1-C_4)$alkoxy-$(C_1-C_4)$alkyl, $(C_1-C_4)$ alkyl optionally substituted with up to five fluoro and $(C_1-C_4)$alkoxy optionally substituted with up to five fluoro; said morpholinyl in the definition of $R^{11}$, $R^{12}$, $R^{13}$ and $R^{14}$ is optionally substituted with up to two substituents independently selected from $(C_1-C_4)$alkyl; said pyrrolidinyl in the definition of $R^{11}$, $R^{12}$, $R^{13}$ and $R^{14}$ is optionally substituted with up to two substituents independently selected from hydroxy, hydroxy-$(C_1-C_3)$alkyl, $(C_1-C_4)$alkoxy-$(C_1-C_4)$alkyl, $(C_1-C_4)$ alkyl optionally substituted with up to five fluoro and $(C_1-C_4)$alkoxy optionally substituted with up to five fluoro; said piperazinyl in the definition of $R^{11}$, $R^{12}$, $R^{13}$ and $R^{14}$ is optionally substituted with up to three substituents independently selected from $(C_1-C_4)$ alkoxy-$(C_1-C_4)$alkyl, hydroxy-$(C_1-C_3)$alkyl, phenyl, pyridyl, $(C_0-C_4)$alkylsulfamoyl, $(C_1-C_4)$alkyl optionally substituted with up to five fluoro and $(C_1-C_4)$ alkoxy optionally substituted with up to five fluoro; said triazolyl in the definition of $R^{11}$, $R^{12}$, $R^{13}$ and $R^{14}$ is optionally substituted with hydroxy, halo, hydroxy-$(C_1-C_4)$alkyl, $(C_1-C_4)$alkoxy-$(C_1-C_4)$alkyl, $(C_1-C_4)$ alkyl optionally substituted with up to five fluoro and $(C_1-C_4)$alkoxy optionally substituted with up to five fluoro; said tetrazolyl in the definition of $R^{11}$, $R^{12}$, $R^{13}$ and $R^{14}$ is optionally substituted with hydroxy-$(C_2-C_3)$ alkyl or $(C_1-C_4)$alkyl optionally substituted with up to five fluoro; and said phenyl and pyridyl which are optionally substituted on piperazine in the definition of $R^{11}$, $R^{12}$, $R^{13}$ and $R^{14}$ are optionally substituted with up to three hydroxy, halo, hydroxy-$(C_1-C_4)$alkyl, $(C_1-C_4)$ alkoxy-$(C_1-C_4)$alkyl, $(C_1-C_4)$alkyl optionally substituted with up to five fluoro and $(C_1-C_4)$alkoxy optionally substituted with up to five fluoro; or $R^{11}$ and $R^{12}$ are taken together on adjacent carbon atoms and are —$CH_2OC(CH_3)_2OCH_2$— or —O—$(CH_2)_p$—O—, and $R^{13}$ and $R^{14}$ are taken separately and are each independently hydrogen or $(C_1-C_4)$alkyl;

p is 1, 2 or 3;

$R^{15}$ and $R^{16}$ are taken separately and are each independently hydrogen, $(C_1-C_4)$alkyl optionally substituted with up to five fluoro; or $R^{15}$ and $R^{16}$ are taken separately and $R^{15}$ is hydrogen and $R^{16}$ is $(C_3-C_6)$ cycloalkyl, hydroxy-$(C_1-C_3)$alkyl, phenyl, pyridyl, pyrimidyl, thienyl, furanyl, thiazolyl, oxazolyl, imidazolyl, benzothiazolyl or benzoxazolyl; or $R^{15}$ and $R^{16}$ are taken together and are $(C_3-C_6)$alkylene;

$G^3$, $G^4$ and $G^5$ are taken separately and are each hydrogen; r is 0; $R^{18}$ is hydrogen, $(C_1-C_4)$alkyl, $(C_1-C_4)$ alkoxycarbonyl, $(C_1-C_4)$alkoxy-$(C_1-C_4)$alkyl, hydroxy-$(C_1-C_4)$alkyl or phenyl optionally independently substituted with up to three hydroxy, halo, hydroxy-$(C_1-C_4)$alkyl, $(C_1-C_4)$alkoxy-$(C_1-C_4)$alkyl, $(C_1-C_4)$alkyl or $(C_1-C_4)$alkoxy, wherein said $(C_1-C_4)$ alkyl in the definition of $R^6$ and said $(C_1-C_4)$alkoxy in the definition of $R^6$ are optionally and independently substituted with up to five fluoro; and $R^{19}$ and $R^{20}$ are each independently $(C_1-C_4)$alkyl; or $G^3$, $G^4$ and $G^5$ are taken separately and are each hydrogen; r is 1; $R^{18}$ is hydrogen, $(C_1-C_4)$alkyl, $(C_1-C_4)$ alkoxycarbonyl, $(C_1-C_4)$alkoxy-$(C_1-C_4)$alkyl, hydroxy-$(C_1-C_4)$alkyl or phenyl optionally independently substituted with up to three hydroxy, halo, hydroxy-$(C_1-C_4)$alkyl, $(C_1-C_4)$alkoxy-$(C_1-C_4)$alkyl, $(C_1-C_4)$alkyl or $(C_1-C_4)$alkoxy, wherein said $(C_1-C_4)$ alkyl in the definition of $R^6$ and said $(C_1-C_4)$alkoxy in the definition of $R^6$ are optionally and independently substituted with up to five fluoro; and $R^{19}$ and $R^{20}$ are each independently hydrogen or $(C_1-C_4)$alkyl; or $G^3$ and $G^4$ are taken together and are $(C_1-C_3)$alkylene; r is 0 or 1; and $R^{18}$, $R^{19}$, $R^{20}$ and $G^5$ are hydrogen; or $G^4$ and $G^5$ are taken together and are $(C_1-C_3)$alkylene; r is 0 or 1; and $R^{18}$, $R^{19}$, $R^{20}$ and $G^3$ are hydrogen;

$R^{17}$ is $SO_2NR^{21}R^{22}$, $CONR^{21}R^{22}$, $(C_1-C_6)$ alkoxycarbonyl, $(C_1-C_6)$alkylcarbonyl, $Ar_2$-carbonyl, $(C_1-C_6)$alkylsulfonyl, $(C_1-C_6)$alkylsulfinyl, $Ar^2$-sulfonyl, $Ar^2$-sufinyl and $(C_1-C_6)$alkyl;

$R^{21}$ and $R^{22}$ are taken separately and are each independently selected from hydrogen, $(C_1-C_6)$alkyl, $(C_3-C_7)$ cycloalkyl and $Ar^2$—$(C_0-C_4)$alkylenyl; or $R^{21}$ and $R^{22}$ are taken together with the nitrogen atom to which they are attached to form azetidinyl, pyrrolidinyl, piperidinyl, piperazinyl, morpholinyl, azepinyl, azabicyclo[3.2.2]nonanyl, azabicyclo[2.2.1] heptyl, 6,7-dihydro-5H-dibenzo[c,e]azepinyl, 1,2,3,4-tetrahydro-isoquinolyl or 5,6,7,8-tetrahydropyrido[4,3-d]pyrimidyl; said azetidinyl in the definition of $R^{21}$ and $R^{22}$ is optionally substituted independently with one substituent selected from hydroxy, amino, hydroxy-$(C_1-C_4)$alkyl, $(C_1-C_4)$alkoxy-$(C_1-C_4)$alkyl, $(C_1-C_4)$ alkyl optionally substituted with up to five fluoro and $(C_1-C_4)$alkoxy optionally substituted with up to five fluoro; said pyrrolidinyl, piperidinyl, azepinyl in the definition of $R^{21}$ and $R^{22}$ are optionally substituted independently with up to two substituents independently selected from hydroxy, amino, hydroxy-$(C_1-C_4)$ alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said morpholinyl in the definition of $R^{21}$ and $R^{22}$ is optionally substituted with up to two substituents independently selected from hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said piperazinyl in the definition of $R^{21}$ and $R^{22}$ is optionally substituted independently with up to three substituents independently selected from phenyl, pyridyl, pyrimidyl, $(C_1-C_4)$alkoxycarbonyl and $(C_1-C_4)$alkyl optionally substituted with up to five fluoro; said 1,2,3,4-tetrahydro-isoquinolyl and said 5,6,7,8-tetrahydropyrido[4,3-d]pyrimidyl in the definition of $R^{21}$ and $R^{22}$ are optionally substituted independently with up to three substituents independently selected from hydroxy, amino, halo, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; and said 6,7-dihydro-5H-dibenzo[c,e]azepinyl in the definition of $R^{21}$ and $R^{22}$ is optionally substituted with up to four substituents independently selected from hydroxy, amino, halo, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said pyrimidyl, pyridyl and phenyl which are optionally substituted on said piperazine in the definition of $R^{21}$ and $R^{22}$ is optionally substituted with up to three substituents selected from hydroxy, amino, hydroxy-$(C_1-C_4)$alkyl, $(C_1-C_4)$ alkoxy-$(C_1-C_4)$alkyl, $(C_1-C_4)$alkyl optionally substituted with up to five fluoro and $(C_1-C_4)$alkoxy optionally substituted with up to five fluoro;

$Ar^2$ is independently defined as set forth for Ar and $Ar^1$ above;

said $Ar^2$ is optionally independently substituted as set forth for Ar and $Ar^1$ above;

$R^{23}$ is $CONR^{25}R^{26}$ or $SO_2R^{25}R^{26}$, wherein $R^{25}$ is hydrogen $(C_1-C_4)$alkyl or $Ar^3$—$(C_0-C_4)$alkylenyl and $R^{26}$ is $Ar^3$—$(C_0-C_4)$alkylenyl; provided that when $Ar^3$ is phenyl, naphthyl or biphenyl, then $R^{23}$ cannot be $CONR^{25}R^{26}$ where $R^{25}$ is hydrogen or $Ar^3$ and $R^{26}$ is $Ar^3$;

$R^{24}$ is hydrogen, $(C_1-C_4)$alkyl, $(C_1-C_4)$alkoxycarbonyl, $(C_1-C_4)$alkoxy-$(C_1-C_4)$alkyl, hydroxy-$(C_1-C_4)$alkyl or phenyl optionally independently substituted with up to three hydroxy, halo, hydroxy-$(C_1-C_4)$alkyl, $(C_1-C_4)$ alkoxy-$(C_1-C_4)$alkyl, $(C_1-C_4)$alkyl or $(C_1-C_4)$alkoxy, wherein said $(C_1-C_4)$alkyl in the definition of $R^6$ and said $(C_1-C_4)$alkoxy in the definition of $R^6$ are optionally and independently substituted with up to five fluoro;

$Ar^3$ is independently defined as set forth for Ar and $Ar^1$ above;

said $Ar^3$ is optionally independently substituted as set forth for Ar and $Ar^1$ above;

$R^{27}$ is hydrogen or $(C_1-C_4)$alkyl;

$R^{28}$ and $R^{29}$ are each independently hydrogen, hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro, $(C_1-C_4)$alkoxy optionally substituted with up to five fluoro, phenyl, pyridyl, pyrimidyl, thienyl, furanyl, thiazolyl, oxazolyl, phenoxy, thiophenoxy, $SO_2NR^{30}R^{31}$, $CONR^{30}R^{31}$ or $NR^{30}R^{31}$; said thienyl, pyrimidyl, furanyl, thiazolyl and oxazolyl in the definition of $R^{28}$ and $R^{29}$ are optionally substituted by up to two hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro; said phenyl, pyridyl, phenoxy and thiophenoxy in the definition of $R^{28}$ and $R^{29}$ are optionally substituted by up to three hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro;

$R^{30}$ and $R^{31}$ are each independently hydrogen, $(C_1-C_4)$alkyl, $(C_3-C_7)$cycloalkyl or phenyl, said phenyl is optionally substituted with up to three hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro; or $R^{30}$ and $R^{31}$ are taken together with the nitrogen to which they are attached to form indolinyl, pyrrolidinyl, piperidinyl, piperazinyl or morpholinyl; said pyrrolidinyl and piperidinyl in the definition of $R^{30}$ and $R^{31}$ are optionally substituted with up to two hydroxy, amino, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro; said indolinyl and piperazinyl in the definition of $R^{30}$ and $R^{31}$ are optionally substituted with up to three hydroxy, amino, hydroxy-$(C_1-C_4)$alkyl, $(C_1-C_4)$alkoxy-$(C_1-C_4)$alkyl, $(C_1-C_4)$alkoxycarbonyl, $(C_1-C_4)$alkyl optionally substituted with up to five fluoro or $(C_1-C_4)$alkoxy optionally substituted with up to five fluoro; said morpholinyl in the definition of $R^{30}$ and $R^{31}$ is optionally substituted with up to two substituents independently selected from hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro;

A is N optionally substituted with hydrogen or $(C_1-C_4)$ alkyl and B is carbonyl; or A is carbonyl and B is N optionally substituted with hydrogen or $(C_1-C_4)$alkyl;

$R^{32}$ is hydrogen or $(C_1-C_4)$alkyl;

$R^{33}$ is phenyl, pyridyl, pyrimidyl, thiazolyl, oxazolyl, benzyl, quinolyl, isoquinolyl, phthalizinyl, quinoxanlyl, benzothiazoyl, benzoxazolyl, benzofuranyl or benzothienyl; said phenyl, pyridyl, pyrimidyl, thiazolyl, oxazolyl, benzyl, quinolyl, isoquinolyl, phthalizinyl, quinoxanlyl, benzothiazoyl, benzoxazolyl, benzofuranyl and benzothienyl in the definition of $R^{33}$ are optionally substituted with up to three phenyl, phenoxy, $NR^{34}R^{35}$, halo, hydroxy, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro;

$R^{34}$ and $R^{35}$ are each independently hydrogen, $(C_1-C_4$ alkyl), phenyl or phenylsulfonyl; said phenyl and phenylsulfonyl in the definition of $R^{34}$ and $R^{35}$ are optionally substituted with up to three halo, hydroxy, $(C_1-C_4)$ alkyl optionally substituted with up to five fluoro or $(C_1-C_4)$alkoxy optionally substituted with up to five fluoro;

D is CO, CHOH or $CH_2$;

E is O, NH or S;

$R^{36}$ and $R^{37}$ are taken separately and are each independently hydrogen, halo, cyano, hydroxy, amino, $(C_1-C_6)$ alkylamino, di-$(C_1-C_6)$alkylamino, pyrrolidino, piperidino, morpholino, $(C_1-C_4)$alkoxy-$(C_1-C_4)$alkyl, hydroxy-$(C_1-C_4)$alkyl, $Ar^4$, $(C_1-C_4)$alkyl optionally substituted with up to five fluoro or $(C_1-C_4)$alkoxy optionally substituted with up to five fluoro;

$R^{38}$, $R^{39}$ and $R^{40}$ are each independently hydrogen or $(C_1-C_4)$-alkyl;

$Ar^4$ is phenyl, furanyl, thienyl, pyridyl, pyrimidyl, pyrazinyl or pyridazinyl; said $Ar^4$ being optionally substituted with up to three hydroxy, $(C_1-C_4)$alkoxy-$(C_1-C_4)$alkyl, halo, hydroxy-$(C_1-C_4)$alkyl, $(C_1-C_4)$alkyl optionally substituted with up to five fluoro or $(C_1-C_4)$alkoxy optionally substituted with up to five fluoro; or $R^{36}$ and $R^{37}$ are taken together on adjacent carbon atoms and are —O—$(CH_2)_t$—O—;

t is 1, 2 or 3;

Y is $(C_2-C_6)$alkylene;

$R^{44}$, $R^{45}$ and $R^{46}$ are each independently hydrogen or $(C_1-C_4)$alkyl;

m and n are each independently 1, 2 or 3, provided that the sum of m and n is 2, 3 or 4;

k is 0, 1, 2, 3 or 4;

$Y^1$ is a covalent bond, carbonyl, sulfonyl or oxycarbonyl;

$R^{43}$ is $(C_3-C_7)$cycloalkyl, $Ar^5$—$(C_0-C_4)$alkylenyl, $NR^{47}R^{48}$ or $(C_1-C_6)$ substituted with one to five fluoro; provided that when $Y^1$ is a covalent bond or oxycarbonyl, then $R^{43}$ is not $NR^{47}R^{48}$;

$R^{47}$ and $R^{48}$ are taken separately and are each independently selected from hydrogen, $Ar^5$, $(C_1-C_6)$alkyl and $Ar^5$—$(C_0-C_4)$alkylenyl; or $R^{47}$ and $R^{48}$ are taken together with the nitrogen atom to which they are attached to form azetidinyl, pyrrolidinyl, piperidinyl, piperazinyl, morpholinyl, azepinyl, azabicyclo[3.2.2]nonanyl, azabicyclo[2.2.1] heptyl, 1,2,3,4-tetrahydroisoquinolyl, 6,7-dihydro-5H-dibenzo[c,e]azepinyl or 5,6,7,8-tetrahydropyrido[4,3-d]pyrimidyl; said azetidinyl in the definition of $R^{47}$ and $R^{48}$ are optionally substituted with one hydroxy, amino, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro; said pyrrolidinyl, piperidinyl and azepinyl in the definition of $R^{47}$ and $R^{48}$ are optionally substituted with up to two hydroxy, amino, hydroxy-$(C_1-C_4)$alkyl, $(C_1-C_4)$alkoxy-$(C_1-C_4)$alkyl, $(C_1-C_4)$ alkyl optionally substituted with up to five fluoro or $(C_1-C_4)$alkoxy optionally substituted with up to five fluoro; said morpholinyl in the definition of $R^{47}$ and $R^{48}$ is optionally substituted with up to two substituents independently selected from hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said piperazinyl, 1,2,3,4-tetrahydroisoquinolyl and 5,6,7,8-tetrahydro[4,3-d]pyrimidyl in the definition of $R^{47}$ and $R^{48}$ are optionally substituted with up to three hydroxy, amino, halo, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro; and said 6,7-dihydro-5H-dibenzo[c,e]azepinyl in the definition of $R^{47}$ and $R^{48}$ are optionally substituted with up to four hydroxy, amino, halo, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro;

$Ar^5$ is independently defined as set forth for Ar and $Ar^1$ above;

$Ar^5$ is optionally independently substituted as set forth for Ar and $Ar^1$ above;

$R^{42}$ and $R^{42a}$ are independently hydrogen, $(C_3-C_7)$ cycloalkyl, $Ar^5$—$(C_0-C_3)$alkylenyl, $Ar^6$—$(C_2-C_4)$ alkenyl, $Ar^6$-carbonyl or $(C_1-C_6)$alkyl optionally substituted with up to five fluoro;

$Ar^6$ is independently defined as set forth for Ar and $Ar^1$ above;

$Ar^6$ is optionally independently substituted as set forth for Ar and $Ar^1$ above; and $R^{41}$ and $R^{41a}$ are each independently hydrogen or $(C_1-C_4)$ alkyl.

A preferred group of compounds within the compound of formula $I^B$ are those compounds wherein $R^{81}$ is the acyl radical of ponalrestat, tolrestat, zenarastat, zopolrestat, epalrestat, ZD5522 or sorbinil.

Especially preferred mutual prodrugs of this invention are selected from (E)-[4-oxo-3-(5-trifluoromethyl-benzbthiazol-2-ylmethyl)-3,4-dihydro-phthalazin-1-yl]-acetic acid 1R-[4-(4-quinoxalin-2-yl-piperazin-1-yl)-pyrimidin-2-yl]-ethyl ester and (E)-[4-Oxo-3-(5-trifluoromethyl-benzothiazol-2-ylmethyl)-3,4-dihydro-phthalazin-1-yl]-acetic acid 1R-{4-[4-(3-thiophen-2-yl-acryloyl)-piperazin-1-yl]-pyrimidin-2-yl}-ethyl ester.

This invention is also directed to intermediate compounds of the formula Z

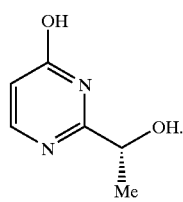

Z

This invention is still further directed to intermediate compounds, designated Group M, of the formula ZZ,

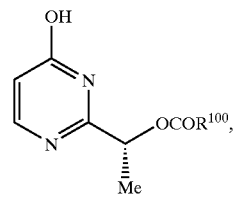

ZZ wherein $R^{100}$ is $(C_1-C_8)$alkyl, benzyl or phenyl wherein said benzyl and phenyl are optionally substituted with up to three halo or $(C_1-C_4)$alkyl.

A preferred group of compounds within Group AA, designated Group AB, are those compounds wherein $R^{100}$ is $(C_1-C_4)$alkyl.

More preferred compounds within the Group AB are those compounds wherein $R^{100}$ is n-butyl or ethyl.

This invention is still further directed to a compound of the formula ZZZ,

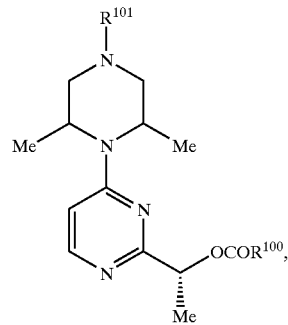

wherein:

$R^{100}$ is $(C_1-C_8)$alkyl, benzyl or phenyl wherein said benzyl and phenyl are optionally substituted with up to three halo or $(C_1-C_4)$alkyl; and $R^{101}$ is hydrogen or a suitable amine protecting group.

A preferred group of compounds of formula ZZZ, designated Group AC, are those compounds wherein $R^{100}$ is $(C_1-C_4)$alkyl and $R^{101}$ is benzyl or tert-butyloxycarbonyl.

A preferred group of compounds within the Group AC are those compounds wherein $R^{100}$ is n-butyl or ethyl and $R^{101}$ is benzyl.

Another preferred group of compounds within the Group AC are those compounds wherein $R^{100}$ is n-butyl or ethyl and $R^{101}$ is tert-butyloxycarbonyl.

This invention is also directed to a process for preparing a compound of the formula Z,

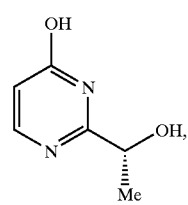

Z comprising:

a) reacting R-(+)-2-hydroxy-propionamide with triethyloxonium tetrafluoroborate in a reaction inert solvent for 10 minutes to 24 hours at 0° C. to ambient temperature to form the corresponding imidate;

b) reacting said corresponding imidate with anhydrous ammonia in a reaction inert solvent for 2 hours to 24 hours at 0° C. to ambient temperature to form R-(+)-2-hydroxy-propionamidine hydrochloride; and c) reacting said R-(+)-2-hydroxy-propionamidine hydrochloride with ethyl 3-hydroxy-acrylate sodium salt and a suitable base in a reaction inert solvent to form said compound of formula Z.

This invention is also directed to a pharmaceutical composition, designated Composition AA, comprising a compound of claim 1, a prodrug thereof or a pharmaceutically acceptable salt of said prodrug or said compound, and a glycogen phosphorylase inhibitor (GPI), a prodrug of said GPI or a pharmaceutically acceptable salt of said GPI or said prodrug.

This invention is also directed to a kit comprising:

a. a compound of claim 1, a prodrug thereof or a pharmaceutically acceptable salt of said prodrug or said compound in a first unit dosage form;

b. a glycogen phosphorylase inhibitor (GPI), a prodrug thereof or a pharmaceutically acceptable salt of said prodrug or said GPI in a second unit dosage form; and c. a container.

This invention is also directed to a method of treating or preventing diabetic complications in a mammal comprising administering to said mammal a pharmaceutical composition of Composition AA.

This invention is also directed to a method of treating hyperglycemia in a mammal comprising administering to said mammal a pharmaceutical composition of Composition AA.

This invention is also directed to a method of treating ischemia in a mammal suffering from ischemia comprising administering to said mammal a pharmaceutical composition of Composition AA.

This invention is also directed to a method of treating diabetes in a mammal comprising adminstering to said mammal a pharmaceutical composition of Composition AA.

This invention is also directed to a method of treating diabetic complications in a mammal comprising adminstering to said mammal a compound of formula I, a prodrug thereof or a pharmaceutically acceptable salt of said compound or said prodrug and a glycogen phosphorylase inhibitor (GPI), a prodrug of said GPI or a pharmaceutically acceptable salt of said GPI or said prodrug.

This invention is also directed to a method of treating hyperglycemia in a mammal comprising administering to said mammal a compound of formula I, a prodrug thereof or a pharmaceutically acceptable salt of said compound or said prodrug and a glycogen phosphorylase inhibitor (GPI), a prodrug of said GPI or a pharmaceutically acceptable salt of said GPI or said prodrug.

This invention is also directed to a method of treating ischemia in a mammal comprising adminstering to said mammal a compound of formula I, a prodrug thereof or a pharmaceutically acceptable salt of said compound or said prodrug and a glycogen phosphorylase inhibitor (GPI), a prodrug of said GPI or a pharmaceutically acceptable salt of said GPI or said prodrug.

This invention is also directed to a method of treating diabetes in a mammal comprising administering to said mammal a compound of formula I, a prodrug thereof or a pharmaceutically acceptable salt of said compound or said prodrug and a glycogen phosphorylase inhibitor (GPI), a prodrug of said GPI or a pharmaceutically acceptable salt of said GPI or said prodrug.

The subject invention also includes isotopically-labeled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which racioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of Formula I of this invention and prodrugs thereof can generally be prepared by carrying out the procedures disclosed in the Schemes and/or in the Examples and Preparations below, by substituting a readily available isotopically labeled reagent for a non-isotopically labeled reagent.

The term "reduction" is intended to include partial prevention or prevention which, although greater than that which would result from taking no compound or from taking a placebo, is less than 100% in addition to substantially total prevention.

The term "damage resulting from ischemia" as employed herein refers to conditions directly associated with reduced blood flow to tissue, for example due to a clot or obstruction of blood vessels which supply blood to the subject tissue and which result, inter alia, in lowered oxygen transport to such tissue, impaired tissue performance, tissue dysfunction and/or necrosis. Alternatively, where blood flow or organ perfusion may be quantitatively adequate, the oxygen carrying capacity of the blood or organ perfusion medium may be reduced, e.g., in hypoxic environment, such that oxygen supply to the tissue is lowered, and impaired tissue performance, tissue dysfunction, and/or tissue necrosis ensues.

The term "treating", "treat" or "treatment" as used herein includes preventative (e.g., prophylactic) and palliative treatment.

By "pharmaceutically acceptable" it is meant the carrier, diluent, excipients, and/or salt must be compatible with the other ingredients of the formulation, and not deleterious to the recipient thereof.

The expression "prodrug" refers to compounds that are drug precursors which following administration, release the drug in vivo via some chemical or physiological process (e.g., a prodrug on being brought to the physiological pH or through enzyme action is converted to the desired drug form).

This invention is further directed to compounds which are mutual prodrugs of aldose reductase inhibitors and sorbitol dehydrogenase inhibitors. By mutual prodrug is meant a compound which contains two active components, in this case, an aldose reductase inhibitor and a sorbitol dehydrogenase inhibitor, which, following administration, is cleaved, releasing each individual active component. Such mutual prodrugs of an aldose reductase inhibitor and a sorbitol dehydrogenase inhibitor are formed under standard esterification conditions well known to those skilled in the art.

By alkylene is meant saturated hydrocarbon (straight chain or branched) wherein a hydrogen atom is removed from each of the terminal carbons. Exemplary of such groups (assuming the designated length encompasses the particular example) are methylene, ethylene, propylene, butylene, pentylene, hexylene, heptylene.

By halo is meant chloro, bromo, iodo, or fluoro.

By alkyl is meant straight chain saturated hydrocarbon or branched saturated hydrocarbon. Exemplary of such alkyl groups (assuming the designated length encompasses the particular example) are methyl, ethyl, propyl, isopropyl, butyl, sec-butyl, tertiary butyl, pentyl, isopentyl, neopentyl, tertiary pentyl, 1-methylbutyl, 2-methylbutyl, 3-methylbutyl, hexyl, isohexyl, heptyl and octyl.

By alkoxy is meant straight chain saturated alkyl or branched saturated alkyl bonded through an oxygen. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy and octoxy.

It is to be understood that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3-, or 4-pyridyl, the term "thienyl" means 2-, or 3-thienyl, and so forth.

The expression "pharmaceutically-acceptable salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate, methanesulfonate and 4-toluene-sulfonate. Where more than one basic moiety exists the expression includes multiple salts (e.g., di-salt). The expression also refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methyl-glucamine), benethamine (N-benzylphenethylamine), piperazine or tromethamine (2-amino-2-hydroxymethyl-1,3-propanediol).

As used herein, the expressions "reaction inert solvent" and "inert solvent" refers to a solvent or mixture of solvents which does not interact with starting materials, reagents, intermediates or products in a manner which adversely affects the yield of the desired product.

The chemist of ordinary skill will recognize that certain compounds of formula I of this invention will contain one or more atoms which may be in a particular stereochemical or geometric configuration, giving rise to stereoisomers and configurational isomers. All such isomers and mixtures thereof are included in this invention. Compounds of formula I may be chiral. In such cases, the isomer wherein $R^1$ has the R configuration is preferred. Hydrates of the compounds of formula I of this invention are also included.

The chemist of ordinary skill in the art will also recognize that certain compounds of formula I of this invention can exist in tautomeric form, i.e., that an equilibrium exists between two isomers which are in rapid equilibrium with each other. A common example of tautomerism is keto-enol tautomerism, i.e.,

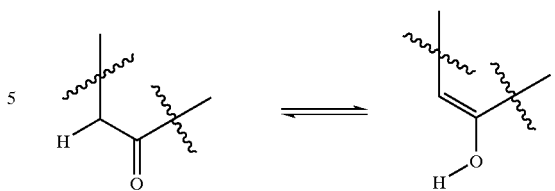

Examples of compounds which can exist as tautomers include hydroxypyridines, hydroxypyrmidines and hydroxyquinolines. Other examples will be recognized by those skilled in the art. All such tautomers and mixtures thereof are included in this invention.

DMF means N,N-dimethylformamide. DMSO means dimethyl sulfoxide. THF means tetrahydrofuran.

Whenever the structure of a cyclic radical is shown with a bond drawn from outside the ring to inside the ring, it will be understood by those of ordinary skill in the art to mean that the bond may be attached to any atom on the ring with an available site for bonding. If the cyclic radical is a bicyclic or tricyclic radical, then the bond may be attached to any atom on any of the rings with an available site for bonding. For example,

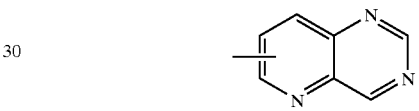

represents any or all of the following radicals:

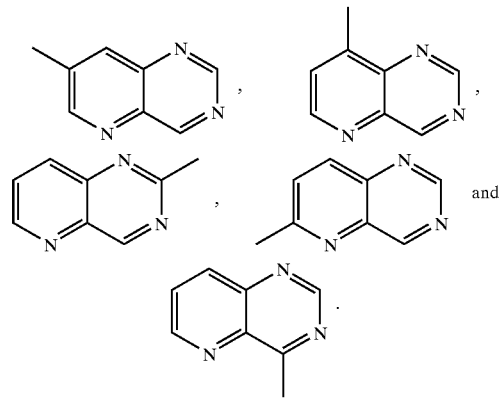

Other features and advantages will be apparent from the specification and claims which describe the invention.

DETAILED DESCRIPTION OF THE INVENTION

In general the compounds of formula I of this invention can be made by processes which include processes known in the chemical arts, particularly in light of the description contained herein. Certain processes for the manufacture of the compounds of formula I of this invention are provided as further features of the invention and are illustrated by the following reaction schemes. Other processes are described in the experimental section.

Scheme 1

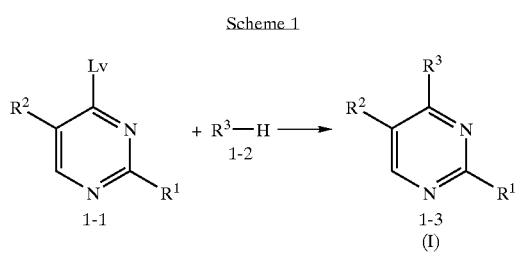

Compounds of formula 1-3 (i.e., formula I) are prepared as set forth in Scheme 1, particularly as described below.

Compounds of formula 1-3 are prepared by the displacement reaction of a pyrimidine of the formula 1-1 where $R^1$ and $R^2$ are defined herein. Lv is a leaving group preferably selected from fluoro, chloro, bromo, iodo, thiomethyl, methylsulfone, or $OSO_2J$ wherein J is $(C_1-C_6)$-lower alkyl, trifluoromethyl, pentafluoroethyl, phenyl optionally substituted with up to three $(C_1-C_4)$alkyl, nitro or halo. The leaving group Lv is displaced by an amine of the formula 1-2 where $R^3$ is defined above. The reaction is conducted in the presence of a non-aqueous base, preferably an organic amine or an inorganic base. Preferred organic amines include triethylamine, pyridine, dimethylaminopyridine and N,N'-diisopropylethylamine (Hunig's base). Preferred inorganic bases include alkaline metal carbonates and bicarbonates such as sodium or potassium carbonate and sodium or potassium bicarbonate. An especially preferred inorganic base is potassium carbonate. An especially preferred organic amine is triethylamine. Alternatively, an excess of the reacting amine 1-2 can be used as the base for this reaction. The reaction can be conducted in the absence of solvent or in a reaction inert solvent. Where used herein, "reaction inert solvent" refers to a solvent which does not interact with starting materials, reagents, intermediates or products in a manner which adversely affects the yield of the desired product. Preferred reaction inert solvents include aqueous media, pyridine, $(C_1-C_4)$alcohol, $(C_2-C_6)$glycol, halocarbon, aliphatic/aromatic hydrocarbon, ethereal solvent, polar aprotic solvent, ketonic solvent, or combinations thereof. The reaction time ranges from 15 minutes to 3 days and the reaction temperature ranges from 0° C. to 180° C. Conveniently, the reaction may be conducted at the reflux temperature of the solvent being used. The reaction is preferably conducted at ambient pressure. The term ambient pressure, where used herein, refers to the pressure of the room in which the reaction is being conducted. The term ambient temperature, where used herein, refers to the temperature of the room in which the reaction is being conducted.

When $R^1$ contains a hydroxy group, the hydroxyl group may or may not be protected. When the hydroxyl group is protected, the protecting group may be any suitable hydroxyl protecting group. The conditions used to remove such optional hydroxyl protecting groups contained in $R^1$ in compounds of formula 1-3 are as follows. When the protecting group is an ester, removal of such ester protecting groups is conducted under basic conditions using inorganic hydroxides or carbonates, preferably lithium hydroxide, sodium hydroxide, potassium hydroxide or potassium carbonate. The reaction is carried out in a reaction inert solvent, preferably an alcoholic solvent. Especially preferred is methanol or methanol in combination with co-solvents such as water, tetrahydrofuran, or dioxane. The reaction time ranges from 15 minutes to 24 hours and the reaction temperature ranges from 0° C. to 100° C. or to the reflux temperature of the solvents) of use. Alternatively, ester cleavage may be accomplished under acidic conditions. It is preferred to utilize aqueous hydrochloric acid, generally 2 N to concentrated, with or without a co-solvent. When a co-solvent is used, dioxane or methanol are preferred. The reaction time ranges from 4 hours to 3 days and the reaction temperature ranges from 0° C. to 60° C.

When the protecting group is an alkyl ether, removal of such alkyl ether protecting groups is conducted using well known dealkylative conditions. For example, the alkyl ether may be cleaved by reaction with boron tribromide or diethylboron bromide in a reaction inert solvent, preferably a halocarbon solvent. It will be recognized by those skilled in the art that a buffer such as triethylamine may facilitate the reaction. The reaction times range from 15 minutes to 24 hours and the reaction temperature ranges from 0° C. to 60° C. In addition, a benzyl ether protecting group can be removed via standard or transfer hydrogenolysis using a palladium catalyst such as palladium on carbon. The hydrogenolysis reaction is conducted under a hydrogen atmosphere at ambient pressure to 50 psi in a reaction inert solvent, preferably methanol. The hydrogen source may be hydrogen gas, ammonium formate or trialkylammonium formate or cyclohexene. The reaction temperature ranges from room temperature to the reflux temperature of the solvent employed. The reaction time ranges from 15 minutes to 24 hours.

When a silyl ether protecting group is employed, removal of such silyl ether protecting groups is conducted under acidic conditions, preferably with aqueous hydrochloric acid such as 1 N to 6 N hydrochloric acid. The de-protection may be carried out in the presence of a co-solvent such as methanol or tetrahydrofuran. The reaction time ranges from 2 hours to 48 hours and the reaction temperature ranges from 0° C. to 100° C. Alternatively, the silyl ether protecting group may be removed via fluoride-mediated deprotection. In this case, deprotection is conducted using tetrabutylammonium fluoride or one of a variety of hydrofluoric acid sources in a reaction inert solvent. It is preferred to use ethereal solvents such as diethyl ether, dioxane or tetrahydrofuran, with tetrahydrofuran being especially preferred. The reaction time ranges from 2 hours to 48 hours and the reaction temperatures range from 0° C. to the reflux temperature of the solvent being used. Other methods for removal of the aforementioned protecting groups are well known to those skilled in the art or can be found in Greene, T. W.; Wuts, P. G. M., *Protective Groups in Organic Synthesis*, $2^{nd}$ ed.; John Wiley and Sons Inc.: New York, 1991. Other suitable hydroxyl protecting groups and methods for their removal may be found also be found therein.

The method of Scheme I is preferred when $R^3$ is $R^{3k, l, m, n, o, p \text{ and } q}$. Thus, compounds of formula 1-2 are reacted with compounds of formula 1-1. Compounds of formula 1-2 where $R^3$ is $R^{3k, l, m, n, o, p \text{ or } q}$ are commercially available or can be prepared by methods well known to those skilled in the art.

Scheme 2

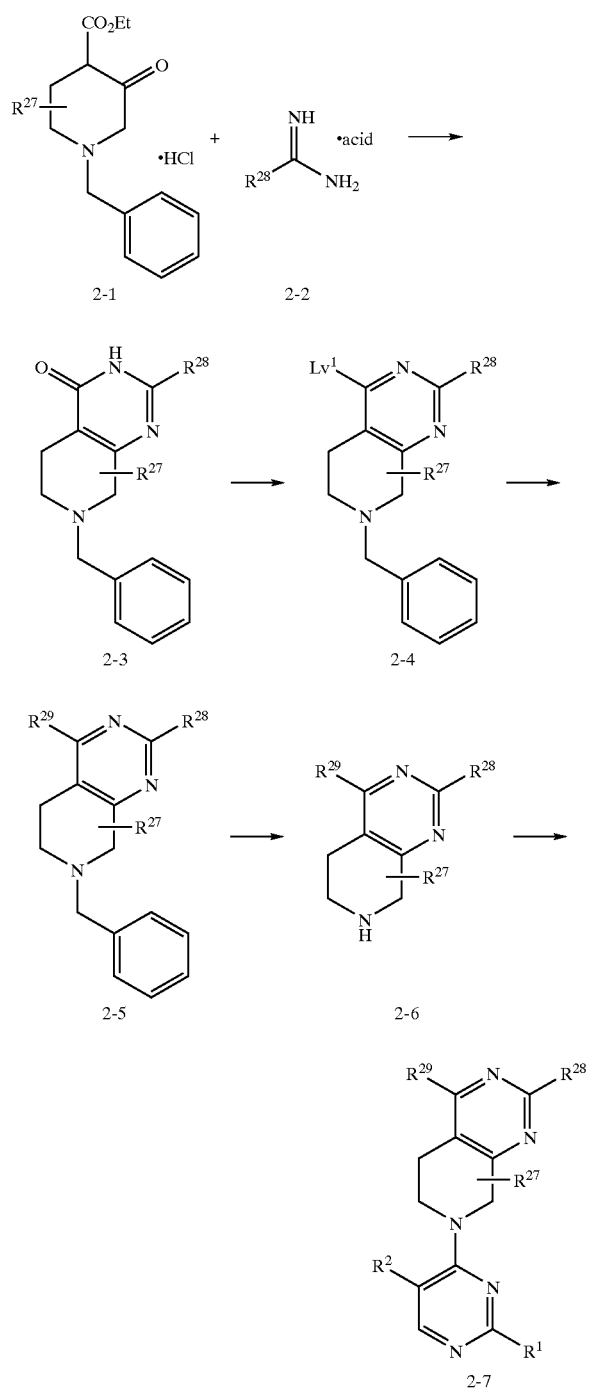

Compounds of formula 2-7 are prepared as set forth in Scheme 2, particularly as described below.

Where $R^{27}$ is H, ethyl 1-benzyl-3-oxo-4-piperidine-carboxylate hydrochloride, the compound of formula 2-1, which is available from Aldrich, is condensed with compounds of formula 2-2 to give compounds of formula 2-3. The compounds of formula 2-1 where $R^{27}$ is not H can be prepared according to methods well known to those skilled in the art. The reaction is conducted in the presence of excess base including non-aqueous bases, organic amines and inorganic bases. Preferred organic amines include triethylamine and pyridine. Preferred non-aqueous bases include alkaline metal ($C_1$–$C_4$)alkoxides. Preferred inorganic bases include potassium carbonate. The reaction is conducted in a reaction inert solvent. Preferred such solvents include ($C_1$–$C_4$) alcohols, aromatic or aliphatic hydrocarbons, polar aprotic solvents, halocarbons, and ethereal solvents. ($C_1$–$C_4$) Alcohols are especially preferred. The reaction time ranges from 2 hours to 3 days. The reaction temperature ranges from ambient temperature to the reflux temperature of the solvent being employed. The reaction is preferably run at ambient pressure but may be conducted at pressures up to 250 psi.

Compounds of formula 2-4 are prepared from compounds of formula 2-3 by converting a compound of formula 2-3 into an activated compound of formula 2-4 where $Lv^1$ is selected from fluoro, chloro, bromo, iodo, trifluoromethanesulfonate, ($C_1$–$C_6$)alkylsulfonate, or phenylsulfonate, wherein said phenyl is optionally substituted with up to three ($C_1$–$C_4$)alkyl, halo or nitro. This reaction is accomplished by reacting compounds of formula 2-3 with a chlorinating agent such as phosphorus oxychloride and/or phosphorus pentachloride to provide compounds of formula 24 where $Lv^1$ is chloro. This reaction is conducted at ambient pressure in the absence of solvent or in a reaction inert solvent, preferably a halocarbon solvent at temperatures ranging from ambient temperature to 180° C. Treatment of the chloro compound thus formed with the requisite mineral acid provides a compound of formula 2-4 where $Lv^1$ is bromo or iodo. A sulfonate of formula 2-4 is prepared by reaction of a compound of formula 2-3 with a sulfonic acid chloride or anhydride in the presence of an organic amine base, preferably triethylamine or pyridine. In certain cases recognized by those skilled in the art, it may be necessary to add a catalyst to the reaction. In those cases, a preferred catalyst is 4-dimethylaminopyridine. This reaction is conducted at ambient pressure in a reaction inert solvent, preferably pyridine, a halocarbon such as chloroform, dichloromethane or carbon tetrachloride, an aromatic or aliphatic hydrocarbon, an ethereal solvent, or combinations thereof. The reaction temperature ranges from –20° C. to 100° C. and the reaction time ranges from 15 minutes to 1 day.

Compounds of formula 2-5 wherein $R^{29}$ is defined above are prepared from compounds of formula 24 by a reduction reaction or by displacement of $Lv^1$ with a nucleophile. The reduction is conducted with a reducing agent, preferably ammonium formate or hydrogen gas, in a reaction inert solvent. The reduction is conducted in the presence of a palladium catalyst at ambient pressure or under a hydrogen pressure of up to 50 psi. Preferred solvents include ($C_1$–$C_4$) alcohols such as methanol and ethanol, and ether solvents such as diethyl ether, dioxane and tetrahydrofuran. The nucleophilic displacement reaction may be conducted by adding the nucleophile directly or by pre-forming the nucleophile separately or in situ from a nucleophile precursor. Preferred nucleophiles include organoaluminum, organoboron, organocopper, organotin, organozinc or Grignard reagent; $R^{29}$—H; or, where $R^{29}$ contains a hydroxyl or thiol group, the anion of $R^{29}$. The term "organo" in the terms organoaluminum, organoboron, organocopper, organotin and organozinc refers to an organic radical selected from $R^{29}$. It will be recognized by those skilled in the art that transition-metal catalysts may be required to effect reaction in certain displacement reactions. When required, such transition metal catalysts may include palladium(0), palladium(II), nickel(0), and nickel(II) complexes. Palladium(II) bis(diphenylphosphinobutane) dichloride is a preferred such catalyst. Additionally, an aqueous or non-aqueous base may be required in the displacement reaction. Preferred such bases include sodium carbonate, sodium hydride, triethylamine and sodium tert-butoxide. The reaction is conducted at ambient pressure in a reaction inert solvent such as a halocarbon, an aromatic or aliphatic hydrocarbon, an ether or a polar aprotic solvent or a combination thereof. In certain cases, a ($C_1$–$C_4$)alcohol is used as a solvent or co-solvent. The reaction temperature ranges from −20° C. to the reflux temperature of the solvent employed. The reaction time ranges from 1 hour to 3 days.

Compounds of formula 2-6 are prepared by removal of the benzyl protecting group from compounds of formula 2-3 or 2-5. This transformation is accomplished using the freebase, or preferably the pre-formed hydrochloride or similar salt, under standard or transfer hydrogenolysis conditions. The catalysts which may be used in the hydrogenolysis reaction include, but are not limited to, palladium on carbon, palladium hydroxide on carbon and platinum(IV) oxide. The reaction is conducted in a reaction inert solvent, preferably methanol or ethanol and the reaction temperature ranges from room temperature to the reflux temperature of the solvent being employed. The hydrogen source is hydrogen gas, ammonium formate, trialkylammonium formate, or cyclohexene. The reaction time ranges from 15 minutes to 3 days. Generally the reaction is conducted at ambient pressure but pressures of up to 50 psi of hydrogen may be employed. Alternatively, if appropriate, the benzyl protecting group is removed in two steps via chloroformate-induced acylative dealkylation. This involves reaction with a chloroformate derivative to form a carbamate followed by cleavage of the carbamate. While this reaction is preferably conducted with 1-chloroethyl chloroformate and sodium iodide catalysis, it will be recognized by those skilled in the art that catalysis may not be required in certain cases. The reaction is conducted at ambient temperature in a reaction inert solvent such as a halocarbon, an aromatic or aliphatic hydrocarbon, a ketone, an ether or a polar aprotic solvent. The reaction temperature ranges from −78° C. to the reflux temperature of the solvent being employed and the reaction time ranges from 15 minutes to 1 day. Cleavage of the carbamate formed by reaction with 1-chloroethyl chloroformate is accomplished upon exposure to methanol or ethanol at ambient pressure to give compounds of formula 2-6 as a hydrochloride salt. The reaction proceeds at temperatures from room temperature to the reflux temperature of the solvent being employed and the reaction time ranges from 15 minutes to 1 day. Deprotection conditions for other carbamates can be found in Greene, T. W.; Wuts, P. G. M. *Protective Groups in Organic Synthesis*, $2^{nd}$ ed.; John Wiley and Sons Inc.: New York, 1991, pp 315–348.

Compounds of formula 2-7 are prepared from the displacement reaction of amine 2-6 as described in Scheme 1, where the amine 2-6 is equivalent to $R^3$—NH.

Alternatively, compounds of formula 2-7 where $R^{29}$ is as defined above are prepared from compounds of formula 2-3 wherein $R^{29}$ is OH according to the sequence outlined in Scheme 2a below, wherein the conditions are as set forth as described for Scheme 2.

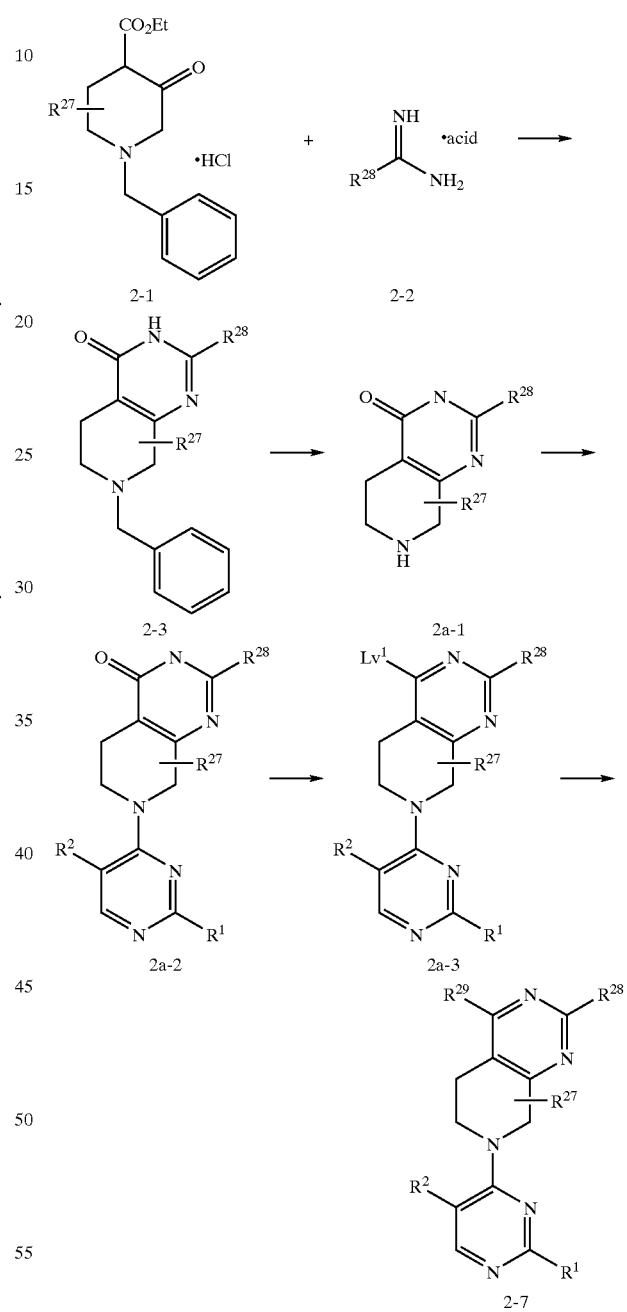

Compounds of formula 2-2 which are used in Schemes 2 and 2a above are commercially available or are prepared according to methods well known to those skilled in the art, such as those described in March, J. *Advanced Organic Chemistry*, $3^{rd}$ ed.; John Wiley and Sons.: New York, 1985, p 359, 374.

Scheme 3

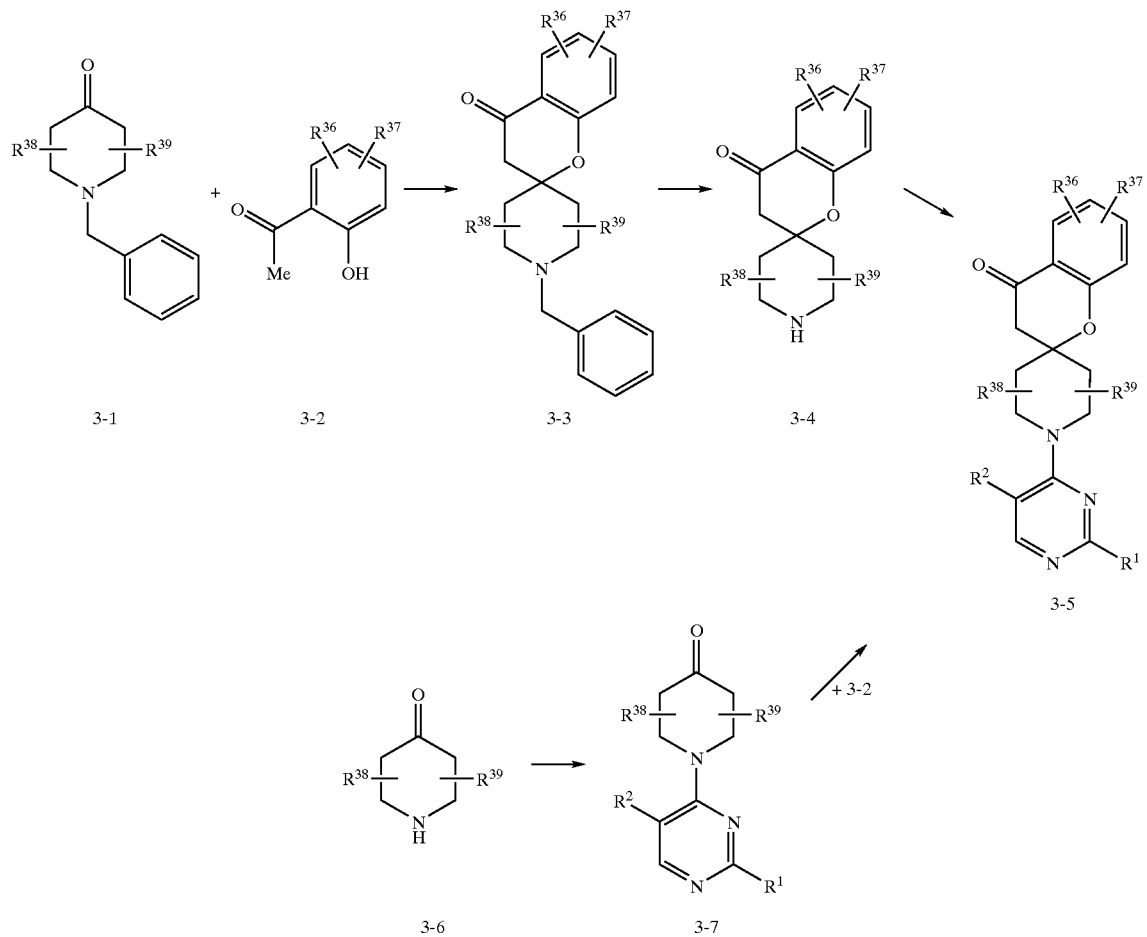

Compounds of formula 3-5 are prepared as set forth in Scheme 3 above and more particularly as described below.

Compounds of formula 3-3 are prepared by condensing a compound of formula 3-1 with a compound of formula 3-2. Where $R^{38}$ and $R^{39}$ are each H, the compound of formula 3-1 is 1-benzyl-4-piperidone, which is commercially available from Aldrich. Compounds of formula 3-2 are either commercially available or can be prepared according to methods well known to those skilled in the art, particularly according to methods set forth in March, J. *Advanced Organic Chemistry*, $3^{rd}$ ed.; John Wiley and Sons Inc.: New York, 1985, pp 499–500. The reaction is conducted at ambient pressure in the presence of a secondary amine. Generally an excess of the secondary amine, preferably pyrrolidine, piperidine, morpholine or diethylamine, is used. An especially preferred secondary amine is pyrrolidine. The reaction is conducted in a reaction inert solvent, preferably a $(C_1-C_4)$ alcohol, an aromatic or aliphatic hydrocarbon, a polar aprotic solvent, a halocarbon or an ether. An especially preferred solvent is ethanol. The reaction time ranges from 2 hours to 3 days and the reaction temperature ranges from ambient temperature to the reflux temperature of the solvent being employed.

Compounds of the formula 3-4 are prepared by removal of the benzyl protecting group from compounds of formula 3-3. This transformation is conducted in a manner analogous to the procedure set forth for the preparation of compounds of formula 2-6 above.

Compounds of formula 3-5 are prepared from the displacement reaction of amine 34 as described in Scheme 1, where the amine 3-4 is equivalent to $R^3$—NH.

Scheme 3a

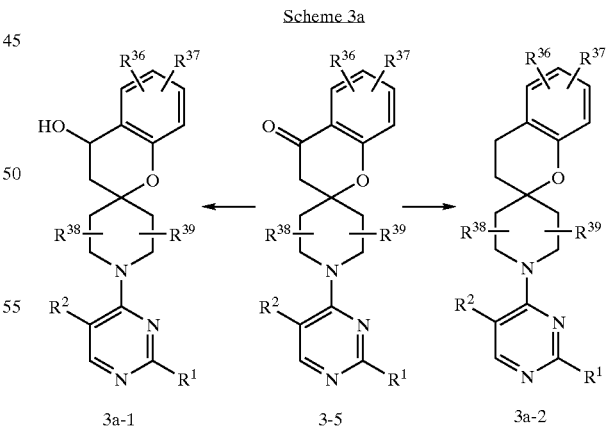

Compounds of formulas 3a-1 and 3a-2 are prepared as shown in Scheme 3a from compounds of formula 3-5. Thus, to prepare a compound of 3a-1, a compound of formula 3-5 is reduced with a common reducing agent, such as, for example, sodium borohydride, lithium aluminum hydride or diisobutylaluminum hydride. Other reducing agents capable of effecting the reduction of a ketone to an alcohol are well known to those skilled in the art (e.g., Larock, R. D. *Comprehensive Organic Transformations*, VCH Publishers, Inc.: New York, 1989, pp 527–547). Likewise, compounds of formula 3a-2 are prepared from compounds of formula 3-5 by reduction with reducing agents capable of reducing a ketone completely to a methylene group. A preferred such reducing agent is aluminum trichloride/borane-tert-butylamine complex. Other such reducing agents are well known to those skilled in the art (e.g., *J. Org. Chem.* 1989, 54, 4350; Larock, R. D. *Comprehensive Organic Transformations*, VCH Publishers, Inc.: New York, 1989, pp 35–37). It will be recognized by those skilled in the art that the transformation of 3-5 to 3a-1 or 3a-2 can be conducted at different points in Scheme 3, depending upon the dynamics of the particular system.

Alternatively, compounds of formula 3-5 wherein $R^{38}$ and $R^{39}$ are hydrogen can be prepared from 4-piperidone monohydrate monochloride in a manner analogous to the procedure described in Scheme 1, where the amine 3-6 is equivalent to $R^3$—NH to give compounds of formula 3-7. Compounds of formula 3-7 can be reacted with compounds of formula 3-2 in a manner analogous to the procedure set forth for the synthesis of compounds of formula 3-3 to afford compounds of formula 3-5.

Compounds of formula 4-5 are prepared according to Scheme 4 and more particularly as described below.

Compounds of formula 4-3 are prepared by reacting a compound of formula 4-2 with a compound of formula 4-1 or 4-1 a. Compounds of formula 4-1 and 4-1 a are prepared according to methods well known to those skilled in the art. Where $R^{32}$ is hydrogen, 4-oxo-piperidine-1,3-dicarboxylic acid 1-tert-butyl ester 3-ethyl ester is condensed with a compound of formula 4-2 to afford a compound of formula 4-3. Said compounds of formula 4-2 are readily available from well known commercial vendors, known in the literature, or are synthesized under standard conditions well known to those skilled in the art. Preferred conditions to prepare compounds of formula 4-3 from a compound of formula 4-1 where A is CO and B is NH or from a compound of formula 4-1a where A is NH and B is CO can be found in March, J. *Advanced Organic Chemistry*, $3^{rd}$ ed.; John Wiley and Sons Inc.: New York, 1985, p 1163. The reaction is conducted at ambient pressure in a reaction inert solvent. Preferred such solvents include aqueous media, a $(C_1–C_4)$ alcohol, glacial acetic acid, an aromatic or aliphatic hydrocarbon, a polar aprotic solvent, a halocarbon and

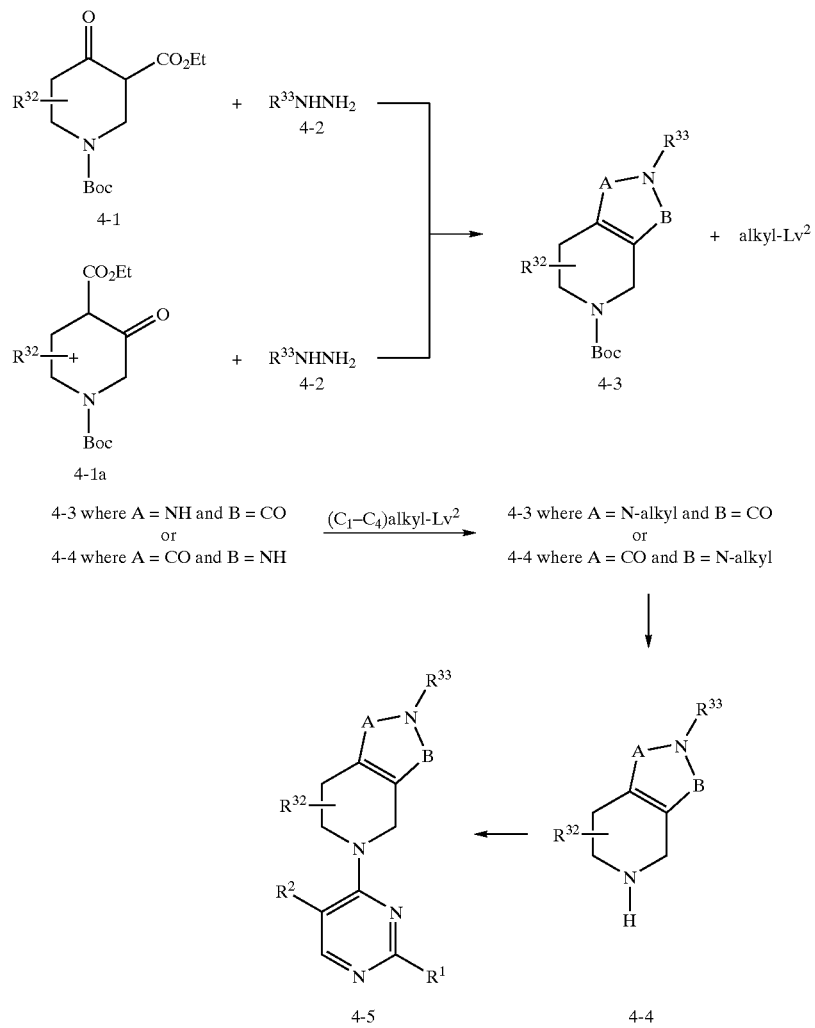

Scheme 4 ethers or combinations thereof. The reaction time ranges from 2 hours to 3 days and the reaction temperature ranges from ambient temperature to the reflux temperature of the solvent being used. An optional second step using aqueous or non-aqueous base may be employed in certain cases which will be recognized by those skilled in the art. This second step is conducted at ambient pressure in a reaction inert solvent. Preferred such solvents include aqueous media, a $(C_1-C_4)$alcohol, glacial acetic acid, an aromatic or aliphatic hydrocarbon, a polar aprotic solvent, a halocarbon and ethers or combinations thereof. The reaction time ranges from 2 hours to 3 days and the reaction temperature ranges from ambient temperature to the reflux temperature of the solvent being used.

Compounds of formula 4-3 wherein B is CO and A is N-alkyl or wherein B is N-alkyl and A is CO are prepared by alkylation of compounds of formula 4-3 where B is CO and A is NH or wherein B is NH and A is CO, respectively. The anion of those compounds of formula 4-3 is formed by reaction with an appropriate base. Preferred such bases include sodium hydride and sodium hexamethyldisilazide, although other bases may be used where conditions warrant, as determined by the skilled person. The reaction is conducted in a reaction inert solvent, preferably an ether such as tetrahydrofuran, diethyl ether, dioxane or diglyme or polar aprotic solvent such as dimethylformamide. The reaction proceeds at ambient pressure and at temperatures ranging from −100° C. to ambient temperature. The reaction times are from 10 minutes to 2 hours. Addition of $(C_1-C_4)$alkyl halides or $(C_1-C_4)$alkylsulfonates such as mesylate, tosylate or nosylate to the anion of 4-3 proceeds at ambient pressure and at temperatures ranging from −20° C. to 50° C. The reaction times range from 10 minutes to 1 day.

Compounds of formula 4-4 are prepared form compounds of formula 4-3 wherein A is N-alkyl and B is CO or A is CO and B is N-alkyl via acid-catalyzed deprotection of the Boc carbamate under standard conditions, for example, hydrochloric acid or trifluoroacetic acid in a reaction inert solvent or in the absence of solvent. Such conditions are known to those skilled in the art. Exemplary conditions are disclosed in Greene, T. W.; Wuts, P. G. M. *Protective Groups in Organic Synthesis*, 2$^{nd}$ ed.; John Wiley and Sons Inc.: New York, 1991, pp 327–330.

Compounds of formula 4-5 are prepared by the displacement reaction of amine 44 as described in Scheme 1, where the amine 4-4 is equivalent to $R^3$—H.

Scheme 5

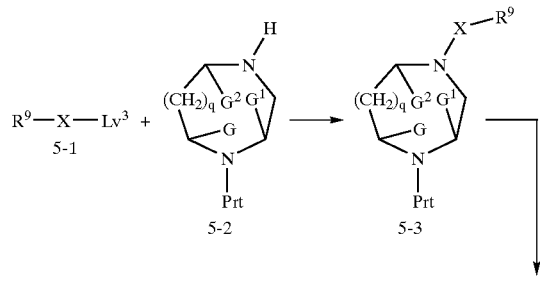

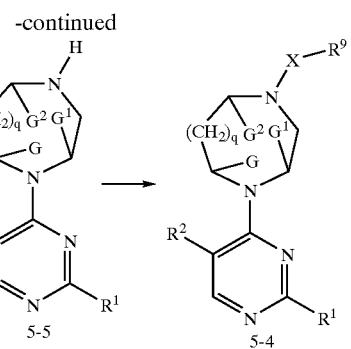

Compounds of formula 5-4 where X is a covalent bond and G, $G^1$, $G^2$, q, $R^1$, $R^2$, $R^6$, $R^7$ and $R^8$ are as defined above are prepared according to Scheme 5 above and particularly as described below.

Compounds of formula 5-3 are prepared by reaction of a compound of formula 5-1 with a compound of formula 5-2 where Prt is an optional amine protecting group selected from benzyl and $CO_2R^{90}$, where $R^{90}$ is selected from $(C_1-C_4)$alkyl, $(C_1-C_4)$allyl, trichloroethyl and benzyl substituted by up to two $(C_1-C_4)$alkoxy. Compounds of formula 5-1 where $R^9$ is $Ar^1$ and $Lv^3$ is halo, $(C_1-C_4)$alkylsulfide, $(C_1-C_4)$alkylsulfone, trifluoromethanesulfonate, $(C_1-C_6)$alkylsulfonate or phenylsulfonate, where said phenyl is optionally substituted with up to three halo, nitro or $(C_1-C_4)$alkyl are commercially available or are readily prepared according to methods well known to those skilled in the art. For example, to prepare compounds of formula 5-1 wherein $Lv^3$ is chloro, a compound of formula $Ar^1$—OH, or the $Ar^1$—(═O) tautomer thereof, is reacted with a chlorinating agent such as phosphorus oxychloride and/or phosphorus pentachloride. This chlorinating reaction is conducted at ambient pressure in the absence of solvent or in a reaction inert solvent, preferably a halocarbon solvent, at temperatures ranging from ambient temperature to 180° C. Treatment of the chloro compound with the requisite mineral acid provides compounds of formula 5-1 where $Lv^3$ is bromo or iodo. Compounds of formula 5-1 wherein $Lv^3$ is trifluoromethanesulfonate, $(C_1-C_6)$alkylsulfonate or phenylsulfonate are prepared from a compound of formula $Ar^1$—OH, or the $Ar^1$—(═O) tautomer thereof, by reaction with a sulfonic acid chloride or anhydride in the presence of a base, preferably an organic amine such as triethylamine, N,N'-diisopropylethylamine, dimethylaminopyridine or pyridine. In certain cases it will be recognized by those skilled in the art that a catalyst will be required to effect reaction. In those cases, a preferred catalyst is 4-dimethylaminopyridine. This reaction is conducted at ambient pressure in a reaction inert solvent such as pyridine, a halocarbon, an aromatic or aliphatic hydrocarbon, an ether, or a combination thereof. The reaction temperature ranges from −20° C. to 100° C. and the reaction time ranges from 15 minutes to 1 day. Compounds of formula 5-1 where $Lv^3$ is thiomethyl are prepared by reacting a compound of formula $Ar^1$—SH, or the $Ar^1$—(═S) tautomer thereof, with methyl iodide or dimethylsulfate in the presence of an inorganic base, preferably potassium carbonate. These reactions are conducted at ambient pressure in a reaction inert solvent, preferably an ether or a polar aprotic solvent. An especially preferred polar aprotic solvent is dimethylformamide at a temperature ranging from 0° C. to 100° C. Compounds of formula 5-1 where $Lv^3$ is methylsulfone are prepared from a compound of formula 5-1 where $Lv^3$ is thiomethyl by oxidation thereof according to procedures well known to those skilled in the art, specifically as set forth in March, J. *Advanced Organic Chemistry*, 3$^{rd}$ ed.; John Wiley and Sons.: New York, 1985, pp 1089–1090.

A representative set of compounds of formula 5-1 which are commercially available or which can be prepared according to methods analogous to a literature procedure include 4-chloropyridine (Aldrich, P.O. Box 355, Milwaukee, Wis. 53201, USA), 3-chloro-6-methyl-pyridazine (Maybridge, c/o Ryan Scientific, 443 Long Point Road, Suite D, Mount Pleasant, S.C. 29464, USA), 2-chloro-pyrazine (Aldrich), 2,6-dichloro-pyrazine (Aldrich), 3-chloro-2,5-dimethylpyrazine (Aldrich), 2,4-dichloro-pyrimidine (Aldrich), 4,6-dichloro-pyrimidine (Aldrich), 4-chloro-2-methyl-pyrimidine (*Chem. Ber.* 1904, 37, 3641), 4-chloro-6-methyl-pyrimidine (*Chem. Ber.* 1899, 32, 2931), 4-chloro-2,6-dimethyl-pyrimidine (*J. Am. Chem. Soc.* 1946, 68, 1299), 4-chloro-2,6-bis(trifluoromethyl)-pyrimidine (*J. Org. Chem.* 1961, 26, 4504), 4-chloro-2-methylsulfanyl-pyrimidine (Aldrich), 4-chloro-2-methoxymethyl-pyrimidine (U.S. Pat. No. 5,215,990), 1-chloro-isoquinoline (*J. Am. Chem. Soc.* 1946, 68, 1299), 2-chloro-quinoline (Aldrich), 4-chloro-quinazoline (*J. Am. Chem. Soc.* 1909, 31, 509), 2-chloro-quinoxaline (U.S. Pat. No. 2,537,870), 2-chloro-3-methyl-quinoxaline (Aldrich), 2,6,7-trichloro-quinoxaline (*J. Chem. Soc., Chem. Commun.* 1956, 4731), 4-chloro-pteridine (*J. Chem. Soc., Chem. Commun.* 1954, 3832), 7-chloro-pteridine (*J. Chem. Soc., Chem. Commun.* 1954, 3832), and 6-chloro-9H-purine (Aldrich). Other compounds of formula 5-1 can be prepared using methods well known to those skilled in the art or by using methods analogous to those described in the foregoing references.

Compounds of formula 5-3 are prepared by the displacement reaction of a compound of formula 5-1 with an amine of the formula 5-2. The reaction is conducted in the presence of a non-aqueous base, prefeably an organic amine such as pyridine, 4-dimethylaminopyridine, triethylamine or N,N'-diisopropylethylamine; an inorganic base such as potassium or sodium carbonate or bicarbonate; or an alkaline metal alkoxide such as potassium t-butoxide. Alternatively, an excess of the reacting amine 5-2 can be used in lieu of the added base. In cases where the leaving group $Lv^3$ is unactivated, or in specific cases which will be recognized by those skilled in the art, the use of a transition-metal catalyst such as palladium(0), palladium (II), nickel(0) or nickel(II), along with phosphine-based ligands, such as 2,2'-bis (diphenylphosphino)-1,1'-binaphthyl (BINAP), may be required to effect reaction. More specific details concerning this reaction are available in the following references: *J. Org. Chem.* 1997, 62, 1264; *J. Org. Chem.* 1997, 62, 1568; *SynLett* 1997, 329. The reaction can be conducted in the absence of solvent or in a reaction inert solvent. Preferable reaction inert solvents include aqueous media, $(C_1-C_4)$ alcohol, $(C_2-C_6)$glycol, a halocarbon, an aliphatic or aromatic hydrocarbon, an ether, a polar aprotic solvent, a ketone, or combinations thereof. The reaction time ranges from 15 minutes to 3 days and the reaction temperature ranges from 0° C. to 180° C. or to the reflux temperature of the solvent being used. The reactions are preferably conducted at ambient pressure.

In certain cases which will be recognized by those skilled in the art, transformations of existing functionality in $Ar^1$ of compound 5-3 may be necessary to produce compounds of formula 5-4. This pertains in particular to those cases where, for example, $R^9$ in 5-3 contains an aromatic or heteroaromatic halide, $(C_1-C_4)$alkylsulfonate or triflate. Said compounds of formula 5-3 wherein $Ar^1$ contains up to two substituents selected from halide, $(C_1-C_4)$alkylsulfonate or triflate, may be converted to a compound of formula $Ar^1$ where said halide, $(C_1-C_4)$alkylsulfonate or triflate is transformed into another functional group by a reduction reaction or by a displacement reaction of said halide, $(C_1-C_4)$ alkylsulfonate or triflate with a nucleophile. The reduction reaction is conducted with a reducing agent, preferably ammonium formate or hydrogen gas, in a reaction inert solvent. The reduction is conducted in the presence of a palladium catalyst at ambient pressure or under a hydrogen pressure of up to 50 psi. Preferred solvents include $(C_1-C_4)$ alcohols such as methanol and ethanol, and ether solvents such as diethyl ether, dioxane and tetrahydrofuran. The nucleophilic displacement reaction may be conducted by adding the nucleophile directly or by pre-forming the nucleophile separately or in situ from a nucleophile precursor. Preferred nucleophiles include organoaluminum, organoboron, organocopper, organotin, organozinc or Grignard reagent; $R^{11}$-oxide or $R^{11}$-thioxide; or anilino where anilino is within the scope of $R^{11}$. It will be recognized by those skilled in the art that transition-metal catalysts may be required to effect reaction in certain displacement reactions. When required, such transition metal catalysts may include palladium(0), palladium(II), nickel(0), and nickel(II) complexes. Palladium(II) bis(diphenylphosphinobutane) dichloride is a preferred such catalyst. Additionally, an aqueous or non-aqueous base may be required in the displacement reaction. Preferred such bases include sodium carbonate, sodium hydride, triethylamine and sodium tert-butoxide. The reaction is conducted at ambient pressure in a reaction inert solvent such as a halocarbon, an aromatic or aliphatic hydrocarbon, an ether or a polar aprotic solvent or a combination thereof. In certain cases, a $(C_1-C_4)$alcohol is used as a solvent or co-solvent. The reaction temperature ranges from −20° C. to the reflux temperature of the solvent employed. The reaction time ranges from 1 hour to 3 days.

Optional protecting groups which may be present in compounds of formula 5-3 are removed according to methods set forth above, or according to methods well known to those skilled in the art, particularly as set forth in: Greene, T. W.; Wuts, P. G. M. *Protective Groups in Organic Synthesis*, 2nd ed.; John Wiley and Sons Inc.: New York, 1991.

Compounds of formula 54 are prepared from the displacement reaction of amine 5-3 as described in Scheme 1, where the amine 5-3 is equivalent to $R^3$—NH. A representative set of amines of formula 5-3 which are commercially available or which can be prepared by a literature procedure include 1-phenyl-piperazine (Aldrich), 1-pyridin-2-yl-piperazine (Aldrich), 3-piperazin-1-yl-benzo[d]isoxazole (*J. Med. Chem.* 1986, 29, 359), 3-piperazin-1-yl-benzo[d]isothiazole (*J. Med. Chem.* 1986, 29, 359), 2-piperazin-1-yl-quinoxaline (*J. Med. Chem.* 1981, 24, 93), 1-naphthalen-2-yl-piperazine (cf. *Tetrahedron Lett.* 1994, 35, 7331), and 1-(3,5-dimethylphenyl)-piperazine (cf. *Tetrahedron Lett.* 1994, 35, 7331). Other compounds of formula 5-3 can be prepared using methods well known to those skilled in the art or by using methods analogous to those described in the foregoing references.

Alternatively, compounds of formula 54 can be prepared from reaction with compounds of formula 5-1 with compounds of formula 5-5 using conditions set forth above to prepare 5-3. Compounds of formula 5-5 can be prepared in a manner analogous to the method used to prepare compounds of formula 1-3.

Compounds of formula 54 wherein X is oxycarbonyl, vinylenylcarbonyl, oxy($C_1$–$C_4$)alkylenylcarbonyl, ($C_1$–$C_4$) alkylenylcarbonyl, ($C_3$–$C_4$)alkenylcarbonyl, thio($C_1$–$C_4$) alkenylcarbonyl, vinylenylsulfonyl or carbonyl($C_0$–$C_4$) alkylenylcarbonyl; wherein said oxy($C_1$–$C_4$) alkylenylcarbonyl, ($C_1$–$C_4$)alkylenylcarbonyl, ($C_3$–$C_4$) alkenylcarbonyl, and thio($C_3$–$C_4$)alkenylcarbonyl in the definition of X are each optionally and independently substituted with up to two ($C_1$–$C_4$)alkyl, benzyl, or Ar; said vinylenylsulfonyl and said vinylenylcarbonyl in the definition of X are each optionally and independently substituted with up to three ($C_1$–$C_4$)alkyl, benzyl, or Ar are also prepared according to Scheme 5 above and particularly as described below.

Compounds of formula 54 where X is as defined in the immediately preceding paragraph are prepared by reacting a compound of formula 5-5 with a compound of formula 5-1 where $R^9$ is described above, X is as defined in the immediately preceding paragraph and $Lv^3$ is chloro. The reaction is conducted under anhydrous conditions in the presence of a non-aqueous base, which includes organic amines such as triethylamine, N,N'-diisopropylethylamine and pyridine and derivatives thereof. The reaction is generally conducted in a reaction inert solvent. Preferred solvents include halocarbon, aliphatic or aromatic hydrocarbon, ethers, ethyl acetate, pyridine and combinations thereof. The reaction time ranges from 15 minutes to 24 hours and the reaction temperature ranges from 0° C. to 80° C. or to the reflux temperature of the solvent being used. The reactions are preferably conducted at from 0° C. to ambient temperature and at ambient pressure. Removal of optional protecting groups is carried out as described in Scheme I.

Compounds of formula 5-4 wherein X is vinylenylcarbonyl, oxy($C_1$–$C_4$)alkylenylcarbonyl, ($C_1$–$C_4$) alkylenylcarbonyl, ($C_3$–$C_4$)alkenylcarbonyl, thio($C_2$–$C_4$) alkenylcarbonyl, or carbonyl($C_0$–$C_4$)alkylenylcarbonyl; wherein said oxy($C_1$–$C_4$)alkylenylcarbonyl, ($C_1$–$C_4$) alkylenylcarbonyl, ($C_3$–$C_4$)alkenylcarbonyl, and thio ($C_2$–$C_4$)alkenylcarbonyl in the definition of X are each optionally and independently substituted with up to two ($C_1$–$C_4$)alkyl, benzyl, or Ar; and said vinylenylcarbonyl in the definition of X are each optionally and independently substituted with up to three ($C_1$–$C_4$)alkyl, benzyl, or Ar are also prepared according to Scheme 5 above and particularly as described below.

Compounds of formula 54 are prepared by reacting a compound of formula 5-5 with a compound of formula $R^9$—X-$Lv^3$ where $R^9$ is described above, X is as defined in the immediately preceding paragraph and $Lv^3$ is OH. The reaction is conducted in the presence of coupling agents, preferably dicyclohexylcarbodiimide or 1-(3-dimethylaminopropyl)-3-ethylcarbodiimide hydrochloride as described in *J. Amer. Chem. Soc.* 1996, 118, 4952. The reaction is conducted in a reaction inert solvent. Preferred solvents include halocarbon, aliphatic or aromatic hydrocarbon and ethers. Especially preferred solvents include dichloromethane and chloroform. Other coupling agents that can be used are well known to those skilled in the art and include, but are not limited to, various phosphine reagents, ethyl chloroformate, and N-hydroxysuccinimide. These reagents and procedures are described in "Compendium of Organic Synthetic Methods" (Ed., l. T. Harrison and S. Harrison, John Wiley & Sons). Specific references include the following: *J. Org. Chem*, 1971, 36, 1305; *Bull. Soc. Chim. Fr.*, 1971, 3034; *Bull. Chem. Soc. Japan*, 1971, 44, 1373; *Tetrahedron Lett.*, 1973, 28, 1595; *Tetrahedron Lett.*, 1971, 26, 2967, and *J. Med. Chem.*, 1968, 11, 534. Removal of optional protecting groups is carried out as described in Scheme I.

Compounds of formula 5-4 wherein X is a covalent bond and $R^9$ is ($C_3$–$C_7$)cycloalkyl or $Ar^1$—($C_1$–$C_3$)alkylenyl are also prepared according to Scheme 5 above and particularly as described below.

Compounds of formula 5-4 wherein X is a covalent bond and $R^9$ is ($C_3$–$C_7$)cycloalkyl or $Ar^1$—($C_1$–$C_3$)alkylenyl are prepared by reacting a compound of formula 5-1 wherein X is a covalent bond, $R^9$ is ($C_3$–$C_7$)cycloalkyl or $Ar^1$—($C_1$–$C_3$)alkylenyl and $Lv^3$ is halo, methanesulfonate, p-toluenesulfonate or trifluoromethanesulfonate. The reaction is conducted under anhydrous conditions in the presence of a non-aqueous base, which includes organic amines such as triethylamine, N,N'-diisopropylethylamine and pyridine and derivatives thereof. The reaction is conducted in a reaction inert solvent. Preferred solvents for the reaction include halocarbons, aliphatic or aromatic hydrocarbons, ethers, ethyl acetate, pyridine and combinations thereof. The reaction time ranges from 15 minutes to 24 hours and the reaction temperature ranges from –20° C. to 80° C. or to the reflux temperature of the solvent being used. The reactions are preferably conducted at ambient temperature of the solvent being used and at ambient pressure. Removal of optional protecting groups is conducted as set forth in Scheme I.

Scheme 6

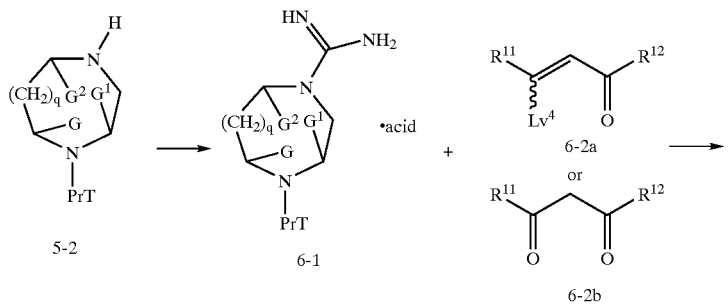

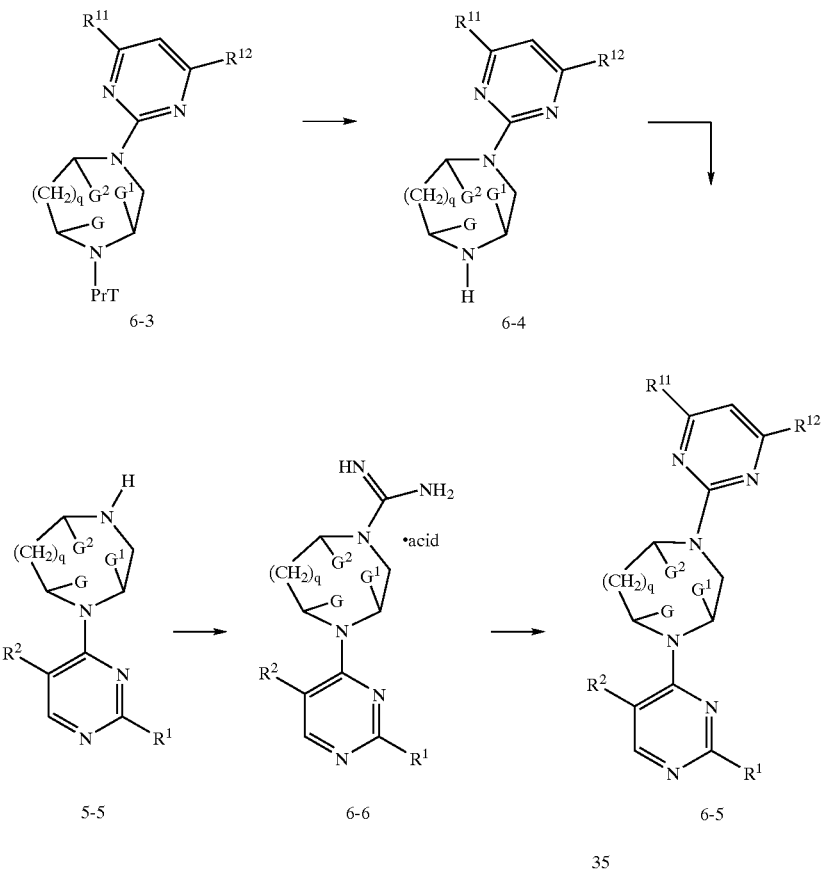

Compounds of formula 6-5 wherein G, $G^1$, $G^2$, q, $R^1$, $R^2$, $R^6$, $R^7$ and $R^8$ are as defined above are prepared as set forth in Scheme 6 above and particularly as described below.

Compounds of formula 6-1 are prepared from an amine of the formula 5-2 where Prt is an optional amine protecting group selected from benzyl and $CO_2R^{90}$, where $R^{90}$ is selected from $(C_1-C_4)$alkyl, $(C_1-C_4)$allyl, trichloroethyl and benzyl substituted with up to two $(C_1-C_4)$alkoxy. The preferred procedure for preparing compounds of formula 6-1 can be found in *Tetrahedron Lett.* 1993, 48, 7767 or *J. Org. Chem* 1997, 62, 1540.

Compounds of formula 6-3 are prepared by condensation of β-diketones or β-ketoesters of the formula 6-2b, where $R^{11}$ and $R^{12}$ are independently substituted as set forth above, or compounds of the formula 6-2a where $Lv^4$ is, for example, hydroxy, chloro or dimethylamino with guanidines of the formula 6-1. The reaction is conducted in the presence of an aqueous or non-aqueous base, preferably potassium or sodium hydroxide, potassium or sodium $(C_1-C_4)$-alkoxide, triethylamine, pyridine, 4-dimethylaminopyridine, potassium or sodium carbonate or potassium or sodium bicarbonate. The reaction is conducted in a reaction inert solvent, preferably aqueous media, a $(C_1-C_4)$alcohol, a $(C_2-C_6)$ dialcohol, an aromatic hydrocarbon, a polar aprotic solvent, or combinations thereof. The reaction time ranges from 2 hours to 3 days and the reaction temperature ranges from room temperature to reflux of the solvent employed. The reaction is preferably run at ambient pressure, but may be conducted at pressures up to 250 psi.

Removal of of optional protecting groups in compounds of formula 6-3 to afford compounds of formula 64 is accomplished as set forth above.

Compounds of formula 6-5 are prepared from the displacement reaction of amine 6-4 as described in Scheme 1, where the amine 6-4 is equivalent to $R^3$—NH.

Alternatively, compounds of formula 6-5 are prepared from compounds of formula 5-5 by formation of a compound of formula 6-6, or by reaction with compounds of formula 6-2a or 6-2b under the conditions outlined above in Scheme 6. Removal of optional protecting groups is conducted as described in Scheme 1. Compounds of formula 5-5 are prepared as set forth above.

Scheme 7

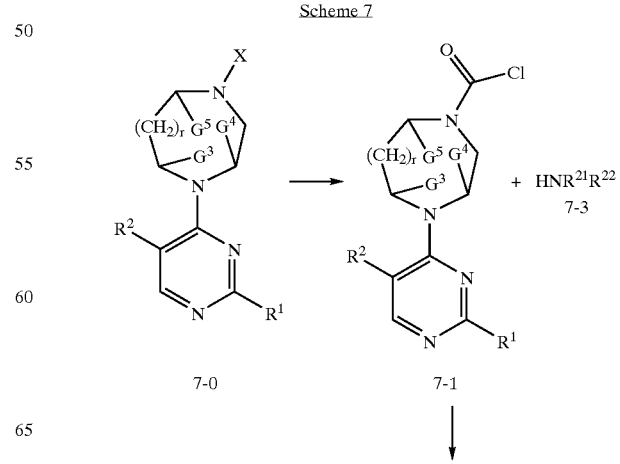

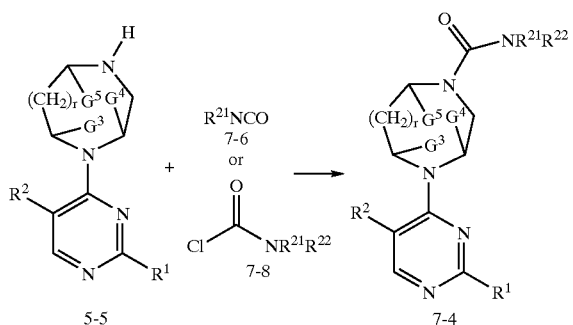

Compounds of formula 74 wherein $G^3$, $G^4$, $G^5$, r, $R^1$, $R^2$, $R^{18}$, $R^{19}$ and $R^{20}$ are d as set forth above are prepared as set forth in Scheme 7 and particularly as described below.

Compounds of formula 7-1 are prepared by reaction of an amine of the formula 7-0 with phosgene or a phosgene equivalent such as triphosgene. Compounds of 7-1 wherein the chloro group is replaced by an imidazolyl group are also useful in this reaction. Such compounds are prepared by reaction of an amine of formula 7-0 with carbonyl diimidazole. The reaction is conducted under anhydrous conditions in the presence of a nonaqueous base. Preferred such bases include triethylamine and other tertiary amines and pyridine and derivatives thereof. The reaction is conducted in a reaction inert solvent at −78° C. to 80° C. or at the reflux temperature of the solvent being used for 15 minutes to 24 hours. Preferred solvents for this reaction include a halocarbon, an aliphatic or aromatic hydrocarbon, an ether, ethyl acetate, pyridine and combinations thereof. The reactions are preferably conducted at from 0° C. to ambient temperature and at ambient pressure.

Compounds of formula 7-4 are prepared by reaction of carbamoyl chlorides of the formula 7-1 with amines of the formula 7-3, where $R^{21}$ and $R^{22}$ are defined above. The reaction can be conducted in the absence of solvent, or in a reaction inert solvent. Preferred such solvents include aqueous media, a $(C_1-C_4)$alcohol, a $(C_2-C_6)$dialcohol, an aromatic or aliphatic hydrocarbon, a halocarbon, an ether, a polar aprotic solvent, a ketone, pyridine or combinations thereof. The reaction time ranges from 15 minutes to 3 days and the reaction temperature ranges from 0° C. to the reflux temperature of the solvent being used. The reaction is preferably conducted at ambient pressure. It will be recognized by those skilled in the art that addition of a base may be required to effect reaction. In those cases, preferred bases include potassium or sodium hydroxide, triethylamine and other tertiary amines, pyridine and its derivatives and inorganic bases such as sodium or potassium carbonate and sodium or potassium bicarbonate. Removal of optional hydroxyl protecting groups contained in $R^1$ is carried out according to methods set forth in Scheme 1.

Alternatively, compounds of formula 74 are prepared from compounds of formula 7-0 by reaction with isocyanates of the formula 7-6 or with carbamoyl chlorides of the formula 7-8. Said isocyanates are commercially available, known in the literature, or synthesized under standard conditions known to those skilled in the art, particularly as described in March, J. *Advanced Organic Chemistry*, $3^{rd}$ ed.; John Wiley and Sons Inc.: New York, 1985, p 1166. A preferred method of forming such isocyanates is the Curtius rearrangement of a suitable acyl azide. Said carbamoyl chlorides are synthesized using methods analogous to that described for the preparation of compounds of formula 7-1 in Scheme 7. Removal of optional hydroxyl protecting groups contained in $R^1$ is carried out according to methods set forth in Scheme 1.

Compounds of formula I containing the radical $R^{3c}$ are prepared according to the procedures set forth in Scheme 7 using the corresponding starting materials and reagents.

Scheme 8

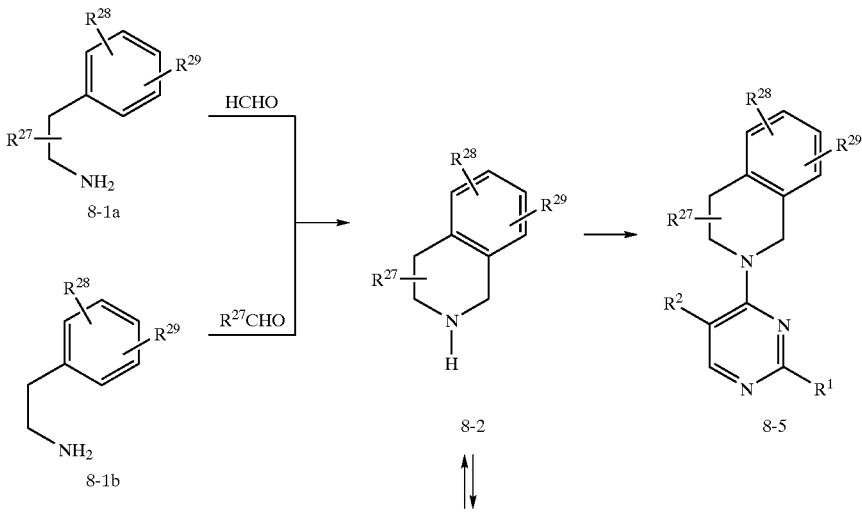

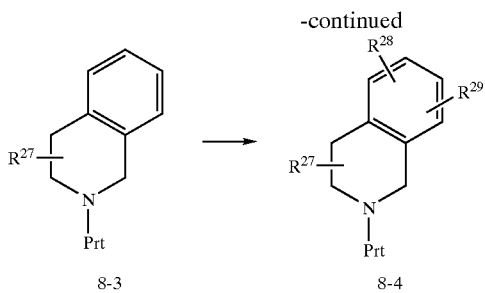

Compounds of formula 8-5 are prepared as set forth in Scheme 8 and particularly as described below.

Compounds of formula 8-2 are readily prepared from commercially available phenethylamines of formula 8-1a and formaldehyde or an aldehyde of the formula $R^{27}$—CHO under Pictet-Spengler conditions. The Pictet-Spengler reaction is reviewed in *Chem. Rev.* 1995, 95, 1797. A similar route route to 1,2,3,4-tetrahydroisoquinolines using the Bischler-Napieralski reaction, as disclosed in March, J. *Advanced Organic Chemistry*, $3^{rd}$ ed.; John Wiley and Sons.: New York, 1985, 495, followed by standard reduction of the imine formed may also be employed.

Compounds of formula 84 are prepared from compounds of formula 8-3 by aromatic electrophilic substitution using the appropriate electrophile. A general reference for this type of reaction can be found in March, J. *Advanced Organic Chemistry*, $3^{rd}$ ed.; John Wiley and Sons.: New York, 1985, 447–511.

Compounds of formula 8-2 are also prepared by removal of the protecting group from a compound of formula 8-4. Preferably the protecting group is trifluoroacetamide which may be removed under basic conditions using inorganic hydroxides or carbonates in a reaction inert solvent. Suitable such solvents include $(C_1-C_4)$alcohols and preferably methanol. Optionally, one or more co-solvents, preferably selected from water, tetrahydrofuran and dioxane may be employed. The reaction time ranges from 15 minutes to 24 hours and the reaction temperature ranges from 0° C. to 100° C. or to the reflux temperature of the solvent or solvent system being used. The reaction is preferably conducted at ambient temperature. Other conditions for deprotection of trifluoroacetamides and deprotection conditions for other suitable protecting groups can be found in Greene, T. W.; Wuts, P. G. M. *Protective Groups in Organic Synthesis*, $2^{nd}$ ed.; John Wiley and Sons Inc.: New York, 1991.

Compounds of formula 8-4 are prepared by adding a protecting group to compounds of formula 8-2. Preferably the protecting group is trifluoroacetamide or tert-butoxycarbonyl (BOC). The protecting group is attached by reaction of a compound of formula 8-2 with trifluoroacetyl chloride or di-tert-butyl dicarbonate or an equivalent thereof in the presence of a base, preferably triethylamine or pyridine. The reaction is conducted in a reaction inert solvent. Preferred such solvents include ethers such as tetrahydrofuran, diethyl ether, dioxane or dimethoxyethane; a halocarbon such as dichloromethane, chloroform or carbon tetrachloride; and aromatic or aliphatic hydrocarbons such as benzene, toluene or hexanes. The reaction time ranges from 15 minutes to 3 days and the reaction temperature ranges from 0° C. to the reflux temperature of the solvent being used. The reaction is preferably conducted at ambient pressure. Other conditions for protection of amines with trifluoroacetamides or tert-butoxycarbonyl groups as well as other suitable protecting groups can be found in Greene, T. W.; Wuts, P. G. M. *Protective Groups in Organic Synthesis*, $2^{nd}$ ed.; John Wiley and Sons Inc.: New York, 1991.

Manipulation of the substituents $R^{28}$ and $R^{29}$ is carried out to provide isoquinolines with altered substitution. Preferably, transition metal-catalyzed cross-coupling of a compound of formula 8-4 where $R^{28}$ or $R^{29}$ is bromide or triflate is employed to afford compounds of formula 8-4 wherein $R^{28}$ or $R^{29}$ are as set forth above. This reaction is conducted according to methods well known to those skilled in the art, particularly as set forth in *Tetrahedron*, 1998, 54, 263 for Stille and Suzuki Reactions and in *Acc. Chem. Res.* 1998, 31, 805 for Buchwald Amination Reactions.

Compounds of formula 8-5 are prepared from the displacement reaction of amine 8-2 as described in Scheme 1, where the amine 8-2 is equivalent to $R^3$—NH.

Scheme 9

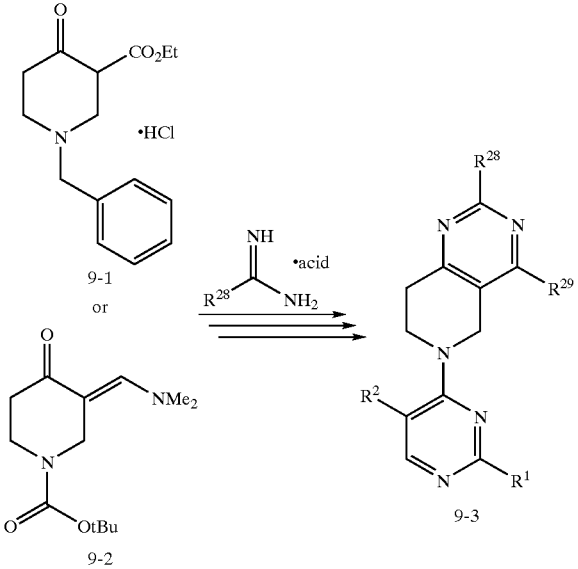

Compounds of formula 9-3 are prepared according to the general procedures set forth in Scheme 2 starting from ethyl 1-benzyl-4-oxo-3-piperidine carboxylate hydrochloride (9-1). In certain cases, where $R^{29}$ is H, N-tertbutoxycarbonyl-3-(dimethylaminomethylene)-4-piperidone (9-2, Chemical Abstracts 121:157661) is used as the starting material.

Scheme 10

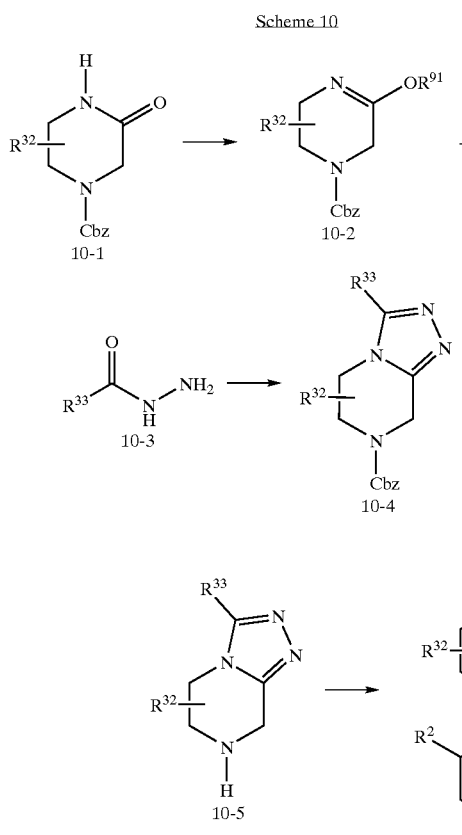

Compounds of formula 10-6 wherein $R^1$, $R^2$, $R^{32}$ and $R^{33}$ are as defined above are prepared as set forth in Scheme 10 and more particularly as described below.

Compounds of formula 10-2 where $R^{91}$ is $(C_1$–$C_4)$alkyl are prepared by reacting a compound of formula 10-1, where Cbz is benzyloxycarbonyl, with an O-alkylating agent. A preferred compound of formula 10-1 is 3-oxo-piperazine-1-carboxylic acid benzyl ester. A preferred O-alkylating agent is triethyloxonium tetrafluoroborate. The reaction is conducted at ambient pressure in a reaction inert solvent. Preferred solvents include an aromatic or aliphatic hydrocarbons, halocarbons and ethers. Dichloromethane is especially preferred. The reaction time ranges from 2 hours to 3 days and the reaction temperature ranges from –100° C. to ambient temperature.

Compounds of formula 10-4 are prepared by condensation of a compound of formula 10-2 with a compound of formula 10-3. Said compounds of formula 10-3 are commercially available, are known in the literature, or are readily prepared via standard amidation of hydrazine and an activated carboxylic acid, such as a carboxylic acid chloride. Such reactions are well known by those skilled in the art. The condensation reaction is preferably run at ambient pressure, although higher pressures up to 250 psi may be employed if necessary. The reaction is conducted in a reaction inert solvent, preferably selected from $(C_1$–$C_4)$ alcohols, aromatic or aliphatic hydrocarbons, polar aprotic media, halocarbons and ethers, or combinations thereof. The reaction is conducted at temperatures ranging from ambient temperature to 180° C. The reaction times are from 2 hours to 3 days.

Compounds of formula 10-5 are prepared form compounds of formula 10-4 via Lewis acid-catalyzed cleavage or hydrogenolysis of the Cbz carbamate under standard conditions which are well known to those skilled in the art, particularly as set forth in Greene, T. W.; Wuts, P. G. M. *Protective Groups in Organic Synthesis*, $2^{nd}$ ed.; John Wiley and Sons Inc.: New York, 1991, pp 335–338.

Compounds of formula 10-6 are prepared from the displacement reaction of an amine of the formula 10-5 as described in Scheme 1, where the amine 10-5 is equivalent to $R^3$—NH.

Scheme 11

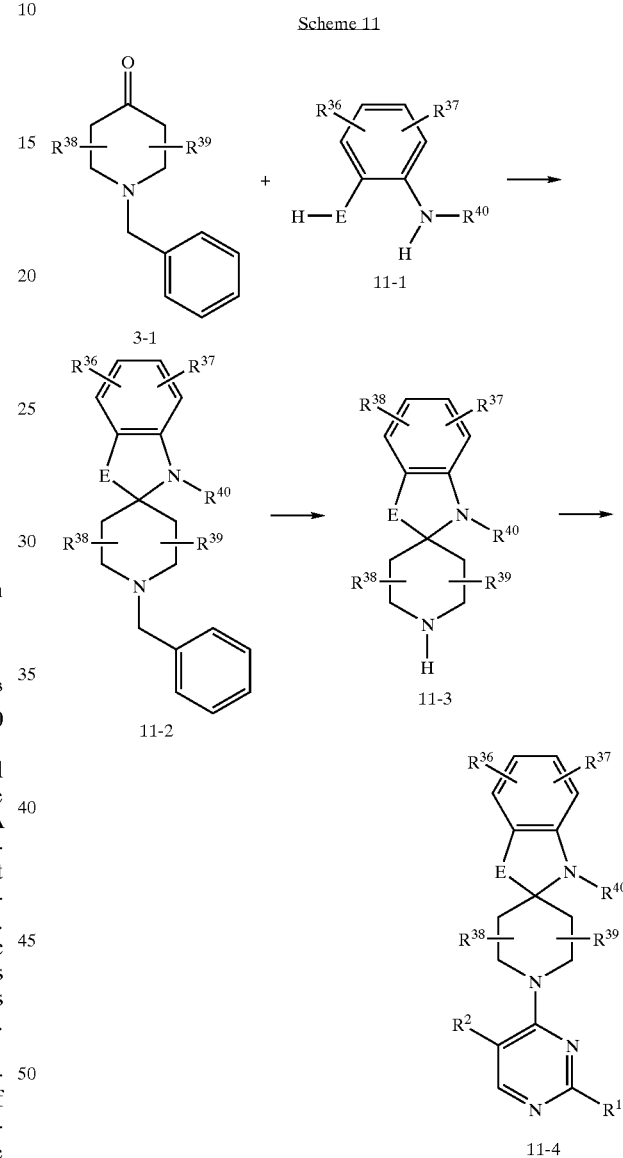

Compounds of formula 11-4, wherein $R^1$, $R^2$, $R^{36}$, $R^{37}$, $R^{38}$, $R^{39}$ and $R^{40}$ are as defined above are prepared as set forth in Scheme 11 and more particularly as described below.

Where $R^{38}$ and $R^{39}$ are hydrogen, 1-benzyl-4-piperidone (3-1), available from Aldrich, is condensed with a compound of formula 11-1, which are either commercially available or well known to those skilled in the art, to give compounds of formula 11-2. Where $R^{38}$ and $R^{39}$ are not hydrogen, compounds of formula 3-1 can be prepared according to methods well known to those skilled in the art. The reaction is conducted at ambient pressure in the absence of solvent or in a reaction inert solvent. Preferred solvents include ($C_1$–$C_4$)alcohols, aromatic or aliphatic hydrocarbons, polar aprotic solvents, halocarbons and ethers. The reaction time ranges from 2 hours to 3 days and the reaction temperature ranges from ambient temperature to the reflux temperature of the solvent being employed. More specific conditions can be found in *Indian J. Chem.* 1976, 14B, 984 and *J. Chem. Soc., Perkin Trans.* 1 1984, 2465.

Compounds of formula 11-3 are prepared by removal of the benzyl protecting group from a compound of formula 11-2 in a manner analogous to the method employed for the preparation of compounds of 2–6 described above.

Compounds of formula 11-4 are prepared by the displacement reaction of an amine of the formula 11-3 as described in Scheme 1, where the amine 11-3 is equivalent to $R^3$—H.

Scheme 12

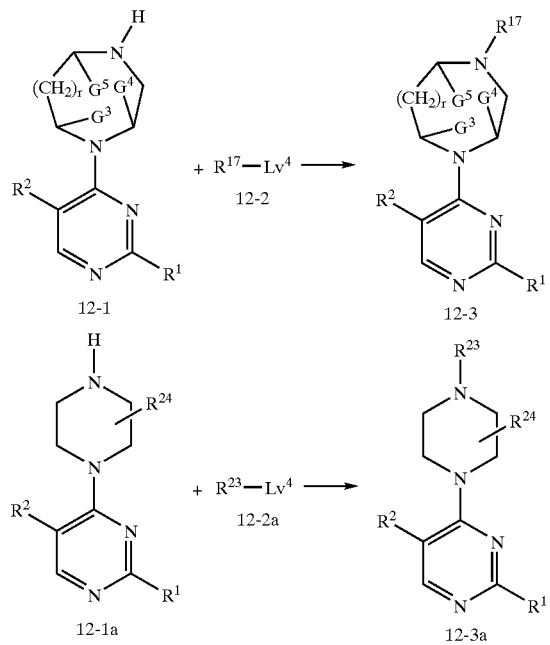

Compounds of formula 12-3 and 12-3a where $R^{17}$ and $R^{23}$ are ($C_1$–$C_6$)alkoxycarbonyl, ($C_1$–$C_6$)alkylcarbonyl, $Ar^2$-carbonyl, ($C_1$–$C_6$)alkylsulfonyl, $A^2$—sulfonyl, or $Ar^2$-sulfinyl are prepared according to Scheme 12 above and particularly as set forth below.

Compounds of formula 12-3 and 12-3a where $R^{17}$ and $R^{23}$ are as defined in the immediately preceding paragraph are prepared by condensation with a compound of formula 12-2 and 12-2a, wherein $Lv^4$ is chloro, respectively. Examples of compounds of formula 12-2 and 12-2a include ($C_1$–$C_6$)alkoxyCOCl, ($C_1$–$C_6$)alkylCOCl, $Ar^2$—COCl, ($C_1$–$C_6$)alkylSO$_2$Cl, $Ar^2$—SO$_2$Cl, or $Ar^2$—SOCl. The reaction is conducted under anhydrous conditions in the presence of a non-aqueous base, which includes organic amines such as triethylamine, N,N'-diisopropylethylamine and pyridine and derivatives thereof. The reaction is conducted in a reaction inert solvent. Preferred solvents for the reaction include halocarbon, aliphatic or aromatic hydrocarbon, ethers, ethyl acetate, pyridine and combinations thereof. The reaction time ranges from 15 minutes to 24 hours and the reaction temperature ranges from 0° C. to 80° C. or to the reflux temperature of the solvent being used. The reactions are preferably conducted at from 0° C. to ambient temperature and at ambient pressure. Removal of optional protecting groups is carried out as described in Scheme I.

Compounds of formula 12-3 and 12-3a wherein $R^{17}$ and $R^{23}$ are ($C_1$–$C_6$)alkylcarbonyl or $Ar^2$-carbonyl are also prepared according to Scheme 12 above and particularly as described below.

Compounds of formula 12-3 and 12-3a wherein $R^{17}$ and $R^{23}$ are ($C_1$–$C_6$)alkylcarbonyl or $Ar^2$-carbonyl are prepared by a condensation reaction with a compound of formula 12-2 or 12-2a, respectively, wherein $Lv^4$ is hydroxy in the presence of coupling agents such as dicyclohexylcarbodiimide or 1-(3-dimethylaminopropyl)-3-ethylcarbodiimide hydrochloride. The reaction is conducted in a reaction inert solvent. Preferred solvents include halocarbon, aliphatic/aromatic hydrocarbons and ethers. Especially preferred solvents include dichloromethane and chloroform. Other coupling agents that can be used are well known to those skilled in the art and include, but are not limited to, various phosphine reagents, ethyl chloroformate, and N-hydroxysuccinimide. Removal of optional protecting groups is carried out as described in Scheme I.

Compounds of formula 12-3 where $R^{17}$ is ($C_1$–$C_6$)alkyl are also prepared according to Scheme 12 and particularly as described below.

Compounds of formula 12-3 where $R^{17}$ is ($C_1$–$C_6$)alkyl are prepared by reacting a compound of formula 12-1 with a compound of formula 12-2 where $R^{17}$ is ($C_1$–$C_4$)alkyl and $Lv^4$ is Cl, Br, I, methanesulfonyloxy, p-toluenesulfonyloxy or trifluoromethanesulfonyloxy. The reaction is conducted under anhydrous conditions in the presence of a nonaqueous base, which includes organic amines such as triethylamine, Hunig's base and pyridine and derivatives thereof. The reaction is conducted in a reaction inert solvent. Preferred solvents for the reaction include halocarbons, aliphatic or aromatic hydrocarbons, ethers, ethyl acetate, pyridine and combinations thereof. The reaction time ranges from 15 minutes to 24 hours and the reaction temperature ranges from ambient temperature to 80° C. or to the reflux temperature of the solvent being used. The reactions are preferably conducted at ambient temperature and pressure.

The starting materials and reagents for the above described compounds are also readily available or can be easily synthesized by those skilled in the art using conventional methods of organic synthesis. For example, many of the compounds used herein are related to, or are derived from, compounds found in nature, in which there is a large scientific interest and commercial need, and accordingly many such compounds are commercially available or are reported in the literature or are easily prepared from other commonly available substances by methods which are reported in the literature.

The compounds of the instant invention inhibit the formation of sorbitol dehydrogenase and as such have utility in the treatment of diabetic complications including but not limited to such complications as diabetic nephropathy, diabetic neuropathy, diabetic retinopathy, diabetic microangiopathy and diabetic microangiopathy and diabetic cardiomyopathy. The utility of the compounds of the present invention as medical agents in the treatment of diseases, such as are detailed herein in mammals (e.g., humans) for example, diabetic complications such as diabetic cardiomyopathy, diabetic neuropathy, diabetic nephropathy, diabetic retinopathy, diabetic microangiopathy and diabetic microangiopathy is demonstrated by the activity of the compounds of formula I of this invention in conventional assays. Such assays also provide a means whereby the activities of the compounds of formula I of this invention can be compared with the activities of other known compounds. The results of these comparisons are useful for determining dosage levels in mammals, including humans, for the treatment of such diseases.

Measurement of SDH Activity

Male Sprague-Dawley rats (350–400 g) are used for these experiments. Diabetes is induced in some of the rats by a tail vein injection of streptozocin, 85 mg/kg. Twenty-four hours later, 4 groups of diabetic rats are given a single dose of the test compound of formula I of this invention (0.001 to 100 mg/kg) by oral gavage. Animals are sacrificed 4–6 hours after dosing and blood and sciatic nerves are harvested. Tissues and cells are extracted with 6% perchloric acid.

Sorbitol in erythrocytes and nerves is measured by a modification of the method of R. S. Clements et al. (Science, 166: 1007–8,1969). Aliquots of tissue extracts are added to an assay system which has final concentrations of reagents of 0.033 M glycine, pH 9.4, 800 mM β-nicotine adenine dinucleotide, and 4 units/ml of sorbitol dehydrogenase. After incubation for 30 minutes at room temperature, sample fluorescence is determined on a fluorescence spectrophotometer with excitation at 366 nm and emission at 452 nm. After subtracting appropriate blanks, the amount of sorbitol in each sample is determined from a linear regression of sorbitol standards processed in the same manner as the tissue extracts.

Fructose is determined by a modification of the method described by M. Ameyama, *Methods in Enzymology*, 89: 20–25 (1982). Resazurin is substituted for ferricyanide. Aliquots of tissue extracts are added to the assay system, which has final concentrations of reagents of 1.2 M citric acid, pH 4.5, 13 mM resazurin, 3.3 units/ml of fructose dehydrogenase and 0.068% Triton X-100. After incubation for 60 minutes at room temperature, sample fluorescence is determined on a fluorescence spectrophotometer with excitation at 560 nm and emission at 580 nm. After subtracting appropriate blanks, the amount of fructose in each sample is determined from a linear regression of fructose standards processed in the same manner as the tissue extracts.

SDH activity is measured by a modification of the method described by U. Gerlach, *Methodology of Enzymatic Analyses*, edited by H. U. Bergmeyer, 3, 112–117 (1983). Aliquots of sera or urine are added to the assay system, which has final concentrations of reagents of 0.1 M potassium phosphate buffer, pH 7.4, 5 mM NAD, 20 mM sorbitol, and 0.7 units/ml of sorbitol dehydrogenase. After incubation for 10 minutes at room temperature, the average change in sample absorbance is determined at 340 nm. SDH activity was presented as milliOD$_{340}$ units/minute (OD$_{340}$=optical density at 340 nm).

Any aldose reductase inhibitor may be used as the second compound (active agent) of this invention for combination therapies. The term aldose reductase inhibitor refers to compounds which inhibit the bioconversion of glucose to sorbitol catalyzed by the enzyme aldose reductase. Such inhibition is readily determined by those skilled in the art according to standard assays (J. Malone, *Diabetes*, 29:861–864, 1980. "Red Cell Sorbitol, an Indicator of Diabetic Control"). A variety of aldose reductase inhibitors are described and referenced below, however, other aldose reductase inhibitors will be known to those skilled in the art. The disclosures of U.S. patents listed below are hereby incorporated by reference. Also, common chemical USAN names or other designation are in parentheses where applicable, together with reference to appropriate patent literature disclosing the compound.

The activity of an aldose reductase inhibitor in a tissue can be determined by testing the amount of aldose reductase inhibitor that is required to lower tissue sorbitol (i.e., by inhibiting the further production of sorbitol consequent to blocking aldose reductase) or lower tissue fructose (by inhibiting the production of sorbitol consequent to blocking aldose reductase and consequently the production of fructose). While not wishing to be bound by any particular theory or mechanism, it is believed that an aldose reductase inhibitor, by inhibiting aldose reductase, prevents or reduces ischemic damage as described hereinafter.

Accordingly, examples of aldose reductase inhibitors useful in the compositions and methods of this invention include:

1. 3-(4-bromo-2-fluorobenzyl)-3,4-dihydro-4-oxo-1-phthalazineacetic acid (ponalrestat, U.S. Pat. No. 4,251,528);
2. N[[(5-trifluoromethyl)-6-methoxy-1-naphthalenyl]thioxomethyl]-N-methylglycine (tolrestat, U.S. Pat. No. 4,600,724);
3. 5-[(Z,E)-β-methylcinnamylidene]-4-oxo-2-thioxo-3-thiazolideneacetic acid (epalrestat, U.S. Pat. Nos. 4,464,382, 4,791,126, 4,831,045);
4. 3-(4-bromo-2-fluorobenzyl)-7-chloro-3,4-dihydro-2,4-dioxo-1(2H)-quinazolineacetic acid (zenarestat, U.S. Pat. Nos. 4,734,419, and 4,883,800);
5. 2R,4R-6,7-dichloro-4-hydroxy-2-methylchroman-4-acetic acid (U.S. Pat. No. 4,883,410);
6. 2R,4R-6,7-dichloro-6-fluoro-4-hydroxy-2-methylchroman-4-acetic acid (U.S. Pat. No. 4,883,410);
7. 3,4-dihydro-2,8-diisopropyl-3-oxo-2H-1,4-benzoxazine-4-acetic acid (U.S. Pat. No. 4,771,050);
8. 3,4-dihydro-3-oxo-4-[(4,5,7-trifluoro-2-benzothiazolyl)methyl]-2H-1,4-benzothiazine-2-acetic acid (SPR-210, U.S. Pat. No. 5,252,572);
9. N-[3,5-dimethyl-4-[(nitromethyl)sulfonyl]phenyl]-2-methyl-benzeneacetamide (ZD5522, U.S. Pat. Nos. 5,270,342 and 5,430,060);
10. (S)-6-fluorospiro(chroman-4,4'-imidazolidine)-2,5'-dione (sorbinil, U.S. Pat. No. 4,130,714);
11. d-2-methyl-6-fluoro-spiro(chroman-4',4'-imidazolidine)-2',5'-dione (U.S. Pat. No. 4,540,704);
12. 2-fluoro-spiro(9H-fluorene-9,4'-imidazolidine)-2',5'-dione (U.S. Pat. No. 4,438,272);
13. 2,7-di-fluoro-spiro(9H-fluorene-9,4'-imidazolidine)-2',5'-dione (U.S. Pat. Nos. 4,436,745, 4,438,272);
14. 2,7-di-fluoro-5-methoxy-spiro(9H-fluorene-9,4'-imidazolidine)-2',5'-dione (U.S. Pat. Nos. 4,436,745, 4,438,272);
15. 7-fluoro-spiro(5H-indenol[1,2-b]pyridine-5,3'-pyrrolidine)-2,5'-dione (U.S. Pat. Nos. 4,436,745, 4,438,272);
16. d-cis-6'-chloro-2',3'-dihydro-2'-methyl-spiro-(imidazolidine-4,4'-4'H-pyrano(2,3-b)pyridine)-2,5-dione (U.S. Pat. No. 4,980,357);
17. spiro[imidazolidine-4,5'(6H)-quinoline]-2,5-dione-3'-chloro-7',8'-dihydro-7'-methyl-(5'-cis) (U.S. Pat. No. 5,066,659);
18. (2S,4S)-6-fluoro-2',5'-dioxospiro(chroman-4,4'-imidazolidine)-2-carboxamide (U.S. Pat. No. 5,447,946); and
19. 2-[(4-bromo-2-fluorophenyl)methyl]-6-fluorospiro[isoquinoline-4(1H),3'-pyrrolidine]-1,2',3,5'(2H)-tetrone (ARI-509, U.S. Pat. No. 5,037,831).

Other aldose reductase inhibitors include compounds having formula ARI,

ARI

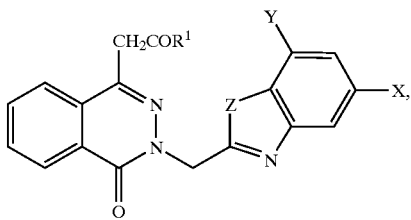

or a pharmaceutically acceptable salt thereof, wherein

Z in the compound of formula ARI is O or S;

$R^1$ in the compound of formula ARI is hydroxy or a group capable of being removed in vivo to produce a compound of formula ARI wherein $R^1$ is OH; and X and Y in the compound of formula ARI are the same or different and are selected from hydrogen, trifluoromethyl, fluoro, and chloro.

A preferred subgroup within the above group of aldose reductase inhibitors includes numbered compounds 1, 2, 3, 4, 5, 6, 9, 10, and 17, and the following compounds of Formula ARI:

20. 3,4-dihydro-3-(5-fluorobenzothiazol-2-ylmethyl)-4-oxophthalazin-1-yl-acetic acid [$R^1$=hydroxy; X=F; Y=H];

21. 3-(5,7-difluorobenzothiazol-2-ylmethyl)-3,4-dihydro-4-oxophthalazin-1-ylacetic acid [$R^1$=hydroxy; X=Y=F];

22. 3-(5-chlorobenzothiazol-2-ylmethyl)-3,4-dihydro-4-oxophthalazin-1-ylacetic acid [$R^1$=hydroxy; X=Cl; Y=H];

23. 3-(5,7-dichlorobenzothiazol-2-ylmethyl)-3,4-dihydro-4-oxophthalazin-1-ylacetic acid [$R^1$=hydroxy; X=Y=Cl];

24. 3,4-dihydro-4-oxo-3-(5-trifluoromethylbenzoxazol-2-ylmethyl)phthalazin-1-ylacetic acid [$R^1$=hydroxy; X=$CF_3$; Y=H];

25. 3,4-dihydro-3-(5-fluorobenzoxazol-2-ylmethyl)-4-oxophthalazin-1-yl-acetic acid [$R^1$=hydroxy; X=F; Y=H];

26. 3-(5,7-difluorobenzoxazol-2-ylmethyl)-3,4-dihydro-4-oxophthalazin-1-ylacetic acid [$R^1$=hydroxy; X=Y=F];

27. 3-(5-chlorobenzoxazol-2-ylmethyl)-3,4-dihydro-4-oxophthalazin-1-ylacetic acid [$R^1$=hydroxy; X=Cl; Y=H];

28. 3-(5,7-dichlorobenzoxazol-2-ylmethyl)-3,4-dihydro-4-oxophthalazin-1-ylacetic acid [$R^1$=hydroxy; X=Y=Cl]; and 29. zopolrestat; 1-phthalazineacetic acid, 3,4-dihydro-4-oxo-3-[[5-(trifluoromethyl)-2-benzothiazolyl]methyl]- [$R^1$=hydroxy; X=trifluoromethyl; Y=H].

In compounds 20–23, and 29 Z is S. In compounds 24–28, Z is O.

Of the above subgroup, compounds 20–29 are more preferred with 29 especially preferred.

An especially preferred aldose reductase inhibitor is 1-phthalazineacetic acid, 3,4-dihydro-4-oxo-3-[[5-trifluoromethyl)-2-benzothiazolyl]methyl]-.

The term "acyl radical of a carboxylic acid aldose reductase inhibitor" refers to any of the above-mentioned aldose reductase inhibitors which contains a carboxylic acid group in which the carboxylic acid group is replaced with a carbonyl radical.

The aldose reductase inhibitor compounds of this invention are readily available or can be easily synthesized by those skilled in the art using conventional methods of organic synthesis, particularly in view of the pertinent patent specification descriptions.

An amount of the aldose reductase inhibitor of this invention that is effective for the activities of this invention may be used. Typically, an effective dosage for the aldose reductase inhibitors of this invention is in the range of about 0.1 mg/kg/day to 100 mg/kg/day in single or divided doses, preferably 0.1 mg/kg/day to 20 mg/kg/day in single or divided doses.

Any sodium hydrogen ion exchange (NHE-1) inhibitor may be used as the second compound (active agent) of this invention for combination therapies. The term NHE-1 inhibitor refers to compounds which inhibit the sodium/proton ($Na^+/H^+$) exchange transport system and hence are useful as a therapeutic or prophylactic agent for diseases caused or aggravated by the acceleration of the sodium/proton ($Na^+/H^+$) exchange transport system, for example, cardiovascular diseases [e.g., arteriosclerosis, hypertension, arrhythmia (e.g. ischemic arrhythmia, arrhythmia due to myocardial infarction, myocardial stunning, myocardial dysfunction, arrhythmia after PTCA or after thrombolysis, etc.), angina pectoris, cardiac hypertrophy, myocardial infarction, heart failure (e.g. congestive heart failure, acute heart failure, cardiac hypertrophy, etc.), restenosis after PTCA, PTCI, shock (e.g. hemorrhagic shock, endotoxin shock, etc.)], renal diseases (e.g. diabetes mellitus, diabetic nephropathy, ischemic acute renal failure, etc.) organ disorders associated with ischemia or ischemic reperfusion [e.g. heart muscle ischemic reperfusion associated disorders, acute renal failure, or disorders induced by surgical treatment such as coronary artery bypass grafting (CABG) surgeries, vascular surgeries, organ transplantation, non-cardiac surgeries or percutaneous transluminal coronary angioplasty (PTCA)], cerebrovascular diseases (e.g. ischemic stroke, hemorrhagic stroke, etc.), cerebro ischemic disorders (e.g. disorders associated with cerebral infarction, disorders caused after cerebral apoplexy as sequelae, or cerebral edema. NHE-1 inhibitors can also be used as an agent for myocardial protection during coronary artery bypass grafting (CABG) surgeries, vascular surgeries, percutaneous transluminal coronary angioplasty (PTCA), PTCI, organ transplantation, or non-cardiac surgeries. The utility of NHE-1 inhibitors as medical agents in the treatment of diseases, such as are detailed herein in mammals (e.g. humans) for example, myocardial protection during surgery or mycardial protection in patients presenting with ongoing cardiac or cerebral ischemic events or chronic cardioprotection in patients with diagnosed coronary heart disease, or at risk for coronary heart disease, cardiac dysfunction or myocardial stunning is demonstrated by the activity of the compounds of formula I of this invention in conventional preclinical cardioprotection assays [see the in vivo assay in Klein, H. et al., *Circulation* 92:912–917 (1995); the isolated heart assay in Scholz, W. et al., Cardiovascular Research 29:260–268 (1995); the antiarrhythmic assay in Yasutake M. et al., Am. J. Physiol., 36:H2430–H2440 (1994); the NMR assay in Kolke et al., J. Thorac. Cardiovasc. Surg. 112: 765–775 (1996)] and the additional in vitro and in vivo assays described below. Such assays also provide a means whereby the activities of the compounds of formula I of this invention can be compared with the activities of other known compounds. The results of these comparisons are useful for determining dosage levels in mammals, including humans, for the treatment of such diseases.

NHE-1 inhibitors are disclosed in U.S. Pat. No. 5,698, 581, European Patent Application Publication No. EP 803 501 A1, International Patent Application Publication Nos. WO 94/26709 and PCT/JP97/04650, each of which is incorporated herein by reference. The NHE-1 inhibitors disclosed therein have utility in the combination of this invention. Said NHE-1 inhibitors can be prepared as disclosed therein.

Preferred NHE-1 inhibitors include compounds of the formula NHE,

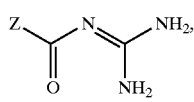

NHE a prodrug thereof or a pharmaceutically acceptable salt of said compound or of said prodrug, wherein Z in the compound of formula NHE is carbon connected and is a five-membered, diaza, diunsaturated ring having two contiguous nitrogens, said ring optionally mono-, di-, or tri-substituted with up to three substituents independently selected from $R^1$, $R^2$ and $R^3$; or Z in the compound of formula NHE carbon connected and is a five-membered, triaza, diunsaturated ring, said ring optionally mono- or di-substituted with up to two substituents independently selected from $R^4$ and $R^5$;

wherein $R^1$, $R^2$, $R^3$, $R^4$ and $R^5$ in the compound of formula NHE are each independently hydrogen, hydroxy-$(C_1-C_4)$alkyl, $(C_1-C_4)$alkyl, $(C_1-C_4)$ alkylthio, $(C_3-C_4)$cycloalkyl, $(C_3-C_7)$cycloalkyl $(C_1-C_4)$alkyl, $(C_1-C_4)$alkoxy, $(C_1-C_4)$alkoxy$(C_1-C_4)$ alkyl, mono-N— or di-N,N—$(C_1-C_4)$alkylcarbamoyl, M or M$(C_1-C_4)$alkyl, any of said previous $(C_1-C_4)$ alkyl moieties optionally having from one to nine fluorines; said $(C_1-C_4)$alkyl or $(C_3-C_4)$cycloalkyl optionally mono-or di-substituted independently with hydroxy, $(C_1-C_4)$alkoxy, $(C_1-C_4)$alkylthio, $(C_1-C_4)$ alkylsulfinyl, $(C_1-C_4)$alkylsulfonyl, $(C_1-C_4)$alkyl, mono-N— or di-N,N—$(C_1-C_4)$alkylcarbamoyl or mono-N— or di-N,N—$(C_1-C_4)$alkylaminosulfonyl; and said $(C_3-C_4)$cycloalkyl optionally having from one to seven fluorines;

wherein M in the compound of formula NHE is a partially saturated, fully saturated or fully unsaturated five to eight membered ring optionally having one to three heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

said M in the compound of formula NHE is optionally substituted, on one ring if the moiety is monocyclic, or one or both rings if the moiety is bicyclic, on carbon or nitrogen with up to three substituents independently selected from $R^6$, $R^7$ and $R^8$, wherein one of $R^6$, $R^7$ and $R^8$ is optionally a partially saturated, fully saturated, or fully unsaturated three to seven membered ring optionally having one to three heteroatoms selected independently from oxygen, sulfur and nitrogen optionally substituted with $(C_1-C_4)$alkyl and additionally $R^6$, $R^7$ and $R^8$ are optionally hydroxy, nitro, halo, $(C_1-C_4)$ alkoxy, $(C_1-C_4)$alkoxycarbonyl, $(C_1-C_4)$alkyl, formyl, $(C_1-C_4)$alkanoyl, $(C_1-C_4)$alkanoyloxy, $(C_1-C_4)$ alkanoylamino, $(C_1-C_4)$alkoxycarbonylamino, sulfonamido, $(C_1-C_4)$alkylsulfonamido, amino, mono-N— or di-N,N—$(C_1-C_4)$alkylamino, carbamoyl, mono-N— or di-N,N—$(C_1-C_4)$alkylcarbamoyl, cyano, thiol, $(C_1-C_4)$alkylthio, $(C_1-C_4)$alkylsulfinyl, $(C_1-C_4)$ alkylsulfonyl, mono-N— or di-N,N—$(C_1-C_4)$ alkylaminosulfonyl, $(C_2-C_4)$alkenyl, $(C_2-C_4)$alkynyl or $(C_5-C_7)$cycloalkenyl, wherein said $(C_1-C_4)$alkoxy, $(C_1-C_4)$alkyl, $(C_1-C_7)$ alkanoyl, $(C_1-C_4)$alkylthio, mono-N— or di-N,N— $(C_1-C_4)$alkylamino or $(C_3-C_7)$cycloalkyl $R^6$, $R^7$ and $R^8$ substituents are optionally mono-substituted independently with hydroxy, $(C_1-C_4)$alkoxycarbonyl, $(C_3-C_7)$cycloalkyl, $(C_1-C_4)$alkanoyl, $(C_1-C_4)$ alkanoylamino, $(C_1-C_4)$alkanoyloxy, $(C_1-C_4)$ alkoxycarbonylamino, sulfonamido, $(C_1-C_4)$ alkylsulfonamido, amino, mono-N— or di-N,N— $(C_1-C_4)$alkylamino, carbamoyl, mono-N— or di-N, N—$(C_1-C_4)$alkylcarbamoyl, cyano, thiol, nitro, $(C_1-C_4)$alkylthio, $(C_1-C_4)$alkylsulfinyl, $(C_1-C_4)$ alkylsulfonyl or mono-N— or di-N,N—$(C_1-C_4)$ alkylaminosulfonyl or optionally substituted with one to nine fluorines.

Especially preferred NHE-1 inhibitors include [1-(8-bromoquinolin-5-yl)-5-cyclopropyl-1H-pyrazole-4-carbonyl]guanidine; [1-(6-chloroquinolin-5-yl)-5-cyclopropyl-1H-pyrazole-4-carbonyl]guanidine; [1-(indazol-7-yl)-5-cyclopropyl-1H-pyrazole-4-carbonyl] guanidine; [1-(benzimidazol-5-yl)-5-cyclopropyl-1H-pyrazole-4-carbonyl]guanidine; [1-(1-isoquinolyl)-5-cyclopropyl-1H-pyrazole-4-carbonyl]guanidine; [5-cyclopropyl-1-(4-quinolinyl)-1H-pyrazole-4-carbonyl] guanidine; [5-cyclopropyl-1-(quinolin-5-yl)-1H-pyrazole-4-carbonyl]guanidine; [5-cyclopropyl-1-(quinolin-8-yl)-1H-pyrazole-4-carbonyl]guanidine; [1-(indazol-6-yl)-5-ethyl-1H-pyrazole-4-carbonyl]guanidine; [1-(indazol-5-yl)-5-ethyl-1H-pyrazole-4-carbonyl]guanidine; [1-(benzimidazol-5-yl)-5-ethyl-1H-pyrazole-4-carbonyl]guanidine; [1-(1-methylbenzimidazol-6-yl)-5-ethyl-1H-pyrazole-4-carbonyl] guanidine; [1-(5-quinolinyl)-5-n-propyl-1H-pyrazole-4-carbonyl]guanidine; [1-(5-quinolinyl)-5-isopropyl-1H-pyrazole-4-carbonyl]guanidine; [5-ethyl-1-(6-quinolinyl)-1H-pyrazole-4-carbonyl]guanidine; [1-(2-methylbenzimidazol-5-yl)-5-ethyl-1H-pyrazole-4-carbonyl] guanidine; [1-(1,4-benzodioxan-6-yl)-5-ethyl-1H-pyrazole-4-carbonyl]guanidine; [1-(benzotriazol-5-yl)-5-ethyl-1H-pyrazole-4-carbonyl]guanidine; [1-(3-chloroindazol-5-yl)-5-ethyl-1H-pyrazole-4-carbonyl]guanidine; [1-(5-quinolinyl)-5-butyl-1H-pyrazole-4-carbonyl]guanidine; [5-propyl-1-(6-quinolinyl)-1H-pyrazole-4-carbonyl] guanidine; [5-isopropyl-1-(6-quinolinyl)-1H-pyrazole-4-carbonyl]guanidine; [1-(2-chloro-4-methylsulfonylphenyl)-5-cyclopropyl-1H-pyrazole-4-carbonyl]guanidine; [1-(2-chlorophenyl)-5-cyclopropyl-1H-pyrazole-4-carbonyl] guanidine; [1-(2-trifluoromethyl-4-fluorophenyl)-5-cyclopropyl-1H-pyrazole-4-carbonyl]guanidine; [1-(2-bromophenyl)-5-cyclopropyl-1H-pyrazole-4-carbonyl] guanidine; [1-(2-fluorophenyl)-5-cyclopropyl-1H-pyrazole-4-carbonyl]guanidine; [1-(2-chloro-5-methoxyphenyl)-5-cyclopropyl-1H-pyrazole-4-carbonyl]guanidine; [1-(2-chloro-4-methylaminosulfonylphenyl)-5-cyclopropyl-1H-pyrazole-4-carbonyl]guanidine; [1-(2,5-dichlorophenyl)-5-cyclopropyl-1H-pyrazole-4-carbonyl]guanidine; [1-(2,3-dichlorophenyl)-5-cyclopropyl-1H-pyrazole-4-carbonyl]

guanidine; [1-(2-chloro-5-aminocarbonylphenyl)-5-cyclopropyl-1H-pyrazole-4-carbonyl]guanidine; [1-(2-chloro-5-aminosulfonylphenyl)-5-cyclopropyl-1H-pyrazole-4-carbonyl]guanidine; [1-(2-fluoro-6-trifluoromethylphenyl)-5-cyclopropyl-1H-pyrazole-4-carbonyl]guanidine; [1-(2-chloro-5-methylsulfonylphenyl)-5-cyclopropyl-1H-pyrazole-4-carbonyl]guanidine; [1-(2-chloro-5-dimethylaminosulfonylphenyl)-5-cyclopropyl-1H-pyrazole-4-carbonyl]guanidine; [1-(2-trifluoromethyl-4-chlorophenyl)-5-cyclopropyl-1H-pyrazole-4-carbonyl]guanidine; [1-(2-chlorophenyl)-5-methyl-1H-pyrazole-4-carbonyl]guanidine; [5-methyl-1-(2-trifluoromethylphenyl)-1H-pyrazole-4-carbonyl]guanidine; [5-ethyl-1-phenyl-1H-pyrazole-4-carbonyl]guanidine; [5-cyclopropyl-1-(2-trifluoromethylphenyl)-1H-pyrazole-4-carbonyl]guanidine; [5-cyclopropyl-1-phenyl-1H-pyrazole-4-carbonyl]guanidine; [5-cyclopropyl-1-(2,6-dichlorophenyl)-1H-pyrazole-4-carbonyl]guanidine or or a pharmaceutically acceptable salt thereof.

The preferred and especially preferred NHE-1 inhibitors disclosed in the above two paragraphs can be prepared according to methods set forth in International Patent Application No. PCT/IB99/00206 or as set forth below, where the variables in the following schemes and description refer only to the NHE-1 compounds.

SCHEME I

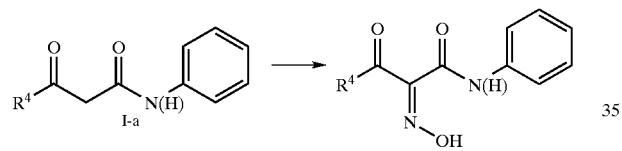

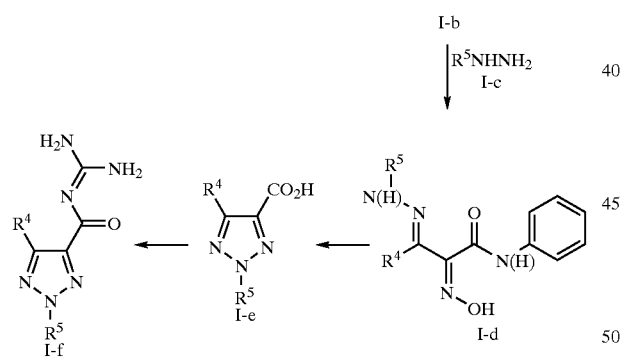

SCHEME II

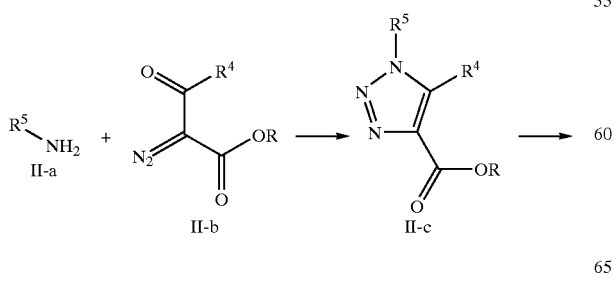

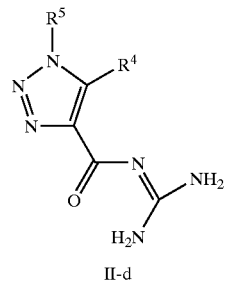

SCHEME III

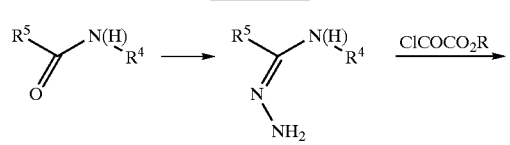

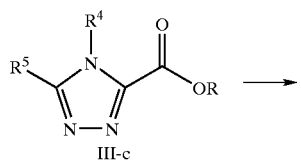

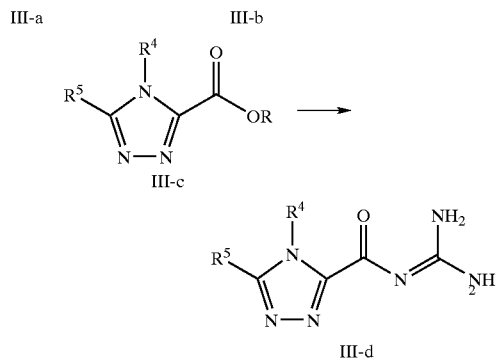

SCHEME IV

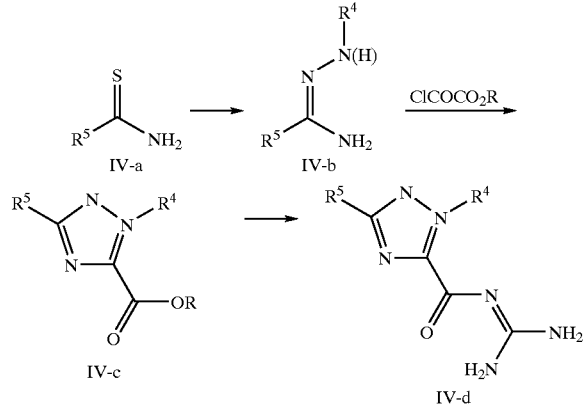

SCHEME V

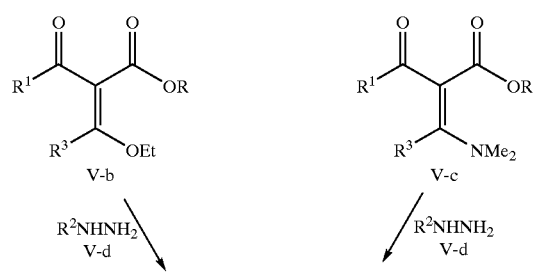

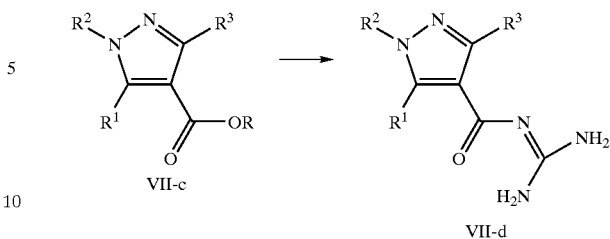

SCHEME VIII

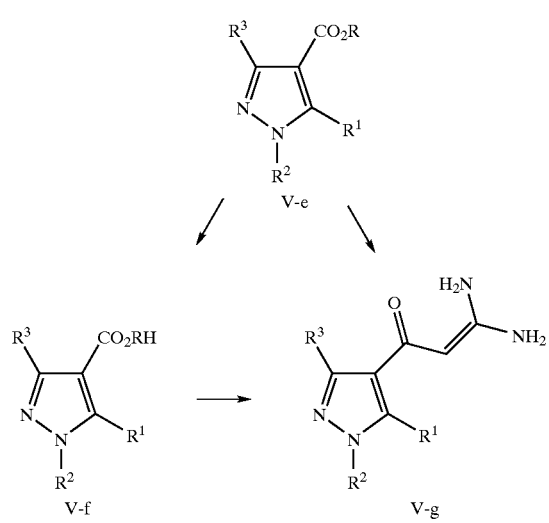

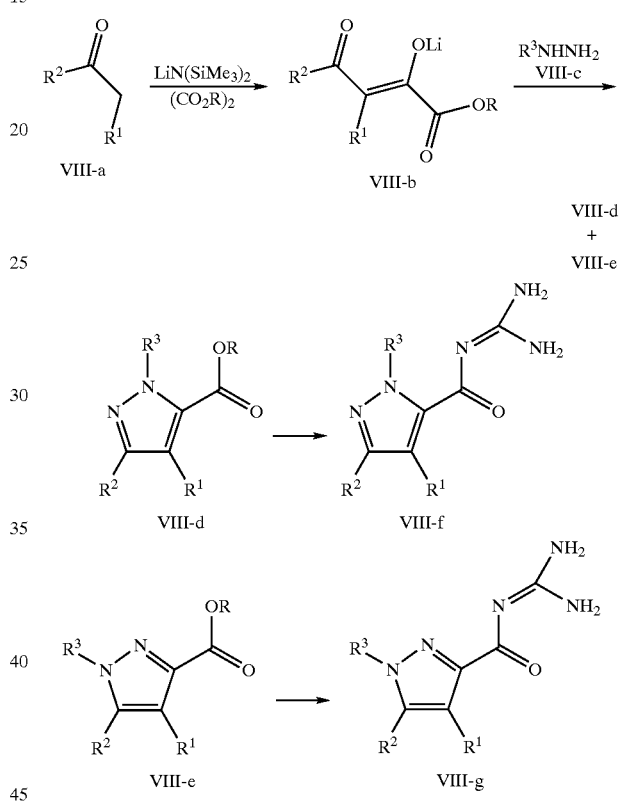

SCHEME VI

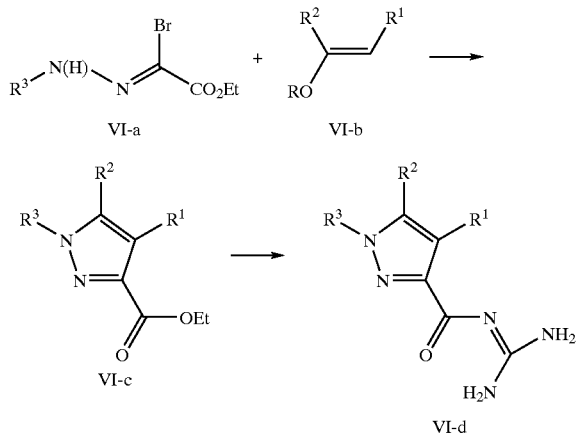

SCHEME VII

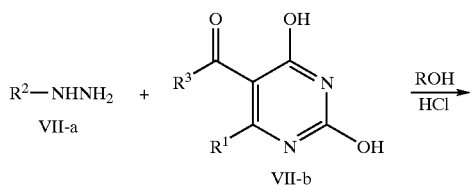

According to Scheme I, the Formula I-a compound, wherein $R^4$ is as described above for the compound of formula NHE, is dissolved or suspended in an aqueous alkali metal hydroxide solution (e.g. 1 N sodium hydroxide) along with sodium nitrite and the mixture is added to an aqueous acidic solution (e.g. 10% v/v sulfuric acid) at a pH of about 0 at a temperature of about 0° C. to about 5° C. for about 30 min to about 1 hour. The resulting mixture is filtered to yield the Formula I-b oxime. Alternatively, the Formula I-a compound is dissolved in 1:1 acetic acid/propionic acid and solid sodium nitrite is added at about 0° C. The reaction mixture is stirred at about 0° C. for about 2 hours, then poured into ice water and the Formula I-b oxime is obtained by filtration.

The Formula I-b compound is reacted with a Formula I-c compound, wherein $R^5$ is as described above for the compound of formula NHE in a protic solvent such as ethanol at a temperature of about 50° C. to about 110° C. for about 10 min to about 1 hour to form the Formula I-d hydrazone.

The Formula I-d hydrazone is cyclized and hydrolyzed to the Formula I-e triazole in an alcoholic solvent such as 2-ethoxyethanol under basic conditions (e.g., potassium hydroxide) at a temperature of about 100° C. to about 175° C. for about ½ hour to about 2 hours followed by acidification to yield the Formula I-e triazole acid.

The Formula I-e acid is coupled with guanidine in the presence of a suitable coupling agent. A suitable coupling agent is one which transforms a carboxylic acid into a reactive species which forms an amide linkage on reaction with an amine.

The coupling agent may be a reagent which effects this condensation in a one pot process when mixed together with the carboxylic acid and guanidine. Exemplary coupling reagents are 1-(3-dimethylaminopropyl)-3-ethylcarbodiimide hydrochloride-hydroxybenzotriazole (EDC/HBT), dicyclohexylcarbodiimide/ hydroxybenzotriazole(HBT), 2-ethoxy-1-ethoxycarbonyl-1, 2-dihydroquinoline (EEDQ), and diethylphosphorylcyanide. The coupling is performed in an inert solvent, preferably an aprotic solvent at a temperature of about −20° C. to about 50° C. for about 1 to about 48 hours, in the presence of excess guanidine as base. Exemplary solvents include acetonitrile, dichloromethane, dimethylformamide and chloroform or mixtures thereof.

The coupling agent may also be that agent which converts the carboxylic acid to an activated intermediate which is isolated and/or formed in a first step and allowed to react with guanidine in a second step. Examples of such coupling agents and activated intermediates are thionyl chloride or oxalyl chloride to form the acid chloride, cyanuric fluoride to form an acid fluoride or an alkyl chloroformate such as isobutyl or isopropenyl chloroformate or propanephosphonic anhydride (propanephosphonic acid anhydride, PPA) (with a tertiary amine base) to form a mixed anhydride of the carboxylic acid, or carbonyldiimidazole to form an acylimidazole. If the coupling agent is oxalyl chloride, it is advantageous to employ a small amount of dimethylformamide as cosolvent with another solvent (such as dichloromethane) to catalyze the formation of the acid chloride. This activated acid derivative may be coupled by mixing with excess guanidine in an appropriate solvent together with an appropriate base. Appropriate solvent/base combinations are for example, dichloromethane, dimethylformamide or acetonitrile or mixtures thereof in the presence of excess guanidine as base. Other appropriate solvent/base combinations include water or a ($C_1$–$C_5$)alcohol or a mixture thereof together with a cosolvent such as dichloromethane, tetrahydrofuran or dioxane and a base such as sodium, potassium or lithium hydroxide in sufficient quantity to consume the acid liberated in the reaction. Use of these coupling agents and appropriate selection of solvents and temperatures are known to those skilled in the art or can be readily determined from the literature. These and other exemplary conditions useful for coupling carboxylic acids are described in Houben-Weyl, Vol XV, part II, E. Wunsch, Ed., G. Theime Verlag, 1974, Stuttgart; M. Bodansky, Principles of Peptide Synthesis, Springer-Verlag, Berlin 1984; and The Peptides, Analysis, Synthesis and Biology (ed. E. Gross and J. Meienhofer), vols 1–5 (Academic Press, NY 1979–1983).

According to Scheme II, the Formula II-a primary amine wherein $R^5$ is as described above for the compound of formula NHE is reacted with a Formula II-b α-diazo-β-ketoester wherein $R^4$ is as described above for the compound of formula NHE, and R is lower alkyl, in the presence of titanium tetrachloride analogously to the method described in Eguchi S. et al. *Synthesis* 1993, 793 to form the Formula II-c triazole carboxylic acid ester. The Formula II-c ester is converted directly to the acylguanidine II-d by reaction with guanidine in an alcoholic solvent at a temperature of about 60 to about 110° C., preferably refluxing methanol, for a period of 8 to 20 hours.

According to Scheme III, the Formula III-a compound wherein $R^4$ and $R^5$ are as described above for the compound of formula NHE is treated with Lawesson's reagent (i.e., 2,4-bis(4-methoxyphenyl)-1,3-dithia-2,4-diphosphetane-2, 4-disulfide) in an aprotic solvent such as dimethoxyethane at a temperature of about 20° C. to about 120° C. for about one to eight hours. The resulting thioamide is treated with an alkylating agent such as methyl iodide in a polar, inert solvent such as acetone, conveniently at ambient temperature for about eight hours to about forty-eight hours. The resulting compound is reacted with anhydrous hydrazine in an alcoholic solvent at a temperature of about 0° C. to about 25° C. for about one to eight hours to provide the Formula III-b compound (analogously as described in Doyle and Kurzer, *Synthesis* 1974, 583).

The Formula III-b compound is treated with a monoalkyloxalyl chloride in an aprotic solvent at a temperature of about 25° C. to about 50° C. for about one to eight hours to provide the Formula III-c carboxylic ester compound wherein R is lower alkyl. The Formula III-c ester is directly coupled with guanidine in an alcoholic solvent at a temperature of about 60° C. to about 110° C., preferably refluxing methanol, for a period of eight to twenty hours, to prepare the Formula III-d triazole carbonyl guanidines.

According to Scheme IV the Formula IV-a compound wherein $R^5$ is as described above for the compound of formula NHE is treated with methyl iodide in an inert solvent, conveniently at ambient temperature for about four to twenty-four hours. The resulting compound is reacted with anhydrous $R^4$-hydrazine (wherein $R^4$ is as described above for the compound of formula NHE) in an alcoholic solvent at a temperature of about 0° C. to about 25° C. for about one to eight hours to provide the Formula IV-b amidrazone compound (analogously as described in Doyle and Kurzer, *Synthesis* 1974, 583).

The Formula IV-b compound is treated with a monoalkyloxalyl chloride in an aprotic solvent at a temperature of about 25° C. to about 50° C. for about one to eight hours to provide the Formula IV-c carboxylic ester compound wherein R is lower alkyl. The Formula IV-c ester is directly coupled with guanidine in an alcoholic solvent at a temperature of about 60° C. to about 110° C., preferably refluxing methanol, for a period of eight to twenty hours to prepare the Formula IV-d triazole carbonyl guanidines.

According to Scheme V the Formula V-a compound wherein $R^1$ is as described above for the compound of formula NHE is combined with excess $(CH_3O)_2C(R^3)N(CH_3)_2$ (N,N-dimethyl amide dimethyl acetal) wherein $R^3$ is as described above for the compound of formula NHE, optionally in the presence of an acid catalyst such as p-toluenesulfonic acid at a temperature of about 90° C. to about 110° C. for about one to about two hours to prepare the Formula V-c compound above.

The Formula V-c compound is cyclized with a Formula V-d compound, wherein $R^2$ is as described above for the compound of formula NHE, in an inert solvent such as ethanol at a temperature of about 20° C. to about 30° C. for about 5 minutes to about one hour followed by heating to a temperature of about 70° C. to about 110° C. for about two hours to about four hours to form the Formula V-f pyrazole.

Alternatively, according to Scheme V the Formula V-a compound, wherein $R^1$ is as described above for the compound of formula NHE, is combined with a triethylorthoester (i.e., $R^3C(OEt)_3$ wherein $R^3$ is as described above for the compound of formula NHE) and acetic anhydride at a temperature of about 120° C. to about 150° C. for about two to about five hours to prepare the Formula V-b compound.

The Formula V-b compound is cyclized with a Formula V-d compound, wherein $R^2$ is as described above for the compound of formula NHE, to form the Formula V-c pyrazole.

The Formula V-c pyrazole is hydrolyzed with a base such as sodium hydroxide or lithium hydroxide in a solvent such as water and/or methanol and/or THF conveniently at ambient temperature or at elevated temperature (e.g., reflux) for about one hour to about five hours to prepare the Formula V-f acid.

The Formula V-f acid is coupled with guanidine in the presence of a suitable coupling agent as described for the above coupling of the Formula I-e acid and guanidine. In one embodiment, the Formula V-f acid is activated with thionyl chloride at a temperature of about 60° C. to about 90° C. for about fifteen minutes to about two hours. The resulting activated acid chloride is combined with guanidine hydrochloride and an inorganic base (e.g., sodium hydroxide) in anhydrous tetrahydrofuran and optionally methanol and/or water. The solution is heated, conveniently at reflux, for about one hour to about eight hours to prepare the Formula V-g compound.

Alternatively according to Scheme V the Formula V-e compound can be directly converted to the Formula V-g compound by several methods. For example, the Formula V-e compound can be heated in the presence of excess guanidine, in a polar protic solvent for example, methanol or isopropanol at a suitable temperature conveniently, at reflux for about one to about seventy-two hours. This transformation may also be performed by repeatedly removing the solvent, for example removing ethanol or toluene about four times, from a mixture of the Formula V-e compound and excess guanidine at a pressure of about one to about 100 mmHg and at a temperature of about 25° C. to about 95° C. This reaction may also be performed in the absence of solvent by heating the mixture of the Formula V-e compound and excess guanidine at a temperature of about 100° C. to about 180° C., optionally at about a pressure of about 1 to about 100 mmHg for about five minutes to about eight hours.

According to Scheme VI, the Formula VI-a compound, wherein $R^3$ is as described above for the compound of formula NHE, is reacted with the Formula VI-b compound, wherein $R^1$ and $R^2$ are as described above for the compound of formula NHE, in an aprotic solvent at a temperature of about 0° C. to about 25° C. for about two hours to about twenty-four hours in the presence of an appropriate amine base, such as triethylamine, to form the Formula VI-c compound.

The resulting Formula VI-c compound is hydrolyzed and coupled with guanidine using one of the methods described in earlier Schemes, such as the method employing carbonyldiimidazole, to form the Formula VI-d compound.

According to Scheme VII, the Formula VII-a hydrazine, wherein $R^2$ is as described above for the compound of formula NHE, is reacted with the appropriate Formula VII-b compound to form the Formula VII-c pyrazole ester wherein R is lower alkyl according to the method of Bajnati, A. and Hubert-Habart, M. *Bull. Soc. Chim. France* 1988, 540. The resulting pyrazole ester is converted to the Formula VII-d acyl guanidine using the hydrolysis and coupling methods described above.

According to Scheme VIII, the Formula VIII-a compound wherein $R^2$ and $R^1$ are as described above for the compound of formula NHE is transformed to the Formula VIII-b lithium salt where R is lower alkyl according to the method described in *J. Het. Chem.* 1989, 26, 1389. The Formula VII-b lithium salt is combined with the Formula VIII-c hydrazine, wherein $R^3$ is as described above for the compound of formula NHE, in an inert solvent such as ethanol, in the presence of a mineral acid, at a temperature of about 20° C. to about 30° C. for about five minutes to about one hour followed by heating to a temperature of about 70° C. to about 110° C. for two hours to about four hours to form both the Formula VIII-d and VIII-e pyrazoles. The Formula VIII-d and VIII-e pyrazoles are converted to the Formula VIII-f and VIII-G acyl guanidines respectively using the hydrolysis and coupling methods described above.

Some of the methods useful for the preparation of the compounds described herein may require protection of remote functionality (e.g., primary amine, secondary amine, carboxyl in Formula I precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, *Protective Groups in Organic Synthesis*, John Wiley & Sons, New York, 1991.

The compounds of formula I of the present invention, when used in combination with NHE-1 inhibitors, inhibit the sodium/proton ($Na^+/H^+$) exchange transport system and hence are useful as a therapeutic or prophylactic agent for diseases caused or aggravated by the acceleration of the sodium/proton ($Na^+/H^+$) exchange transport system, for example, cardiovascular diseases [e.g., arteriosclerosis, hypertension, arrhythmia (e.g. ischemic arrhythmia, arrhythmia due to myocardial infarction, myocardial stunning, myocardial dysfunction, arrhythmia after PTCA or after thrombolysis, etc.), angina pectoris, cardiac hypertrophy, myocardial infarction, heart failure (e.g. congestive heart failure, acute heart failure, cardiac hypertrophy, etc.), restenosis after PTCA, PTCI, shock (e.g. hemorrhagic shock, endotoxin shock, etc.)], renal diseases (e.g. diabetes mellitus, diabetic nephropathy, ischemic acute renal failure, etc.) organ disorders associated with ischemia or ischemic reperfusion [e.g. heart muscle ischemic reperfusion associated disorders, acute renal failure, or disorders induced by surgical treatment such as coronary artery bypass grafting (CABG) surgeries, vascular surgeries, organ transplantation, non-cardiac surgeries or percutaneous transluminal coronary angioplasty (PTCA)], cerebrovascular diseases (e.g. ischemic stroke, hemorrhagic stroke, etc.), cerebro ischemic disorders (e.g. disorders associated with cerebral infarction, disorders caused after cerebral apoplexy as sequelae, or cerebral edema.

Preferably, the compounds of formula I of this invention can be used in combination with NHE-1 inhibitors as agents for myocardial protection before, during, or after coronary artery bypass grafting (CABG) surgeries, vascular surgeries, percutaneous transluminal coronary angioplasty (PTCA), organ transplantation, or non-cardiac surgeries.

Preferably, the compounds of formula I of this invention can be used in combination with NHE-1 inhibitors as agents for myocardial protection in patients presenting with ongoing cardiac (acute coronary syndromes, e.g. myocardial infarction or unstable angina) or cerebral ischemic events (e.g. stroke).

Preferably, the compounds of formula I of this invention can be used in combination with NHE-1 inhibitors as agents for chronic myocardial protection in patients with diagnosed coronary heart disease (e.g. previous myocardial infarction or unstable angina) or patients who are at high risk for myocardial infarction (age greater than 65 and two or more risk factors for coronary heart disease).

In addition, a combination of the compounds of formula I of this invention with NHE-1 inhibitors has a strong inhibitory effect on the proliferation of cells, for example the proliferation of fibroblast cells and the proliferation of the smooth muscle cells of the blood vessels. For this reason, the combination of the compounds of formula I of this invention with NHE-1 inhibitors of this invention is a valuable therapeutic agent for use in diseases in which cell proliferation represents a primary or secondary cause and may, therefore, be used as antiatherosclerotic agents, and as agents against diabetic late complications, cancerous diseases, fibrotic diseases such as pulmonary fibrosis, hepatic fibrosis or renal fibrosis, glomerular nephrosclerosis, organ hypertrophies or hyperplasias, in particular hyperplasia or hypertrophy of the prostate, pulmonary fibrosis, diabetic complications or recurrent stricture after PTCA, or diseases caused by endothelial cell injury.

The utility of the combination of compounds of the present invention with NHE-1 inhibitors as medical agents in the treatment of diseases, such as are detailed herein in mammals (e.g. humans) for example, myocardial protection during surgery or mycardial protection in patients presenting with ongoing cardiac or cerebral ischemic events or chronic cardioprotection in patients with diagnosed coronary heart disease, or at risk for coronary heart disease, cardiac dysfunction or myocardial stunning is demonstrated by the activity of said combination in conventional preclinical cardioprotection assays [see the in vivo assay in Klein, H. et al., Circulation 92:912–917 (1995); the isolated heart assay in Scholz, W. et al., Cardiovascular Research 29:260–268 (1995); the antiarrhythmic assay in Yasutake M. et al., Am. J. Physiol., 36:H2430–H2440 (1994); the NMR assay in Kolke et al., J. Thorac. Cardiovasc. Surg. 112: 765–775 (1996)] and the additional in vitro and in vivo assays described below. Such assays also provide a means whereby the activities of the compounds of formula I of this invention can be compared with the activities of other known compounds. The results of these comparisons are useful for determining dosage levels in mammals, including humans, for the treatment of such diseases.

Measurement of Human NHE-1 Inhibitory Activity

Methodologies for measurement of human NHE-1 activity and inhibitor potency are based on those published by Watson et al., Am. J. Physiol., 24:G229–G238, 1991), where NHE-mediated recovery of intracellular pH is measured following intracellular acidification. Thus, fibroblasts stably expressing human NHE-1 (Counillon, L. et al., Mol. Pharmacol., 44:1041–1045 (1993) are plated onto collagen coated 96 well plates (50,000/well) and grown to confluence in growth media (DMEM high glucose, 10% fetal bovine serum, 50 u/ml penicillin and streptomycin). Confluent plates are incubated for 30 minutes at 37° C. with the pH sensitive fluorescent probe BCECF (5 $\mu$M; Molecular Probes, Eugene, Oreg.). BCECF loaded cells are incubated for 30 minutes at 37° C. in acid loading media (70 mM choline chloride, 50 mM NHCl$_4$, 5 mM KCl, 1 mM MgCl$_2$, 1.8 mM CaCl$_2$, 5 mM glucose, 10 mM HEPES, pH 7.5), and then placed in a Fluorescent Imaging Plate Reader (Molecular Devices, CA). BCECF fluorescence is monitored using excitation and emission wavelengths of 485 nM and 525 nM, respectively. Intracellular acidification is initiated via rapid replacement of acid loading media with recovery media (120 mM NaCl, 5 mM KCl, 1 mM MgCl$_2$, 1.8 mM CaCl$_2$, 5 mM glucose, 10 mM HEPES, pH 7.5) ±test combination, and NHE-mediated recovery of intracellular pH is monitored as the subsequent time-dependent increase BCECF fluorescence. The potency of the combinations of the compounds of formula I of this invention with NHE-1 inhibitors is calculated as the concentration that reduces recovery of intracellular pH by 50% (IC$_{50}$). Under these conditions reference NHE inhibitors amiloride and HOE-642 had IC$_{50}$ values for human NHE-1 of 50 $\mu$M and 0.5 $\mu$M, respectively.

As background information, it is noted that brief periods of myocardial ischemia followed by coronary artery reperfusion protects the heart from subsequent severe myocardial ischemia (Murry et al., Circulation 74:1124–1136, 1986).

The therapeutic effects of the combination of the compounds of formula I of this invention with NHE-1 inhibitors in preventing heart tissue damage resulting from an ischemic insult can be demonstrated in vitro along lines presented in Liu et al. (Cardiovasc. Res., 28:1057–1061, 1994), as described specifically herein. Cardioprotection, as indicated by a reduction in infarcted myocardium, can be induced pharmacologically using adenosine receptor agonists in isolated, retrogradely perfused rabbit hearts as an in vitro model of myocardial ischemic preconditioning (Liu et al., Cardiovasc. Res., 28:1057–1061, 1994). The in vitro test described below demonstrates that a test compound or, in this case a test combination (i.e., a combination of a compound of formula I with an NHE-1 antagonist) can also pharmacologically induce cardioprotection, i.e., reduced myocardial infarct size, when administered to a rabbit isolated heart. The effects of the test combination are compared to ischemic preconditioning and the A1/A3 adenosine agonist, APNEA (N$^6$-[2-(4-aminophenyl)ethyl]adenosine), that has been shown to pharmacologically induce cardioprotection in the rabbit isolated heart (Liu et al., Cardiovasc. Res., 28:1057–1061, 1994). The exact methodology is described below.

The protocol used for these experiments closely follows that described by Liu et al., Cardiovasc. Res., 28:1057–1061, 1994. Male New Zealand White rabbits (3–4 kg) are anesthetized with sodium pentobarbital (30 mg/kg, i.v.). After deep anesthesia is achieved (determined by the absence of an ocular blink reflex) the animal is intubated and ventilated with 100% O$_2$ using a positive pressure ventilator. A left thoracotomy is performed, the heart exposed, and a snare (2-0 silk) is placed loosely around a prominent branch of the left coronary artery, approximately ⅔ of the distance towards the apex of the heart. The heart is removed from the chest and rapidly (<30 sec) mounted on a Langendorff apparatus. The heart is retrogradely perfused in a non-recirculating manner with a modified Krebs solution (NaCl 118.5 mM, KCl 4.7 mM, Mg SO$_4$ 1.2 mM, KH$_2$PO$_4$ 1.2 mM, NaHCO$_3$ 24.8 mM, CaCl$_2$ 2.5 mM, and glucose 10 mM), at a constant pressure of 80 mmHg and a temperature of 37° C. Perfusate pH is maintained at 7.4–7.5 by bubbling with 95% O$_2$/5% CO$_2$. Heart temperature is tightly controlled by using heated reservoirs for the physiological solution and water jacketing around both the perfusion tubing and the isolated heart. Heart rate and left ventricular pressures are determined via a latex balloon which is inserted in the left ventricle and connected by stainless steel tubing to a pressure transducer. The intraventricular balloon is inflated to provide a systolic pressure of 80–100 mmHg, and a diastolic pressure ≦10 mmHg. Total coronary flow is also continuously monitored using an in-line flow probe and normalized for heart weight.

The heart is allowed to equilibrate for 30 minutes, over which time the heart must show stable left ventricular pressures within the parameters outlined above. If the heart rate falls below 180 bpm at any time prior to the 30 minutes period of regional ischemia, the heart is paced at about 200 bpm for the remainder of the experiment. Ischemic preconditioning is induced by total cessation of cardiac perfusion (global ischemia) for 5 minutes, followed by reperfusion for 10 minutes. The regional ischemia is provided by tightening the snare around the coronary artery branch. Following the 30 minutes regional ischemia, the snare is released and the heart reperfused for an additional 120 minutes.

Pharmacological cardioprotection is induced by infusing the test combination, i.e., a combination of a compound of formula I with an NHE-1 inhibitor, at predetermined concentrations, starting 30 minutes prior to the 30 minutes regional ischemia, and continuing until the end of the 120 minutes reperfusion period. Hearts which receive the test combination do not undergo the period of ischemic preconditioning. The reference compound, APNEA (500 nM) is perfused through hearts (which do not receive the test compound) for a 5 minutes period which ends 10 minutes before the 30 minutes regional ischemia.

At the end of the 120 minutes reperfusion period, the coronary artery snare is tightened, and a 0.5% suspension of fluorescent zinc cadmium sulfate particles (1–10 $\mu$M) Duke Scientific Corp.(Palo Alto, Calif.) is perfused through the heart; this stains all of the myocardium, except that area-at-risk for infarct development (area-at-risk). The heart is removed from the Langendorff apparatus, blotted dry, wrapped in aluminum foil and stored overnight at $-20°$ C. The next day, the heart is sliced into 2 mm transverse sections from the apex to the top of the ventricles. The slices are stained with 1% triphenyl tetrazolium chloride (TTC) in phosphate-buffered saline for 20 minutes at $37°$ C. Since TTC reacts with living tissue (containing NAD-dependent dehydrogenases), this stain differentiates between living (red stained) tissue, and dead tissue (unstained infarcted tissue). The infarcted area (no stain) and the area-at-risk (no fluorescent particles) are calculated for each slice of left ventricle using a precalibrated image analyzer. To normalize the ischemic injury for differences in the area-at-risk between hearts, the data is expressed as the ratio of infarct area vs. area-at-risk (% IA/AAR). All data are expressed as mean±SE and compared statistically using a Mann-Whitney non-parametric test with a Bonferroni correction for multiple comparisons. Significance is considered as $p<0.05$.

The results from the above in vitro test demonstrate that a combination of a compound of this invention with an NHE-1 inhibitor induce significant cardioprotection relative to the control group.

The therapeutic effects of a combination of a compound of formula I of this invention with an NHE-1 inhibitor in preventing heart tissue damage otherwise resulting from an ischemic insult can also be demonstrated in vivo along lines presented in Liu et al. (Circulation, Vol. 84:350–356, 1991) as described specifically herein. The in vivo assay tests the cardioprotection of the test combination, i.e., a compound of formula I together with an NHE-1 inhibitor, relative to the control group which receives saline vehicle. Cardioprotection, as indicated by a reduction in infarcted myocardium, can be induced pharmacologically using intravenously administered adenosine receptor agonists in intact, anesthetized rabbits studied as an in situ model of myocardial ischemic preconditioning (Liu et al., Circulation 84:350–356, 1991). The in vivo assay tests whether the instant combination of a compound of formula I with an NHE-1 inhibitor can pharmacologically induce cardioprotection, i.e., reduced myocardial infarct size, when parenterally administered to intact, anesthetized rabbits. The effects of the combination of a compound of formula I of this invention with an NHE-11 inhibitor can be compared to ischemic preconditioning using the A1 adenosine agonist, $N^6$-1-(phenyl-2R-isopropyl) adenosine (PIA) that has been shown to pharmacologically induce cardioprotection in intact anesthetized rabbits studied in situ (Liu et al., Circulation 84:350–356, 1991).

The methodology is described below.

Surgery: New Zealand White male rabbits (34 kg) are anesthetized with sodium pentobarbital (30 mg/kg, i.v.). A tracheotomy is performed via a ventral midline cervical incision and the rabbits are ventilated with 100% oxygen using a positive pressure ventilator. Catheters are placed in the left jugular vein for drug administration and in the left carotid artery for blood pressure measurements. The hearts are then exposed through a left thoracotomy and a snare (00 silk) placed around a prominent branch of the left coronary artery. Ischemia is induced by pulling the snare tight and clamping it in place. Releasing the snare allows the affected area to reperfuse. Myocardial ischemia is evidenced by regional cyanosis; reperfusion is evidenced by reactive hyperemia.

Protocol: Once arterial pressure and heart rate have been stable for at least 30 minutes the test is started. Ischemic preconditioning is induced by occluding the coronary artery for 5 minutes followed by a 10 minutes reperfusion. Pharmacological preconditioning is induced by infusing the test combination, i.e., a combination of a compound of formula I of this invention with an NHE-1 inhibitor, over, for example, 5 minutes and allowing 10 minutes before further intervention or by infusing the adenosine agonist, PIA (0.25 mg/kg). Following ischemic preconditioning, pharmacological preconditioning or no conditioning (unconditioned, vehicle control) the artery is occluded for 30 minutes and then reperfused for two hours to induce myocardial infarction. The test combination and PIA are dissolved in saline or other suitable vehicle and delivered at 1 to 5 mg/kg, respectively.

Staining (Liu et al., *Circulation* 84:350–356, 1991): At the end of the 2 hour reperfusion period, the hearts are quickly removed, hung on a Langendorff apparatus, and flushed for 1 minute with normal saline heated to body temperature ($38°$ C.). The silk suture used as the snare is then tied tightly to reocclude the artery and a 0.5% suspension of fluorescent zinc cadmium sulphate particles (1–10 $\mu$m) Duke Scientific Corp. (Palo Alto, Calif.) is infused with the perfusate to stain all of the myocardium except the area at risk (nonfluorescent ventricle). The hearts are then quickly frozen and stored overnight at $-20°$ C. On the following day, the hearts are cut into 2 mm slices and stained with 1% triphenyl tetrazolium chloride (TTC). Since TTC reacts with living tissue, this stain differentiates between living (red stained) tissue, and dead tissue (unstained infarcted tissue). The infarcted area (no stain) and the area at risk (no fluorescent particles) are calculated for each slice of left ventricle using a precalibrated image analyzer. To normalize the ischemic injury for differences in the area at risk between hearts, the data is expressed as the ratio of infarct area vs. area at risk (% IA/AAR). All data are expressed as Mean±SEM and compared statistically using single factor ANOVA or Mann Whitney non parametric test. Significance is considered as $p<0.05$.

The combination of a compound of formula I of this invention with an NHE-1 inhibitor can be tested for their utility in reducing or preventing ischemic injury in non-cardiac tissues, for example, the brain, or the liver, utilizing procedures reported in the scientific literature. The combination of a compound of formula I of this invention with an NHE-1 inhibitor in such tests can be administered by the preferred route and vehicle of administration and at the preferred time of administration either prior to the ischemic episode, during the ischemic episode, following the ischemic episode (reperfusion period) or during any of the below-mentioned experimental stages.

The benefit of the combination of NHE-1 inhibitors and compounds of formula I of this invention to reduce ischemic brain damage can be demonstrated, for example, in mammals using the method of Park, et al (Ann. Neurol. 1988;24:543–551). According to the procedure of Park, et al., adult male Sprague Dawley rats are anesthetized initially with 2% halothane, and thereafter by mechanical ventilation with a nitrous oxide-oxygen mixture (70%:30%) containing 0.5–1% halothane. A tracheostomy is then performed. The stroke volume of the ventilator is adjusted to maintain arterial carbon dioxide tension at approximately 35 mm Hg and adequate arterial oxygenation ($PaO_2$>90 mm Hg). Body temperature can be monitored by a rectal thermometer, and the animals can be maintained normothermic, if necessary, by external heating. The animals next undergo subtemporal craniectomy to expose the main trunk of the left middle cerebral artery (MCA) under an operating microscope, and the exposed artery is occluded with microbipolar coagulation to generate large ischemic lesions in the cerebral cortex and basal ganglia. After three hours of MCA occlusion, the rats are deeply anesthetized with 2% halothane and a thoracotomy is performed to infuse heparinized saline into the left ventricle. The effluent is collected via an incision of the right atrium. The saline washout is followed by approximately 200 ml of a 40% formaldehyde, glacial acetic acid and absolute methanol solution (FAM; 1:1:8, v/v/v), then the animals are decapitated and the head is stored in fixative for 24 hours. The brain is then removed, dissected, embedded in paraffin wax, and sectioned (approximately 100 sections 0.2 mm per brain). The sections are then stained with hematoxylin-eosin or with a combination of cresyl violet and Luxol fast blue, and examined by light microscopy to identify and quantitate the ischemic damage using a precalibrated image analyzer. The ischemic volumes and areas are expressed in absolute units ($mm^3$ and $mm^2$) and as a percentage of the total region examined. The effect of the compositions and methods of this invention to reduce ischemic brain damage induced by MCA occlusion is noted based on a reduction in the area or volume of relative or absolute ischemic damage in the brain sections from the rats in the treatment group compared to brain sections from rats in a placebo-treated control group.

Other methods which could alternatively be utilized to demonstrate the benefit of the invention to reduce ischemic brain damage include those described by Nakayama, et al. in Neurology 1988, 38:1667–1673; Memezawa, et al. in Stroke 1992, 23:552–559; Folbergrova, et al. in Proc. Natl. Acad. Sci 1995, 92:5057–5059; and Gotti, et al. in Brain Res. 1990, 522:290–307.

The benefit of the compositions and methods of this invention to reduce ischemic liver damage can be demonstrated, for example, in mammals using the method of Yokoyama, et al. (Am. J. Physiol. 1990;258:G564–G570). According to the procedure of Yokoyama, et al., fasted adult male Sprague Dawley rats are anesthetized with sodium pentobarbital (40 mg/kg i.p.), then the animals are tracheotomized and mechanically ventilated with room air. The liver is extirpated and placed in an environmental chamber maintained at constant temperature (37° C.), then perfused through the portal vein at a constant pressure of 15 cm $H_2O$ with a modified, hemoglobin-free Krebs-Henseleit buffer (in mM: 118 NaCl, 4.7 KCl, 27 $NaHCO_3$, 2.5 $CaCl_2$, 1.2 $MgSO_4$, 1.2 $KH_2PO_4$, 0.05 EDTA, and 11 mM glucose, plus 300 U heparin). The pH of the perfusate is maintained at 7.4 by gassing the buffer with 95% $O_2$–5% $CO_2$. Each liver is perfused at a flow rate of 20 ml/minutes in a single-pass manner for a 30 minutes washout and equilibration period (preischemic period), followed by a 2 hour period of global ischemia, and then a 2 hour period of reperfusion under conditions identical to the preischemic period. Aliquots (20 ml) of the perfusate are collected during the preischemic period, immediately after the occlusive ischemic period, and every 30 minutes of the 2 hour reperfusion period. The perfusate samples are assayed for the appearance of hepatocellular enzymes, for example, aspartate amino-transferase (AST), alanine amino-transferase (ALT), and lactate dehydrogenase (LDH), which are taken to quantitatively reflect the degree of ischemic liver tissue damage during the procedure. AST, ALT, and LDH activities in the perfusate can be determined by several methods, for example, by the reflectometry method using an automatic Kodak Ektachem 500 analyzer reported by Nakano, et al. (Hepatology 1995;22:539–545). The effect of the compositions and methods of this invention in reducing ischemic liver damage induced by occlusion is noted based on a reduction in the release of hepatocellular enzymes immediately following the occlusive period and/or during the postischemic-reperfusion period in the perfused livers from the rats in the treatment group compared to perfused livers from rats in a placebo-treated control group.

Other methods and parameters which could alternatively be utilized to demonstrate the benefit of the compositions and methods of this invention in reducing ischemic liver damage include those described by Nakano, et al. (Hepatology 1995;22:539–545).

Any glycogen phosphorylase inhibitor may be used as the second compound of this invention. The term glycogen phosphorylase inhibitor refers to any substance or agent or any combination of substances and/or agents which reduces, retards, or eliminates the enzymatic action of glycogen phosphorylase. The currently known enzymatic action of glycogen phosphorylase is the degradation of glycogen by catalysis of the reversible reaction of a glycogen macromolecule and inorganic phosphate to glucose-1-phosphate and a glycogen macromolecule which is one glucosyl residue shorter than the original glycogen macromolecule (forward direction of glycogenolysis). Such actions are readily determined by those skilled in the art according to standard assays (e.g., as described hereinafter). A variety of these compounds are included in the following published PCT patent applications: PCT application publication WO 96/39384 and WO96/39385. However, other glycogen phosphorylase inhibitors will be known to those skilled in the art.

Compounds of formula I, prodrugs thereof, mutual prodrugs of the compounds of formula I with aldose reductase inhibitors, pharmaceutically acceptable salts of any of the above and pharmaceutical compositions comprising a compound of formula I, a prodrug thereof or a pharmaceutically acceptable salt of said compound or said prodrug and either (a) an aldose reductase inhibitor, a prodrug thereof or a pharmaceutically acceptable salt of said aldose reductase inhibitor or said prod rug, (b) a NHE-1 inhibitor, a prodrug thereof or a pharmaceutically acceptable salt of said NHE-1 inhibitor or said prodrug, or a glycogen phosphorylase inhibitor, a prodrug thereof or a pharmaceutically acceptable salt of said glycogen phosphorylase inhibitor or said prodrug are hereinafter referred to, collectively, as "the active compounds and compositions of this invention."

The active compounds and compositions of this invention may be administered to a subject in need of treatment by a variety of conventional routes of administration, including orally, parenterally and topically. In general, compounds of the formula I and their pharmaceutically acceptable salts will be administered orally or parenterally at dosages between about 0.001 and about 100 mg/kg body weight of the subject to be treated per day, preferably from about 0.01 to 10 mg/kg, in single or divided doses. Mutual prodrugs of compounds of the formula I and aldose reductase inhibitors will generally be administered orally or parenterally at dosages between about 0.001 and about 100 mg/kg body weight of the subject to be treated per day, preferably from about 0.01 to about 10 mg/kg, in single or divided doses. Compositions containing both a compound of the formula I and an aldose reductase inhibitor will generally be administered orally or parenterally at dosages between about 0.001 and about 100 mg of each active component (i.e., the compound of formula I and the aldose reductase inhibitor) per kg body weight of the subject to be treated per day, preferably from about 0.01 to about 10 mg/kg. Compositions containing both a compound of formula I and a NHE-1 inhibitor will generally be administered orally or parenterally at dosages between about 0.001 and 100 mg of said compound of formula I per kg body weight of the subject to be treated per day and about 0.001 to 100 mg/kg/day of the NHE-1 inhibitor. An especially preferred dosage contains between about 0.01 and 10 mg/kg/day of said compound of formula I and between about 0.01 and 50 mg/kg/day of said NHE-1 inhibitor. Compositions containing both a compound of formula I and a glycogen phosphorylase inhibitor will generally be administered orally or parenterally at dosages between about 0.001 and 100 mg of said compound of formula I per kg body weight of the subject to be treated per day and 0.005 to 50 mg/kg/day of said glycogen phosphorylase inhibitor, preferably 0.01 and 10 mg/kg/day of said compound of formula and 0.01 to 25 mg/kg/day of said glycogen phosphorylase inhibitor and most preferably 0.01 and 10 mg/kg/day of said compound of formula and 0.1 to 15 mg/kg/day of said glycogen phosphorylase inhibitor. However, some variation in dosage will necessarily occur depending on the condition of the subject being treated. The person responsible for administration will, in any event, determine the appropriate dose for the individual subject.

The active compounds and compositions of this invention may be administered alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed by combining the active compounds of formula I of this invention and the pharmaceutically acceptable carriers are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions of the active compounds and compositions of this invention in sesame or peanut oil, aqueous propylene glycol, or in sterile aqueous solutions may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

Administration of the compounds of formula I of this invention can be via any method which delivers a compound of this invention preferentially to the desired tissue (e.g., nerve, kidney, retina and/or cardiac tissues). These methods include oral routes, parenteral, intraduodenal routes, etc. Generally, the compounds of the present invention are administered in single (e.g., once daily) or multiple doses or via constant infusion.

The compositions of this invention comprising a compound of formula I in combination with an NHE-1 inhibitor are useful, for example, in reducing or minimizing damage effected directly to any tissue that may be susceptible to ischemia/reperfusion injury (e.g., heart, brain, lung, kidney, liver, gut, skeletal muscle, retina) as the result of an ischemic event (e.g., myocardial infarction). The composition is therefore usefully employed prophylactically to prevent, i.e. (prospectively or prophylactically) to blunt or stem, tissue damage (e.g., myocardial tissue) in patients who are at risk for ischemia (e.g., myocardial ischemia).

Generally, a compounded of formula I of this invention is administered orally, or parenterally (e.g., intravenous, intramuscular, subcutaneous or intramedullary). Topical administration may also be indicated, for example, where the patient is suffering from gastrointestinal disorders or whenever the medication is best applied to the surface of a tissue or organ as determined by the attending physician.

The amount and timing of compounds administered will, of course, be dependent on the subject being treated, on the severity of the affliction, on the manner of administration and on the judgement of the prescribing physician. Thus, because of patient to patient variability, the dosages given below are a guideline and the physician may titrate doses of the drug to achieve the treatment that the physician considers appropriate for the patient. In considering the degree of treatment desired, the physician must balance a variety of factors such as age of the patient, presence of preexisting disease, as well as presence of other diseases.

Thus, for example, in one mode of administration the compounds of formula I of this invention may be administered just prior to surgery (e.g., within twenty-four hours before surgery for example cardiac surgery) during or subsequent to surgery (e.g., within twenty-four hours after surgery) where there is risk of myocardial ischemia. The compounds of formula I of this invention may also be administered in a chronic daily mode.

The compounds of the present invention are generally administered in the form of a pharmaceutical composition comprising at least one of the compounds of formula I of this invention together with a pharmaceutically acceptable vehicle or diluent. Thus, the compounds of formula I of this invention can be administered individually or together in any conventional oral, parenteral, rectal or transdermal dosage form.

For purposes of transdermal (e.g., topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences*, Mack Publishing Company, Easton, Pa., 19th Edition (1995).

Pharmaceutical compositions according to the invention may contain for example 0.0001%–95% of the compound(s) of this invention. In any event, the composition or formulation to be administered will contain a quantity of a compound(s) according to the invention in an amount effective to treat the disease/condition of the subject being treated.

The two different compounds of this combination of this invention can be co-administered simultaneously or sequentially in any order, or as a single pharmaceutical composition comprising a compound of Formula I and an aldose reductase inhibitor as described above or a glycogen phosphorylase inhibitor as described above or a cardiovascular agent.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a compound of Formula I a prodrug thereof or a salt of such compound or prodrug and a second compound as described above. The kit comprises means for containing the separate compositions such as a container, a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc . . . . Second Week, Monday, Tuesday, . . . " etc. Other variations of memory aids will be readily apparent. A "daily dose" can be a single tablet or capsule or several pills or capsules to be taken on a given day. Also, a daily dose of Formula I compound can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of formula I of this invention generally will be administered in a convenient formulation. The following formulation examples are illustrative only and are not intended to limit the scope of the present invention.

In the formulations which follow, "active ingredient" means a compound(s) of this invention.

Formulation 1: Gelatin Capsules

Hard gelatin capsules are prepared using the following:

| Ingredient | Quantity (mg/capsule) |
|---|---|
| Active ingredient | 0.25–100 |
| Starch, NF | 0–650 |
| Starch flowable powder | 0–50 |
| Silicone fluid 350 centistokes | 0–15 |

A tablet formulation is prepared using the ingredients below:

Formulation 2: Tablets

| Ingredient | Quantity (mg/tablet) |
|---|---|
| Active ingredient | 0.25–100 |
| Cellulose, microcrystalline | 200–650 |
| Silicon dioxide, fumed | 10–650 |
| Stearate acid | 5–15 |

The components are blended and compressed to form tablets.

Alternatively, tablets each containing 0.25–100 mg of active ingredients are made up as follows:

Formulation 3: Tablets

| Ingredient | Quantity (mg/tablet) |
|---|---|
| Active ingredient | 0.25–100 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25–100 mg of active ingredient per 5 ml dose are made as follows:

Formulation 4: Suspensions

| Ingredient | Quantity (mg/5 ml) |
|---|---|
| Active ingredient | 0.25–100 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified Water to | 5 mL |

The active ingredient is passed through a No. 45 mesh U.S. sieve and mixed with the sodium carboxymethyl cellulose and syrup to form smooth paste. The benzoic acid solution, flavor, and color are diluted with some of the water and added, with stirring. Sufficient water is then added to produce the required volume. An aerosol solution is prepared containing the following ingredients:

Formulation 5: Aerosol

| Ingredient | Quantity (% by weight) |
|---|---|
| Active ingredient | 0.25 |
| Ethanol | 25.75 |
| Propellant 22 (Chlorodifluoromethane) | 74.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

Formulation 6: Suppositories

| Ingredient | Quantity (mg/suppository) |
|---|---|
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

Formulation 7: Intravenous Solution

| Ingredient | Quantity |
|---|---|
| Active ingredient | 25 mg–10,000 mg |
| Isotonic saline | 1,000 mL |

The solution of the above ingredients is intravenously administered to a patient.

The active ingredient above may also be a combination of agents.

General Experimental Procedures

Melting points were determined on a Thomas-Hoover capillary melting point apparatus, and are uncorrected. $^1$H NMR spectra were obtained on a Bruker AM-250 (Bruker Co., Billerica, Mass.), a Bruker AM-300, a Varian XL-300 (Varian Co., Palo Alto, Calif.), or a Varian Unity 400 at about 23° C. at 250, 300, or 400 MHz for proton. Chemical shifts are reported in parts per million (δ) relative to residual chloroform (7.26 ppm), dimethylsulfoxide (2.49 ppm), or methanol (3.30 ppm) as an internal reference. The peak shapes and descriptors for the peak shapes are denoted as follows: s, singlet; d, doublet; t, triplet; q, quartet; m, multiplet; c, complex; br, broad; app, apparent. Low-resolution mass spectra were obtained under thermospray (TS) conditions on a Fisons (now Micromass) Trio 1000 Mass Spectrometer (Micromass Inc., Beverly, Mass.), under chemical-ionization (CI) conditions on a Hewlett Packard 5989A Particle Beam Mass Spectrometer (Hewlett Packard Co., Palo Alto, Calif.), or under atmospheric pressure chemical ionization (APCI) on a Fisons (now Micromass) Platform II Spectrometer. Optical rotations were obtained on a Perkin-Elmer 241 MC Polarimeter (Perkin-Elmer, Norwalk, Conn.) using a standard path length of 1 dcm at about 23° C. at the indicated concentration in the indicated solvent.

Liquid column chromatography was performed using forced flow (flash chromatography) of the indicated solvent on either Baker Silica Gel (40 μm, J. T. Baker, Phillipsburg, N.J.) or Silica Gel 60 (EM Sciences, Gibbstown, N.J.) in glass columns or using low nitrogen or air pressure in Flash 40™ or Flash 12™ (Biotage, Charlottesville, Va.) cartridges. Radial chromatography was performed using a Chromatron (Harrison Research, Palo Alto, Calif.). The terms "concentrated" and "evaporated" refer to removal of solvent using a rotary evaporator at water aspirator pressure or at similar pressures generated by a Büchi B-171 Vacobox (Brinkmann Instruments, Inc., Westbury, New York) or a Büchi B-177 Vacobox with a bath temperature equal to or less than 50° C. Reactions requiring the use of hydrogen gas at pressures greater than 1 atmosphere were run using a Parr hydrogen apparatus (Parr Instrument Co., Moline, Ill.). Unless otherwise specified, reagents were obtained from commercial sources. The abbreviations "d", "h", and "min" stand for "day(s)", "hour(s)", and "minute(s)", respectively.

EXAMPLE 1

(R)-1-[4-(4-Quinoxalin-2-yl-piperazin-1-yl)-pyrimidin-2-yl]-ethanol.

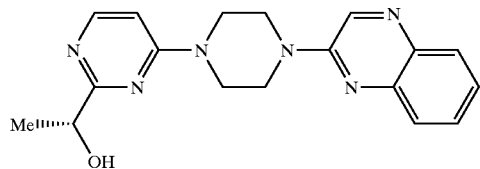

Step A: (R)-1-[4-(4-Quinoxalin-2-yl-piperazin-1-yl)-pyrimidin-2-yl]-ethyl acetate. To a solution of (R)-1-(4-chloro-pyrimidin-2-yl)-ethyl acetate (prepared according to the method of Preparation Five, 7.3 g, 36.2 mmol) in isopropanol (240 mL) was added triethylamine (10.1 mL, 72.4 mmol) followed by 2-(1-piperazinyl)quinoxaline (10.1 g, 47.1 mmol; J. Med. Chem. 1981, 24, 93). This mixture was stirred at room temperature overnight then concentrated. The residue was diluted with saturated aqueous sodium bicarbonate and extracted with chloroform (5×). The combined organic extracts were dried over sodium sulfate, filtered, evaporated, and purified by flash column chromatography (2% methanol/chloroform) to give 12.4 g (91%) of the title compound of Example 1, Step A as a yellow foam. $^1$H NMR (CDCl$_3$, 250 MHz) δ 8.61 (s, 1H), 8.27 (d, 1H), 7.91 (dd, 1H), 7.72 (dd, 1H), 7.61 (td, 1H), 7.44 (td, 1H), 6.43 (d, 1H), 5.70 (q, 1H), 3.96–3.84 (c, 8H), 2.18 (s, 3H), 1.61 (d, 3H); MS(CI/NH$_3$) 379 (MH$^+$).

Step B: (R)-1-[4-(4-Quinoxalin-2-yl-piperazin-1-yl)-pyrimidin-2-yl]-ethanol. To a solution of (R)-1-[4-(4-quinoxalin-2-yl-piperazin-1-yl)-pyrimidin-2-yl]-ethyl acetate (prepared according to the method of Example 1, Step A, 14.1 g, 37.2 mmol) in a 3:1:1 mixture of tetrahydrofuran/water/methanol (375 mL) was added lithium hydroxide hydrate (4.7 g, 112 mmol). This mixture was stirred at room temperature for 1 h 45 min, concentrated, and extracted with chloroform (6×). The combined organic extracts were dried over sodium sulfate, filtered, evaporated, and purified by flash column chromatography (2×; 2% methanol/chloroform) to give 11.3 g (90%) of the title compound as a pale yellow solid after tritration with hexanes. mp: 106.5–108° C.; $^1$H NMR (CDCl$_3$, 250 MHz) δ 8.62 (s, 1H), 8.26 (d, 1H), 7.92 (dd, 1H), 7.72 (dd, 1H), 7.61 (td, 1H), 7.44 (td, 1H), 6.45 (d, 1H), 4.75 (m, 1H), 3.95–3.85 (c, 8), 1.54 (d, 3H); MS (CI/NH$_3$) 337 (MH$^+$); [α]$_D$+15.3 (c 2.3, MeOH).

EXAMPLE 2

(R)-1-[4-(4-Oxazolo[5,4-c]pyridin-2-yl-piperazin-1-yl)-pyrimidin-2-yl]-ethanol.

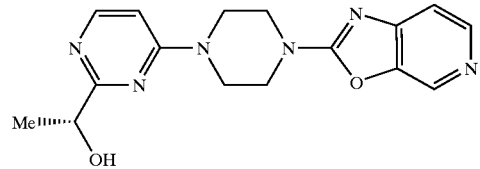

Step A: (R)-1-[4-(4-Oxazolo[5,4-c]pyridin-2-yl-piperazin-1-yl)-pyrimidin-2-yl]-ethyl butyrate. To a solution of 2-(1-piperazinyl)oxazolo[5,4-c]pyridine (775 mg, 3.8 mmol; J. Org. Chem. 1995, 60, 5721) in isopropanol (38 mL) was added (R)-1-(4-chloro-pyrimidin-2-yl)-ethyl butyrate (prepared according to the method of Preparation Seven, 868 mg, 3.8 mmol) followed by triethylamine (1.6 mL, 11.4 mmol). This mixture was stirred at reflux overnight, cooled to room temperature, and evaporated. The residue was diluted with saturated aqueous sodium bicarbonate and extracted with chloroform (3×). The combined organic extracts were dried over sodium sulfate, filtered, evaporated, and purified by flash column chromatography (2×; 3% methanol/chloroform then 6→8% methanol/ethyl acetate, where used herein, the arrow symbol, →, indicates a gradient) to give 1.2 g (79%) of the title compound of Example 2, Step A as a pale yellow oil which solidified upon standing. $^1$H NMR (CDCl$_3$, 250 MHz) δ 8.57 (s, 1H), 8.39 (d, 1H), 8.28 (d, 1H), 7.30 (d, 1H), 6.44 (d, 1H), 5.70 (q, 1H), 3.85 (s, 8H), 2.42 (t, 2H), 1.78–1.61 (c, 2H), 1.60 (d, 3H), 0.98 (t, 3H); MS (APCI) 397 (MH$^+$).

Step B: (R)-1-[4-(4-Oxazolo[5,4-c]pyridin-2-yl-piperazin-1-yl)-pyrimidin-2-yl]-ethanol. To a solution of (R)-1-[4-(4-oxazolo[5,4-c]pyridin-2-yl-piperazin-1-yl)-pyrimidin-2-yl]-ethyl butyrate (prepared according to the method of Example 2, Step A, 1.2 g, 3.0 mmol) in methanol (30 mL) was added potassium carbonate (823 mg, 6.0 mmol). This mixture was stirred at room temperature for 5 h, diluted with saturated aqueous ammonium chloride, concentrated, and extracted with chloroform (3×). The combined organic extracts were dried over sodium sulfate, filtered, evaporated, and purified by flash column chromatography (6% methanol/chloroform) to give 915 mg (94%) of the title compound as a white solid after tritration with hexanes. mp: 181–183° C.; $^1$H NMR (CDCl$_3$, 300 MHz) δ 8.54 (d, 1H), 8.35 (d, 1H), 8.25 (d, 1H), 7.27 (dd, 1H), 6.44 (d, 1H), 4.71 (q, 1H), 4.25 (br s, 1H), 3.86–3.83 (c, 8H), 1.50 (d, 3H); MS (APCI) 327 (MH$^+$); [α]$_D$+15.3 (c 0.5, MeOH).

EXAMPLE 3

1R-(4-{1'-[2-(1R-Hydroxy-ethyl)-pyrimidin-4-yl]-[4,4']bipiperidinyl-1-yl}-pyrimidin-2-yl)-ethanol.

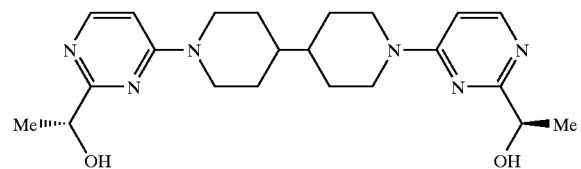

A mixture of (R)-1-(4-chloro-pyrimidin-2-yl)-ethanol (prepared according to the method of Preparation Ten, 100 mg, 0.63 mmol), 4,4'-bipiperidine dihydrochloride (76 mg, 0.32 mmol), and triethylamine (0.44 mL, 3.2 mmol) in isopropanol (3 mL) was refluxed overnight and cooled to room temperature. The reaction mixture was diluted with saturated aqueous sodium bicarbonate and extracted with chloroform (4×). The combined organic extracts were dried over sodium sulfate, filtered, evaporated, and purified by flash column chromatography (Biotage Flash 40S™, 5% methanol/chloroform) to give 110 mg (85%) of the title compound as a white solid. mp: 144–153° C., $^1$H NMR (CDCl$_3$, 400 MHz) δ 8.14 (d, 2H), 6.36 (d, 2H), 4.67 (q, 2H), 4.53–4.28 (c, 4H), 2.84 (t, 4H), 1.82 (d, 4H), 1.49 (d, 6H), 1.43–1.40 (c, 2H), 1.30–1.18 (c, 4H); MS (APCI) 413 (MH$^+$); [a]$_D$+22.6 (c 1.0, MeOH).

EXAMPLES 4 TO 8

Examples 4 to 8 were prepared from the appropriate starting materials in a manner analogous to the method of Example 3.

EXAMPLE 4
1R-(4-{4-[2-(1R-Hydroxy-ethyl)-pyrimidin-4-yl]-2R,5S-dimethyl-piperazin-1-yl}-pyrimidin-2-yl)-ethanol.

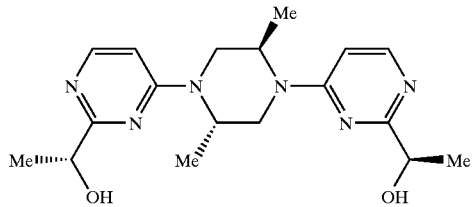

mp: 153–155° C., $^1$H NMR (CDCl$_3$, 400 MHz) δ 8.23 (d, 2H), 6.40 (d, 2H), 4.71 (m, 2H), 4.28 (dd, 2H), 3.51–3.45 (c, 4H), 1.51 (d, 6H), 1.23 (d, 6H); MS (APCI) 359 (MH$^+$); [α]$_D$+18.6 (c 1.2, CHCl$_3$).

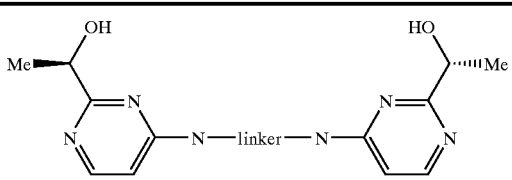

| Example | N-linker-N | mp (° C.) | MS (MH$^+$) |
|---|---|---|---|
| 5 | N,N'-ethylenediamine | 141–143 | 333 |
| 6 | [1,4]diazepane | 136–138 | 345 |
| 7 | 4,4'-ethylenebipiperidine |  | 441 |
| 8 | methyl-piperidin-4-ylmethyl-amine |  | 373 |

EXAMPLE 9
(R)-1-[4-(4-Oxazolo[5,4-b]pyridin-2-yl-piperazin-1-yl)-pyrimidin-2-yl]-ethanol.

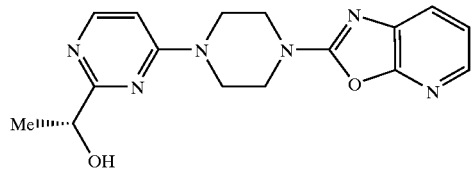

Step A: 2-(1-Piperazinyl)oxazolo[5,4-b]pyridine. A mixture of 2-(thiomethyl)oxazolo[5,4-b]pyridine (9.2 g, 55.5 mmol; *J. Org. Chem.* 1995, 60, 5721) and piperazine (23.9 g, 277 mmol), with a small amount of ethyl acetate which was used for washing the compound down the sides of the flask, was heated at 90° C. for 1.5 h. The reaction mixture was cooled to room temperature, diluted with ~20% saturated aqueous sodium bicarbonate solution, and extracted with chloroform (4×). The combined organic extracts were washed with saturated aqueous sodium bicarbonate (1×), dried over sodium sulfate, filtered, evaporated, and purified by flash column chromatography (3→5% methanol/chloroform+1% ammonium hydroxide) to give 9.1 g (81%) of the title compound of Example 9, Step A as an off-white solid. $^1$H NMR (CDCl$_3$, 300 MHz) δ 7.92 (dd, 1H), 7.55 (dd, 1H), 7.10 (dd, 1H), 3.74–3.70 (c, 4H), 3.02–2.97 (c, 4H); MS (APCI) 205 (MH$^+$).

Step B: (R)-1-[4-(4-Oxazolo[5,4-b]pyridin-2-yl-piperazin-1-yl)-pyrimidin-2-yl]-ethyl butyrate. To a solution of (R)-1-(4-chloro-pyrimidin-2-yl)-ethyl butyrate (prepared according to the method of Preparation Seven, 6.8 g, 29.9 mmol) and triethylamine (12.5 mL, 89.6 mmol) in isopropanol (100 mL) was added 2-(1-piperazinyl)oxazolo[5,4-b]pyridine (prepared according to the method of Example 9, Step A, 6.1 g, 29.9 mmol). This mixture was stirred at reflux overnight, cooled to room temperature, and evaporated. The residue was diluted with saturated aqueous sodium bicarbonate and extracted with chloroform (3×). The combined organic extracts were dried over sodium sulfate, filtered, evaporated, and purified by flash column chromatography (1.5→2% methanol/chloroform) to give 11.1 g (94%) of the title compound of Example 9, Step B as a yellow oil which solidified upon standing.

$^1$H NMR (CDCl$_3$, 250 MHz) δ 8.28 (d, 1H), 7.97 (dd, 1H), 7.60 (dd, 1H), 7.25 (dd, 1H), 6.44 (d, 1H), 5.70 (q, 1H), 3.85 (app s, 8H), 2.42 (t, 2H), 1.78–1.61 (c, 2H), 1.60 (d, 3H), 0.98 (t, 3H); MS (APCI) 397 (MH$^+$).

Step C: (R)-1-[4-(4-Oxazolo[5,4-b]pyridin-2-yl-piperazin-1-yl)-pyrimidin-2-yl]-ethanol. To a solution of (R)-1-[4-(4-oxazolo[5,4-b]pyridin-2-yl-piperazin-1-yl)-pyrimidin-2-yl]-ethyl butyrate (prepared according to the method of Example 9, Step B, 11.0 g, 27.6 mmol) in dioxane (11.5 mL) was added concentrated hydrochloric acid (23 mL, 276 mmol). This mixture was stirred at room temperature overnight, neutralized with 6 N aqueous sodium hydroxide, and extracted with chloroform (3×). The combined organic extracts were dried over sodium sulfate, filtered, evaporated, and purified by flash column chromatography (3.5% methanol/chloroform) to give 8.4 g (93%) of the title compound as a white solid. mp: 153–156° C.; $^1$H NMR (CDCl$_3$, 300 MHz) δ 8.25 (d, 1H), 7.95 (dd, 1H), 7.58 (dd, 1H), 7.15 (dd, 1H), 6.45 (d, 1H), 4.72 (q, 1H), 4.25 (br s, 1H), 3.85–3.82 (c, 8H), 1.51 (d, 3H); MS (CI/NH$_3$) 327 (MH$^+$); [α]$_D$+16.1 (c, 1.0, MeOH).

EXAMPLES 10 TO 15

Examples 10 to 15 were prepared from the appropriate starting materials in a manner analogous to the method of Example 9.

Ar$^1$—X—N(piperazine)N—pyrimidine-R$^1$

| Example | X—Ar$^1$ | R$^1$ | mp (° C.) | MS (MH$^+$) |
|---|---|---|---|---|
| 10 | oxazolo[4,5-c]pyridin-2-yl | (R)—CH(CH$_3$)OH | 178–180 | 327 |
| 11 | oxazolo[5,4-c]pyridin-2-yl | —C(CH$_3$)$_2$OH | 181–184 | 341 |
| 12 | oxazolo[5,4-c]pyridin-2-yl | (±)-CH(CH$_3$)OH | 153–158 | 327 |
| 13 | oxazolo[5,4-c]pyridin-2-yl | (S)—CH(CH$_3$)OH | 175–179 | 327 |
| 14 | quinoxalin-2-yl | (±)-CH(CH$_3$)OH | 102–105 | 337 |
| 15 | (5-iodo)-benzoxazol-2-yl | (R)—CH(CH$_3$)OH |  | 452 |

EXAMPLE 16

1R-[4-(3S-Methyl-4-oxazolo[5,4-b]pyridin-2-yl-piperazin-1-yl)-pyrimidin-2-yl]-ethanol.

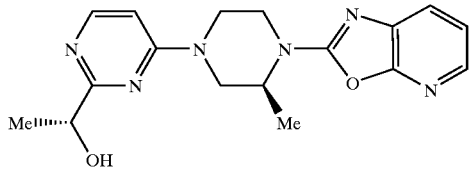

Step A: (S)-2-(4-Benzyl-2-methyl-piperazin-1-yl)-oxazolo[5,4-b]pyridine. A mixture of 2-(thiomethyl)oxazolo[5,4-b]pyridine (44 g, 264 mmol; *J. Org. Chem.* 1995, 60, 5721) and (S)-1-benzyl-3-methyl-piperazine (25 g, 132 mmol; *J. Org. Chem.* 1995, 60, 4177) was stirred at 130° C. for 3 d, cooled to room temperature, and purified by flash column chromatography (17→83% ethyl acetate/hexanes) to give 30 g (74%) of the title compound of Example 16, Step A as a dark yellow oil. $^1$H NMR (CDCl$_3$, 400 MHz) δ 7.89 (d, 1H), 7.53 (d, 1H), 7.34–7.25 (c, 5H), 7.10 (dd, 1H), 4.45 (m, 1H), 4.11 (d, 1H), 3.59 (d, 1H), 3.52–3.45 (c, 2H), 2.90 (d, 1H), 2.73 (d, 1H), 2.32 (dd, 1H), 2.21 (td, 1H), 1.41 (d, 3H); MS (APCI) 309(MH$^+$).

Step B: (S)-2-(2-Methyl-piperazin-1-yl)-oxazolo[5,4-b]pyridine. To a solution of (S)-2-(4-benzyl-2-methyl-piperazin-1-yl)-oxazolo[5,4-b]pyridine (prepared according to the method of Example 16, Step A, 30 g, 97 mmol) in methanol (970 mL) was added hydrogen chloride (5.85 M in methanol, 20 mL, 116 mmol), ammonium formate (122 g, 1.95 mol), and 10% palladium on carbon (60 g, 200 wt %). This mixture was stirred at reflux for 50 min, cooled, and filtered through Celite. The filtrate was concentrated, diluted with saturated aqueous sodium bicarbonate, and extracted with chloroform (1×) followed by 10% isopropanol/chloroform (4×). The combined organic extracts were dried over sodium sulfate, filtered, and evaporated to give 16 g (76%) of the title compound of Example 16, Step B as a green oil. $^1$H NMR (CDCl$_3$, 400 MHz) δ 7.89 (m, 1H), 7.53 (m, 1H), 7.09 (m, 1H), 4.42 (m, 1H), 4.11 (d, 1H), 3.35 (td, 1H), 3.09–3.03 (c, 2H), 2.85 (d, 1H), 2.82 (td, 1H), 1.38 (d, 3H); MS (APCI) 219 (MH$^+$).

Step C: 1R-[4-(3S-Methyl-4-oxazolo[5,4-b]pyridin-2-yl-piperazin-1-yl)-pyrimidin-2-yl]-ethyl butyrate. A mixture of (S)-2-(2-methyl-piperazin-1-yl)-oxazolo[5,4-b]pyridine (prepared according to the method of Example 16, Step B, 10 g, 45.9 mmol), (R)-1-(4-chloro-pyrimidin-2-yl)-ethyl butyrate (prepared according to the method of Preparation Seven, 9.5 g, 41.7 mmol), and triethylamine (17.3 mL, 125 mmol) in isopropanol (230 mL) was heated at reflux for 30 h, cooled to room temperature, diluted with saturated aqueous sodium bicarbonate, and extracted with chloroform (4×). The combined organic extracts were dried over sodium sulfate, filtered, evaporated, and purified by flash column chromatography (1.5% methanol/chloroform) to give 16 g (93%) of the title compound of Example 16, Step C as a yellow oil. $^1$H NMR (CDCl$_3$, 400 MHz) δ 8.23 (d, 1H), 7.93 (dd, 1H), 7.57 (d, 1H), 7.13 (dd, 1H), 6.39 (d, 1H), 5.67 (q, 1H), 4.61 (m, 1H), 4.42 (m, 1H), 4.28 (m, 1H), 4.18 (dt, 1H), 3.51 (td, 1H), 3.41 (dd, 1H), 3.17 (td, 1H), 2.39 (t, 2H), 1.72–1.59 (c, 2H), 1.57 (d, 3H), 1.30 (d, 3H), 0.95 (t, 3H); MS (APCI) 411 (MH$^+$).

Step D: 1R-[4-(3S-Methyl-4-oxazolo[5,4-b]pyridin-2-yl-piperazin-1-yl)-pyrimidin-2-yl]-ethanol. A mixture of 1R-[4-(3S-methyl-4-oxazolo[5,4-b]pyridin-2-yl-piperazin-1-yl)-pyrimidin-2-yl]-ethyl butyrate (prepared according to the method of Example 16, Step C, 16 g, 39.0 mmol) and potassium carbonate (10.8 g, 78.1 mmol) in methanol (195 mL) was stirred at room temperature for 4 h, diluted with saturated aqueous sodium bicarbonate, and extracted with chloroform (1×) followed by 10% isopropanol/chloroform (3×). The combined organic extracts were dried over sodium sulfate, filtered, evaporated, and purified by flash column chromatography (1→2.5% methanol/chloroform) to give a white foam that was recrystallized from ether/chloroform to give 8.9 g (67%) of the title compound as a white solid. mp: 147–149° C.; $^1$H NMR (CDCl$_3$, 400 MHz) δ 8.24 (d, 1H), 7.94 (dd, 1H), 7.58 (d, 1H), 7.14 (dd, 1H), 6.42 (d, 1H), 4.72 (m, 1H), 4.64 (m, 1H), 4.42 (m, 1H), 4.32 (m, 1H), 4.25 (d, 1H), 4.21 (dt, 1H), 3.54 (td, 1H), 3.46 (dd, 1H), 3.24 (td, 1H), 1.51 (d, 3H), 1.33 (d, 3H); MS (APCI) 411 (MH$^+$); [α]$_D$+70.4 (c 1.1, MeOH).

EXAMPLES 17 TO 25

Examples 17 to 25 were prepared from the appropriate starting materials in a manner analogous to the method of Example 16.

EXAMPLE 17

1R-[4-(3S-Methyl-4-quinoxalin-2-yl-piperazin-1-yl)-pyrimidin-2-yl]-ethanol.

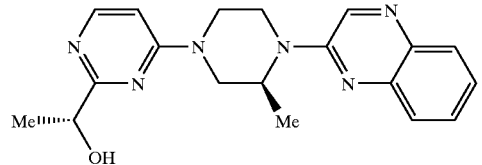

$^1$H NMR (CDCl$_3$, 400 MHz) δ 8.56 (d, 1H), 8.23 (d, 1H), 7.89 (d, 1H), 7.69 (d, 1H), 7.59 (t, 1H), 7.41 (t, 1H), 6.42 (d, 1H), 4.78 (m, 1H), 4.73 (m, 1H), 4.43 (m, 1H), 4.38–4.23 (c, 2H), 3.64–3.52 (c, 2H), 3.38 (m, 1H), 1.52 (d, 3H), 1.30 (d, 3H); MS (APCI) 351 (MH$^+$); [α]$_D$+57.0 (c 1.2, CHCl$_3$).

EXAMPLE 18

1R-{4-[4-(4,6-Dimethyl-pyrimidin-2-yl)-3S-methyl-piperazin-1-yl]-pyrimidin-2-yl}-ethanol.

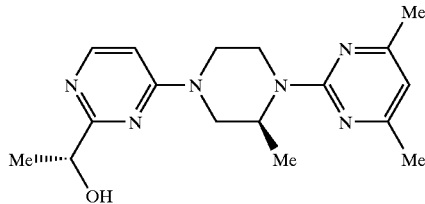

$^1$H NMR (CDCl$_3$, 400 MHz) δ 8.18 (d, 1H), 6.37 (d, 1H), 6.30 (s, 1H), 5.04 (m, 1H), 4.70 (q, 1H), 4.60 (dt, 1H), 4.37 (br s, 1H), 4.36–4.12 (c, 2H), 3.40 (dd, 1H), 3.34 (td, 1H), 3.16 (td, 1H), 2.28 (s, 6H), 1.51 (d, 3H), 1.16 (d, 3H); MS (APCI) 329 (MH$^+$); [α]$_D$+78.8 (c 1.6, MeOH).

EXAMPLE 19
1R-{4-[4-(2-Hydroxymethyl-6-methyl-pyrimidin-4-yl)-3S-methyl-piperazin-1-yl]-pyrimidin-2-yl}-ethanol.

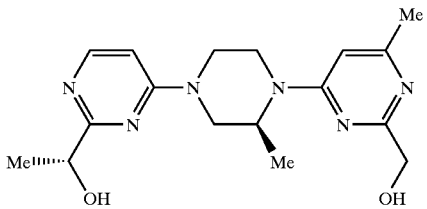

$^1$H NMR (CDCl$_3$, 400 MHz) δ 8.23 (d, 1H), 6.38 (d, 1H), 6.23 (s, 1H), 4.71 (q, 1H), 4.58 (s, 3H), 4.36–4.18 (c, 4H), 3.86 (br s, 1H), 3.57 (dd, 1H), 3.46 (td, 1H), 3.32 (td, 1H), 2.38 (s, 3H), 1.51 (d, 3H), 1.22 (d, 3H); MS (APCI) 345 (MH$^+$); [α]$_D$72.6 (c, 1.1, MeOH).

EXAMPLE 20
1R-[4-(3S-Methyl-4-oxazolo[4,5-b]pyridin-2-yl-piperazin-1-yl)-pyrimidin-2-yl]-ethanol.

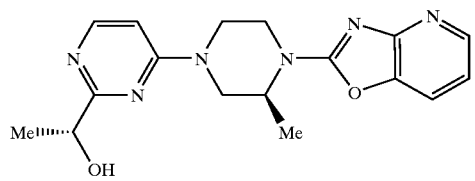

mp: 158–161° C.; $^1$H NMR (CDCl$_3$, 400 MHz) δ 8.22–8.15 (c, 2H), 7.40 (dd, 1H), 6.86 (dd, 1H), 6.40 (d, 1H), 4.65 (m, 1H), 4.61 (m, 1H), 4.44–4.20 (c, 3H), 4.18(dt, 1H), 3.50 (td, 1H), 3.41 (dd, 1H), 3.19 (td, 1H), 1.45 (d, 3H), 1.26 (d, 3H); MS (APCI) 341 (MH$^+$); [α]$_D$+58.2 (c 1.1, MeOH).

EXAMPLE 21
1R-[4-(3S-Methyl-4-oxazolo[4,5-c]pyridin-2-yl-piperazin-1-yl)-pyrimidin-2-yl]-ethanol.

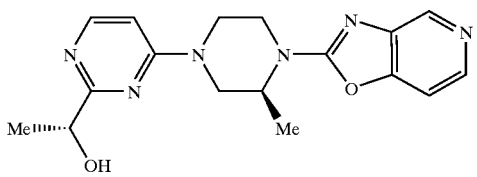

$^1$H NMR (CDCl$_3$, 400 MHz) δ 8.68 (d, 1H), 8.32 (d, 1H), 8.24 (d, 1H), 7.25(dd, 1H), 6.42 (d, 1H), 4.71 (m, 1H), 4.60 (m, 1H), 4.42 (m, 1H), 4.32–4.23 (c, 2H), 4.17 (dt, 1H), 3.56 (td, 1H), 3.47 (dd, 1H), 3.24 (td, 1H), 1.51 (d, 3H), 1.32 (d, 3H); MS (APCI) 341 (MH$^+$); [α]$_D$+57.9 (c 1.6, MeOH).

EXAMPLE 22
1R-[4-(3S-Methyl-4-oxazolo[5,4-c]pyridin-2-yl-piperazin-1-yl)-pyrimidin-2-yl]-ethanol.

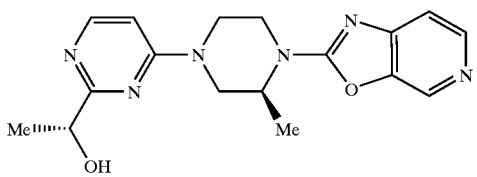

$^1$H NMR (CDCl$_3$, 400 MHz) δ 8.56 (s, 1H), 8.37 (d, 1H), 8.25 (d, 1H), 7.29 (d, 1H), 6.43 (d, 1H), 4.72 (m, 1H), 4.65 (m, 1H), 4.45 (m, 1H), 4.29 (m, 1H), 4.26–4.20 (c, 2H), 3.58 (td, 1H), 3.48 (dd, 1H), 3.26 (td, 1H), 1.51 (d, 3H), 1.34 (d, 3H); MS (APCI) 341 (MH$^+$); [α]$_D$+61.1 (c 1.0, MeOH).

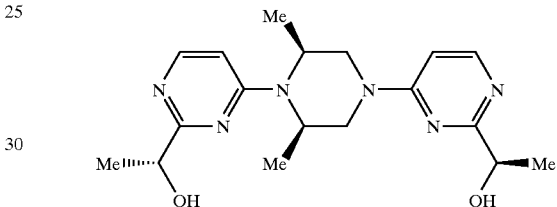

| Example | X—Ar$^1$ | C* | mp (° C.) | MS (MH$^+$) |
|---|---|---|---|---|
| 23 | quinoxalin-2-yl | R | | 351 |
| 24 | (2-[C(CH$_3$)$_2$OH])-pyrimidin-4-yl | S | | 359 |
| 25 | benzoxazol-2-yl | S | | 340 |

EXAMPLE 26
1R-(4-{4-[2-(1R-Hydroxy-ethyl)-pyrimidin-4-yl]-2R,6S-dimethyl-piperazin-1-yl}-pyrimidin-2-yl)-ethanol.

Method 1: To a solution of 1R-[4-(2R,6S-dimethyl-piperazin-1-yl)-pyrimidin-2-yl]-ethyl butyrate (prepared according to the method of Preparation Four, 72.8 g, 238 mmol) and triethylamine (50 mL, 357 mmol) in isopropanol (793 mL) was added (R)-1-(4-chloro-pyrimidin-2-yl)-ethyl butyrate (prepared according to the method of Preparation Seven, 54.3 g, 238 mmol). This mixture was stirred at reflux for 12 h and concentrated. The residue was dissolved in a 3:1:1 mixture of tetrahydrofuran/methanol/water (1200 mL) and lithium hydroxide hydrate (60 g, 1.43 mol) was added. This mixture was stirred at room temperature for 2.5 h, concentrated somewhat, diluted with saturated aqueous sodium bicarbonate, and extracted with 10% isopropanol/chloroform (6×). The combined organic extracts were dried over sodium sulfate, filtered, and evaporated. The residue was diluted with 1:1 ethyl acetate/methanol (1100 mL) and stirred at room temperature for 1 h. The precipitate was collected by filtration and the filtrate was concentrated to about 850 mL. After 1 h, more precipitate had formed and this material was collected by filtration. The filtrate was concentrated somewhat and ethyl acetate was added. After 1 h more precipitate had again formed and this material was collected by filtration. This was repeated one more time to give in total 65.9 g (77%) of the title compound as a white solid. mp: 163–164.5° C.; $^1$H NMR (CDCl$_3$, 400 MHz) δ 8.24 (d, 1H), 8.23 (d, 1H), 6.46 (d, 1H), 6.36 (d, 1H), 4.74–4.70 (c, 2H), 4.70–4.50 (c, 2H), 4.50–4.30 (c, 2H), 4.30 (d, 1H), 4.27 (d, 1H), 3.31 (dt, 2H), 1.51 (d, 6H), 1.26 (d, 6H); MS (APCI) 359 (MH$^+$); [α]$_D$+42.3 (c 1.0, MeOH).

Method 2, Step A: 1R-(4-{4-[2-(1R-Butyryloxy-ethyl)-pyrimidin-4-yl]-2R,6S-dimethyl-piperazin-1-yl}-pyrimidin-2-yl)-ethyl butyrate. To a solution of (R)-2-(1-butyryloxy-ethyl)-3H-pyrimidin-4-one (828 g, 3.9 mol) in dichloromethane (50 L) was added triethylamine (576 mL, 4.1 mol) and the resulting solution was cooled to 5° C. A solution of trifluoromethanesulfonic anhydride (729 mL, 4.3 mol) in dichloromethane (6 L) was added slowly such that the internal temperature was maintained at <10° C. After the addition was complete, the reaction was judged complete by TLC and quenched by the addition of water (5.3 L). The organic layer was separated, washed with water (20 L) and saturated aqueous sodium bicarbonate (20 L), and dried over sodium sulfate. This solution was then slowly added to a solution of 1R-[4-(2R,6S-dimethyl-piperazin-1-yl)-pyrimidin-2-yl]-ethyl butyrate dibenzoyl-L-tartrate salt (prepared according to the method of Preparation Fifteen, 2.49 kg, 3.75 mol) and triethylamine (1.6 L, 11.6 mol) in dimethylacetamide (18 L) such that the internal temperature was maintained at <10° C. The resulting solution was allowed to stir for 12 h at 10° C. and then diluted with ethyl acetate (40 L) and water (27 L). The aqueous layer was removed and the organic layer was washed twice with water (40 L) and once with brine (20 L), and dried over sodium sulfate. The resulting solution was partially concentrated (8 L) and then hexanes (23 L) was added. The resulting suspension was allowed to granulate for 12 h and then filtered over cotton. The solids were dried under vacuum (40° C.) to provide 1178 gm (63%) of the title compound of Example 26, Method 2, Step A as a white solid. The $^1$H NMR and MS data for this compound are in agreement with that of Example 266.

Method 2, Step B: 1R-(4-{4-[2-(1R-Hydroxy-ethyl)-pyrimidin-4-yl]-2R,6S-dimethyl-piperazin-1-yl}-pyrimidin-2-yl)-ethanol. To a solution of 1R-4-{4-[2-(1R-butyryloxy-ethyl)-pyrimidin-4-yl]-2R,6S-dimethyl-piperazin-1-yl}-pyrimidin-2-yl)-ethyl butyrate (prepared according to the method of Example 26, Method 2, Step A, 1140 g, 2.28 mol) in isopropanol (11.4 L) was added 40% aqueous potassium hydroxide (800 mL) at room temperature. The resulting solution was allowed to stir for 16 h and then diluted with water (5 L) and dichloromethane (4 L). The organic layer was separated and the aqueous layer was extracted with dichloromethane (4 L). The combined organic layers were washed twice with 1 M aqueous sodium hydroxide (10 L) and twice with water (5 L), partially concentrated (5 L), diluted with ethyl acetate (4 L), and again partially concentrated (6 L). Hexanes (10 L) was added and the resulting slurry was allowed to stir at reflux for 12 h, cooled to room temperature, and filtered. The resulting solid was dried under vacuum to provide 758 g (93%) of the title compound as a white solid. The mp, $^1$H NMR, MS, and optical rotation data for this compound are in agreement with that of Example 26, Method 1.

EXAMPLES 27 TO 62

Examples 27 to 62 were prepared from the appropriate starting materials in a manner analogous to the method of Example 26.

EXAMPLE 27

1R-{4-[4-(4,6-Dimethyl-pyrimidin-2-yl)-2R,6S-dimethyl-piperazin-1-yl]-pyrimidin-2-yl}-ethanol.

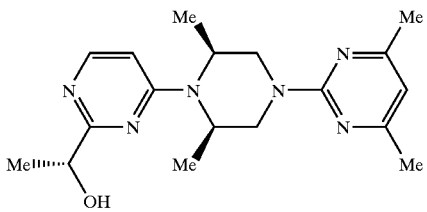

mp: 150.5–152° C.; $^1$H NMR (CD$_3$OD, 300 MHz) δ 8.14 (d, 1H), 6.62 (d, 1H), 6.46 (d, 1H), 6.40 (s, 1H), 4.83 (d, 2H), 4.72–4.52 (c, 3H), 3.30 (dd, 2H), 2.28 (s, 6H), 1.46 (d, 3H), 1.23 (d, 6H); MS (APCI) 343 (MH$^+$); [α]$_D$+12.0 (c 1.3, MeOH).

EXAMPLE 28

1R-[4-(2R,6S-Dimethyl-4-oxazolo[5,4-c]pyridin-2-yl-piperazin-1-yl)-pyrimidin-2-yl]-ethanol.

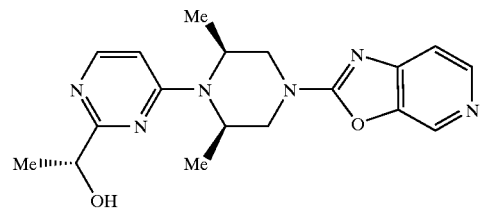

$^1$H NMR (CD$_3$OD, 300 MHz) δ 8.53 (d, 1H), 8.28 (d, 1H), 8.20 (d, 1H), 7.34 (dd, 1H), 6.68 (d, 1H), 4.90–4.72 (c, 2H), 4.69 (q, 1H), 4.32 (d, 2H), 3.56 (dd, 2H), 1.47 (d, 3H), 1.33 (d, 6H); MS (APCI) 343 (MH$^+$); [α]$_D$+8.1 (c 1.3, MeOH).

EXAMPLE 29

1R-{4-[4-(4-Hydroxymethyl-6-methyl-pyrimidin-2-yl)-2R,6S-dimethyl-piperazin-1-yl]-pyrimidin-2-yl}-ethanol.

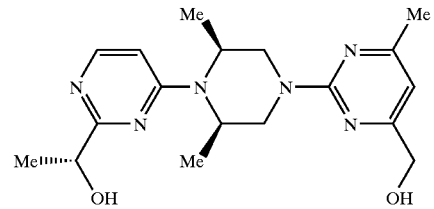

mp: 139–141° C.; $^1$H NMR (CD$_3$OD, 300 MHz) δ 8.24 (d, 1H), 6.51 (d, 1H), 6.38 (s, 1H), 4.90 (m, 1H), 4.84 (d, 2H), 4.77–4.53 (c, 2H), 4.55 (s, 2H), 3.24 (dd, 2H), 2.37 (s, 3H), 1.61 (d, 3H), 1.32 (d, 6H); MS (APCI) 359 (MH$^+$); [α]$_D$+14.8 (c 1.0, MeOH).

EXAMPLE 30

1R-{4-[4-(2,6-Dimethyl-pyrimidin-4-yl)-2R,6S-dimethyl-piperazin-1-yl]-pyrimidin-2-yl}-ethanol.

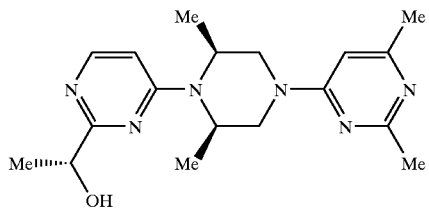

$^1$H NMR (CDCl$_3$, 300 MHz) δ 8.22 (d, 1H), 6.36 (d, 1H), 6.26 (s, 1H), 4.71 (m, 1H), 4.65–4.50 (c, 2H), 4.42–4.28 (c, 3H), 3.24 (dd, 2H), 2.49 (s, 3H), 2.35 (s, 3H), 1.52 (d, 3H), 1.26 (d, 6H); MS (APCI) 343 (MH$^+$); [a]$_D$+11.4 (c 0.8, MeOH).

EXAMPLE 31
1R-[4-(2R,6S-Dimethyl-4-oxazolo[4,5-b]pyridin-2-yl-piperazin-1-yl)-pyrimidin-2-yl]-ethanol.

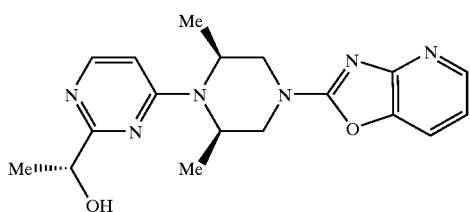

mp: 231–233° C.; ¹H NMR (CDCl₃, 400 MHz) δ 8.26–8.23 (c, 2H), 7.47 (d, 1H), 6.94 (dd, 1H), 6.39 (d, 1H), 4.75–4.53 (c, 2H), 4.72 (q, 1H), 4.35 (d, 1H), 4.28 (m, 1H), 3.44 (dd, 2H), 1.51 (d, 3H), 1.34 (d, 6H); MS (APCI) 355 (MH⁺); [α]$_D$+8.0 (c 0.8, MeOH).

EXAMPLE 32
1R-{4-[4-(2-Hydroxymethyl-6-methyl-pyrimidin-4-yl)-2R,6S-dimethyl-piperazin-1-yl]-pyrimidin-2-yl}-ethanol.

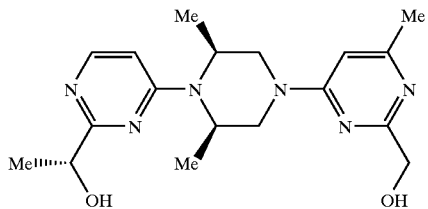

¹H NMR (CD₃OD, 300 MHz) δ 8.16 (d, 1H), 6.66 (s, 1H), 6.63 (d, 1H), 4.85–4.63 (c, 2H), 4.67 (q, 1H), 4.58 (d, 2H), 4.50 (s, 2H), 3.26 (dd, 2H), 2.35 (s, 3H), 1.46 (d, 3H), 1.24 (d, 6H); MS (APCI) 359 (MH⁺); [a]$_D$+11.8 (c 0.9, MeOH).

EXAMPLE 33
1R-[4-(2R,6S-Dimethyl-4-oxazolo[5.4-b]pyridin-2-yl-piperazin-1-yl)-pyrimidin-2-yl]-ethanol.

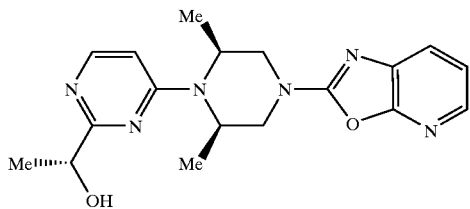

mp: 204–207° C.; ¹H NMR (CDCl₃, 400 MHz) δ 8.25 (d, 1H), 7.95 (dd, 1H), 7.59 (dd, 1H), 7.15 (dd, 1H), 6.39 (d, 1H), 4.80–4.57 (c, 2H), 4.73 (q, 1H), 4.30 (d, 2H), 3.42 (dd, 2H), 1.51 (d, 3H), 1.35 (d, 6H); MS (APCI) 355 (MH⁺); [α]$_D$+7.5 (c 0.7, MeOH).

EXAMPLE 34
2-(4-{4-[2-(1R-Hydroxy-ethyl)-pyrimidin-4-yl]-3R,5S-dimethyl-piperazin-1-yl}-pyrimidin-2-yl)-propan-2-ol.

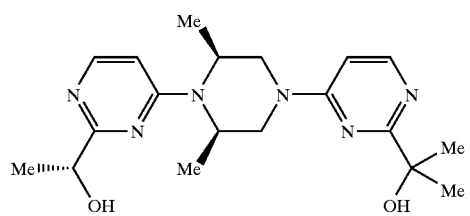

mp: 138–140° C.; ¹H NMR (CDCl₃, 400 MHz) δ 8.23 (d, 2H), 6.45 (d, 1H), 6.36 (d, 1H), 4.86 (s, 1H), 4.70 (m, 1H), 4.67–4.33 (c, 4H), 4.30 td, 1H), 3.31 (dd, 2H), 1.53 (s, 6H), 1.51 (d, 3H), 1.25 (d, 6H); MS (APCI) 373 (MH⁺); [α]$_D$+15.5 (c 1.2, MeOH).

EXAMPLE 35
1R-{4-[4-(4-Hydroxymethyl-6-methyl-pyrimidin-2-yl)-2S-methyl-piperazin-1-yl]-pyrimidin-2-yl}-ethanol.

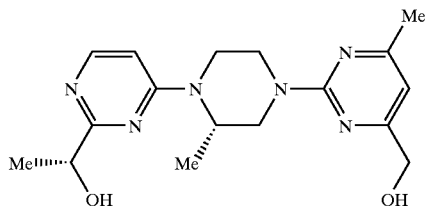

¹H NMR (CDCl₃, 400 MHz) δ 8.18 (d, 1H), 6.36 (d, 1H), 6.32 (s, 1H), 4.69 (q, 1H), 4.60–4.53 (c, 3H), 4.52 (s, 2H), 4.38–4.18 (c, 2H), 3.63 (m, 1H), 3.40–3.29 (c, 2H), 3.24 (m, 1H), 2.32 (s, 3H), 1.49 (d, 3H), 1.20 (d, 3H); MS (APCI) 345 (MH⁺); [α]$_D$ +66.5 (c 1.0, MeOH).

EXAMPLE 36
1R-{4-[4-(4-Hydroxymethyl-6-methyl-pyrimidin-2-yl)-2R-methyl-piperazin-1-yl]-pyrimidin-2-yl}-ethanol.

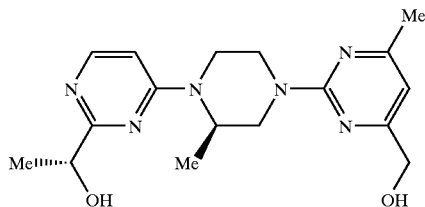

¹H NMR (CDCl₃, 400 MHz) δ 8.21 (d, 1H), 6.37 (d, 1H), 6.33 (s, 1H), 4.72 (m, 1H), 4.67–4.54 (c, 3H), 4.54 (s, 2H), 4.34 (d, 1H), 4.20 (d, 1H), 3.58 (br s, 1H), 3.42–3.32 (c, 2H), 3.26 (td, 1H), 2.34 (s, 3H), 1.51 (d, 3H), 1.21 (d, 3H); MS (APCI) 345 (MH⁺); [α]$_D$–35.0 (c 1.1, MeOH).

EXAMPLE 37
1R-{4-[4-(2-Hydroxymethyl-pyrimidin-4-yl)-3S-methyl-piperazin-1-yl]-pyrimidin-2-yl}-ethanol.

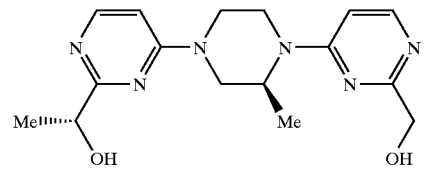

mp: 178–181° C.; ¹H NMR (CDCl₃, 400 MHz) δ 8.23 (d, 2H), 6.38 (d, 2H), 4.60 (q, 1H), 4.60 (s, 2H), 4.56 (m, 1H), 4.28–4.15 (c, 4H), 3.72 (br s, 1H), 3.58 (dd, 1H), 3.48 (m, 1H), 3.33 (td, 1H), 1.51 (d, 3H), 1.23 (d, 3H); MS (APCI) 331 (MH⁺); [a]$_D$+88.9 (c 1.1, MeOH).

EXAMPLE 38

1R-(4-{4-[2-(1R-Hydroxy-ethyl)-pyrimidin-4-yl]-2S-methyl-piperazin-1-yl}-pyrimidin-2-yl)-ethanol.

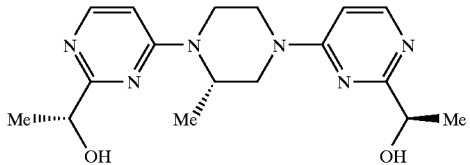

mp: 158–160° C.; ¹H NMR (CDCl₃, 400 MHz) δ 8.24 (d, 2H), 6.39 (d, 1H), 6.38 (d, 1H), 4.71 (m, 2H), 4.55 (br s, 1H), 4.32–4.16 (c, 5H), 3.60 (dd, 1H), 3.48 (td, 1H), 3.38 (td, 1H), 1.52 (d, 6H), 1.24 (d, 3H); MS (APCI) 345 (MH⁺); [α]$_D$+82.5 (c 1.0, MeOH).

EXAMPLE 39

1R-(4-{4-[2-(1R-Hydroxy-ethyl)-pyrimidin-4-yl]-2R-methyl-piperazin-1-yl}-pyrimidin-2-yl)-ethanol.

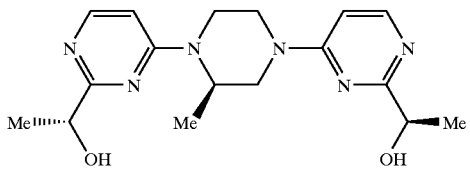

mp: 155–157° C.; ¹H NMR (CDCl₃, 400 MHz) δ 8.24 (d, 2H), 6.39 (d, 1H), 6.38 (d, 1H), 4.73 (m, 2H), 4.58 (br s, 1H), 4.32–4.16 (c, 5H), 3.59 (dd, 1H), 3.50 (m, 1H), 3.38 (m, 1H), 1.52 (d, 6H), 1.25 (d, 3H); MS (APCI) 345 (MH⁺); [α]$_D$−30.4 (c 0.9, MeOH).

EXAMPLE 40

1R-(4-{3-[2-(1R-Hydroxy-ethyl)-pyrimidin-4-yl]-3,9-diaza-bicyclo[3.3.1]non-9-yl}-pyrimidin-2-yl)-ethanol.

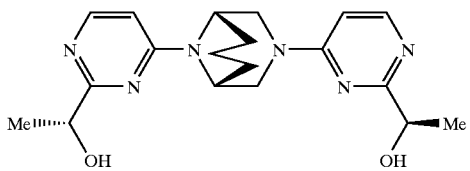

mp: 151–158° C.; ¹H NMR (CDCl₃, 400 MHz) δ 8.24 (d, 2H), 6.42 (d, 1H), 6.41 (d, 1H), 4.72 (m, 2H), 4.48–4.18 (c, 2H), 4.29 (dd, 2H), 3.28 (d, 2H), 2.03 (m, 1H), 1.98–1.82 (c, 4H), 1.58 (m, 1H), 1.51 (d, 3H), 1.50 (d, 3H); MS (APCI) 371 (MH⁺); [α]$_D$+27.6 (c 0.9, MeOH).

EXAMPLE 41

1R-(4-{4-[2-(1S-Hydroxy-ethyl)-pyrimidin-4-yl]-2R,6S-dimethyl-piperazin-1-yl}-pyrimidin-2-yl)-ethanol.

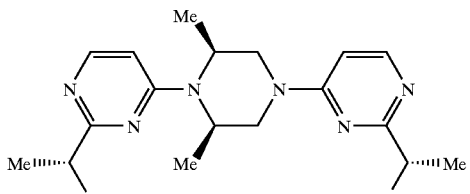

mp: 222–223.5° C.; ¹H NMR (CDCl₃, 400 MHz) δ 8.24 (d, 1H), 8.23 (d, 1H), 6.46 (d, 1H), 6.36 (d, 1H), 4.75–4.51 (c, 4H), 4.50–4.30 (c, 4H), 3.31 (dt, 2H), 1.51 (d, 6H), 1.26 (d, 6H); MS (APCI) 359 (MH⁺); [α]$_D$−3.4 (c 0.5, CHCl₃).

EXAMPLE 42

1S-(4-{4-[2-(1R-Hydroxy-ethyl)-pyrimidin-4-yl]-2R,6S-dimethyl-piperazin-1-yl}-pyrimidin-2-yl)-ethanol.

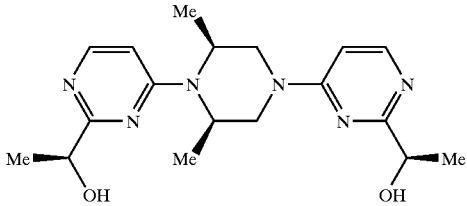

mp: 224–226° C.; ¹H NMR (CDCl₃, 400 MHz) δ 8.24 (d, 1H), 8.23 (d, 1H), 6.46 (d, 1H), 6.36 (d, 1H), 4.76–4.51 (c, 4H), 4.50–4.23 (c, 4H), 3.33 (dt, 2H), 1.51 (d, 6H), 1.25 (d, 6H); MS (APCI) 359 (MH⁺); [α]$_D$+64.2 (c 0.5, CHCl₃).

EXAMPLE 43

1 S-(4-{4-[2-(1S-Hydroxy-ethyl)-pyrimidin-4-yl]-2R,6S-dimethyl-piperazin-1-yl}-pyrimidin-2-yl)-ethanol.

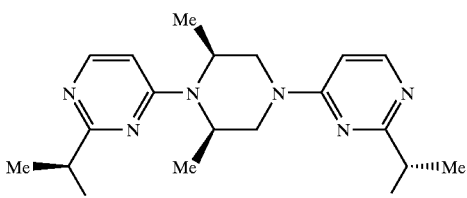

mp: 164–165.5° C.; ¹H NMR (CDCl₃, 400 MHz) δ 8.24 (d, 1H), 8.23 (d, 1H), 6.46 (d, 1H), 6.36 (d, 1H), 4.75–4.51 (c, 4H), 4.50–4.23 (c, 4H), 3.47–3.28 (c, 2H), 1.51 (d, 6H), 1.25 (d, 6H); MS (APCI) 359 (MH⁺); [α]$_D$−43.8 (c 1.0, MeOH).

EXAMPLE 44

1RS-(4-{4-[2-(1RS-Hydroxy-ethyl)-pyrimidin-4-yl]-2R*,6S*-dimethyl-piperazin-1-yl}-pyrimidin-2-yl)-ethanol.

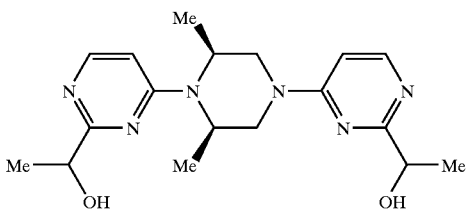

mp: 180–186° C.; ¹H NMR (CDCl₃, 400 MHz) δ 8.24 (d, 1H), 8.23 (d, 1H), 6.46 (d, 1H), 6.36 (d, 1H), 4.75–4.51 (c, 4H), 4.50–4.23 (c, 4H), 3.47–3.28 (c, 2H), 1.51 (d, 6H), 1.25 (d, 6H); MS (APCI) 359 (MH⁺).

EXAMPLE 45

1-(4-{4-[2-(1R-Hydroxy-ethyl)-pyrimidin-4-yl]-2R,6S-dimethyl-piperazin-1-yl}-pyrimidin-2-yl)-ethanone.

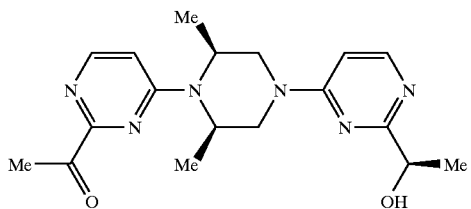

mp: 123–127° C.; $^1$H NMR (CDCl$_3$, 400 MHz) δ 8.41 (d, 1H), 8.24 (d, 1H), 6.56 (d, 1H), 6.47 (d, 1H), 4.75–4.53 (c, 3H), 4.52–4.28 (c, 2H), 4.26 (m, 1H), 3.36–3.29 (c, 2H), 2.68 (s, 3H), 1.51 (d, 3H), 1.28 (d, 6H); MS (APCI) 357 (MH$^+$); [α]$_D$+19.4 (c 1.0, MeOH).

EXAMPLE 46

1-(4-{4-[2-(1R-Hydroxy-ethyl)-pyrimidin-4-yl]-3R,5S-dimethyl-piperazin-1-yl}-pyrimidin-2-yl)-ethanone.

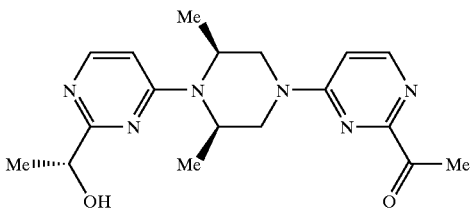

mp: 150–164° C.; $^1$H NMR (CDCl$_3$, 400 MHz) δ 8.40 (d, 1H), 8.24 (d, 1H), 6.66 (d, 1H), 6.37 (d, 1H), 4.74–4.52 (c, 3H), 4.51–4.31 (c, 2H), 4.29 (m, 1H), 3.36 (dd, 2H), 2.69 (s, 3H), 1.51 (d, 3H), 1.27 (d, 6H); MS (APCI) 357 (MH$^+$); [α]$_D$+21.8 (c 1.1, MeOH).

EXAMPLE 47

1R-(4-{4-[2-(1R-Hydroxy-ethyl)-pyrimidin-4-yl]-2R,6R-dimethyl-piperazin-1-yl}-pyrimidin-2-yl)-ethanol.

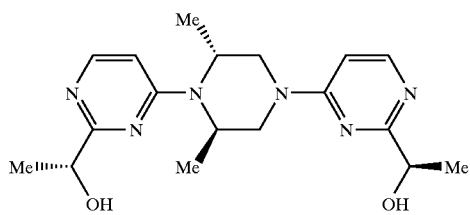

mp: 168–171° C.; $^1$H NMR (CDCl$_3$, 400 MHz) δ 8.27 (d, 1H), 8.23d, 1H), 6.33 (d, 1H), 6.30 (d, 1H), 4.78–4.69 (c, 2H), 4.68–4.28 (c, 5H), 3.83–3.69 (c, 2H), 3.54 (m, 1H), 1.53 (d, 3H), 1.52 (d, 3H), 1.43–1.22 (c, 6H); MS (APCI) 359 (MH$^+$); [α]$_D$+92.2 (c 0.5, MeOH).

EXAMPLE 48

1R-(4-{4-[2-(1R-Hydroxy-ethyl)-pyrimidin-4-yl]-2S,6S-dimethyl-piperazin-1-yl}-pyrimidin-2-yl)-ethanol.

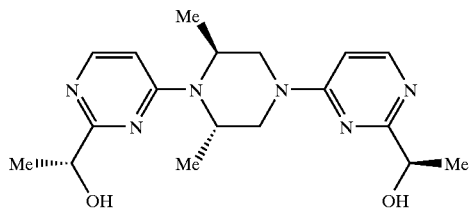

mp: 168–178° C.; $^1$H NMR (CDCl$_3$, 400 MHz) δ 8.26 (d, 1H), 8.23 (d, 1H), 6.32 (d, 1H), 6.29 (d, 1H), 4.78–4.68 (c, 2H), 4.65–4.27 (c, 5H), 3.82–3.71 (c, 2H), 3.55 (m, 1H), 1.52 (d, 3H), 1.51 (d, 3H), 1.43–1.20 (c, 6H); MS (APCI) 359 (MH$^+$); [α]$_D$−32.4 (c 0.7, MeOH).

| Example | X—Ar$^1$ | R$^6$ | R$^7$ | mp (° C.) | MS (MH$^+$) |
|---|---|---|---|---|---|
| 49 | benzoxazol-2-yl | (R)—Me | (S)—Me | | 354 |
| 50 | benzothiazol-2-yl | (R)—Me | (S)—Me | | 370 |
| 51 | oxazolo[4,5-c]pyridin-2-yl | (R)—Me | (S)—Me | | 355 |
| 52 | quinoxalin-2-yl | (R)—Me | H | | 351 |
| 53 | quinoxalin-2-yl | (S)—Me | H | | 351 |
| 54 | quinoxalin-2-yl | (R)—Me | (S)—Me | | 365 |
| 55 | (4,6-dimethyl)-pyrimidin-2-yl | H | H | 132–133 | 315 |
| 56 | (4,6-dimethyl)-pyrimidin-2-yl | (S)—Me | H | | 329 |
| 57 | (2,6-dimethyl)-pyrimidin-4-yl | H | H | 125.5–127 | 314 |

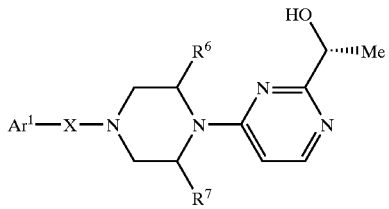

| Example | X—Ar¹ | R⁶ | R⁷ | mp (° C.) | MS (MH⁺) |
|---|---|---|---|---|---|
| 58 | (2-hydroxymethyl)-pyrimidin-4-yl | (S)—Me | H | 146–148 | 331 |
| 59 | (2-hydroxymethyl)-pyrimidin-4-yl | (R)—Me | (S)—Me | 168–171 | 345 |
| 60 | (2-hydroxymethyl-6-methyl)-pyrimidin-4-yl | (S)—Me | H | | 345 |

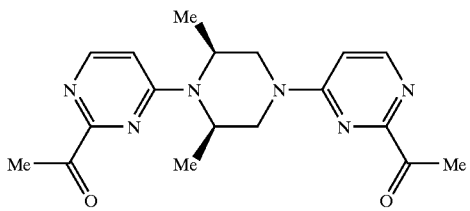

| Example | X—Ar¹ | mp (° C.) | MS (MH⁺) |
|---|---|---|---|
| 61 | (4-hydroxymethyl-6-methy)-lpyrimidin-2-yl | | 357 |
| 62 | (R)-[2-(1-hydroxy-ethyl)]-pyrimidin-4-yl | | 357 |

EXAMPLE 63

1-{4-[4-(2-Acetyl-pyrimidin-4-yl)-2R*,6S*-dimethyl-piperazin-1-yl]-pyrimidin-2-yl}-ethanone.

A mixture of 1S-(4-{4-[2-(1R-hydroxy-ethyl)-pyrimidin-4-yl]-2R,6S-dimethyl-piperazin-1-yl}-pyrimidin-2-yl)-ethanol (prepared according to the method of Example 42, 1.05 g, 2.93 mmol) and manganese(IV) oxide (5.15 g, 59.3 mmol) in dichloroethane (28 mL) was heated at reflux for 7 h, and filtered through Celite (hot). The filtrate was concentrated and purified by flash column chromatography (Flash 40M™, 5% methanol/chloroform) to give 0.67 g (64%) of the title compound as a white solid. mp: >235° C. (dec); ¹H NMR (CDCl₃, 400 MHz) δ 8.42 (d, 1H), 8.41 (d, 1H), 6.68 (d, 1H), 6.57 (d, 1H), 4.81–4.36 (c, 4H), 3.39 (dd, 2H), 2.69 (s, 3H), 2.68 (s, 3H), 1.29 (d, 6H); MS (APCI) 355 (MH⁺).

EXAMPLE 64

1R-{4-[4-(4-Hydroxymethyl-6-methyl-pyrimidin-2-yl)-3R,5S-dimethyl-piperazin-1-yl]-pyrimidin-2-yl}-ethanol.

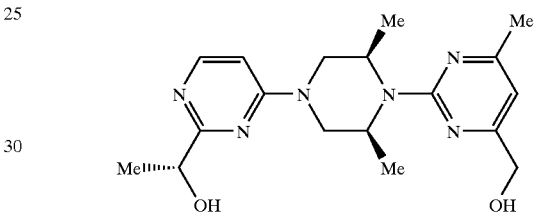

Step A: 1R-{4-[4-(tert-Butoxycarbonylamino-tert-butoxycarbonylimino-methyl)-3R,5S-dimethyl-piperazin-1-yl]-pyrimidin-2-yl}-ethyl butyrate. To a mixture of 1R-[4-(3R,5S-dimethyl-piperazin-1-yl)-pyrimidin-2-yl]-ethyl butyrate (prepared according to the method of Preparation Three, 10 g, 32.7 mmol), N,N'-bis(tert-butoxycarbonyl) thiourea (8.6 g, 32.7 mmol; Synth. Commun. 1993, 23, 1443), and triethylamine (9.0 mL, 65.4 mmol) in dimethylformamide (110 mL) at 0° C. was added mercury(II) chloride (9.8 g, 36.0 mmol). This mixture was stirred overnight with warming to room temperature, diluted with ethyl acetate, and washed with water (3×) and brine (1×). The organic phase was dried over sodium sulfate, filtered, and evaporated to give 17.9 g (100%) of the title compound of Example 64, Step A as a yellow foam. ¹H NMR (CDCl₃, 300 MHz) δ 9.61 (s, 1H), 8.19 (d, 1H), 6.37 (d, 1H), 5.66 (q, 1H), 4.51–4.14 (c, 4H), 3.36–3.23 (c, 2H), 2.37 (t, 2H), 1.75–1.60 (c, 2H), 1.55 (d, 3H), 1.49 (s, 9H), 1.46 (s, 9H), 1.28 (d, 3H), 1.26 (d, 3H), 0.94 (t, 3H); MS (APCI) 549 (MH⁺).

Step B: 1R-[4-(4-Carbamimidoyl-3R,5S-dimethyl-piperazin-1-yl)-Pyrimidin-2-yl]-ethyl butyrate trifluoroacetic acid salt. A mixture of 1R-{4-[4-(tert-butoxycarbonylamino-tert-butoxycarbonylimino-methyl)-3R,5S-dimethyl-piperazin-1-yl]-pyrimidin-2-yl}-ethyl butyrate (prepared according to the method of Example 64, Step A, 17.9 g, 32.7 mmol) in a 3:1 mixture of dichloromethane/trifluoroacetic acid (300 mL) was stirred at room temperature overnight and concentrated to provide ~36 g of the title compound of Example 64, Step B as an oil that was used as is. ¹H NMR (CD₃OD, 400 MHz) δ 8.24 (d, 1H), 7.25 (d, 1H), 5.69 (q, 1H), 4.19–4.10 (c, 4H), 3.79–3.42 (c, 2H), 2.45 (t, 2H), 1.67–1.45 (c, 2H), 1.63 (d, 3H), 1.32–1.25 (c, 6H), 0.95 (t, 3H); MS (APCI) 3.49 (MH⁺).

Step C: 1R-{4-[4-(4-Methoxymethyl-6-methyl-pyrimidin-2-yl)-3R,5S-dimethyl-piperazin-1-yl]-pyrimidin- 2-yl}-ethanol. A solution of 1 M sodium isopropoxide in isopropanol was prepared by adding sodium metal (3.8 g, 160 mmol) to isopropanol (160 mL) and heating at reflux until all the metal was consumed. 1R-[4-(4-Carbamimidoyl-3R,5S-dimethyl-piperazin-1-yl)-pyrimidin-2-yl]-ethyl butyrate trifluoroacetic acid salt (prepared according to the method of Example 64, Step B, 32.7 mmol theory) was added to the refluxing sodium isopropoxide/isopropanol solution followed, after 1 h, by 1-methoxy-pentane-2,4-dione (21.2 g, 163 mmol; J. Am. Chem. Soc. 1944, 22, 2092). After 12 h, another aliquot of sodium isopropoxide (1 M in isopropanol, 65 mL, 65 mmol) was added. After refluxing overnight, the reaction mixture was cooled to room temperature and diluted with water (100 mL). Lithium hydroxide hydrate (6.9 g, 163 mmol) was added and this mixture was stirred for 3 h, concentrated, and extracted with 10% isopropanol/chloroform (3×). The combined organic extracts were dried over sodium sulfate, filtered, evaporated, and purified by flash column chromatography (1→2.5% methanol/chloroform) to give 10.5 g (87%, 2 steps) of the title compound of Example 64, Step C as a yellow solid.
$^1$H NMR (CDCl$_3$, 400 MHz) δ 8.18 (d, 1H), 6.54 (s, 1H), 6.43 (d, 1H), 5.00–4.94 (c, 2H), 4.69 (m, 1H), 4.37–4.34 (c, 2H), 4.33 (s, 2H), 3.45 is, 3H), 3.29–3.23 (c, 2H), 2.33 (s, 3H), 1.51 (d, 3H), 1.20 (s, 6H); MS (APCI) 373 (MH$^+$).

Step D: 1R-{4-[4-(4-Hydroxymethyl-6-methyl-pyrimidin-2-yl)-3R,5S-dimethyl-piperazin-1-yl]-pyrimidin-2-yl}-ethanol. To a solution of 1R-{4-[4-(4-methoxymethyl-6-methyl-pyrimidin-2-yl)-3R,5S-dimethyl-piperazin-1-yl]-pyrimidin-2-yl}-ethanol (prepared according to the method of Example 64, Step C, 8.0 g, 21.5 mmol) in dichloromethane (150 mL) at 0° C. was added boron tribromide (1 M in dichloromethane, 64.3 mL, 64.3 mmol). This mixture was stirred overnight with warming to room temperature and quenched by careful addition of saturated aqueous sodium bicarbonate. The layers were separated and the aqueous phase was extracted with 10% isopropanol/chloroform (3×). The combined organic extracts were washed with brine (1×), dried over sodium sulfate, filtered, and evaporated. The resulting solid was refluxed in ethyl acetate and filtered (hot). This procedure was repeated and the combined filtrates were concentrated to a minimal volume. After standing at room temperature overnight, a tan solid was collected by filtration. The resulting filtrate was again allowed to stand at room temperature overnight to yield an additional crop of the desired product to give all together 6.0 g (78%) of the title compound as a tan solid. mp: 149–151° C.; $^1$H NMR (CDCl$_3$, 400 MHz) δ 8.19 (d, 1H), 6.45 (d, 1H), 6.32 (s, 1H), 5.02–4.96 (c, 2H), 4.71 (q, 1H), 4.53 (s, 2H), 4.50–4.23 (c, 2H), 3.31–3.25 (c, 2H), 2.33 (s, 3H), 1.51 (d, 3H), 1.23 (s, 6H); MS (APCI) 359 (MH$^+$); [α]$_D$+18.9 (c 1.1, MeOH).

EXAMPLES 65 TO 74

Examples 65 to 74 were prepared from the appropriate starting materials in a manner analogous to the method of Example 64.

EXAMPLE 65
(R)-1-{4-[4-(4-Hydroxymethyl-6-methyl-pyrimidin-2-yl)-piperazin-1-yl]-pyrimidin-2-yl}-ethanol.

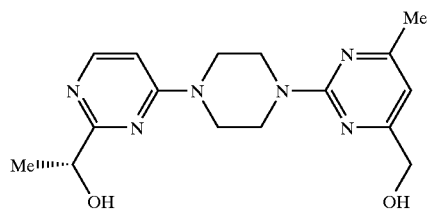

mp: 139–140° C.; $^1$H NMR (CDCl$_3$, 300 MHz) δ 8.21 (d, 1H), 6.41 (d, 1H), 6.37 (s, 1H), 4.71 (m, 1H), 4.54 (s, 2H), 4.32 (d, 1H), 4.02–3.93 (c, 4H), 3.78–3.68 (c, 4H), 3.65 (br s, 1H), 2.34 (s, 3H), 1.19 (d, 3H); MS (TS) 331 (MH$^+$); [α]$_D$+21.6 (c 2.0, MeOH).

EXAMPLE 66

1R-{4-[4-(4,6-Dimethyl-pyrimidin-2-yl)-3R,5S-dimethyl-piperazin-1-yl]-pyrimidin-2-yl}-ethanol.

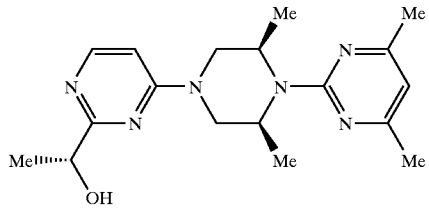

mp: 141.5–142.5° C.; $^1$H NMR (CDCl$_3$, 400 MHz) δ 8.17 (d, 1H), 6.43 (d, 1H), 6.28 (s, 1H), 5.03–4.97 (c, 2H), 4.70 (q, 1H), 4.44–4.18 (c, 2H), 3.32–3.20 (c, 2H), 2.27 (s, 6H), 1.50 (d, 3H), 1.20 (d, 6H); MS (APCI) 343 (MH$^+$); [α]$_D$+19.2 (c 1.1, MeOH).

EXAMPLE 67

1R-{4-[4-(4-Methoxymethyl-6-methyl-pyrimidin-2-yl)-3R,5S-dimethyl-piperazin-1-yl]-pyrimidin-2-yl}-ethanol.

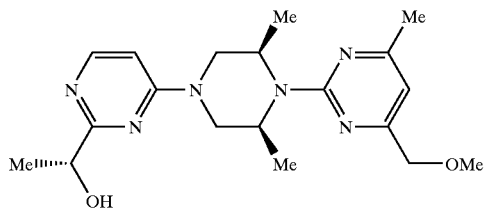

$^1$H NMR (CDCl$_3$, 400 MHz) δ 8.18 (d, 1H), 6.55 (s, 1H), 6.43 (d, 1H), 5.02–4.93 (c, 2H), 4.69 (m, 1H), 4.43–4.20 (c, 2H), 4.36 (d, 1H), 4.33 (s, 2H), 3.46 (s, 3H), 3.30–3.21 (c, 2H), 2.34 (s, 3H), 1.51 (d, 3H), 1.20 (d, 6H); MS (APCI) 373 (MH$^+$); [α]$_D$+16.0 (c 0.9, MeOH).

EXAMPLE 68

1R-{4-[4-(4-Hydroxymethyl-6-methyl-pyrimidin-2-yl)-3R-methyl-piperazin-1-yl]-pyrimidin-2-yl}-ethanol.

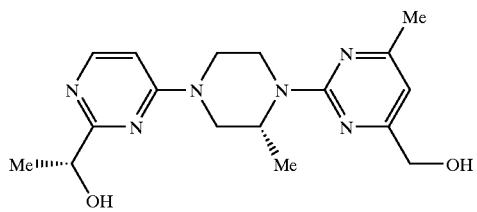

¹H NMR (CdCl₃, 400 MHz) δ 8.17 (d, 1H), 6.36 (d, 1H), 6.32 (s, 1H), 4.98 (m, 1H), 4.69 (q, 1H), 4.58 (dt, 1H), 4.51 (s, 2H), 4.37–4.11 (c, 3H), 3.62 (br s, 1H), 3.48–3.36 (c, 2H), 3.18 (td, 1H), 2.31 (s, 3H), 1.49 (d, 3H), 1.17 (s, 3H); MS (APCI) 359 (MH⁺); [α]$_D$ −40.6 (c 1.0, MeOH).

EXAMPLE 69

1R-{4-[4-(4-Hydroxymethyl-6-methyl-pyrimidin-2-yl)-3S-methyl-piperazin-1-yl]-pyrimidin-2-yl}-ethanol.

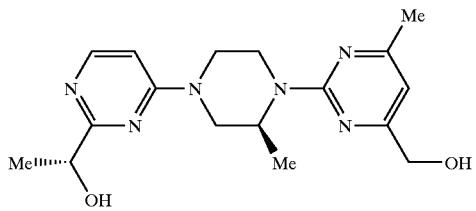

¹H NMR (CDCl₃, 400 MHz) δ 8.17 (d, 1H), 6.36 (d, 1H), 6.33 (s, 1H), 4.99 (m, 1H), 4.69 (q, 1H), 4.58 (m, 1H), 4.52 (s, 2H), 4.40–4.11 (c, 3H), 3.60 (br s, 1H), 3.45–3.34 (c, 2H), 3.19 (td, 1H), 2.32 (s, 3H), 1.49 (d, 3H), 1.16 (s, 3H); MS (APCI) 359 (MH⁺); [α]$_D$+68.1 (c 0.7, MeOH).

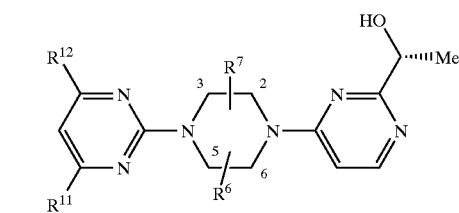

| Example | R¹¹ | R¹² | R⁷ | R⁶ | mp (° C.) | MS (MH⁺) |
|---|---|---|---|---|---|---|
| 70 | H | OH | 3R—Me | 5S—Me | | 331 |
| 71 | Me | OH | 3R—Me | 5S—Me | 231–232 | 345 |
| 72 | Ph | OH | 3R—Me | 5S—Me | | 407 |
| 73 | Me | ethoxymethyl | 3R—Me | 5S—Me | | 387 |
| 74 | Me | ethoxymethyl | 2R—Me | 6S—Me | 106–108 | 387 |

EXAMPLE 75

(R)-5-[2-(1-Hydroxy-ethyl)-pyrimidin-4-yl]-1-methyl-2-quinoxalin-2-yl-1,2,4,5,6,7-hexahydro-pyrazolo[4.3-c]pyridin-3-one.

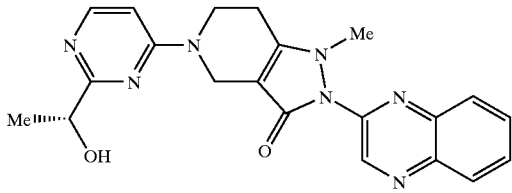

Step A: 3-Oxo-2-quinoxalin-2-yl-1,2,3,4,6,7-hexahydro-pyrazolo[4,3-c]pyridine-5-carboxylic acid tert-butyl ester. To a solution of 4-oxo-piperidine-1,3-dicarboxylic acid 1-tert-butyl ester 3-ethyl ester (500 mg, 1.84 mmol; Tetrahedron 1994, 50, 515) in toluene (10 mL) was added quinoxalin-2-yl-hydrazine (295 mg, 1.85 mmol; Heterocycles 1985, 23, 2603). This mixture was stirred at reflux overnight, cooled to room temperature, concentrated, and purified by flash column chromatography (25→75% ethyl acetate/hexanes) to give 600 mg (89%) of the title compound of Example 75, Step A as a light orange solid. ¹H NMR (CDCl₃, 250 MHz, 5:1 mixture of tautomers) δ 11.94 (br s, 0.83H), 10.16 (s, 0.17H), 9.57 (s, 0.83H), 8.13 (dd, 1H), 7.91–7.69 (c, 3H), 4.45 (s, 1.66H), 4.33 (s, 0.34H), 3.79–3.72 (c, 2H), 2.82–2.72 (c, 2H), 1.52 (s, 9H); MS (APCI) 368 (MH⁺).

Step B: 1-Methyl-3-oxo-2-quinoxalin-2-yl-1,2,3,4,6,7-hexahydro-pyrazolo[4,3-c]pyridine-5-carboxylic acid tert-butyl ester. To a solution of 3-oxo-2-quinoxalin-2-yl-1,2,3,4,6,7-hexahydro-pyrazolo[4,3-c]pyridine-5-carboxylic acid tert-butyl ester (prepared according to the method of Example 75, Step A, 250 mg, 0.68 mmol) in dimethylformamide (2 mL) at 0° C. with stirring under nitrogen was added sodium hydride (60% dispersion in mineral oil, 41 mg, 1.02 mmol). After 10 min, iodomethane (51 μL, 0.82 mmol) was added. This mixture was allowed to stir at 0° C. for 2 h, quenched by addition of saturated aqueous sodium bicarbonate and extracted with ethyl acetate (4×). The combined organic extracts were dried over sodium sulfate, filtered, evaporated, and purified by flash column chromatography (40% ethyl acetate/hexanes) to give 164 mg (63%) of the title compound of Example 75, Step B as a yellow foam. ¹H NMR (CDCl₃, 250 MHz) δ 9.71 (s, 1H), 8.15 (dd, 1H), 8.02 (m, 1H), 7.80–7.70 (c, 2H), 4.29 (s, 2H), 4.14 (t, 2H), 3.79 (s, 3H), 2.72–2.67 (c, 2H), 1.50 (s, 9H); MS (APCI) 382 (MH⁺).

Step C: 1-Methyl-2-quinoxalin-2-yl-1.2.4,5,6,7-hexahydro-pyrazolo[4,3-c]pyridin-3-one hydrochloride. To a solution of 1-methyl-3-oxo-2-quinoxalin-2-yl-1,2,3,4,6,7-hexahydro-pyrazolo[4,3-c]pyridine-5-carboxylic acid tert-butyl ester (prepared according to the method of Example 75, Step B, 279 mg, 0.73 mmol) in methanol (6 mL) was added hydrogen chloride (5.85 M in methanol, 1.25 mL, 7.3 mmol). This mixture was heated at 60° C. for 30 min, cooled to room temperature, and concentrated to give 249 mg (>100%) of the title compound of Example 75, Step C as a dark red solid. ¹H NMR (CD₃OD, 250 MHz) δ 9.45 (s, 1H), 8.13 (dd, 1H), 8.05 (m, 1H), 7.91–7.83 (c, 2H), 4.05 (s, 2H), 3.64 (t, 2H), 3.56 (s, 3H), 3.12 (t, 2H), MS (APCI) 282 (MH⁺).

Step D: (R)-1-[4-(1-Methyl-3-oxo-2-quinoxalin-2-yl-1,2,3,4,6,7-hexahydro-pyrazolo[4.3-c]pyridin-5-yl)-pyrimidin-2-yl]-ethyl butyrate. To a stirred solution of 1-methyl-2-quinoxalin-2-yl-1,2,4,5,6,7-hexahydro-pyrazolo[4,3-c]pyridin-3-one hydrochloride (prepared according to the method of Example 75, Step C, 175 mg, 0.55 mmol) and (R)-1-(4-chloro-pyrimidin-2-yl)-ethyl butyrate (prepared according to the method of Preparation Seven, 126 mg, 0.55 mmol) in isopropanol (6 mL) was added triethylamine (230 μL, 1.66 mmol). This mixture was heated to reflux overnight, cooled to room temperature, and evaporated. The residue was diluted with saturated aqueous sodium bicarbonate and extracted with chloroform (3×). The combined organic extracts were dried over sodium sulfate, filtered, evaporated, and purified by flash column chromatography (1.5% methanol/chloroform) to give 248 mg (95%) of the title compound of Example 75, Step D as a yellow oil. ¹H NMR (CDCl₃, 250 MHz) δ 9.70 (s, 1H), 8.29 (d, 1H), 8.15 (dd, 1H), 8.03 (m, 1H), 7.82–7.70 (c, 2H), 6.48 (d, 1H) 5.72 (q, 1H), 4.36 (s, 2H), 4.354.15 (c, 2H), 3.42 (s, 3H), 2.77–2.82 (c, 2H), 2.43 (t, 2H), 1.79–1.60 (c, 2H), 1.61 (d, 3H), 0.99 (t, 3H); MS (APCI) 474 (MH⁺).

Step E: (R)-5-[2-(1-Hydroxy-ethyl)-pyrimidin-4-yl]-1-methyl-2-quinoxalin-2-yl-1,2,4,5,6,7-hexahydro-pyrazolo

[4.3-c]pyridin-3-one. To a solution of (R)-1-[4-(1-methyl-3-oxo-2-quinoxalin-2-yl-1,2,3,4,6,7-hexahydro-pyrazolo[4,3-c]pyridin-5-yl)-pyrimidin-2-yl]-ethyl butyrate (prepared according to the method of Example 75, Step D, 248 mg, 0.52 mmol) in a 5:2 mixture of methanol/tetrahydrofuran (7 mL) was added potassium carbonate (218 mg, 1.57 mmol). This mixture was stirred at room temperature overnight and evaporated. The residue was diluted with saturated aqueous sodium bicarbonate and extracted with chloroform (3×). The combined organic extracts were dried over sodium sulfate, filtered, evaporated, and purified by flash column chromatography (1.5→3% methanol/chloroform) to give 150 mg (71%) of the title compound as a white solid. mp: 217–219° C. (dec); $^1$H NMR (CDCl$_3$, 250 MHz) δ 9.66 (s, 1H), 8.25 (d, 1H), 8.12 (dd, 1H), 7.99 (m, 1H), 7.68–7.78 (c, 2H), 6.47 (d, 1H), 4.72 (q, 12H), 4.32 (s, 2H), 4.19–4.14 (c, 3H), 3.41 (s, 3H), 2.80 (t, 2H), 1.51 (d, 3H); MS (APCI) 404 (MH$^+$); [a]$_D$+13.4 (c 1.5, CHCl$_3$).

EXAMPLES 76 AND 77

Examples 76 and 77 were prepared from the appropriate starting materials in a manner analogous to the method of Example 75.

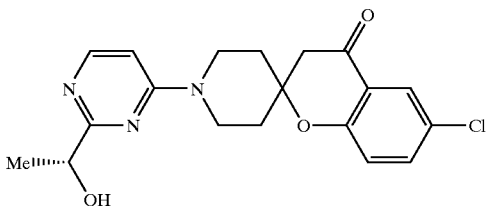

| Example | A | R$^{33}$ | B | mp (° C.) | MS (MH$^+$) |
|---|---|---|---|---|---|
| 76 | N—Me | benzothiazol-2-yl | CO | 176–178 | 409 |
| 77 | CO | quinoxalin-2-yl | N—Me | 201–204 (dec) | 404 |

EXAMPLE 78

(R)-6-Chloro-1'-[2-(1-hydroxy-ethyl)-pyrimidin4-yl]-spiro[chroman-2,4'-piperidin]-4-one.

Step A: 6-Chloro-spiro[chroman-2,4'-piperidin]-4-one hydrochloride. To a solution of 1'-benzyl-6-chloro-spiro[chroman-2,4'-piperidin]4-one (300 mg, 0.88 mmol, Chem. Pharm. Bull. 1981, 29, 3494) in acetone (5 mL) at 0° C. was added 1-chloroethyl chloroformate (0.29 mL, 2.64 mmol). This mixture was warmed to room temperature, stirred overnight, and concentrated. The residue was purified by flash column chromatography (10→20% ethyl acetate/hexanes) to give the intermediate carbamate which was refluxed in methanol (3 mL) for 1 h. Evaporation of the reaction mixture provided 149 mg (59%) of the title compound of Example 78, Step A as a colorless solid. $^1$H NMR (CD$_3$OD, 250 MHz) 67.77 (d, 1H), 7.58 (dd, 1H), 7.15 (d, 1H), 3.33 (buried, 4H), 2.90 (s, 2H), 2.46–2.20 (c, 2H), 2.04–1.81 (c, 2H); MS (APCI) 252, 254 (MH$^+$).

Step B: (R)-1'-[2-(1-Butyryloxy-ethyl)-pyrimidin-4-yl]-6-chloro-spiro[chroman-2,4'-piperidin]-4-one. To a solution of 6-chloro-spiro[chroman-2,4'-piperidin]-4-one hydrochloride (prepared according to the method of Example 78, Step A, 175 mg, 0.61 mmol) in isopropanol (5 mL) was added (R)-1-(4-chloro-pyrimidin-2-yl)-ethyl butyrate (prepared according to the method of Preparation Seven, 160 mg, 0.70 mmol) followed by triethylamine (0.29 mL, 2.1 mmol). This mixture was stirred at reflux for 1.5 h, concentrated, and purified by flash column chromatography (1% methanol/chloroform) to give 270 mg (100%) of the title compound of Example 78, Step B as a yellow oil. $^1$H NMR (CDCl$_3$, 400 MHz) δ 8.19 (d, 1H), 7.83 (d, 1H), 7.44 (dd, 1H), 6.97 (d, 1H), 6.37 (d, 1H), 5.64 (q, 1H), 4.18 (app s, 2H), 3.34 (t, 2H), 2.72 (s, 2H), 2.37 (t, 2H), 2.10 (d, 2H), 1.71–1.60 (c, 4H), 1.55 (d, 3H), 0.94 (t, 3H); MS (APCI) 444, 446 (MH$^+$).

Step C: (R)-6-Chloro-1'-[2-(1-hydroxy-ethyl)-pyrimidin4-yl]-spiro[chroman-2,4'-piperidin]-4-one. A mixture of (R)-1'-[2-(1-butyryloxy-ethyl)-pyrimidin4-yl]-6-chloro-spiro[chroman-2,4'-piperidin]4-one (prepared according to the method of Example 78, Step B, 270 mg, 0.61 mmol) and lithium hydroxide hydrate (80 mg, 1.83 mmol) in a 3:1:1 mixture of tetrahydrofuran/methanol/water (5 mL) was stirred at room temperature for 1.5 h. The organic solvents were evaporated and the residue was extracted with chloroform (4×). The combined organic extracts were dried over sodium sulfate, filtered, evaporated, and purified by flash column chromatography (ethyl acetate) to give 41 mg (18%) of the title compound as a reddish foam. $^1$H NMR (CDCl$_3$, 300 MHz) δ 8.19 (d, 1H), 7.82 (d, 1H), 7.44 (dd, 1H), 6.96 (d, 1H), 6.40 (d, 1H), 4.65 (q, 1H), 4.20 (app s, 2H), 3.42–3.32 (c, 2H), 2.73 (s, 2H), 2.14 (d, 2H), 1.67 (td, 2H), 1.48 (d, 3H); MS (APCI) 374, 376 (MH$^+$); [α]$_D$+12.6 (c 0.5, MeOH).

EXAMPLES 79 TO 85

Examples 79 to 85 were prepared from the appropriate starting materials in a manner analogous to the method of Example 78.

| Example | R$^{36}$ | R$^{37}$ | D | mp (° C.) | MS (MH$^+$) |
|---|---|---|---|---|---|
| 79 | 6-Ph | H | CH$_2$ | | 402 |
| 80 | 6-Ph | H | CHOH | | 418 |
| 81 | 6-Ph | H | CO | | 416 |
| 82 | 6-OMe | H | CO | 156.5–157.5 | 370 |
| 83 | 7-Br | H | CO | | 418,420 |
| 84 | 5-Cl | 6-Cl | CO | | 408,410 |
| 85 | 6-OMe | 7-OMe | CO | | 400 |

EXAMPLE 86

(R)-1-[4-(2-Methyl-4-phenyl-5,8-dihydro-6H-pyrido[3,4-d]pyrimidin-7-yl)-pyrimidin-2-yl]-ethanol.

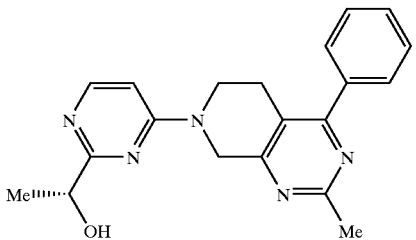

Step A: 7-Benzyl-2-methyl-5,6,7,8-tetrahydro-3H-pyrido[3.4-d]pyrimidin-4-one. A solution of sodium ethoxide in ethanol was prepared by addition of sodium metal (5.7 g, 247 mmol) to absolute ethanol (141 mL). After the sodium metal had all dissolved, ethyl 1-benzyl-3-oxo-4-piperidine carboxylate hydrochloride (21 g, 70.5 mmol) was added followed by acetamidine hydrochloride (13.3 g, 141 mmol). This mixture was stirred at reflux for 1 h, cooled to room temperature, and concentrated. The residue was dissolved in a minimum amount of water and the pH was adjusted to about 7 with glacial acetic acid. The resulting yellow precipitate was filtered, washed with water (3x), air-dried for 2 h, then vacuum-dried overnight to provide 17.1 g (95%) of the title compound of Example 86, Step A as a yellow solid. $^1$H NMR (CDCl$_3$, 250 MHz) δ 7.35–7.25 (c, 5H), 3.70 (s, 2H), 3.42 (s, 2H), 2.73–2.64 (c, 2H), 2.64–2.60 (c, 2H), 2.41 (s, 3H); MS (APCI) 256 (MH$^+$).

Step B: 7-Benzyl-4-chloro-2-methyl-5,8-dihydro-6H-pyrido[3,4-d]pyrimidine. 7-Benzyl-2-methyl-5,6,7,8-tetrahydro-3H-pyrido[3,4-d]pyrimidin-4-one (prepared according to the method of Example 86, Step A, 17.1 g, 67.0 mmol) was suspended in phosphorus oxychloride (66 mL, 335 mmol). This mixture was stirred at reflux for 1 h, cooled to room temperature, evaporated, then chased with toluene. The residue was carefully diluted with ice/water/chloroform and the layers were separated. The aqueous phase was extracted with chloroform (3x) and the combined organic extracts were washed with saturated aqueous sodium bicarbonate (1x) and water (1x), dried over sodium sulfate, filtered, and evaporated to give the title compound of Example 86, Step B as a brown oil that was used without purification in the next step.

$^1$H NMR (CDCl$_3$, 250 MHz) δ 7.36–7.23 (c, 5H), 3.73 (s, 2H), 3.63 (s, 2H), 2.63 (app s, 4H), 2.36 (s, 3H); MS (APCI) 274, 276 (MH$^+$).

Step C: 7-Benzyl-2-methyl-4-phenyl-5,8-dihydro-6H-Pyrido[3,4-d]pyrimidine. To a suspension of 1,4-diphenylphosphinobutane (1.43 g, 3.35 mmol) in toluene (50 mL) was added bis(benzonitrile)palladium(II) chloride (1.28 g, 3.35 mmol). This mixture was stirred for 25 min at room temperature, then was added to a suspension of 7-benzyl-4-chloro-2-methyl-5,8-dihydro-6H-pyrido[3,4-d]pyrimidine (prepared according to the method of Example 86, Step B, 67.0 mmol, assumed) and phenylboronic acid (10.6 g, 87.1 mmol) in a mixture of absolute ethanol (40 mL), toluene (175 mL), and 2 N aqueous sodium carbonate (33.5 mL). This mixture was stirred at reflux for 6.5 h, cooled to room temperature and stirred for ~2.5 d, then filtered through a pad of Celite. The filtrate was concentrated and the residue was diluted with water and extracted with chloroform (3x). The combined organic extracts were dried over sodium sulfate, filtered, evaporated, and purified by flash column chromatography (45→50% ethyl acetate/hexanes) to give 16.5 g (78%, two steps) of the title compound of Example 86, Step C as a yellow oil. $^1$H NMR (CDCl$_3$, 250 MHz) δ 7.57–7.54 (c, 2H), 7.48–7.24 (c, 8H), 3.71 (app s, 4H), 2.85 (t, 2H), 2.71–2.67 (c, 2H), 2.69 (s, 3H); MS (APCI) 316 (MH$^+$).

Step D: 2-Methyl-4-phenyl-5,8-dihydro-6H-pyrido[3.4-d]pyrimidine. 7-Benzyl-2-methyl-4-phenyl-5,8-dihydro-6H-pyrido[3,4-d]pyrimidine hydrochloride was formed in situ by addition of hydrogen chloride (1.9 M in methanol, 31.1 mL, 51.1 mmol) to a solution of 7-benzyl-2-methyl-4-phenyl-5,8-dihydro-6H-pyrido[3,4-d]pyrimidine (prepared according to the method of Example 86, Step C, 16.5 g, 52.2 mmol) in methanol (75 mL). After stirring 10 min at room temperature, a precipitate formed, and another aliquot of methanol (100 mL) was added to obtain a homogeneous solution. To this mixture was added a slurry of 10% palladium on carbon (3.3 g, 20 wt %) in methanol followed by ammonium formate (16.5 g, 261 mmol). This mixture was stirred at reflux for 5 h, cooled to room temperature, and filtered through Celite. The filtrate was evaporated, diluted with saturated aqueous sodium bicarbonate, and extracted with chloroform (3x). The combined organic extracts were dried over sodium sulfate, filtered, evaporated, and purified by flash column chromatography (3% methanol/chloroform+1% ammonium hydroxide) to give 6.7 g (57%) of the title compound of Example 86, Step D as an off-white solid and 2.4 g (19%) of 7-formyl-2-methyl-4-phenyl-5,8-dihydro-6H-pyrido[3,4-d]pyrimidine as a yellow gum. Treatment of the 7-formyl byproduct with methanolic hydrogen chloride at room temperature overnight followed by aqueous workup and column chromatography provided an additional 1.4 g (12%) of the title compound of Example 86, Step D. $^1$H NMR (CDCl$_3$, 250 MHz) δ 7.55–7.40 (c, 5H), 4.09 (s, 2H), 3.05 (t, 2H), 2.75 (t, 2H), 2.79 (s, 3H); MS (APCI) 226 (MH$^+$).

Step E: (R)-1-[4-(2-Methyl-4-phenyl-5,8-dihydro-6H-pyrido[3,4-d]pyrimidin-7-yl)-pyrimidin-2-yl]-ethyl butyrate. To a solution of 2-methyl-4-phenyl-5,8-dihydro-6H-pyrido[3,4-d]pyrimidine (prepared according to the method of Example 86, Step D, 6.8 g, 30.0 mmol) in isopropanol (125 mL) was added (R)-1-(4-chloro-pyrimidin-2-yl)-ethyl butyrate (prepared according to the method of Preparation Seven, 6.8 g, 30 mmol) followed by triethylamine (12.5 mL, 89.9 mmol). This mixture was stirred at reflux for 8 h, cooled to room temperature overnight, and evaporated. The residue was diluted with saturated aqueous sodium bicarbonate and extracted with ethyl acetate (3x). The combined organic extracts were dried over sodium sulfate, filtered, evaporated, and purified by flash column chromatography (2% methanol/ethyl acetate) to give 11.0 g (88%) of the title compound of Example 86, Step E, as a yellow oil. $^1$H NMR (CDCl$_3$, 250 MHz) δ 8.28 (d, 1H), 7.62–7.40 (c, 5H), 6.45 (d, 1H ), 5.69 (q, 1H), 4.78 (s, 2H), 3.93 (app s, 2H), 2.95 (t, 2H), 2.77 (s, 3H), 2.40 (t, 2H), 1.77–1.63 (c, 2H), 1.60 (d, 3H), 0.98 (t, 3H); MS (APCI) 418 (MH$^+$).

Step F: (R)-1-[4-(2-Methyl-4-phenyl-5.8-dihydro-6H-pyrido[3,4-d]pyrimidin-7-yl)-pyrimidin-2-yl]-ethanol. To a solution of (R)-1-[4-(2-methyl-4-phenyl-5,8-dihydro-6H-pyrido[3,4-d]pyrimidin-7-yl)-pyrimidin-2-yl]-ethyl butyrate (prepared according to the method of Example 86, Step E, 11.0 g, 26.4 mmol) in dioxane (13 mL) was added concentrated hydrochloric acid (22 mL, 264 mmol). This mixture was stirred at room temperature overnight, cooled to 0° C., neutralized via slow addition of 6 N aqueous sodium hydroxide, and extracted with ethyl acetate (4x). The combined organic extracts were dried over sodium sulfate, filtered, evaporated, and purified by flash column chromatography (2→5% methanol/ethyl acetate) to give an oil which after titration with hexanes provided 8.0 g (88%) of the title compound as a white solid. mp: 114–116° C.; $^1$H NMR (CD$_3$OD, 250 MHz) δ 8.26 (d, 1H), 7.62–7.47 (c, 5H), 6.52 (d, 1H), 4.79 (s, 2H), 4.66 (q, 1H), 4.24 (br s, 1H), 3.90–3.80 (c, 2H), 2.95 (t, 2H), 2.70 (s, 3H), 1.49 (d, 3H); MS (APCI) 348 (MH$^+$), [α]$_D$+15.6 (c 1.0, MeOH).

EXAMPLES 87 TO 100

Examples 87 to 100 were prepared from the appropriate starting materials in a manner analogous to the method of Example 86.

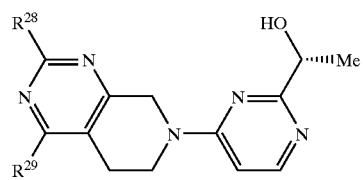

| Example | R$^{29}$ | R$^{28}$ | mp (° C.) | MS (MH$^+$) |
|---|---|---|---|---|
| 87 | H | Ph | 72–74 | 334 |
| 88 | Ph | H | | 334 |
| 89 | Ph | Et | | 362 |
| 90 | Ph | NH$_2$ | 225–228 (dec) | 349 |
| 91 | Ph | Ph | 73–75 | 410 |
| 92 | Ph | 4-pyridyl | | 411 |
| 93 | (4-OMe)Ph | Me | 62–64 | 378 |
| 94 | (4-F)Ph | Me | 55–58 | 366 |
| 95 | (4-Cl)Ph | H | | 368, 370 |
| 96 | OMe | Me | | 302 |
| 97 | OPh | Me | 156–158 | 364 |
| 98 | SPh | Me | 103–105 | 380 |
| 99 | N-indolinyl | Me | 128–131 | 389 |
| 100 | NMe$_2$ | Et | | 329 |

EXAMPLE 101

{4-[2-(1R-Hydroxy-ethyl)-pyrimidin-4-yl]-2R,6S-dimethyl-piperazin-1-yl}-(2-phenyl-7,8-dihydro-5H-pyrido[4,3-d]pyrimidin-6-yl)-methanone.

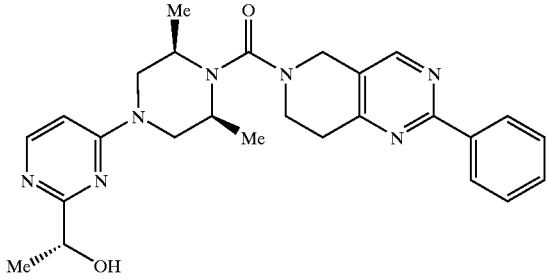

Step A: 4-Oxo-piperidine-1-carboxylic acid tert-butyl ester. A mixture of 4-piperidone monohydrate hydrochloride (9.22 g, 60 mmol) and di-tert-butyl dicarbonate (10.9 g, 50 mmol) in a 1:1 mixture of dichloromethane/saturated aqueous sodium bicarbonate (100 mL) was stirred at room temperature for 15.5 h. The layers were separated and the aqueous layer was extracted with chloroform (3×). The combined organic extracts were washed with 1 N aqueous phosphoric acid (3×), dried over sodium sulfate, filtered, and evaporated to give 10.0 g (100%) of the title compound of Example 101, Step A as a white solid. $^1$H NMR (CDCl$_3$, 400 MHz) δ 3.70 (t, 4H), 2.42 (t, 4H), 1.47 (s, 9H).

Step B: 3-Dimethylaminomethylene-4-oxo-piperidine-1-carboxylic acid tert-butyl ester. To a solution of 4-oxo-piperidine-1-carboxylic acid tert-butyl ester (prepared according to the method of Example 101, Step A, 4.0 g, 20.0 mmol) in dimethylformamide (40 mL) was added tert-butoxybis(dimethylamino)methane (4.35 mL, 22 mmol). This mixture was stirred at reflux for 15 h, cooled to room temperature, diluted with water, and extracted with ethyl acetate (5×). The combined organic extracts were washed with water (3×) and brine (1×), dried over sodium sulfate, filtered, and evaporated to give 3.64 g (72%) of the title compound of Example 101, Step B as a brown oil that was sufficiently pure to carry on to the next step. $^1$H NMR (CDCl$_3$, 400 MHz) δ 7.47 (s, 1H), 4.53 (s, 2H), 3.58 (t, 2H), 3.09 (s, 6H), 2.43 (t, 2H), 1.46 (s, 9H); MS (APCI) 255 (MH$^+$).

Step C: 2-Phenyl-7,8-dihydro-5H-pyrido[4,3-d]pyrimidine-6-carboxylic acid tert-butyl ester. A mixture of 3-dimethylaminomethylene-4-oxo-piperidine-1-carboxylic acid tert-butyl ester (prepared according to the method of Example 101, Step B, 509 mg, 2.0 mmol), benzamidine hydrochloride hydrate (470 mg, 3.0 mmol), and sodium ethoxide (1 M in ethanol, 6.0 mL, 6.0 mmol) in absolute ethanol (4 mL) was heated to reflux for about 3 d, cooled to room temperature, and concentrated. The residue was diluted with saturated aqueous sodium bicarbonate and extracted with chloroform (3×). The combined organic extracts were dried over sodium sulfate, filtered, evaporated, and purified by flash column chromatography (Biotage Flash 40S™, 10→15% ethyl acetate/hexanes) to give 304 mg (49%) of the title compound of Example 101, Step C as a yellow oil. $^1$H NMR (CDCl$_3$, 400 MHz) δ 8.52 (s, 1H), 8.40–8.38 (c, 2H), 7.50–7.44 (c, 3H), 4.62 (s, 2H), 3.78 (t, 2H) 3.02 (t, 2H), 1.50 (s, 9H); MS (APCI) 312 (MH$^+$).

Step D: 2-Phenyl-7,8-dihydro-5H-pyrido[4,3-d]pyrimidine hydrochloride. To a solution of 2-phenyl-7,8-dihydro-5H-pyrido[4,3-d]pyrimidine-6-carboxylic acid tert-butyl ester (prepared according to the method of Example 101, Step C, 304 mg, 0.98 mmol) in ethyl acetate (2 mL) was added hydrogen chloride (2.5 M in ethyl acetate, 3.9 mL, 9.76 mmol). This mixture was stirred at room temperature for 16 h and concentrated to give 256 mg (>100%) of the title compound of Example 101, Step D as a pale yellow solid. $^1$H NMR (CD$_3$OD, 400 MHz) δ 8.75 (s, 1H), 8.42–8.38 (c, 2H), 7.51–7.45 (c, 3H), 4.48 (s, 2H), 3.68 (t, 2H) 3.35–3.25 (buried, 2H); MS (APCI) 212 (MH$^+$).

Step E: 1R-[4-(4-Chlorocarbonyl-3R,5S-dimethyl-piperazin-1-yl)-pyrimidin-2-yl]-ethyl butyrate. To a solution of 1R-[4-(3R,5S-dimethyl-piperazin-1-yl)-pyrimidin-2-yl]-ethyl butyrate (prepared according to the method of Preparation Three, 1.36 g, 4.44 mmol) in dichloromethane (22 mL) at 0° C. under nitrogen was added pyridine (0.36 mL, 4.44 mmol) followed by triphosgene (883 mg, 2.97 mmol). This mixture was stirred with warming to room temperature for 1.5 h and quenched with saturated aqueous sodium bicarbonate. The layers were separated and the aqueous phase was extracted with chloroform (3×). The combined organic extracts were dried over sodium sulfate, filtered, evaporated, and purified by flash column chromatography (1→2% methanol/chloroform) to give 1.59 g (97%) of the title compound of Example 101, Step E as a brown oil. $^1$H NMR (CDCl$_3$, 400 MHz) δ 8.23<d, 1H), 6.39<d, 1H), 5.66 (q, 1H), 4.54–4.47 (c, 2H), 4.35 (m, 1H), 4.25 (m, 1H), 3.20

(dt, 2H), 2.38 (t, 2H), 1.72–1.62 (c, 2H), 1.56 (d, 3H), 1.31 (d, 3H), 1.30 (d, 3H), 0.95 (t, 3H); MS (APCI) 369, 371 (MH⁺).

Step F: {4-[2-(1R-Hydroxy-ethyl)-pyrimidin-4-yl]-2R,6S-dimethyl-piperazin-1-yl}-(2-phenyl-7,8-dihydro-5H-pyrido[4,3-d]pyrimidin-6-yl)-methanone. A mixture of 2-phenyl-7,8-dihydro-5H-pyrido[4,3-d]pyrimidine hydrochloride (prepared according to the method of Example 101, Step D, 160 mg, 0.65 mmol), 1R-[4-(4-chlorocarbonyl-3R,5S-dimethyl-piperazin-1-yl)-pyrimidin-2-yl]-ethyl butyrate (prepared according to the method of Example 101, Step E, 200 mg, 0.54 mmol), and triethylamine (0.19 mL, 1.36 mmol) in tetrahydrofuran (5 mL) was stirred at reflux for 3 h, cooled to room temperature overnight, and concentrated. The residue was diluted with a 4:1 mixture of methanol/water (5 mL) and lithium hydroxide hydrate (114 mg, 2.71 mmol) was added. This mixture was stirred for 2.5 h, concentrated, and partitioned between saturated aqueous sodium bicarbonate and chloroform. The layers were separated and the aqueous phase was extracted with 20% isopropanol/chloroform (3×). The combined organic extracts were dried over sodium sulfate, filtered, evaporated, and purified by flash column chromatography (2→5% methanol/chloroform) to give 183 mg (71%) the title compound as a white foam. ¹H NMR (CDCl₃, 400 MHz) δ 8.56 (s, 1H), 8.41–8.39 (c, 2H), 8.20 (d, 1H), 7.50–7.46 (c, 3H), 6.38 (d, 1H), 4.71 (s, 2H), 4.69 (m, 1H), 4.28 (d, 1H), 3.89 (t, 2H) 3.83 (d, 2H), 3.60–3.56 (c, 2H), 3.46–3.39 (c, 2H), 3.09 (t, 2H), 1.50 (d, 3H), 1.18 (d, 6H); MS (APCI) 212 (MH⁺); [α]$_D$+6.1 (c 1.8, CHCl₃).

EXAMPLES 102 TO 110

Examples 102 to 110 were prepared from the appropriate starting materials in a manner analogous to the method of Example 101.

EXAMPLE 111

(E)-1R-{4-[4-(2-Phenyl-ethenesulfonyl)-piperazin-1-yl]-pyrimidin-2-yl}-ethanol.

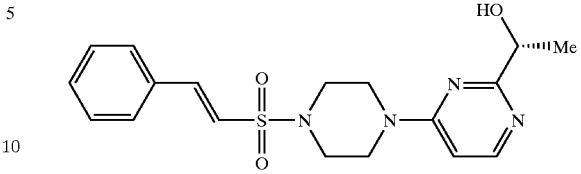

Step A: (E)-1R-{4-[4-(2-Phenyl-ethenesulfonyl)-piperazin-1-yl]-pyrimidin-2-yl}-ethyl acetate. To a solution of (R)-1-[4-piperazin-1-yl)-pyrimidin-2-yl]-ethyl acetate (prepared according to the method of Preparation Two, 0.25 g, 1.0 mmol) and triethylamine (0.10 g, 1.0 mmol) in tetrahydrofuran (5 mL) was added β-styrenesulfonyl chloride (0.21 g, 1.0 mmol) at ambient temperature and stirred for 1 h. The mixture was diluted with water and extracted twice with ethyl acetate. The extract was dried over magnesium sulfate, filtered, and the filtrate was concentrated to an oil, which was purified by flash chromatography (9:1 dichloromethane:methanol) to give the title compound of Example 111, Step A as an oil, 0.15 g (34%). ¹H NMR (CDCl₃, 300 MHz) δ 1.48 (d, 3H), 2.15 (s, 3H), 3.23 (m, 4H), 3.84 (m, 4H), 5.61 (q, 1H), 6.40 (d, 1H), 6.65 (d, 1H), 7.39–7.52 (m, 6H), 8.21 (d, 1H); MS (TS) 417 (MH⁺).

Step B: (E)-1R-{4-[4-(2-Phenyl-ethenesulfonyl)-piperazin-1-yl]-pyrimidin-2-yl}-ethanol.

To a solution (E)-1R-{4-[4-(2-phenyl-ethenesulfonyl)-piperazin-1-yl]-pyrimidin-2-yl}-ethyl acetate (prepared according the method of Example 111, Step A, 0.14 g, 0.33 mmol) in methanol (1 mL) was added at ambient temperature 6 N aqueous potassium hydroxide (0.25 mL). After stirring for 3 h, the solution was diluted with ethyl acetate

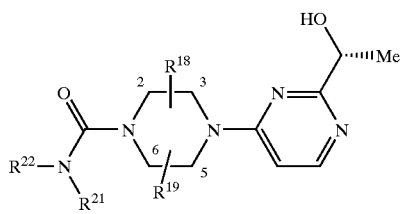

| Example | R²² | R²¹ | R¹⁸ | R¹⁹ | mp (° C.) | MS (MH⁺) |
|---|---|---|---|---|---|---|
| 102 | quinolin-2-yl | H | 3R—Me | 5S—Me | 172–174.5 | 407 |
| 103 | quinolin-3-yl | H | 2R—Me | 6S—Me | | 407 |
| 104 | quinolin-4-yl | H | 3R—Me | 5S—Me | | 407 |
| 105 | quinolin-6-yl | H | 3R—Me | 5S—Me | | 407 |
| 106 | pyridin-3-yl-methyl | pyridin-3-yl-methyl | 2R—Me | 6S—Me | | 462 |

| Example | NR²¹R²² | R¹⁸ | R¹⁹ | mp (° C.) | MS (MH⁺) |
|---|---|---|---|---|---|
| 107 | 2-amino-7,8-dihydro-5H-pyrido[4,3-d]pyrimidin-6-yl | 2R—Me | 6S—Me | 225–228 | 413 |
| 108 | 2-(1-hydroxy-1-methyl-ethyl)-7,8-dihydro-5H-pyrido[4,3-d]pyrimidin-6-yl | 2R—Me | 6S—Me | | 456 |
| 109 | 5,7-dihydro-dibenzo[c,e]azepin-6-yl | 2R—Me | 6S—Me | | 458 |
| 110 | 4-[2-(1R-hydroxy-ethyl)-pyrimidin-4-yl]-3R,5S-dimethyl-piperazin-1-yl | 3R—Me | 5S—Me | | 499 | and washed twice with water. The organic layer was separated, dried over magnesium sulfate, filtered, and the filtrate was concentrated to give the title compound as a white solid, 0.09 g (69%). $^1$H NMR (CDCl$_3$, 300 MHz) δ 1.48 (d, 3H), 3.23 (m, 4H), 3.84 (m, 4H), 4.20 (br s, 1H), 4.71 (q, 1H), 6.40 (d, 1H), 6.65 (d, 1H), 7.39–7.52 (m, 6H), 8.21 (d, 1H); mp: 68–70 IC; MS (TS) 375 (MH$^+$); [α]$_D$+20.9 (c 1.0, MeOH).

EXAMPLES 112 AND 113

Examples 112 and 113 were prepared from the appropriate starting materials in a manner analogous to the method of Example 111.

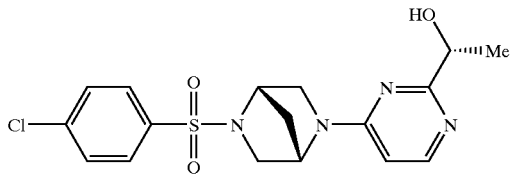

| Example | R$^{18}$ | R$^{19}$ | R$^{17}$ | mp (° C.) | MS (MH$^+$) |
|---|---|---|---|---|---|
| 112 | (R)—Me | (S)—Me | isopropylsulfonyl | 152–154 | 343 |
| 113 | (R)—Me | (S)—Me | 1-methyl-1H-imidazol-4-yl-sulfonyl | 157–158 | 381 |

EXAMPLE 114

1R-{4-[5-(4-Bromobenzenesulfonyl)-2R,5S-diaza-bicyclo[2.2.1]hept-2-yl]-pyrimidin-2-yl}-ethanol.

Step A: 1R-[4-(2R,5S-Diaza-bicyclo[2.2.1]hept-2-yl)-pyrimidin-2-yl]-ethyl butyrate. To a suspension of 2,5-diaza-bicyclo[2.2.1]heptane dihydrobromide (7.57 g, 88.0 mmol; Synthesis 1990, 10, 925) in dichloromethane (90 mL) was added 1,8-diazabicyclo[5.4.0]undec-7-ene (13.7 g, 90 mmol) and stirred until homogeneous. A solution of (R)-1-(4-chloro-pyrimidin-2-yl)-ethyl butyrate (prepared according to the method of Preparation Seven, 10.2 g, 45 mmol) in dichloromethane (10 mL) was added and stirred at reflux for 14 h. The mixture was filtered and washed with saturated aqueous sodium bicarbonate. The organic layer was dried over sodium sulfate and filtered. The filtrate was concentrated to obtain a crude product which was purified by flash chromatography (9:1→5:1 dichloromethane:methanol) to give the title compound of Example 114, Step A as an oil, 6.75 g (51%). $^1$H NMR (CDCl$_3$, 300 MHz) δ 0.92 (t, 3H), 1.54 (d, 3H), 1.68–1.78 (m, 5H), 2.68 (t, 2H), 3.38 (m, 1H), 3.76 (m, 3H), 4.42 (m, 1H), 5.35 (q, 1H), 6.16 (d, 1H), 8.12 (d, 1H); MS (CI) 291 (MH$^+$).

Step B: 1R-{4-[5-(4-Bromobenzenesulfonyl)-2R,5S-diaza-bicyclo[2.2.1]hept-2-yl]-pyrimidin-2-yl}-ethyl butyrate. To a solution of 1R-[4-(2R,5S-diaza-bicyclo[2.2.1]hept-2-yl)-pyrimidin-2-yl]-ethyl butyrate (prepared according to the method of Example 114, Step A, 0.58 g, 2.0 mmol) and triethylamine (0.22 g, 2.2 mmol) in chloroform (10 mL) was added 4-bromobenzenesulfonyl chloride (0.56 g, 2.2 mmol) and stirred at ambient temperature for 16 h. The mixture was washed once with water, once with brine, dried over magnesium sulfate, filtered, and the filtrate was concentrated to give the title compound of Example 114, Step B as a clear oil, 0.92 g (90%). $^1$H NMR (CDCl$_3$, 300 MHz) δ 0.92 (t, 3H), 1.54 (d, 3H), 1.68–1.78 (m, 5H), 2.68 (t, 2H), 3.25 (m, 1H), 3.46 (m, 3H), 4.28 (m, 1H), 5.25 (q, 1H), 6.16 (d, 1H), 7.58–7.64 (m, 4H), 8.12 (d, 1H); MS (CI) 510 (MH$^+$).

Step C: 1R-{4-[5-(4-Bromobenzenesulfonyl)-2R,5S-diaza-bicyclo[2.2.1]hept-2-yl]-pyrimidin-2-yl}-ethanol. To a solution of 1R-{4-[5-(4-bromobenzenesulfonyl)-2R,5S-diaza-bicyclo[2.2.1]hept-2-yl]-pyrimidin-2-yl}-ethyl butyrate (prepared according to the method of Example 114, Step B, 0.85 g, 1.6 mmol) in a 2:1 mixture of tetrahydrofuran:methanol (10 mL) was added at ambient temperature 6 N aqueous potassium hydroxide (1 mL). After stirring for 6 h the solution was diluted with dichloromethane and washed twice with water. The organic layer was separated, dried over magnesium sulfate, filtered, and the filtrate was concentrated to a viscous oil which was purified by flash chromatography (9:1 dichloromethane:methanol) to give the title compound as a white foam, 0.49 g (66%). $^1$H NMR (CDCl$_3$, 300 MHz) δ 1.54 (d, 3H), 1.68 (m, 2H), 1.78 (m, 1H), 3.25 (m, 1H), 3.46 (m, 3H), 4.28 (m, 1H), 4.78 (q, 1H), 6.16 (d, 1H), 7.64 (m, 4H), 8.12 (d, 1H); mp: 83–88° C.; MS (CI) 4.40 (MH$^+$); [α]$_D$–49.2 (c 1.0, MeOH).

EXAMPLES 115 TO 120

Examples 115 to 120 were prepared from the appropriate starting materials in a manner analogous to the method of Example 114.

| Example | R$^{17}$ | mp (° C.) | MS (MH$^+$) |
|---|---|---|---|
| 115 | 4-chlorophenylsulfonyl | 83–88 | 395, 397 |
| 116 | 2-thienylsulfonyl | 84–86 | 367 |
| 117 | 2-(5-chlorothienyl)-sulfonyl | 62–64 | 401, 403 |
| 118 | 4-carboxamidoylphenyl-sulfonyl | 148–151 | 404 |
| 119 | 4-(tert-butylphenyl)-sulfonyl | 72–75 | 417 |
| 120 | N,N-dimethylsulfamoyl | 110–111 | 328 |

EXAMPLE 121

{4-[4-(Pyrrolidine-1-sulfonyl)-piperazin-1-yl]-pyrimidin-2-yl}-methanol.

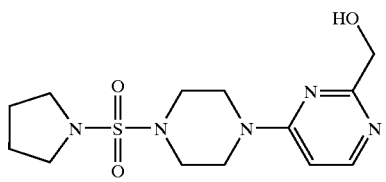

Step A: 2-Methoxymethyl-4-[4-(pyrrolidine-1-sulfonyl)-piperazin-1-yl]-pyrimidine. To a solution of 2-methoxymethyl-4-piperazin-1-yl-pyrimidine (prepared according to the method of Preparation One, 2.08 g, 10 mmol) and triethylamine (1.01 g, 10 mmol) in tetrahydrofuran (20 mL) was added N-pyrrolidinesulfonyl chloride (1.69 g, 10 mmol) at 0° C. and stirred for 3 h at ambient temperature. The mixture was diluted with ethyl acetate and washed twice with water. The organic layer was separated, dried over magnesium sulfate, filtered, and the filtrate was concentrated to an oil which was purified by flash chromatography (95:5 dichloromethane:methanol) to give the title compound of Example 121, Step A as a clear oil, 3.24 g (93%). $^1$H NMR (COCl$_3$, 300 MHz) δ 1.81–1.85 (m, 4H), 3.12–3.18 (m, 8H), 3.59 (s, 3H), 3.81 (m, 4H), 4.43 (s, 2H), 6.71 (d, 1H), 8.18 (d, 1H); MS (TS) 342 (MH$^+$).

Step B: {4-[4-(Pyrrolidine-1-sulfonyl)-piperazin-1-yl]-pyrimidin-2-yl}-methanol. To a solution of 2-methoxymethyl-4-[4-(pyrrolidine-1-sulfonyl)-piperazin-1-yl]-pyrimidine (prepared according to the method of Example 121, Step A, 3.1 g, 9.4 mmol) in dichloromethane (47 mL) was added boron tribromide (1 M in dichloromethane, 19 mL, 18.7 mmol) at 0° C. then stirred at ambient temperature for 2 h. The mixture was washed twice with saturated aqueous sodium bicarbonate, and the organic layer was separated, dried over magnesium sulfate, filtered, and the filtrate was concentrated to give an oil which was crystallized from isopropyl ether to give the title compound as a white solid, 2.43 g (77%). $^1$H NMR (CDCl$_3$, 300 MHz) δ 1.82 (m, 4H), 3.15 (m, 8H), 3.81 (m, 4H), 4.35 (d, 2H), 4.83 (t, 1H), 6.71 (d, 1H), 8.18 (d, 1H); mp: 1.28–131° C.; MS (CI) 328 (MH$^+$).

EXAMPLES 122 TO 125

Examples 122 to 125 were prepared from the appropriate starting materials in a manner analogous to the method of Example 121.

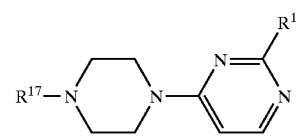

| Example | R$^1$ | R$^{17}$ | mp (° C.) | MS (MH$^+$) |
|---|---|---|---|---|
| 122 | CH$_2$OH | 2,5-dimethylpyrrolidin-1-ylsulfonyl | 128–131 | 356 |
| 123 | CH$_2$OH | piperidin-1-ylsulfonyl | 141–142 | 342 |
| 124 | (R)—CH(Me)OH | aza-bicyclo[3.2.1]octan-8-ylsulfonyl | 111–112 | 382 |
| 125 | (R)—CH(Me)OH | aza-bicyclo[3.2.1]octan-3-one-8-yl-sulfonyl | 113–114 | 396 |

EXAMPLE 126

(E)-1-{4-[2-(1R-Hydroxy-ethyl)-pyrimidin-4-yl]-piperazin-1-yl}-2-methyl-3-phenyl-popenone.

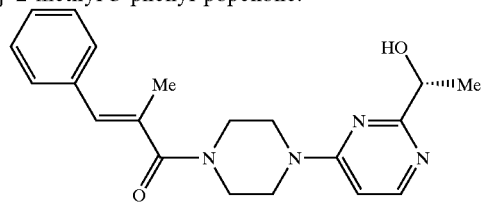

Step A: (E)-1R-{4-[4-(2-Methyl-3-phenyl-acryloyl)-piperazin-1-yl]-pyrimidin-2-yl}-ethyl acetate. To a solution of (R)-1-(4-piperazin-1-yl-pyrimidin-2-yl)-ethyl acetate (prepared according to the method of Preparation Two, 0.54 g, 2.1 mmol) and α-methylcinnamic acid (0.34 g, 2.1 mmol) in dichloromethane (10 mL) was added 1-hydroxybenzotriazole (0.50 g, 3.6 mmol) followed by 1–3-dimethylaminopropyl)-3-ethylcarbodiimide hydrochloride (0.45 g, 2.4 mmol) at ambient temperature and stirred for 48 h. The mixture was washed once with water, once with saturated aqueous sodium chloride, dried over magnesium sulfate, filtered, and the filtrate was concentrated to an oil which was purified by flash chromatography (9:1 dichloromethane:methanol) to give the title compound of Example 126, Step A as a clear viscous oil, 0.53 g (63%). $^1$H NMR (CDCl$_3$, 300 MHz) δ 1.51 (d, 3H), 2.14 (s, 3H), 2.18 (s, 3H), 3.75 (m, 8H), 5.68 (q, 1H), 6.41 (d, 1H), 6.59 (s, 1H), 7.25–7.43 (m, 5H), 8.23 (d, 1H); MS (CI) 395 (MH$^+$); [α]$_D$+38.6 (c 1.0, MeOH).

Step B: (E)-1-{4-[2-(1R-Hydroxy-ethyl)-pyrimidin-4-yl]-piperazin-1-yl}-2-methyl-3-phenyl-propenone. To a solution of (E)-1R-{4-[4-(2-methyl-3-phenyl-acryloyl)-piperazin-1-yl]-pyrimidin-2-yl}-ethyl acetate (prepared according to the method of Example 126, Step A, 0.51 g, 1.3 mmol) in methanol (5 mL) was added at ambient temperature 6 N aqueous potassium hydroxide (1 mL). After stirring for 1 h the solution was diluted with ethyl acetate and washed twice with water. The organic layer was separated, dried over magnesium sulfate, filtered, and the filtrate was concentrated to give the title compound as a white solid, 0.25 g (55%). $^1$H NMR (CDCl$_3$, 300 MHz) δ 1.51 (d, 3H), 2.14 (s, 3H), 3.75 (m, 8H), 4.22 (br s, 1H), 4.71 (q, 1H), 6.41 (d, 1H), 6.59 (s, 1H), 7.25–7.43 (m, 5H), 8.23 (d, 1H); mp: 119–121° C.; MS (CI) 353 (MH$^+$); [α]$_D$+16.0 (c 1.0, MeOH).

EXAMPLES 127 TO 129

Examples 127 to 129 were prepared from the appropriate starting materials in a manner analogous to the method of Example 126.

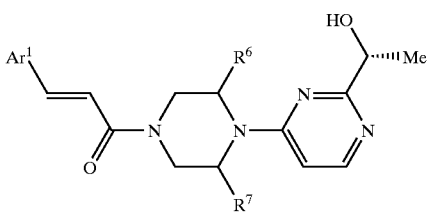

| Example | Ar$^1$ | R$^6$ | R$^7$ | mp (° C.) | MS (MH$^+$) |
|---|---|---|---|---|---|
| 127 | thien-2-yl | H | H | 104–106 | 345 |
| 128 | thien-2-yl | (R)—Me | (S)—Me | 69–73 | 373 |

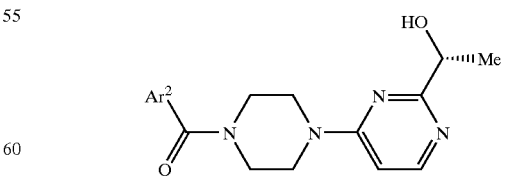

| Example | Ar$^2$ | mp (° C.) | MS (MH$^+$) |
|---|---|---|---|
| 129 | 4-(o-tolylcarbamoyl)-phenyl | 98–103 | 446 |

EXAMPLE 130

(E)-3-Benzofuran-2-yl-1-{4-[2-(1R-hydroxy-ethyl)-pyrimidin4-yl]-2R,6S-dimethyl-piperazin-1-yl}-propenone.

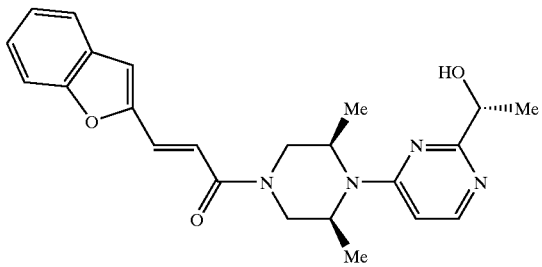

Step A: (E)-1R-{4-[4-(3-Benzofuran-2-yl-acryloyl)-3R,5S-dimethyl-piperazin-1-yl]-pyrimidin-2-yl}-ethyl butyrate. To a solution of 1R-[4-(3R,5S-dimethyl-piperazin-1-yl)-pyrimidin-2-yl]-ethyl butyrate (prepared according to the method of Preparation Three, 0.79 g, 2.6 mmol) and triethylamine (0.26 g, 2.6 mmol) in dichloromethane (90 mL) was added (E)-3-benzofuran-2-yl-acryloyl chloride (0.54 g, 2.6 mmol) and stirred at ambient temperature for 16 h, then at reflux for 2.5 h. The mixture was washed successively with saturated aqueous sodium bicarbonate and water, and the organic layer was dried over sodium sulfate and filtered. The filtrate was concentrated to obtain a crude product, which was purified by flash chromatography (9:1 dichloromethane:methanol) to give the title compound of Example 130, Step A as a viscous oil, 0.79 g (54%). $^1$H NMR (CDCl$_3$, 300 MHz) δ 0.95 (t, 3H), 1.40 (d, 6H), 1.56 (d, 3H), 1.67 (q, 2H), 2.38 (t, 2H), 3.25 (d, 2H), 4.33 (m, 2H), 4.75 (m, 2H), 5.66 (q, 1H), 5.95 (d, 1H), 6.40 (d, 1H), 7.14–7.37, (m, 5H), 8.06 (d, 1H), 8.22 (d, 1H); MS (CI) 477 (MH$^+$); [a]$_D$+49.1 (c 1.0, MeOH).

Step B: (E)-3-Benzofuran-2-yl-1-{4-[2-(1R-hydroxy-ethyl)-pyrimidin-4-yl]-2R,6S-dimethyl-piperazin-1-yl}-propenone. To a solution of (E)-1R-{4-[4-(3-benzofuran-2-yl-acryloyl)-3R,5S-dimethyl-piperazin-1-yl]-pyrimidin-2-yl}-ethyl butyrate (prepared according to the method of Example 130, Step A, 0.51 g, 1.1 mmol) in methanol (5 mL) was added at ambient temperature 6 N aqueous potassium hydroxide (1 mL). After stirring for 1 h the solution was diluted with ethyl acetate and washed twice with water. The organic layer was separated, dried over magnesium sulfate, filtered, and the filtrate was concentrated to give the title compound as a white solid, 0.49 g (75%). $^1$H NMR (CDCl$_3$, 300 MHz) δ 1.40 (d, 6H), 1.56 (d, 3H), 3.25 (d, 2H), 4.33 (m, 2H), 4.75 (m, 2H), 4.68 (q, 1H), 5.95 (d, 1H), 6.40 (d, 1H), 7.14–7.37, (m, 5H), 8.06 (d, 1H), 8.22 (d, 1H); mp: 80–82° C.; MS (CI) 407 (MH$^+$); [α]$_D$+17.7 (c 1.0, MeOH).

EXAMPLE 131

Cyclohexyl-{4-[2-(1R-hydroxy-ethyl)-pyrimidin-4-yl]-2R,6S-dimethyl-piperazin-1-yl}-methanone.

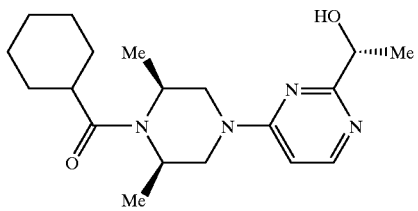

Step A: 1R-[4-(4-Cyclohexanecarbonyl-3R,5S-dimethyl-piperazin-1-yl)-pyrimidin-2-yl]-ethyl butyrate. To a solution of 1R-[4-(3R,5S-dimethyl-piperazin-1-yl)-pyrimidin-2-yl]-ethyl butyrate (prepared according to the method of Preparation Three, 306 mg, 1.0 mmol) and triethylamine (230 mg, 1.2 mmol) in dichloromethane (10 mL) was added at ambient temperature cyclohexanecarbonyl chloride (161 mg, 1.1 mmol). After 1 h the mixture was washed with water, and the dichloromethane layer was dried over magnesium sulfate and filtered. The filtrate was concentrated to give the title compound of Example 131, Step A as an oil, 388 mg (94%). $^1$H NMR (CDCl$_3$, 300 MHz) δ 0.94 (t, 3H), 1.2–1.4 (m, 6H), 1.54 (d, 3H), 1.5–1.83 (m, 12H), 2.44 (m, 3H), 3.2–3.3 (m, 2H), 4.4–4.6 (m, 4H), 5.52 (q, 1H), 6.44 (d, 1H), 8.22 (d, 1H); MS (CI) 417 (MH$^+$).

Step B: Cyclohexyl-{4-[2-(1R-hydroxy-ethyl)-pyrimidin-4-yl]-2R,6S-dimethyl-piperazin-1-yl}-methanone. To a solution of 1R-[4-(4-cyclohexanecarbonyl-3R,5S-dimethyl-piperazin-1-yl)-pyrimidin-2-yl]-ethyl butyrate (prepared according to the method of Example 131, Step A, 375 mg, 9.0 mmol) in methanol (5 mL) was added 6 N aqueous potassium hydroxide (0.5 mL) and stirred at ambient temperature for 4 h. The reaction mixture was concentrated, diluted with water, and extracted into dichloromethane. The extract was washed twice with water, dried over magnesium sulfate, and evaporated to an oil. The crude product was crystallized from ethyl ether to give the title compound as a white solid, 106 mg (34%). $^1$H NMR (CDCl$_3$, 300 MHz) δ 1.2–1.4 (m, 6H), 1.55 (d, 3H), 1.6–1.8 (m, 10H), 2.46 (m, 1H), 3.2–3.3 (m, 2H), 4.2–4.6 (m, 4H), 4.78 (q, 1H), 6.43 (d, 1H), 8.22 (d, 1H); mp: 174–175° C.; MS (CI) 347 (MH$^+$); [α]$_D$+18.4 (c 1.0, MeOH).

EXAMPLE 132

Furo[3,2-c]pyridin-2-yl-{4-[2-(1R-hydroxy-ethyl)-pyrimidin-4-yl]-2R,6S-dimethyl-piperazin-1-yl}-methanone.

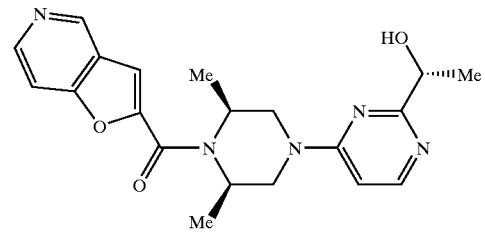

Step A: 7-Chloro-furo[3.2-c]pyridine-2-carboxylic acid. To a solution of n-butyllithium (2.5 M in hexanes, 17 mL, g, 42.6 mmol) in anhydrous ethyl ether (90 mL) was added dropwise a solution of 4-chloro-furo[3,2-c]pyridine (5.81 g, 37.8 mmol; *J. Heterocycl. Chem.* 1975, 12, 705) in ethyl ether (85 mL) at −78° C. under nitrogen atmosphere. This mixture was stirred for 1.5 h at −65° C., poured onto dry ice (100 cc) and warmed to ambient temperature and quenched into water. The separated organic layer was extracted once with water and the combined aqueous layers were acidified to pH 2 with concentrated hydrochloric acid to give the title compound of Example 132, Step A as a white solid, 3.33 g (45%). $^1$H NMR (CDCl$_3$, 300 MHz) δ 7.69 (s, 1H), 7.85 (d, 1H), 8.42 (d, 1H); mp: 233–235° C. (dec); MS (CI) 153 (MH$^+$-CO$_2$).

Step B: 7-Chloro-furo[3,2-c]pyridine-2-carboxylic acid chloride. 7-Chloro-furo[3,2-c]pyridine-2-carboxylic acid (prepared according to the method of Example 132, Step A, 8.94 g, 45.2 mmol) was combined with thionyl chloride (30 mL) and sodium carbonate (9.59 g, 90.5 mmol) and heated to reflux for 16 h under nitrogen atmosphere. The cooled mixture was diluted with dichloromethane and filtered. The filtrate was evaporated to give the title compound of Example 132, Step B as an orange oil, 9.19 g (94%). The acid chloride was used directly without further purification.

Step C: 1R-{4-[4-(4-Chloro-furo[3,2-c]pyridine-2-carbonyl)-3R,5S-dimethyl-piperazin-1-yl]-pyrimidin-2-yl}-ethyl butyrate. To a solution of 1R-[4-(3R,5S-dimethyl-piperazin-1-yl)-pyrimidin-2-yl]-ethyl butyrate (prepared according to the method of Preparation Three, 13.04 g, 42.5 mmol) and triethylamine (8.61 g, 85.1 mmol) in dichloromethane (90 mL) was added 7-chloro-furo[3,2-c]pyridine-2-carboxylic acid chloride (prepared according to the method of Example 132, Step B, 9.1 g, 84.0 mmol) and stirred at ambient temperature for 2 h. The mixture was washed successively with saturated aqueous sodium bicarbonate and water, and the organic layer was dried over sodium sulfate and filtered. The filtrate was concentrated to obtain a crude product which was purified by flash chromatography (9:1 dichloromethane:methanol) to give the title compound of Example 132, Step C as a viscous oil, 18.9 g (91%). $^1$H NMR (CDCl$_3$, 300 MHz) δ 0.95 (t, 3H), 1.40 (d, 6H), 1.56 (d, 3H), 1.67 (m, 2H), 2.38 (t, 2H), 3.25 (d, 2H), 4.33 (m, 2H), 4.75 (m, 2H), 5.66 (q, 1H), 6.40 (d, 1H), 7.33 (s, 1H), 7.41 (d, 1H), 8.23 (d, 1H), 8.35 (d, 1H); MS (CI) 487 (MH$^+$); [α]$_D$+33.3 (c 1.0, MeOH).

Step D: 1R-{4-[4-(Furo[3,2-c]pyridine-2-carbonyl)-3R,5S-dimethyl-piperazin-1-yl]-pyrimidin-2-yl}-ethyl butyrate. To a solution of 1R-{4-[4-(4-chloro-furo[3,2-c]pyridine-2-carbonyl)-3R,5S-dimethyl-piperazin-1-yl]-pyrimidin-2-yl}-ethyl butyrate (prepared according to the method of Example 132, Step C, 18.6 g, 38.4 mmol) in ethanol (160 mL) was added sodium carbonate (4.07 g, 38.4 mmol) and 10% palladium on carbon (6.10 g, 33 wt %). This mixture was hydrogenated at 50 psi hydrogen for 6 h using a Parr apparatus. The catalyst was filtered and the filtrate was evaporated to an oil which was purified by flash chromatography (9:1 dichloromethane:methanol) to give the title compound of Example 132, Step D as a yellow oil, 14.2 g (82%). $^1$H NMR (CDCl$_3$, 300 MHz) δ 0.95 (t, 3H), 1.40 (d, 6H), 1.56 (d, 3H), 1.67 (q, 2H), 2.38 (t, 2H), 3.25 (d, 2H), 4.33 (m, 2H), 4.75 (m, 2H), 5.68 (q, 1H), 6.40 (d, 1H), 7.37 (s, 1H), 7.48 (d, 1H), 8.22 (d, 1H), 9.04 (s, 1H); MS (CI) 452 (MH$^+$); [α]$_D$+36.7 (c 1.0, MeOH).

Step E: Furo[3,2-c]pyridin-2-yl-{4-[2-(1R-hydroxy-ethyl)-pyrimidin-4-yl]-2R,6S-dimethyl-piperazin-1-yl}-methanone. 1R-{4-[4-(Furo[3,2-c]pyridine-2-carbonyl)-3R,5S-dimethyl-piperazin-1-yl]-pyrimidin-2-yl}-ethyl butyrate (prepared according to the method of Example 132, Step D, 5.48 g, 12.1 mmol) was combined with concentrated hydrochloric acid (15 mL) and stirred at ambient temperature for 6 h. The mixture was poured into cold 6 M aqueous sodium hydroxide and extracted twice with ethyl acetate. The organic extract was washed once with water, dried over sodium sulfate and evaporated to a foam which crystallized from isopropyl ether to give the title compound as a white solid, 3.33 g (72%). $^1$H NMR (CDCl$_3$, 300 MHz) δ 1.43 (d, 6H), 1.52 (d, 3H), 3.37 (m, 2H), 4.38 (m, 2H), 4.71 (q, 1H), 4.83 (m, 2H), 6.43 (d, 1H), 7.38 (s, 1H), 7.47 (m, 1H), 8.22 (m, 1H), 8.54 (d, 1H), 8.58 (d, 1H), 9.04 (s, 1H); mp: 142–143° C.; MS (CI) 382 (MH$^+$); [α]$_D$+15.9 (c 1.0, MeOH).

EXAMPLE 133

{4-[2-(1R-Hydroxy-ethyl)-pyrimidin-4-yl]-2R,6S-dimethyl-piperazin-1-yl}-(4-pyrrolidin-1-yl-furo[3,2-c]pyridin-2-yl)-methanone.

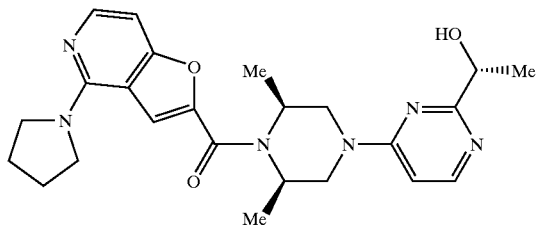

A solution of 1R-{4-[4-(4-chloro-furo[3,2-c]pyridine-2-carbonyl)-3R,5S-dimethyl-piperazin-1-yl]-pyrimidin-2-yl}-ethyl butyrate (prepared according to the method of Example 132, Step C, 0.046 g, 0.11 mmol) in pyrrolidine (0.037 mL, 0.44 mmol) was heated to reflux for 14 h and evaporated to give the title compound as a tan solid, 0.04 g (80%). $^1$H NMR (CDCl$_3$, 300 MHz) δ 1.43 (d, 6H), 1.53 (d, 3H), 2.08 (m, 4H), 3.43 (m, 2H), 3.77 (m, 4H), 4.43 (m, 2H), 4.71 (q, 1H), 4.92 (m, 2H), 6.43 (d, 1H), 6.70 (d, 1H), 7.60 (s, 1H), 8.08 (d, 1H), 8.23 (d, 1H); MS (CI) 451 (MH$^+$).

EXAMPLES 134 TO 158

Examples 140 and 142 to 158 were prepared from the appropriate starting materials in a manner analogous to the method of Example 131. Example 141 was prepared from the appropriate starting materials in a manner analogous to the method of Example 133.

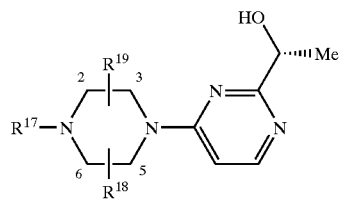

| Example | R$^{17}$ | R$^{18}$ | R$^{19}$ | mp (° C.) | MS (MH$^+$) |
|---|---|---|---|---|---|
| 134 | cyclopropylcarbonyl | 2R—Me | 6S—Me | 110–111 | 305 |
| 135 | cyclobutylcarbonyl | 2R—Me | 6S—Me | 134–135 | 319 |
| 136 | cyclopentylcarbonyl | 2R—Me | 6S—Me | 199–200 | 333 |
| 137 | tert-butylcarbonyl | 2R—Me | 6S—Me | 168–169 | 321 |

-continued

| Example | Ar² | R¹⁸ | R¹⁹ | mp (° C.) | MS (MH⁺) |
|---|---|---|---|---|---|
| 138 | benzofuran-2-yl | 2R—Me | 6S—Me | 124–126 | 381 |
| 139 | furo[3,2-c]pyridin-2-yl | H | H | 55–65 | 354 |
| 140 | furo[3,2-c]pyridin-2-yl | 3R—Me | 5S—Me | | 382 |
| 141 | morpholin-4-yl-furo[3,2-c]pyridin-2-yl | 2R—Me | 6S—Me | | 467 |
| 142 | furo[2,3-c]pyridine-2-yl | 2R—Me | 6S—Me | 129–131 | 382 |
| 143 | 5-chlorobenzofuran-2-yl | H | H | | 387, 389 |
| 144 | 5-chlorobenzofuran-2-yl | 3R—Me | 5S—Me | 114–116 | 415, 417 |
| 145 | 5,7-dichlorobenzofuran-2-yl | 2R—Me | 6S—Me | 136–137 | 450, 452 |
| 146 | 5,7-dichlorobenzofuran-2-yl | 3R—Me | 5S—Me | 152–153 | 450, 452 |
| 147 | 5-nitrobenzofuran-2-yl | 2R—Me | 6S—Me | 153–154 | 426 |
| 148 | 5,7-dimethylbenzofuran-2-yl | 3R—Me | 5S—Me | 134–136 | 409 |
| 149 | 5-methoxybenzofuran-2-yl | 3R—Me | 5S—Me | 137–138 | 411 |
| 150 | 5-methoxybenzofuran-2-yl | 2R—Me | 6S—Me | 118–119 | 411 |
| 151 | imidazo[1,2-a]pyridin-2-yl | H | H | 149–150 | 353 |
| 152 | imidazo[1,2-a]pyridin-2-yl | 3R—Me | 5S—Me | 171–173 | 381 |
| 153 | imidazo[1,2-a]pyridin-2-yl | 2R—Me | 6S—Me | 147–149 | 381 |
| 154 | 6-chloroimidazo[1,2-b]pyridazin-2-yl | 2R—Me | 6S—Me | 76–84 | 416, 418 |
| 155 | 6-methylimidazo[1,2-a]pyridin-2-yl | 3R—Me | 5S—Me | 164–165 | 395 |
| 156 | benzoxazol-2-yl | 2R—Me | 6S—Me | 126–127 | 382 |
| 157 | 4-cyanophenyl | 2R—Me | 6S—Me | 90–100 | 366 |
| 158 | 6-hydroxy-pyridazin-3-yl | 2R—Me | 6S—Me | | 359 |

EXAMPLE 159

1-{4-[2-(1R-Hydroxy-ethyl)-pyrimidin-4-yl]-2R,6S-dimethyl-piperazin-1-yl}-2-(6-methyl-pyridin-3-yloxy)-ethanone.

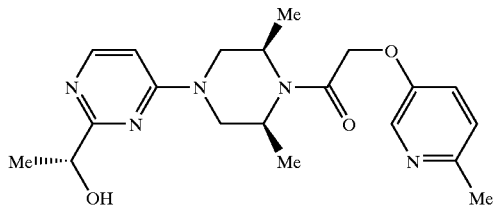

Step A: 1R-[4-(4-Chloroacetyl-3R,5S-dimethyl-piperazin-1-yl)-pyrimidin-2-yl]-ethyl butyrate. To a solution of 1R-[4-(3R,5S-dimethyl-piperazin-1-yl)-pyrimidin-2-yl]-ethyl butyrate (prepared according to the method of Preparation Three, 9.69 g, 31.3 mmol) and triethylamine (4.74 g, 46.9 mmol) in chloroform (150 mL) was added dropwise chloroacetyl chloride (3.00 mL, 37.6 mmol) at 0° C. then stirred at ambient temperature for 12 h under nitrogen atmosphere. The mixture was washed successively with saturated aqueous sodium bicarbonate and water, and the organic layer was dried over sodium sulfate, treated with activated carbon, and filtered. The filtrate was concentrated to obtain an oil which was purified by flash chromatography (9:1 dichloromethane:methanol) to give the title compound of Example 159, Step A as an oil, 8.98 g (75%). ¹H NMR (CDCl₃, 300 MHz) δ 0.96 (d, 3H), 1.32 (d, 6H), 1.59 (d, 3H), 1.71 (m, 2H), 2.40 (t, 2H), 3.28 (m, 2H), 4.28 (s, 2H), 4.35 (m, 4H), 5.68 (q, 1H), 6.41 (d, 1H), 8.23 (d, 1H); MS (CI) 383, 385 (MH⁺).

Step B: 1R-(4-{3R,5S-Dimethyl-4-[(6-methyl-pyridin-3-yloxy)-acetyl]-piperazin-1-yl}-pyrimidin-2-yl)-ethyl butyrate. To a suspension of sodium hydride (60% dispersion in oil, 0.05 g, 1.3 mmol) in tetrahydrofuran (2 mL) was added a solution of 6-methyl-3-pyridinol (0.14 g, 1.3 mmol) in tetrahydrofuran (3 mL) at 0° C. under nitrogen atmosphere and stirred for 0.5 h warming to ambient temperature. Next, a solution of 1R-[4-(4-chloroacetyl-3R,5R-dimethyl-piperazin-1-yl)-pyrimidin-2-yl]-ethyl butyrate (prepared according to the method of Example 159, Step A, 0.40 g, 1.1 mmol) in tetrahydrofuran (2 mL) was added and refluxed for 1 h. The mixture was diluted with dichloromethane and washed with saturated aqueous sodium bicarbonate, dried over sodium sulfate and filtered. The filtrate was evaporated to an oil which was purified by flash chromatography (9:1 dichloromethane:methanol) to give the title compound of Example 159, Step B as an oil, 0.31 g (66%). ¹H NMR (CDCl₃, 300 MHz) δ 0.96 (d, 3H), 1.32 (d, 6H), 1.59 (d, 3H), 1.71 (m, 2H), 2.40 (t, 2H), 2.46 (s, 3H), 3.28 (m, 2H), 3.78 (s, 2H), 4.35 (m, 4H), 5.68 (q, 1H), 6.41 (d, 1H), 6.83 (m, 1H), 7.14 (m, 1H), 8.08, (d, 1H), 8.23 (d, 1H); MS (CI) 456 (MH⁺).

Step C: 1-{4-[2-(1R-Hydroxy-ethyl)-pyrimidin-4-yl]-2R,6S-dimethyl-piperazin-1-yl}-2-(6-methyl-pyridin-3-yloxy)-ethanone. 1R-(4-{3R,5S-Dimethyl-4-[(6-methyl-pyridin-3-yloxy)-acetyl]-piperazin-1-yl}-pyrimidin-2-yl)-ethyl butyrate (prepared according to the method of Example 159, Step B, 0.30 g, 0.65 mmol) was combined with concentrated hydrochloric acid (3 mL) and stirred at ambient temperature for 6 h. The mixture was neutralized with 6 N aqueous sodium hydroxide to pH 9 and extracted twice with ethyl acetate. The organic extract was washed once with water, dried over sodium sulfate and filtered. The filtrate was concentrated to an oil which was purified by flash chromatography (9:1 dichloromethane:methanol) to give the title compound as a white foam, 0.14 g (55%). ¹H NMR (CDCl₃, 300 MHz) δ 1.38 (d, 6H), 1.55 (d, 3H), 2.46 (s, 3H), 3.28 (m, 2H), 3.76 (s, 2H), 4.35–4.65 (m, 4H), 4.67 (q, 1H), 6.38 (d, 1H), 6.83 (m, 1H), 7.11 (m, 1H), 8.08, (d, 1H), 8.21 (d, 1H); mp: 55–65° C.; MS (CI) 330 (MH⁺); [α]_D+16.0 (c 1.0, MeOH).

EXAMPLE 160

1-{4-[2-(1R-Hydroxy-ethyl)-pyrimidin-4-yl]-2R,6S-dimethyl-piperazin-1-yl}-2-(pyrimidin-2-ylsulfanyl)-ethanone.

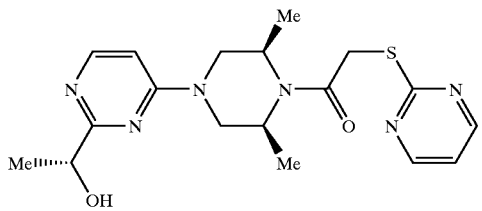

Example 160 was prepared from the appropriate starting materials in a manner analogous to example 159. ¹H NMR (CDCl₃, 300 MHz) 61.38 (m, 6H), 1.48 (d, 3H), 3.28 (m, 2H), 3.96 (s, 2H), 4.35 (m, 4H), 4.65·4.97 (m, 3H), 6.28 (d, 1H), 6.93 (m, 1H), 7.11 (m, 1H), 8.21 (d, 1H), 8.45, (m, 2H); mp: 60–70° C.; MS (CI) 389 (MH⁺); [α]$_D$+16.8 (c 1.0, MeOH).

EXAMPLE 161

4-[2-(1R-Hydroxy-ethyl)-pyrimidin-4-yl]-2R,6S-dimethyl-piperazine-1-carboxylic acid phenyl ester.

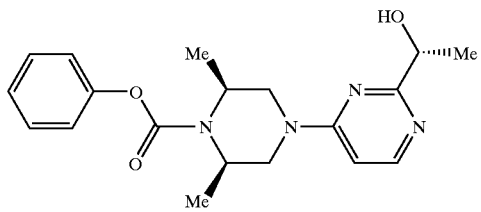

Step A: 4-[2-(1R-Butyryloxy-ethyl)-pyrimidin-4-yl]-2R,6S-dimethyl-piperazine-1-carboxylic acid Phenyl ester. To a solution of 1R-[4-(3R,5S-dimethyl-piperazin-1-yl)-pyrimidin-2-yl]-ethyl butyrate (prepared according to the method of Preparation Three, 0.30 g, 0.98 mmol) and triethylamine (0.20 g, 1.9 mmol) in dichloromethane (5 mL) was added phenyl chloroformate (0.76 g, 4.8 mmol) and stirred at ambient temperature for 2 h under nitrogen atmosphere. The mixture was washed successively with saturated aqueous sodium bicarbonate and water, and the organic layer was dried over sodium sulfate and filtered. The filtrate was concentrated to obtain an oil which was purified by flash chromatography (9:1 dichloromethane:methanol) to give the title compound of Example 161, Step A as an oil, 0.35 g (84%). ¹H NMR (CDCl₃, 300 MHz) δ 0.96 (d, 3H), 1.32 (d, 6H), 1.59 (d, 3H), 1.71 (q, 2H), 2.40 (t, 2H), 3.28 (m, 2H), 4.35 (m, 4H), 5.68 (q, 1H), 6.41 (d, 1H), 7.12 (d, 2H), 7.22 (m, 1H), 7.35 (m, 2H), 8.23 (d, 1H); MS (CI) 427 (MH⁺); [α]$_D$+39.6 (c 1.0, MeOH).

Step B: 4-[2-(1R-Hydroxy-ethyl)-pyrimidin-4-yl]-2R,6S-dimethyl-piperazine-1-carboxylic acid phenyl ester. 4-[2-(1R-Butyryloxy-ethyl)-pyrimidin-4-yl]-2R,6S-dimethyl-piperazine-1-carboxylic acid phenyl ester (prepared according to the method of Example 161, Step A, 0.31 g, 0.70 mmol) was combined with concentrated hydrochloric acid (5 mL) and stirred at ambient temperature for 6 h. The mixture was neutralized with 6 N aqueous sodium hydroxide to pH 9 and extracted twice with ethyl acetate. The organic extract was washed once with water, dried over sodium sulfate and filtered. The filtrate was concentrated to an oil which was purified by flash chromatography (9:1 dichloromethane:methanol) to give the title compound as a white solid, 0.12 g (81%). ¹H NMR (CDCl₃, 300 MHz) δ 1.41 (d, 6H), 1.51 (d, 3H), 3.34 (m, 2H), 4.43 (m, 2H), 4.52 (m, 2H), 4.71 (q, 1H), 6.46 (d, 1H), 7.12 (m, 2H), 7.23 (m, 1H), 7.35 (m, 2H), 8.23 (d, 1H); MS (CI) 357 (MH⁺); [α]$_D$+16.9 (c 1.0, MeOH).

EXAMPLE 162

4-[2-(1R-Hydroxy-ethyl)-pyrimidin-4-yl]-2R,6S-dimethyl-piperazine-1-carboxylic acid pyridin-3-yl ester.

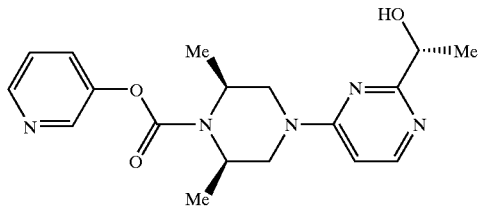

Step A: 4-[2-(1R-Hydroxy-ethyl)-pyrimidin-4-yl]-2R,6S-dimethyl-piperazine-1-carbonyl chloride. To a solution of 1R-[4-(3R,5S-dimethyl-piperazin-1-yl)-pyrimidin-2-yl]-ethyl butyrate (prepared according to the method of Preparation Three, 3.61, 11.8 mmol) and pyridine (0.93 g, 11.8 mmol) in dichloromethane (50 mL) was added triphosgene (1.17 g, 3.9 mmol) and stirred at ambient temperature for 16 h under nitrogen atmosphere. The mixture was washed successively with saturated aqueous sodium bicarbonate and water, and the organic layer was dried over sodium sulfate and filtered. The filtrate was concentrated to obtain an oil which was purified by flash chromatography (ethyl acetate) to give the title compound of Example 162, Step A as a yellow oil, 2.12 g, (51%). ¹H NMR (CDCl₃, 300 MHz) δ 0.90 (t, 3H), 1.31 (d, 6H), 1.56 (d, 3H), 1.68 (m, 2H), 2.38 (t, 2H), 3.21 (m, 2H), 3.88–4.40 (m, 4H), 5.66 (q, 1H), 6.43 (d, 1H), 8.22 (d, 1H); MS (CI) 369, 371 (MH⁺).

Step B: {4-[2-(1R-Butyryloxy-ethyl)-pyrimidin4-yl]-2R,6S-dimethyl-piperazine}-1-carboxylic acid pyridin-3-yl ester. To a suspension of sodium hydride (60% dispersion in oil, 0.046 g, 1.15 mmol) in anhydrous tetrahydrofuran (8 mL) was added 3-hydroxypyridine (0.11 g, 1.15 mmol) at 0° C. After a homogeneous solution was obtained, a solution of 4-[2-(1R-hydroxy-ethyl)-pyrimidin-4-yl]-2R,6S-dimethyl-piperazine-1-carbonyl chloride (prepared according to the method of Example 162, Step A, 0.36 g, 0.96 mmol) in tetrahydrofuran (3 mL) was added at 0° C. and this mixture was warmed to ambient temperature, then heated to reflux for 6 h. The mixture was quenched in water and extracted twice with ethyl acetate. The combined organic layers were dried over sodium sulfate and filtered. The filtrate was concentrated to obtain an oil, which was purified by flash chromatography (ethyl acetate) to give the title compound of Example 162, Step B as a semi-solid, 0.31 g (78%). ¹H NMR (CDCl₃, 300 MHz) δ 0.90 (t, 3H), 1.35 (m, 6H), 1.61 (d, 3H), 1.69 (m, 2H), 2.41 (t, 2H), 3.30 (m, 2H), 4.11·4.38 (m, 4H), 5.69 (q, 1H), 6.41 (d, 1H), 7.32 (m, 1H), 7.52 (m, 1H), 8.22 (d, 1H), 8.46 (s, 1H), 8.48, (d, 1H); MS (CI) 428 (MH⁺).

Step C: 4-[2-(1R-Hydroxy-ethyl)-pyrimidin4-yl]-2R,6S-dimethyl-Piperazine-1-carboxylic acid pyridin-3-yl ester. {4-[2-(1R-Butyryloxy-ethyl)-pyrimidin4-yl]-2R,6S-dimethyl-piperazine}-1-carboxylic acid pyridin-3-yl ester (prepared according to the method of Example 162, Step B, 0.31 g, 0.70 mmol) was combined with concentrated hydrochloric acid (5 mL) and stirred at ambient temperature for 6 h. The mixture was neutralized with 6 N aqueous sodium hydroxide to pH 9 and extracted twice with ethyl acetate.

The extract was washed once with water, dried over sodium sulfate and filtered. The filtrate was concentrated to an oil which was purified by flash chromatography (9:1 dichloromethane:methanol) to give the title compound as a white solid, 0.12 g (81%). $^1$H NMR (CDCl$_3$, 300 MHz) δ 1.41 (d, 6H), 1.51 (d, 3H), 3.33 (m, 2H), 4.254.45 (m, 4H), 4.71 (q, 1H), 6.43 (d, 1H), 7.33 (m, 1H), 7.56 (m, 1H), 8.23 (d, 1H), 8.25 (d, 1H), 8.48 (d, 1H); MS (CI) 358 (MH$^+$); [α]$_D$+18.5 (c 1.0, MeOH).

EXAMPLE 163
4-[2-(1R-Hydroxy-ethyl)-pyrimidin4-yl]-2R-phenyl-piperazine-1-carboxylic acid pyridin-3-yl ester.

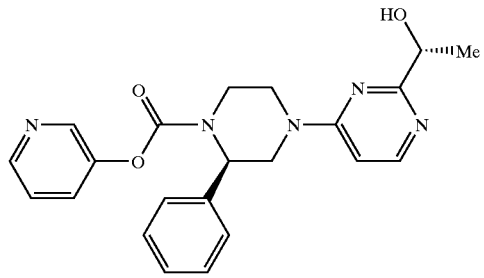

Step A: 1R-[4-(3R-Phenyl-piperazin-1-yl)-pyrimidin-2-yl]-ethyl butyrate. To a solution of (R)-2-phenylpiperazine (0.48 g, 3.0 mmol, *Indian J. Chem. Sect B* 1994, 33, 285) and triethylamine (1.21 g, 12.0 mmol) in tetrahydrofuran (10 mL) was added (R)-1-(4-chloropyrimidin-2-yl)-ethyl butyrate (prepared according to the method of Preparation Seven, 0.68 g, 3.0 mmol) and stirred at ambient temperature for 18 h. The mixture was poured into saturated aqueous sodium bicarbonate and extracted with ethyl acetate. The combined organic layer was dried over sodium sulfate and filtered. The filtrate was concentrated to obtain a crude product which was purified by flash chromatography (95:5 dichloromethane:methanol) to give the title compound of Example 163, Step A as a viscous oil, 0.70 g (67%). $^1$H NMR (CDCl$_3$, 300 MHz) δ 0.95 (t, 3H), 1.56 (d, 3H), 1.67 (m, 2H), 2.40 (t, 2H), 3.55 (m, 2H), 4.0 (m, 2H), 4.32 (m, 2H), 4.70 (m, 1H), 5.69 (q, 1H), 6.49 (d, 1H), 7.40 (m, 5H), 8.21 (d, 1H); MS (CI) 355 (MH$^+$).

Step B: 4-[2-(1R-Butyryloxy-ethyl)-pyrimidin-4-yl]-2R-phenyl-piperazine-1-carboxylic acid pyridin-3-yl ester. To a solution 1R-[4-(3R-phenyl-piperazin-1-yl)-pyrimidin-2-yl]-ethyl butyrate (prepared according to the method of Example 163, Step A, 0.22 g, 0.6 mmol) and triethylamine (0.31 g, 3.1 mmol) in toluene (5 mL) was added dipyridin-3-yl carbonate (0.67 g, 3.1 mmol) and heated to reflux for 3 h. The mixture was poured into saturated aqueous sodium bicarbonate, the organic layer was separated and the aqueous layer was extracted with ethyl acetate. The combined organic layers were dried over sodium sulfate and filtered. The filtrate was concentrated to obtain a crude product which was purified by flash chromatography (9:1 dichloromethane:methanol) to give the title compound of Example 163, Step B as a yellow oil, 0.22 g (73%). MS (CI) 476 (MH$^+$).

Step C: 4-[2-(1R-Hydroxy-ethyl)-pyrimidin-4-yl]-2R-phenyl-piperazine-1-carboxylic acid pyridin-3-yl ester. 4-[2-(1R-Butyryloxy-ethyl)-pyrimidin-4-yl]-2R-phenyl-piperazine-1-carboxylic acid pyridin-3-yl ester (prepared according to the method of Example 163, Step B, 0.21 g, 0.44 mmol) was combined with concentrated hydrochloric acid (2 mL) and stirred at ambient temperature for 6 h. The mixture was neutralized with 6 N aqueous sodium hydroxide to pH 9 and extracted twice with ethyl acetate. The combined extracts were washed once with water, dried over sodium sulfate and filtered. The filtrate was concentrated to an oil which was purified by flash chromatography (9:1 dichloromethane:methanol) to give the title compound as a white solid, 0.13 g (73%). $^1$H NMR (CDCl$_3$, 300 MHz) 31.55 (d, 3H), 3.55 (m, 2H), 4.0 (m, 2H), 4.32 (m, 2H), 4.71 (m, 1H), 4.75 (q, 1H), 6.40 (d, 1H), 7.18–7.41 (m, 7H), 8.24 (d, 1H), 8.35 (br s, 1H), 8.45 (d, 1H); MS (CI) 406 (MH$^+$).

EXAMPLES 164 TO 173

Examples 164 to 173 were prepared from the appropriate starting materials in a manner analogous to the method of Example 163.

| Example | R$^7$ | R$^6$ | Ar$^1$ | mp (° C.) | MS (MH$^+$) |
|---|---|---|---|---|---|
| 164 | 3R—Me | 5S—Me | phenyl | | 357 |
| 165 | 3R—Me | 5S—Me | 2-methyl-pyridin-3-yl | 65–75 | 372 |
| 166 | H | H | pyridin-3-yl | 107–110 | 330 |
| 167 | 3R—Me | 5S—Me | 2-chloro-pyridin-3-yl | 60–70 | 392, 394 |
| 168 | 3R—Me | 5S—Me | 5-chloro-pyridin-3-yl | 65–69 | 392, 394 |
| 169 | 3R—Me | 5S—Me | isoquinolin-5-yl | 60–70 | 407 |
| 170 | 3R—Me | 5S—Me | 4-chloro-pyridin-3-yl | 60–70 | 392, 394 |
| 171 | 3R—Me | 5S—Me | 6-methyl-pyridin-3-yl | 60–70 | 372 |
| 172 | 2RS—CH$_2$OMe | H | pyridin-3-yl | | 388 |
| 173 | 2RS—CO$_2$Et | H | pyridin-3-yl | | 402 |

EXAMPLE 174
(R)-4-Benzyl-1-[2-(1-hydroxy-ethyl)-pyrimidin4-yl]-piperidin-4-ol.

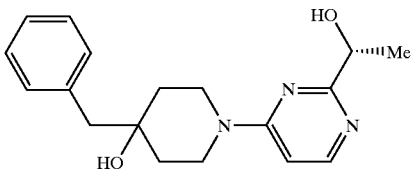

Step A: (R)-1-[4-(4-Benzyl-4-hydroxy-piperidin-1-yl)-pyrimidin-2-yl]-ethyl acetate. To a solution of 4-benzyl-4-hydroxypiperidine (0.95 g, 5.0 mmol) and triethylamine (0.51 g, 5.0 mmol) in dichloromethane (10 mL) was added (R)-1-(4-methanesulfonyloxy-pyrimidin-2-yl)-ethyl butyrate (prepared according to the method of Preparation Eight, 1.23 g, 4.0 mmol) and stirred at ambient temperature for 18 h. The mixture was washed once with water, once with saturated aqueous sodium chloride and the organic layer was dried over sodium sulfate and filtered. The filtrate was evaporated to an oil which was purified by flash chromatography (95:5 dichloromethane:methanol) to give the title compound of Example 174, Step A as a viscous oil, 0.99 g (52%). ¹H NMR (CDCl₃, 300 MHz) δ 0.95 (t, 3H), 1.53 (d, 3H), 1.65–1.78 (m, 4H), 1.88 (m, 2H), 2.08 (m, 2H), 2.48 (t, 2H), 3.45 (m, 2H), 4.42 (br s, 1H), 5.68 (q, 1H), 6.41 (d, 1H), 7.30–7.48 (m, 5H), 8.18 (d, 1H); MS (CI) 384 (MH⁺).

Step B: (R)-4-Benzyl-1-[2-(1-hydroxy-ethyl)-pyrimidin4-yl]-piperidin-4-ol. To a solution of (R)-1-[4-(4-benzyl-4-hydroxy-piperidin-1-yl)-pyrimidin-2-yl]-ethyl butyrate (prepared according to the method of Example 174, Step A, 0.20 g, 0.52 mmol) in methanol (5 mL) was added 1 N aqueous sodium hydroxide (1 mL) and stirred for 4 h at ambient temperature. The mixture was diluted with dichloromethane and washed once with water, once with saturated aqueous sodium chloride and the organic layer was dried over sodium sulfate and filtered. The filtrate was evaporated to give the title compound as a foam, 0.12 g (68%). ¹H NMR (CDCl₃, 300 MHz) δ 1.49 (d, 3H), 1.74 (br s, 2H), 1.82 (m, 2H), 2.08 (m, 2H), 3.42 (m, 2H), 4.42 (br s, 1H), 4.71 (q, 1H), 6.43 (d, 1H), 7.33–7.48 (m, 5H), 8.21 (d, 1H); MS (CI) 314 (MH⁺).

EXAMPLE 175

(R)-4-Phenyl-1-[2-(1-hydroxy-ethyl)-pyrimidin4-yl]-piperidin-4-ol.

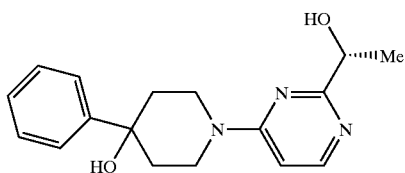

Example 175 was prepared from the appropriate starting materials in a manner analogous to the method of Example 174. mp: 114° C.; MS (CI) 300 (MH⁺).

EXAMPLE 176

(R)-1-{4-[4-(3-Chlorobenzylidene)-piperidin-1-yl]-pyrimidin-2-yl}-ethanol.

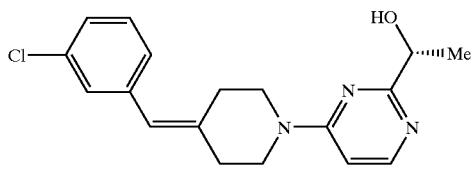

Step A: 1-[4-(3-Chlorobenzylidene)-piperidine-1-yl]-1-carboxylic acid tert-butyl ester. To a suspension of 4-chlorobenzyltriphenylphosphonium chloride (4.23 g, 10.0 mmol) in tetrahydrofuran (40 mL) was added n-butyllithium in hexanes (2.5 M in hexanes, 4.4 mL, 11.0 mmol) at 0° C. under nitrogen atmosphere and stirred 0.5 h. A solution of 4-oxo-piperidine-1-carboxylic acid tert-butyl ester (prepared according to the method of Example 101, Step A, 1.99 g, 10.0 mmol) in tetrahydrofuran (10 mL) was added at 10–15° C. and warmed to ambient temperature. The mixture was evaporated to an oil which was purified by flash chromatography (9:1 hexanes:ethyl acetate) to give the title compound of Example 176, Step A as an oil, 2.63 g (85%). ¹H NMR (CDCl₃, 300 MHz) δ 1.39 (s, 9H), 2.48 (m, 2H), 2.57 (m, 2H), 3.68–3.82 (m, 4H), 6.36 (s, 1H), 7.08 (m, 1H), 7.12–7.28 (m, 3H); MS (CI) 308 (MH⁺).

Step B: 4-(3-Chloro-benzylidene)-piperidine hydrochloride. To a solution of 1-[4-(3-chlorobenzylidene)-piperidine-1-yl]-1-carboxylic acid tert-butyl ester (prepared according to the method of Example 176, Step A, 2.5 g, 8.1 mmol) in dichloromethane (20 mL) was added hydrogen chloride (4 M in dioxane, 4.0 mL, 16.0 mmol) at ambient temperature and stirred for 4 h. The mixture was evaporated to dryness, suspended in ethyl ether and filtered to give the title compound of Example 176, Step B as a white solid, 1.63 g (82%). ¹H NMR (CDCl₃/D₂O, 300 MHz) δ 2.48 (m, 2H), 2.57 (m, 2H), 3.63 (m, 2H), 3.77 (m, 2H), 6.36 (s, 1H), 7.10 (m, 1H), 7.12–7.28 (m, 3H); mp: 147–151° C.

Step C: (R)-1-{4-[4-(3-Chloro-benzylidene)-piperidin-1-yl]-pyrimidin-2-yl}-ethyl butyrate. To a solution of 4-(3-chlorobenzylidene)-piperidine hydrochloride (prepared according to the method of Example 176, Step B, 0.46 g, 2.0 mmol) and triethylamine (0.61 g, 6.0 mmol) in dichloromethane (10 mL) was added (R)-1-(4-chloropyrimidin-2-yl)-ethyl acetate (prepared according to the method of Preparation Five, 0.54 g, 2.2 mmol) and stirred at ambient temperature for 12 h. The mixture was washed successively with saturated aqueous sodium bicarbonate and water, and the organic layer was dried over sodium sulfate and filtered. The filtrate was concentrated to obtain a crude product which was purified by flash chromatography (95:5 dichloromethane:methanol) to give the title compound of Example 176, Step C as a viscous oil, 0.64 g (80%). ¹H NMR (CDCl₃, 300 MHz) δ 0.95 (d, 6H), 1.51 (d, 3H), 1.68 (m, 2H) 2.35 (m, 2H), 2.47–2.64 (m, 4H), 3.67–3.75 (m, 4H), 5.68 (q, 1H), 6.36 (s, 1H), 6.40 (d, 1H), 6.98 (m, 1H), 7.12–7.28 (m, 3H), 8.18 (m, 1H); MS (CI) 400 (MH⁺).

Step D: (R)-1-{4-[4-(3-Chlorobenzylidene)-piperidin-1-yl]-pyrimidin-2-yl}-ethanol. To a solution of (R)-1-{4-[4-(3-chloro-benzylidene)-piperidin-1-yl]-pyrimidin-2-yl}-ethyl butyrate (prepared according to the method of Example 176, Step C, 0.62 g, 1.55 mmol) in methanol (8 mL) was added 1 N aqueous sodium hydroxide (1 mL) then stirred for 4 h at ambient temperature. The mixture was diluted with chloroform and washed once with water, once with saturated aqueous sodium chloride and the organic layer was dried over sodium sulfate and filtered. The filtrate was concentrated to obtain a crude product which was purified by flash chromatography (95:5 dichloromethane:methanol) to give the title compound as a white solid, 0.31 g (61%). ¹H NMR (CDCl₃, 300 MHz) δ1.51 (d, 3H), 2.46 (m, 2H), 2.56 (m, 2H), 3.07 (m, 2H), 3.77 (m, 2H), 4.35 (d, 1H), 4.69 (q, 1H), 6.36 (s, 1H), 6.40 (d, 1H), 7.07 (m, 1H), 7.12–7.28 (m, 3H), 8.18 (m, 1H); mp: 45–55° C.; MS (CI) 330 (MH⁺); [α]_D+16.8 (c 1.0, MeOH).

EXAMPLES 177 TO 181

Examples 177 to 181 were prepared from the appropriate starting materials in a manner analogous to the method of Example 176.

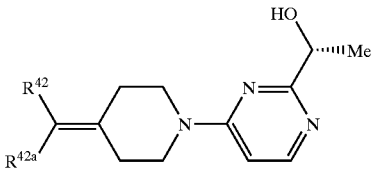

| Example | R⁴² | R⁴²ª | mp (° C.) | MS (MH⁺) |
|---|---|---|---|---|
| 177 | 4-chlorophenyl | H | | 330, 332 |
| 178 | (E)-2-phenyl-ethen-1-yl | H | | 322 |
| 179 | benzoyl | H | 44–59 | 324 |
| 180 | phenyl | phenyl | 108–109 | 372 |
| 181 | phenyl | pyrid-2-yl | 98–101 | 373 |

EXAMPLE 182

(R)-1-[4-(4-pyridin-2-ylmethyl-piperazin-1-yl)-pyrimidin-2-yl]-ethanol.

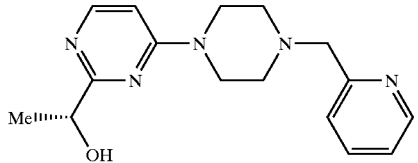

Step A: (R)-1-[4-(4-Pyridin-2-ylmethyl-piperazin-1-yl)-pyrimidin-2-yl]-ethyl acetate. To a solution of (R)-1-[4-piperazin-1-yl)-pyrimidin-2-yl]-ethyl acetate (prepared according to the method of Preparation Two, 1.55 g, 6.2 mmol) and triethylamine (0.86 mL, 6.2 mmol) in tetrahydrofuran (20 mL) was added 2-picoylchloride hydrochloride (1.01 g, 6.2 mmol) at ambient temperature and stirred for 1 h. The mixture was diluted with water and extracted twice with ethyl acetate. The combined extracts were dried over magnesium sulfate, filtered, and the filtrate was concentrated to an oil which was purified by flash chromatography (95:5 dichloromethane:methanol) to give the title compound of Example 182, Step A, 0.98 g (46%). $^1$H NMR (CDCl$_3$, 300 MHz) δ 1.58 (d, 3H), 2.15 (s, 3H) 2.62 (t, 4H), 3.72 (t, 4H), 3.75 (s, 2H), 5.67 (q, 1H), 6.35 (d, 1H), 7.22 (m, 1H), 7.46 (d, 1H), 7.73 (m, 1H), 8.21 (d, 1H), 8.62 (d, 1H); MS (CI) 342 (MH$^+$).

Step B: (R)-1-[4-(4-Pyridin-2-ylmethyl-piperazin-1-yl)-pyrimidin-2-yl]-ethanol. To a solution of (R)-1-[4-(4-pyridin-2-ylmethyl-piperazin-1-yl)-pyrimidin-2-yl]-ethyl acetate (prepared according to the method of Example 182, Step A, 0.14 g, 0.33 mmol) in dioxane (6 mL) was added at ambient temperature 6 N aqueous potassium hydroxide (0.5 mL). After stirring for 3 h the solution was diluted with ethyl acetate and washed twice with water. The organic layer was separated, dried over magnesium sulfate, filtered, and the filtrate was concentrated to give the title compound as a white solid, 0.09 g (69%). $^1$H NMR (CDCl$_3$, 300 MHz) δ 1.52 (d, 3H), 2.38–2.59 (m, 4H), 3.72–3.77 (m, 6H), 4.69 (q, 1H), 6.37 (d, 1H), 7.22 (d, 1H), 7.41 (d, 1H), 7.69 (m, 1H), 8.21 (d, 1H) 8.58, (d, 1H); mp: 68–70 IC; MS (CI) 300 (MH$^+$); [a]$_D$+16.2 (c 1.0, MeOH).

EXAMPLES 183 TO 187

Examples 183 to 187 were prepared from the appropriate starting materials in a manner analogous to the method of Example 182.

| Example | R$^9$ | mp (° C.) | MS (MH$^+$) |
|---|---|---|---|
| 183 | phenylmethyl | | 299 |
| 184 | isoquinolin-2-yl-methyl | | 350 |
| 185 | benzothien-2-yl-methyl | | 355 |
| 186 | benzothiazol-2-yl-methyl | | 356 |
| 187 | benzofuran-2-yl-methyl | | 339 |

EXAMPLE 188

1R-{4-[2R,6S-Dimethyl-4-(2-[1,2,4]triazol-1-yl-pyrimidin-4-yl)-piperazin-1-yl]-pyrimidin-2-yl}-ethanol.

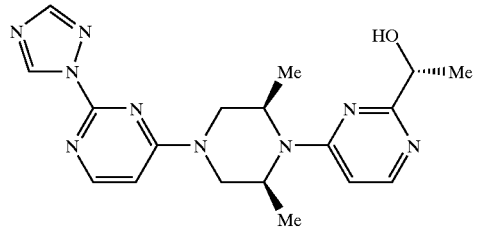

Step A: 4-(3R,5S-Dimethyl-piperazin-1-yl)-2-methanesulfonyl-pyrimidine. To a solution of cis-2,6-dimethylpiperazine (10.7 g, 94.1 mmol) and triethylamine (9.52 g, 94.1 mmol) in chloroform (300 mL) was added 4-chloro-2-methanesulfonylpyrimidine (15.1 g, 78.4 mmol; *Heterocycles* 1985, 23, 611) at ambient temperature and stirred for 1 h. The mixture was partitioned with saturated aqueous sodium bicarbonate and the separated organic layer was washed once with water, once with saturated aqueous sodium chloride and the organic layer was dried over sodium sulfate and filtered. The filtrate was evaporated to an orange solid which was slurried in ethyl ether and filtered to give the title compound of Example 188, Step A as a white solid, 15.4 g (73%). $^1$H NMR (CDCl$_3$, 400 MHz) δ 1.01 (m, 6H), 2.35–2.78 (m, 4H), 2.85 (s, 3H), 3.32 (m, 2H), 6.81 (d, 1H), 8.2 (d, 1H); mp: 182–183° C.; MS (CI) 301 (MH$^+$).

Step B: 4-(3R,5S-Dimethyl-piperazin-1-yl)-2-[1,2,4]triazol-1-yl-pyrimidine. To a slurry of sodium hydride (60% dispersion in oil, 0.37 g, 9.4 mmol) in dimethylformamide (5 mL) was added a solution of 1,2,4-triazole (0.67 g, 9.4 mmol) in dimethylformamide (4 mL) at 0° C. under nitrogen atmosphere. After 10 min, a solution of 4-(3R,5S-dimethyl-piperazin-1-yl)-2-methanesulfonyl-pyrimidine (prepared according to the method of Example 188, Step A, 2.54 g, 9.4 mmol) in warm dimethylformamide (5 mL) was added dropwise and stirred at ambient temperature for 2 h then heated to 100° C. for 0.5 h. The mixture was quenched in saturated aqueous sodium bicarbonate and extracted twice with ethyl acetate. The combined extracts were washed once with water, once with saturated aqueous sodium chloride and the organic layer was dried over sodium sulfate and filtered. The filtrate was evaporated to an oil which was purified by flash chromatography (9:1 dichloromethane:methanol) to give the title compound of Example 188, Step B as an oil, 0.50 g (62%). $^1$H NMR (CDCl$_3$, 400 MHz) δ 1.01 (m, 6H), 2.35–2.88 (m, 5H), 3.32 (m, 1H), 6.81 (d, 1H), 8.16–8.23 (m, 2H), 9.25 (d, 1H); MS (CI) 260 (MH$^+$).

Step C: 1R-{4-[2R,6S-Dimethyl-4-(2-[1,2,3]triazol-1-yl-pyrimidin-4-yl)-piperazin-1-yl]-pyrimidin-2-yl}-ethyl butyrate. To a solution of 4-(3R,5S-dimethyl-piperazin-1-yl)-2-[1,2,4]triazol-1-yl-pyrimidine (prepared according to the method of Example 188, Step B, 0.46 g, 1.8 mmol) in acetonitrile (3 mL) was added (R)-1-(4-methanesulfonyloxy-pyrimidin-2-yl)-ethyl butyrate (prepared according to the method of Preparation Eight, 0.57 g, 2.0 mmol) and heated to reflux for 6 h under nitrogen atmosphere. The mixture was quenched in saturated aqueous sodium bicarbonate and extracted twice with ethyl acetate. The combined extracts were washed once with water, once with saturated aqueous sodium chloride and the organic layer was dried over sodium sulfate and filtered. The filtrate was evaporated to an oil which was purified by flash chromatography (9:1 dichloromethane:methanol) to give the title compound of Example 188, Step C as an oil, 0.22 g (54%). $^1$H NMR (CDCl$_3$, 400 MHz) δ 0.95 (t, 3H), 1.51 (m, 6H), 1.54 (d, 3H), 1.63 (m, 2H), 2.38 (t, 2H), 3.38 (m, 2H), 4.33–4.64 (m, 4H), 5.68 (q, 1H), 6.28 (d, 1H), 6.58 (d, 1H), 8.10 (s, 1H), 8.26–8.32 (m, 2H), 9.10 (d, 1H); MS (CI) 452 (MH$^+$); [α]$_D$+50.0 (c 1.0, MeOH).

Step D: 1R-{4-[2R,6S-Dimethyl-4-(2-[1,2,4]triazol-1-yl-pyrimidin-4-yl)-piperazin-1-yl]-pyrimidin-2-yl}-ethanol. 1R-{4-[2R,6S-Dimethyl-4-(2-[1,2,3]triazol-1-yl-pyrimidin-4-yl)-piperazin-1-yl]-pyrimidin-2-yl}-ethyl butyrate (prepared according to the method of Example 188, Step C, 0.18 g, 0.40 mmol) was combined with concentrated hydrochloric acid (2 mL) and stirred at ambient temperature for 4 h. The mixture was quenched in saturated aqueous sodium bicarbonate and extracted twice with ethyl acetate. The combined extracts were washed once with water, once with saturated aqueous sodium chloride and the organic layer was dried over sodium sulfate and filtered. The filtrate was evaporated to an oil which was purified by flash chromatography (9:1 dichloromethane:methanol) to give the title compound as a white solid, 0.13 g (87%). $^1$H NMR (CDCl$_3$, 400 MHz) δ 1.31 (d, 6H), 1.51 (d, 3H), 3.42 (m, 2H), 4.42–4.73 (m, 5H), 6.41 (d, 1H), 6.56 (d, 1H), 8.12 (s, 1H), 8.24 (d, 1H), 8.30 (d, 1H), 9.10 (s, 1H); MS (CI) 382 (MH$^+$); [a]$_D$+18.6 (c 1.0, MeOH).

EXAMPLES 189 TO 195

Examples 189 to 195 were prepared from the appropriate starting materials in a manner analogous to the method of Example 188.

Step A: 2-Thiomethyl-4-[1,2,4]triazol-1-yl-pyrimidine. To a slurry of sodium hydride (60% dispersion in oil, 24.2 g, 605 mmol) in dimethylformamide (800 mL) was added a solution of 1,2,4-triazole (0.67 g, 9.4 mmol) in dimethylformamide (4.0 mL) at 0° C. under nitrogen atmosphere. After 10 min, a solution of 4-chloro-2-methylthio-pyrimidine (97.2 g, 605 mmol) in dimethylformamide (200 mL) was added dropwise at 10° C. and stirred at ambient temperature for 14 h. The mixture was quenched in water and the solid precipitate was filtered off and dried under vacuum to give the title compound of Example 196, Step A as a white solid, 113 g (94%). $^1$H NMR (CDCl$_3$, 400 MHz) δ 2.82 (s, 3H), 6.82 (d, 1H), 8.18 (d, 1H), 8.19 (s, 1H), 9.35 (s, 1H); mp: 125–126° C.; MS (CI) 194 (MH$^+$).

Step B: 2-Methanesulfonyl-4-[1,2,4]triazol-1-yl-pyrimidine. To a mechanically stirred suspension of 3-chloroperoxybenzoic acid (75%, 127 g, 551 mmol) in chloroform (625 mL) was added a solution of 2-thiomethyl-4-[1,2,4]triazol-1-yl-pyrimidine (prepared according to the method of Example 196, Step A, 50.7 g, 262 mmol) in chloroform (625 mL) and stirred at ambient temperature for 16 h. The mixture was filtered and the filtrate was washed six times with saturated aqueous sodium carbonate. The organic layer was dried over sodium sulfate, filtered, and concentrated to give the title compound of Example 196, Step B as a white solid, 37.8 g (64%). $^1$H NMR (CDCl$_3$, 400 MHz) δ 3.62 (s, 3H), 6.82 (d, 1H), 8.19 (s, 1H), 8.24 (d, 1H), 9.35 (s, 1H); mp: 135–136° C.; MS (CI) 226 (MH$^+$).

Step C: 2-(3R,5S-Dimethyl-piperazin-1-yl)-4-[1,2,4]triazol-1-yl-pyrimidine. 2-Methanesulfonyl-4-[1,2,4]triazol-1-yl-pyrimidine (prepared according to the procedure of

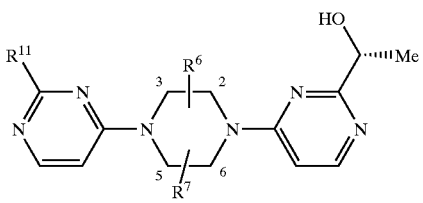

| Example | R$^{11}$ | R$^7$ | R$^6$ | mp (° C.) | MS (MH$^+$) |
|---|---|---|---|---|---|
| 189 | 2-hydroxyphenyl | 2R—Me | 6S—Me | 60–70 | 407 |
| 190 | imidazol-1-yl | 2R—Me | 6S—Me | 60–70 | 381 |
| 191 | [1,2,3]triazol-1-yl | 2R—Me | 6S—Me | 70–80 | 382 |
| 192 | pyrrol-1-yl | 2R—Me | 6S—Me | 70–80 | 380 |
| 193 | 4-methylimidazol-1-yl | 2R—Me | 6S—Me | 70–80 | 395 |
| 194 | 2-methylimidazol-1-yl | 2R—Me | 6S—Me | 70–80 | 395 |
| 195 | 2,4-dimethylimidazol-1-yl | 2R—Me | 6S—Me | 70–80 | 409 |

EXAMPLE 196

1R-{4-[2R,6S-Dimethyl-4-(4-[1.2.4]triazol-1-yl-pyrimidin-2-yl)-piperazin-1-yl]-pyrimidin-2-yl}-ethanol.

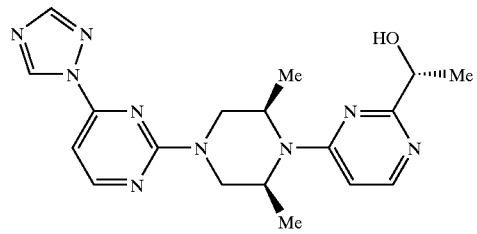

Example 196, Step B, 32.5 g, 144 mmol) was combined with cis-2,6-dimethylpiperazine (34.5 g, 302 mmol) and heated neat at 135° C. for 1 h, cooled, dissolved in 2 N aqueous hydrochloric acid and washed once with ethyl acetate. The acidic aqueous layer was basified to pH 9 with 6 N aqueous sodium hydroxide at 0° C. then extracted four times with ethyl acetate. The combined extracts were washed once with water, once with saturated aqueous sodium chloride and the organic layer was dried over sodium sulfate and filtered. The filtrate was evaporated to an oil which crystallized from hexanes to give the title compound of Example 196, Step C as a white solid, 31.8 g (71%). $^1$H NMR (CDCl$_3$, 400 MHz) δ 0.99 (d, 6H), 2.38 (m, 4H), 3.30 (s, 2H), 6.82 (d, 1H), 8.18 (d, 1H), 8.19 (s, 1H), 9.35 (s, 1H); mp: 143–145° C.; MS (CI) 260 (MH$^+$).

Step D: 1R-{4-[2R,6S-Dimethyl-4-(4-[1,2,4]triazol-1-yl-pyrimidin-2-yl)-piperazin-1-yl]-pyrimidin-2-yl}-ethyl butyrate. To a solution of 2-(3R,5S-dimethyl-piperazin-1-yl)-4-[1,2,4]triazol-1-yl-pyrimidine (prepared according to the method of Example 196, Step C, 8.33 g, 32.1 mmol) in acetonitrile (30 mL) was added (R)-1-(4-trifluoromethanesulfonyloxy-pyrimidin-2-yl)-ethyl butyrate (prepared according to the method of Preparation Nine, 5.50 g, 16.1 mmol) and heated to reflux for 3 h under nitrogen atmosphere. The cooled mixture was filtered and the solids were washed twice with ethyl acetate. The combined extracts were washed once with water, once with saturated aqueous sodium chloride and the organic layer was dried over sodium sulfate and filtered. The filtrate was evaporated to an oil which was purified by flash chromatography (99:1 dichloromethane:methanol) to give the title compound of Example 196, Step D as an oil, 3.61 g (50%). ¹H NMR (CDCl₃, 400 MHz) δ 0.91 (d, 6H), 1.26 (t, 3H), 1.59 (d, 3H), 1.69 (q, 2H), 2.40 (m, 2H), 3.40 (d, 2H), 4.60 (m, 4H), 5.70 (q, 1H), 6.39 (d, 1H), 6.58 (d, 1H), 8.12 (s, 1H), 8.25 (d, 1H), 8.31 (d, 1H), 8.35 (s, 1H); MS (CI) 452 (MH⁺).

Step E: 1R-{4-[2R,6S-Dimethyl-4-(4-[1,2,4]triazol-1-yl-pyrimidin-2-yl)-piperazin-1-yl]-pyrimidin-2-yl}-ethanol. 1R-{4-[2R,6S-Dimethyl-4-(4-[1,2,4]triazol-1-yl-pyrimidin-2-yl)-piperazin-1-yl]-pyrimidin-2-yl}-ethyl butyrate (prepared according to the method of Example 196, Step D, 3.60 g, 8.0 mmol) was combined with concentrated hydrochloric acid (10 mL) and stirred at ambient temperature for 4 h. The mixture was quenched in saturated aqueous sodium bicarbonate and extracted twice with ethyl acetate. The combined extracts were washed once with water, once with saturated aqueous sodium chloride and the organic layer was dried over sodium sulfate and filtered. The filtrate was evaporated to an oil which was purified by flash chromatography (99:1 dichloromethane:methanol) to give the title compound as a white solid, 2.35 g (77%). ¹H NMR (CDCl₃, 400 MHz) δ 1.31 (d, 6H), 1.51 (d, 3H), 3.34 (m, 2H), 4.42 (m, 2H), 4.68–4.82 (m, 3H), 6.42 (d, 1H), 7.11 (d, 1H), 8.11 (s, 1H), 8.23 (d, 1H), 8.49 (d, 1H), 9.12 (s, 1H); mp: 181–182° C.; MS (CI) 382 (MH⁺).

EXAMPLES 197 TO 200

Examples 197 to 200 were prepared from the appropriate starting materials in a manner analogous to the method of Example 196.

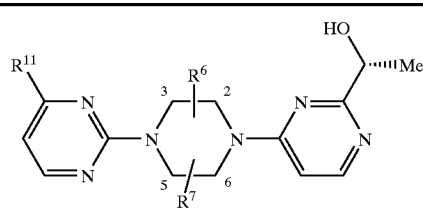

| Example | R¹¹ | R⁷ | R⁶ | mp (° C.) | MS (MH⁺) |
|---|---|---|---|---|---|
| 197 | imidazol-1-yl | 2R—Me | 6S—Me | 60–70 | 381 |
| 198 | morpholin-4-yl | 2R—Me | 6S—Me | 70–80 | 400 |
| 199 | pyrrolidin-1-yl | 2R—Me | 6S—Me | 70–80 | 384 |
| 200 | 4-methylpiperazin-1-yl | 3R—Me | 5S—Me | 168–170 | 413 |

EXAMPLE 201

1R-{4-[2R,6S-Dimethyl-4-(2-pyridin-3-yl-pyrimidin-4-yl)-piperazin-1-yl]-pyrimidin-2-yl}-ethanol.

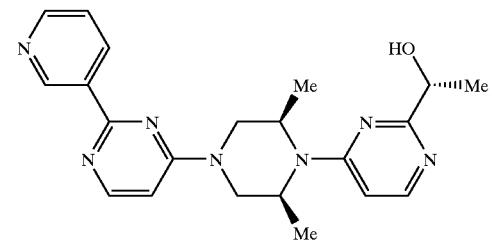

Step A: 2-Pyridin-3-yl-pyrimidin4-yl trifluoromethanesulfonate. To a solution of 2-pyridin-3-yl-3H-pyrimidin-4-one (150 mg, 0.87 mmol; J. Med. Chem. 1990, 33, 1230) and triethylamine (0.13 mL, 0.95 mmol) in dichloromethane (3 mL) was added dropwise a solution of trifluoromethanesulfonic anhydride (0.22 mL, 0.91 mmol) in dichloromethane (2 mL) at 0° C. under nitrogen atmosphere. The mixture was allowed to stir for 30 min at 0° C. then diluted with dichloromethane and washed once with water and the aqueous layer was extracted twice with dichloromethane. The organic extracts were combined, washed sequentially with saturated aqueous sodium carbonate and saturated aqueous sodium chloride, dried over sodium sulfate and filtered. The filtrate was evaporated to give the title compound of Example 201, Step A as an orange oil, 0.22 g (95%), that was used without further purification.

Step B: 1R-{4-[2R,6S-Dimethyl-4-(2-pyridin-3-yl-pyrimidin4-yl)-piperazin-1-yl]-pyrimidin-2-yl}-ethanol. A solution of 2-pyridin-3-yl-pyrimidin4-yl trifluoromethanesulfonate (prepared according to the method of Example 201, Step A, 0.15 g, 0.5 mmol) in tetrahydrofuran (3 mL) at 0° C. was added dropwise to a solution of 1R-[4-(2R,6S-dimethyl-piperazin-1 yl)-pyrmidin-2-yl]-ethyl butyrate (prepared according to the method of Preparation Four, 0.15 g, 0.45 mmol) in tetrahydrofuran (2 mL) and stirred for 1 h at ambient temperature. The mixture was quenched in saturated aqueous sodium bicarbonate and extracted twice with ethyl acetate. The combined extracts were washed once with water, once with saturated aqueous sodium chloride and the organic layer was dried over sodium sulfate and filtered. The filtrate was evaporated to an oil and dissolved in concentrated hydrochloric acid (3 mL) and stirred at ambient temperature for 4 h. The mixture was quenched in saturated aqueous sodium bicarbonate and extracted twice with ethyl acetate. The combined extracts were washed once with water, once with saturated aqueous sodium chloride and the organic layer was dried over sodium sulfate and filtered. The filtrate was evaporated to give the title compound as a white foam, 0.091 g (48%). ¹H NMR (CDCl₃, 400 MHz) δ 1.31 (d, 6H), 1.51 (d, 3H), 3.34 (m, 2H), 4.424.70 (m, 4H), 4.71 (q, 1H), 6.40 (d, 1H), 6.56 (d, 1H), 7.37 (m, 1H), 8.22 (d, 1H), 8.36 (d, 1H), 8.62–8.68 (m, 2H), 9.53 (m, 1H); mp: 61–70° C.; MS (CI) 392 (MH⁺).

EXAMPLE 202

1R-(4-{2R,6S-Dimethyl-4-[2-(4-methyl-piperazin-1-yl)-pyrimidin-4-yl]-piperazin-1-yl}-pyrimidin-2-yl)-ethanol.

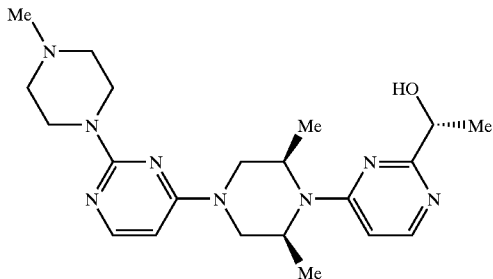

Step A: 1R-{4-[4-(2-Methanesulfonyl-pyrimidin4-yl)-2R,6S-dimethyl-Piperazin-1-yl]-pyrimidin-2-yl}-ethyl butyrate. To a solution of 4-(3R,5S-dimethyl-piperazin-1-yl)-2-methanesulfonyl-pyrimidine (prepared according to the method of Example 188, Step A, 7.70 g, 14.3 mmol) in acetonitrile (30 mL) was added 1R-(4-trifluoromethanesulfonyloxy-pyrimidin-2-yl)-ethyl butyrate (prepared according to the method of Preparation Nine, 5.50 g, 16.1 mmol) and heated to reflux for 3 h under nitrogen atmosphere. The cooled mixture was filtered and the solids were washed twice with ethyl acetate. The combined extracts were washed once with water, once with saturated aqueous sodium chloride and the organic layer was dried over sodium sulfate and filtered. The filtrate was evaporated to an oil which was purified by flash chromatography (98:2 dichloromethane:methanol) to give the title compound of Example 202, Step A as an oil, 4.01 g (62%). $^1$H NMR (CDCl$_3$, 400 MHz) δ 0.93 (t, 3H), 1.21 (d, 6H), 1.55 (d, 3H), 1.64 (q, 2H), 2.36 (t, 2H), 3.25 (s, 3H), 3.37 (m, 2H), 4.54.7 (m, 4H), 5.65 (q, 1H), 6.33 (d, 1H), 6.68 (d, 1H), 8.22 (d, 1H), 8.28 (d, 1H); MS (CI) 463 (MH$^+$).

Step B: 1R-{4-[4-(2-Methanesulfonyl-pyrimidin4-yl)-2R,6S-dimethyl-piperazin-1-yl]-pyrimidin-2-yl}-ethanol. 1R-{4-[4-(2-Methanesulfonyl-pyrimidin-4-yl)-2R,6S-dimethyl-piperazin-1-yl]-pyrimidin-2-yl}-ethyl butyrate (prepared according to the method of Example 202, Step A, 0.42 g, 0.9 mmol) was combined with concentrated hydrochloric acid (3 mL) and stirred at ambient temperature for 4 h. The mixture was quenched in saturated aqueous sodium bicarbonate and extracted twice with ethyl acetate. The combined extracts were washed once with water, once with saturated aqueous sodium chloride and the organic layer was dried over sodium sulfate and filtered. The filtrate was evaporated to an oil which was purified by flash chromatography (99:1 dichloromethane:methanol) to give the title compound of Example 202, Step B as a white foam, 0.25 g (71%). $^1$H NMR (CDCl$_3$, 400 MHz) δ 1.26 (d, 6H), 1.50 (d, 3H), 3.25 (s, 3H), 3.41 (m, 2H), 4.5–4.7 (m, 5H), 6.37 (d, 1H), 6.71 (d, 1H), 8.24 (d, 1H), 8.30 (d, 1H); MS (CI) 393 (MH$^+$).

Step C: 1R-(4-{2R,6S-Dimethyl-4-[2-(4-methyl-piperazin-1-yl)-pyrimidin4-yl]-piperazin-1-yl}-pyrimidin-2-yl)-ethanol. 1R-{4-[4-(2-Methanesulfonyl-pyrimidin4-yl)-2,6-dimethyl-piperazin-1-yl]-pyrimidin-2-yl}-ethanol (prepared according to the method of Example 202, Step B, 0.25 g, 6.4 mmol) was combined with N-methylpiperazine (2.0 mL) and heated at 80° C. for 1 h under nitrogen atmosphere. The mixture was quenched in water and extracted twice with ethyl acetate. The combined extracts were washed once with water, once with saturated aqueous sodium chloride and the organic layer was dried over sodium sulfate and filtered. The filtrate was evaporated to an oil which was purified by flash chromatography (96:4 chloroform:methanol) to give the title compound as a white foam, 0.11 g (41%). $^1$H NMR (CDCl$_3$, 400 MHz) δ 1.31 (d, 6H), 1.51 (d, 3H), 2.47 (s, 3H), 2.63 (m, 4H), 3.23 (m, 2H), 3.94 (m, 4H), 4.33 (m, 2H), 4.57 (m, 2H), 4.71 (q, 1H), 5.96 (d, 1H), 6.46 (d, 1H), 7.98 (d, 1H), 8.23 (d, 1H); mp: 60–70 IC; MS (CI) 413 (MH$^+$).

EXAMPLES 203 TO 207

Examples 203 to 207 were prepared from the appropriate starting materials in a manner analogous to the method of Example 202.

| Example | R$^{11}$ | R$^7$ | R$^6$ | mp (° C.) | MS (MH$^+$) |
|---|---|---|---|---|---|
| 203 | morpholin-4-yl | 2R-Me | 6S-Me | 70–80 | 400 |
| 204 | pyrrolidin-1-yl | 2R-Me | 6S-Me | 70–80 | 384 |
| 205 | 2,6-dimethylmorpholin-4-yl | 2R-Me | 6S-Me | | 428 |
| 206 | 3,5-dimethylpiperidin-1-yl | 2R-Me | 6S-Me | | 426 |
| 207 | 5-methyl-furan-2-yl | 2R-Me | 6S-Me | 123–128 | 395 |

EXAMPLE 208

1R-{4-[3R,5S-Dimethyl-4-[2-(4-methyl-piperazin-1-yl)-pyrimidin-4-yl]-piperazin-1-yl}-pyrimidin-2-yl)-ethanol.

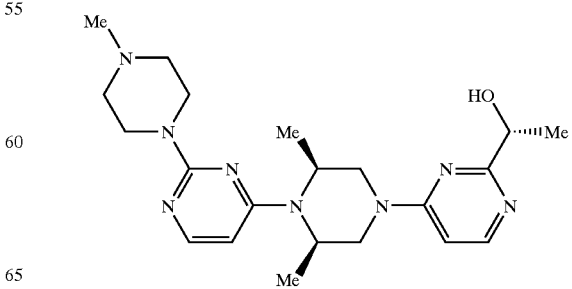

Step A: 4-(4-Benzyl-2R,6S-dimethyl-piperazin-1-yl)-2-methanesulfonyl-pyrimidine. To a solution of cis-1-benzyl-3,5-dimethylpiperazine (24.9 g, 122 mmol, Org. Prep. Proceed. Int. 1976, 8, 19) in dimethylacetamide (60 mL) was added 4-chloro-2-methanesulfonyl pyrimidine (11.8 g, 61.3 mmol) and stirred for 16 h at 120° C. The mixture was partitioned between water and ethyl acetate and the aqueous layer was extracted three times with ethyl acetate. The combined organic layers were washed three times with 1% aqueous copper sulfate, once with saturated aqueous sodium chloride and the organic layer was dried over sodium sulfate and filtered. The filtrate was evaporated to an orange solid which was slurried in isopropyl ether (100 mL) and filtered to give the title compound of Example 208, Step A as an orange solid, 16.5 g (75%). $^1$H NMR (CDCl$_3$, 300 MHz) δ 1.35 (d, 6H), 2.25 (m, 2H), 2.76 (m, 2H), 3.23 (s, 3H), 3.53 (s, 2H), 4.35–4.65 (m, 2H), 6.51 (d, 1H), 7.26 (m, 2H), 7.34 (m, 3H), 8.24 (d, 1H); MS (CI) 361 (MH$^+$).

Step B: 4-(4-Benzyl-2R,6S-dimethyl-piperazin-1-yl)-2-(4-methylpiperazin-1-yl)-pyrimidine. 4-(4-Benzyl-2R,6S-dimethylpiperazin-1-yl)-2-methanesulfonylpyrimidine (prepared according to the method of Example 208, Step A, 11.5 g, 31.9 mmol) was combined with N-methylpiperazine (15 mL, 128 mmol) and heated to 120° C. for 2 h. The mixture was diluted with ethyl acetate and washed once with water, once with saturated aqueous sodium chloride and the organic layer was dried over sodium sulfate and filtered. The filtrate was evaporated to give the title compound of Example 208, Step B as an orange solid, 14.7 g (84%). $^1$H NMR (CDCl$_3$, 300 MHz) δ 1.30 (d, 6H), 2.21 (m, 2H), 2.33 (s, 3H), 2.46 (m, 4H), 2.72 (d, 2H), 3.53 (s, 2H), 3.78 (m, 4H), 4.31 (m, 2H), 5.79 (d, 1H), 7.24 (m, 2H), 7.31 (m, 3H), 7.90 (d, 1H); MS (CI) 381 (MH$^+$).

Step C: 4-(2R,6S-Dimethyl-piperazin-1-yl)-2-(4-methylpiperazin-1-yl)-pyrimidine. To a solution of 4-(4-benzyl-2R,6S-dimethylpiperazin-1-yl)-2–4-methyl-piperazin-1-yl)-pyrimidine (prepared according to the method of Example 208, Step B, 9.8 g, 25.8 mmol) in methanol (200 mL) and hydrochloric acid (1 N in ethyl ether, 38.7 mL, 38.7 mmol) was added ammonium formate (16.3 g, 25.8 mmol). After stirring at ambient temperature for 5 min, 10% palladium on carbon (1.96 g, 20 wt % pre-wetted with isopropanol) was added and this mixture was heated to reflux for 2 h. The cooled reaction was filtered and the filtrate was concentrated to a solid, which was diluted with ethyl acetate and washed twice with water, once with saturated aqueous sodium chloride and the organic layer was dried over sodium sulfate and filtered. The filtrate was evaporated to give the title compound of Example 208, Step C as a clear oil, 6.01 g (81%). $^1$H NMR (CDCl$_3$, 300 MHz) δ 1.25 (s, 6H), 2.31 (s, 3H), 2.24–2.44 (m, 4H), 2.90 (m, 4H), 3.76 (m, 4H), 4.25 (m, 2H), 5.79 (d, 1H), 7.90 (d, 1H); MS (CI) 291 (MH$^+$).

Step D: 1R-(4-[3R,5S-Dimethyl-4-[2-(4-methyl-piperazin-1-yl)-pyrimidin4-yl]-piperazin-1-yl]-pyrimidin-2-yl)-ethyl butyrate. To a solution of 4-(2R,6S-dimethyl-piperazin-1-yl)-2-(4-methyl-piperazin-1-yl)-pyrimidine (prepared according to the method of Example 208, Step C, 9.0 g, 31.1 mmol) and triethylamine (6.5 g, 46.5 mmol) in dimethylformamide (90 mL) was added (R)-1-(4-chloro-pyrimidin-2-yl)-ethyl butyrate (prepared according to the method of Preparation Seven, 7.78 g, 34.1 mmol) and heated to reflux for 3 h under nitrogen atmosphere. The cooled mixture was filtered and the solids were washed twice with ethyl acetate. The combined extracts were washed once with water, once with saturated aqueous sodium chloride and the organic layer was dried over sodium sulfate and filtered. The filtrate was evaporated to an oil which was purified by flash chromatography (95:5 chloroform:methanol) to give the title compound of Example 208, Step D as an oil, 11.4 g (76%). $^1$H NMR(CDCl$_3$, 300 MHz) 60.95 (t, 3H), 1.18 (d, 6H), 1.54 (d, 3H), 2.23–2.35 (m, 7H), 2.51 (m, 4H), 3.21 (m, 2H), 3.81 (m, 4H), 4.32 (m, 2H), 4.52 (m, 2H), 5.65 (q, 1H), 5.82 (d, 1H), 6.38 (d, 1H), 7.39 (d, 1H), 8.18 (d, 1H); MS (CI) 4.83 (MH$^+$).

Step E: 1R-(4-{3R,5S-Dimethyl-4-[2-(4-methyl-piperazin-1-yl)-pyrimidin4-yl]-piperazin-1-yl}-pyrimidin-2-yl)-ethanol. 1R-(4-{3R,5S-dimethyl-4-[2-(4-methyl-piperazin-1-yl)-pyrimidin-4-yl]-piperazin-1-yl}-pyrimidin-2-yl)-ethyl butyrate (prepared according to the method of Example 208, Step D, 11.3 g, 23.5 mmol) was combined with concentrated hydrochloric acid (60 mL) and stirred at ambient temperature for 4 h. The mixture was quenched in saturated aqueous sodium bicarbonate and extracted five times with 10% isopropanol/chloroform. The combined extracts were washed once with saturated aqueous sodium chloride and the organic layer was dried over sodium sulfate and filtered. The filtrate was evaporated to an oil and crystallized from isopropanol to give the title compound as a white solid, 7.34 g (76%). $^1$H NMR (CDCl$_3$, 300 MHz) δ 1.21 (d, 6H), 1.51 (d, 3H), 2.34 (s, 3H), 2.45 (m, 4H), 3.24 (m, 4H), 3.76 (m, 2H), 4.30–4.53 (m, 4H), 4.68 (q, 1H), 5.82 (d, 1H), 6.42 (d, 1H), 7.94 (d, 1H), 8.21 (d, 1H); mp: 181–182° C.; MS (CI) 413 (MH$^+$).

EXAMPLES 209 TO 211

Examples 209 to 211 were prepared from the appropriate starting materials in a manner analogous to the method of Example 208.

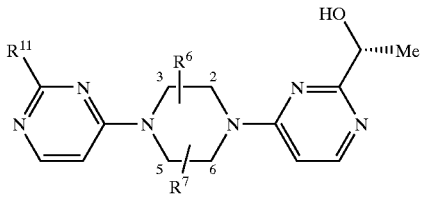

| Example | R$^{11}$ | R$^7$ | R$^6$ | mp (° C.) | MS (MH$^+$) |
|---|---|---|---|---|---|
| 209 | 2,6-dimethylmorpholin-4-yl | 3R-Me | 5S-Me | | 428 |
| 210 | 4-ethylpiperazin-1-yl | 3R-Me | 5S-Me | 144–146 | 427 |
| 211 | 4-isopropylpiperazin-1-yl | 3R-Me | 5S-Me | 137–139 | 441 |

EXAMPLE 212
1R-{4-[2R,6S-Dimethyl-4-(4-morpholino-4-yl-[1,3,5]triazin-2-yl)-piperazin-1-yl]-pyrimidin-2-yl}-ethanol.

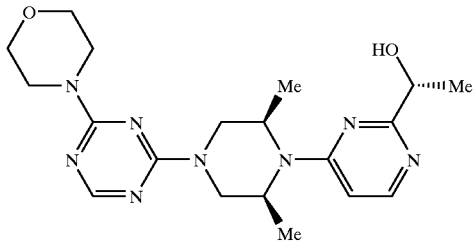

Step A: 1R-{4-[4-(4-Chloro-6-morpholino-[1,3,5]triazin-2-yl)-2R,6S-dimethylpiperazin-1-yl]-pyrimidin-2-yl}-ethyl butyrate. To a solution of 1R-[4-(2R,6S-dimethyl-piperazin-1-yl)-pyrimidin-2-yl]-ethyl butyrate (prepared according to the method of Preparation Four, 0.31 g, 1.0 mmol) and sodium bicarbonate (0.17 g, 2.0 mmol) in dimethylformamide (3 mL) was added 2,4-dichloro-6-morpholino-[1,3,5]triazine (0.24 g, 1.0 mmol; Chem. Pharm. Bull. 1997, 45, 291) and stirred at ambient temperature for 2 hours. The mixture was diluted with ethyl acetate and washed twice with water, once with saturated aqueous sodium chloride, and the organic layer was dried over sodium sulfate and filtered. The filtrate was concentrated to an oil, which was purified by flash chromatography (99:1 chloroform:methanol) to give the title compound of Example 212, Step A as a white solid, 0.19 g (37%). $^1$H NMR (CDCl$_3$, 300 MHz) 80.93 (t, 3H), 1.23 (d, 6H), 1.53 (d, 3H), 1.66 (m, 2H), 2.37 (t, 2H), 3.16 (m, 2H), 3.72–3.78 (m, 10H), 4.12–4.78 (m, 2H), 5.65 (q, 1H), 6.34 (d, 1H), 8.19 (m, 2H); MS (CI) 505, 507 (MH$^+$).

Step B: 1R-{4-[2R,6S-Dimethyl-4-(4-morpholino-4-yl-[1,3,5]triazin-2-yl)-piperazin-1-yl]-pyrimidin-2-yl}-ethanol. To a solution of 1R-{4-[4-(4-chloro-6-morpholino-[1,3,5]triazin-2-yl)-2R,6S-dimethyl-piperazin-1-yl]-pyrimidin-2-yl}-ethyl butyrate (prepared according to the method of Example 212, Step A, 0.15 g, 0.35 mmol) in ethanol (10 mL) was added 10% palladium on carbon (0.75 g, 500 wt %) and hydrogenated at 45–50 psi using a Parr apparatus for 12 hours. The catalyst was filtered off and the filtrate was concentrated to an oil which was added to concentrated hydrochloric acid (2 mL) and stirred at ambient temperature for 6 hours. The mixture was diluted with chloroform and washed twice with water, once with saturated aqueous sodium chloride and the organic layer was dried over sodium sulfate and filtered. The filtrate was concentrated to give the title compound as a white solid, 0.47 g (40%). $^1$H NMR (CDCl$_3$, 300 MHz) δ 1.23 (d, 6H), 1.53 (d, 3H), 3.16 (m, 2H), 3.72–3.78 (m, 10H), 4.12–4.78 (m, 3H), 6.34 (d, 1H), 8.19 (m, 2H); mp: 78–82° C.; MS (CI) 401 (MH$^+$); [α]$_D$+15.1 (c 1.0, MeOH).

EXAMPLE 213
1R-{4-[4-(4-Methoxy-6-methyl-[1,3,5]triazin-2-yl)-3R,5S-dimethylpiperazin-1-yl]-pyrimidin-2-yl}-ethanol.

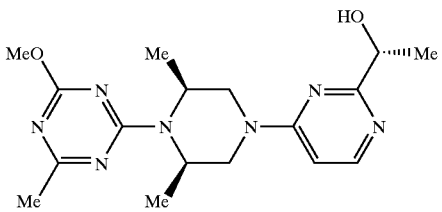

Step A: 1R-{4-[4-(4-Chloro-6-methyl-[1,3,5]triazin-2-yl)-3R,5S-dimethylpiperazin-1-yl]-pyrimidin-2-yl}-ethyl butyrate. To a solution of 1R-[4-(3R,5S-dimethyl-piperazin-1-yl)-pyrimidin-2-yl]-ethyl butyrate (prepared according to the method of Preparation Three, 1.47 g, 6.43 mmol) and sodium bicarbonate (2.25 g, 26.8 mmol) in dimethylformamide (10 mL) was added 2,4-dichloro-6-methyl-[1,3,5]triazine (0.88 g, 5.3 mmol; Monatsh. Chem. 1970, 101, 724) and stirred at ambient temperature for 2 h. The mixture was diluted with ethyl acetate (150 mL) and washed twice with water, once with 10% aqueous CuSO$_4$, once with saturated aqueous sodium chloride, and the organic layer was dried over sodium sulfate and filtered. The filtrate was concentrated to give the title compound of Example 213, Step A as a tan solid, 2.12 g (91%). $^1$H NMR (CDCl$_3$, 300 MHz) δ 0.93 (t, 3H), 1.23 (m, 6H), 1.54 (d, 2H), 1.66 (m, 2H), 2.31 (s, 3H), 2.37 (m, 2H), 2.41 (s, 1H), 3.19 (m, 2H), 4.22–4.55 (m, 2H), 4.91 (m, 2H), 5.65 (q, 1H), 6.40 (d, 1H), 8.20 (d, 1H); MS (CI) 434, 436 (MH$^+$).

Step B: 1R-{4-[4-(4-Methoxy-6-methyl-[1,3,5]triazin-2-yl)-3R,5S-dimethylpiperazin-1-yl]-pyrimidin-2-yl}-ethanol. A solution of sodium methoxide in methanol was freshly prepared by allowing sodium metal (0.4 g, 17.3 mmol) to dissolve in methanol (40 mL). To this mixture was added 1R-{4-[4-(4-chloro-6-methyl-[1,3,5]triazin-2-yl)-3R,5S-dimethyl-piperazin-1-yl]-pyrimidin-2-yl}-ethyl butyrate (prepared according to the method of Example 213, Step A, 1.5 g, 3.46 mmol) which was stirred at ambient temperature for 16 h. The reaction mixture was evaporated to an oil, diluted with chloroform and washed twice with water, once with saturated aqueous sodium chloride, and the organic layer was dried over sodium sulfate and filtered. The filtrate was concentrated to a clear oil which was crystallized from isopropyl ether to give the title compound as a white solid, 0.85 g (72%). $^1$H NMR (CDCl$_3$, 300 MHz) δ 1.23 (d, 6H), 1.48 (d, 3H), 2.36 (s, 3H), 3.20–3.26 (m, 2H), 3.90 (s, 3H), 4.18–4.43 (m, 2H), 4.63 (m, 2H), 4.68 (q, 1H), 4.85 (d, 1H), 6.42 (d, 1H), 8.18 (d, 1H); mp: 161–162° C.; MS (CI) 360 (MH$^+$); [α]$_D$+16.8 (c 1.0, MeOH).

EXAMPLE 214
1R-{4-[4-(4,6-Dimethoxy-[1,3,5]triazin-2-yl)-3R,5S-dimethyl-piperazin-1-yl]-pyrimidin-2-yl}-ethanol.

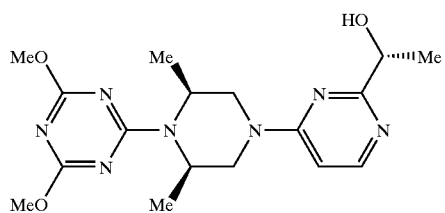

Step A: 1R-{4-[4-(4.6-Dichloro-[1.3,5]triazin-2-yl)-3R,5S-dimethyl-piperazin-1-yl]-pyrimidin-2-yl}-ethyl butyrate. To a solution of 1R-[4-(3R,5S-Dimethyl-piperazin-1-yl)-pyrimidin-2-yl]-ethyl butyrate (prepared according to the method of Preparation Three, 3.25 g, 10.5 mmol) and sodium bicarbonate (1.01 g, 19.2 mmol) in dimethylformamide (8 mL) was added cyanuric chloride (1.76 g, 9.6 mmol) and stirred at ambient temperature for 2 h. The mixture was diluted with ethyl acetate and washed twice with water, once with saturated aqueous sodium chloride, and the organic layer was dried over sodium sulfate and filtered. The filtrate was concentrated to give the title compound of Example 214, Step A as a white semi-solid, 1.42 g (68%). $^1$H NMR (CDCl$_3$, 300 MHz) δ 0.93 (t, 3H), 1.23 (m, 6H), 1.54 (d, 3H), 1.66 (m, 2H), 2.37 (m, 2H), 3.19

(m, 2H), 4.42–4.55 (m, 2H), 4.91 (m, 2H), 5.65 (q, 1H), 6.40 (d, 1H), 8.20 (d, 1H); MS (CI) 446, 448 (MH⁺).

Step B: 1R-{4-[4-(4,6-Dimethoxy-[1,3,5]triazin-2-yl)-3R,5S-dimethyl-piperazin-1-yl]-pyrimidin-2-yl}-ethanol. A solution of sodium methoxide in methanol was freshly prepared by allowing sodium metal (0.18 g, 8.0 mmol) to dissolve in methanol (16 mL). To this mixture was added 1R-{4-[4-(4,6-dichloro-[1,3,5]triazin-2-yl)-3R,5S-dimethyl-piperazin-1-yl]-pyrimidin-2-yl}-ethyl butyrate (prepared according to the method of Example 214, Step A, 0.91 g, 2.0 mmol) at 0° C., then warmed to ambient temperature for 1 h. The mixture was evaporated to an oil, diluted with chloroform and washed once with water, once with saturated aqueous sodium chloride, dried over sodium sulfate and filtered. The filtrate was concentrated to a clear oil which crystallized from isopropyl ether to give the title compound as a white solid, 0.54 g (72%). ¹H NMR (CDCl₃, 300 MHz) δ 1.23 (d, 6H), 1.50 (d, 3H), 3.20 (m, 2H), 3.95 (s, 6H), 4.32 (m, 1H), 4.67–4.86 (m, 4H), 6.34 (d, 1H), 8.22 (d, 1H); mp: 187–188° C.; MS (CI) 376 (MH⁺).

EXAMPLE 215

1R-{2R,6S-Dimethyl-4-(4-phenyl-[1,3,5]triazin-2yl)-piperazin-1-yl]-pyrimidin-2-yl}-ethanol.

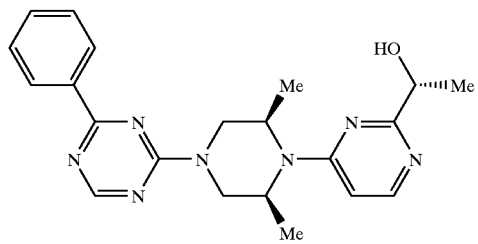

Step A: 1R-{4-[4-(4-Chloro-6-phenyl-[1,3,5]triazin-2-yl)-2R,6S-dimethyl-piperazin-1-yl]-pyrimidin-2-yl}-ethyl butyrate. To a solution of 1R-[4-(2R,6S-dimethyl-piperazin-1yl)-pyrmidin-2yl]-ethyl butyrate (prepared according to the method of Preparation Four, 2.35 g, 7.67 mmol) and sodium bicarbonate (1.29 g, 15.3 mmol) in dimethylformamide (25 mL) at 0° C. was added 2,4-dichloro-6-phenyl[1,3,5]triazine (1.73 g, 7.67 mmol; Helv. Chim. Acta 1950, 33, 1365) portionwise. The reaction mixture was allowed to warm to room temperature and stir under nitrogen for 4 h, poured into water then filtered to give the title compound of Example 215, Step A as a light tan solid, 1.99 g (51%). ¹H NMR (CDCl₃, 400 MHz) δ 0.94 (t, 3H), 1.25 (d, 6H), 1.57 (d, 3H), 1.68 (m, 2H), 2.40 (t, 2H), 3.27 (d, 2H), 4.65 (m, 2H), 4.82 (d, 1H), 5.00 (d, 1H), 5.68 (q, 1H), 6.34 (d, 1H), 7.46 (m, 3H), 8.21 (d, 1H), 8.40 (d, 2H); MS (CI) 496, 498 (MH⁺).

Step B: 1R-{4-[4-(6-Phenyl-[1,3,5]triazin-2-yl)-2R,6S-dimethyl-piperazin-1-yl]-pyrimidin-2-yl}-ethyl butyrate. To a solution of 1R-{4-[4-(4-chloro-6-phenyl-[1,3,5]triazin-2-yl)-2R,6S-dimethyl-piperazin-1-yl]-pyrimidin-2-yl}-ethyl butyrate (prepared according to the method of Example 215, Step A, 4.81 g, 9.7 mmol) in methanol (50 mL) was added 10% palladium on carbon (940 mg, 20 wt %), ammonium formate (5.98 g, 97 mmol), and hydrochloric acid (2 M in ethyl ether, 7.1 mL, 14.2 mmol) and refluxed for 1.5 h. The mixture was allowed to cool, then filtered. The filtrate was concentrated and partitioned between chloroform and saturated aqueous sodium bicarbonate. The organic layer was separated, dried over sodium sulfate, filtered, and the filtrate was evaporated to an oil which was purified by flash chromatography (99:1 chloroform:methanol) to give the title compound of Example 215, Step B as a clear oil, 2.69 g (59%). ¹H NMR (CDCl₃, 400 MHz) δ 0.95 (t, 3H), 1.25 (d, 6H), 1.57 (d, 3H), 1.68 (m, 2H), 2.40 (t, 2H), 3.27 (d, 2H), 4.65 (m, 2H), 4.82 (d, 1H), 5.00 (d, 1H), 5.68 (q, 1H), 6.34 (d, 1H), 7.46 (m, 3H), 8.21 (d, 1H), 8.40 (d, 2H), 8.66 (s, 1H); MS (CI) 462 (MH⁺).

Step C: 1R-{2R,6S-Dimethyl-4-(4-phenyl-[1,3,5]triazin-2yl)-piperazin-1-yl]-pyrimidin-2-yl}-ethanol. Concentrated hydrochloric acid (10 mL) was added to 1R-{4-[4-(6-phenyl-[1,3,5]triazin-2-yl)-2R,6S-dimethyl-piperazin-1 yl]-pyrimidin-2yl}-ethyl butyrate (prepared according to the method of Example 215, Step B, 2.69 g, 5.8 mmol) and allowed to stir for 5 h at ambient temperature. The reaction mixture was cooled to 0° C., diluted with chloroform, and 6 M aqueous sodium hydroxide was added slowly until basic (pH 9). The layers were separated and the aqueous layer was extracted twice with chloroform. The combined organic extracts were washed once with saturated aqueous sodium chloride, dried over sodium sulfate, filtered, and the filtrate was concentrated to an oil which was purified by flash chromatography (97:3 chloroform:methanol) to give a white foam that crystallized from isopropyl ether to give the title compound as a white solid, 1.55 g (68%). ¹H NMR (CDCl₃, 400 MHz) δ 1.28 (d, 6H), 1.54 (d, 3H), 3.31 (d, 2H), 4.63 (m, 2H), 4.77 (q, 1H), 4.85 (d, 1H), 5.50 (d, 1H), 6.42 (d, 1H), 7.50 (m, 3H), 8.25 (d, 1H), 8.41 (d, 2H), 8.68 (s, 1H); mp: 1.33–134° C.; MS (CI) 392 (MH⁺); [a]_D+8.7 (c 1.07, MeOH).

EXAMPLES 216 TO 235

Examples 216 to 235 were prepared from the appropriate starting materials in a manner analogous to the method of Example 215.

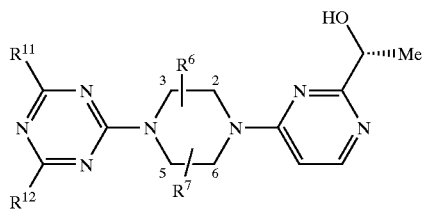

| Example | R¹¹ | R¹² | R⁶ | R⁷ | mp (° C.) | MS (MH⁺) |
|---|---|---|---|---|---|---|
| 216 | Cl | morpholin-4-yl | 2R-Me | 6S-Me | 138–141 | 435, 437 |
| 217 | H | morpholin-4-yl | 3R-Me | 5S-Me | 152 | 401 |

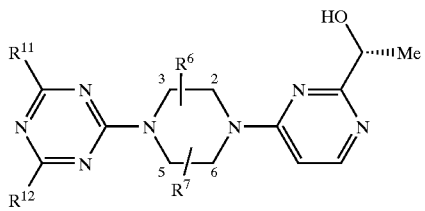

| Example | R¹¹ | R¹² | R⁶ | R⁷ | mp (° C.) | MS (MH⁺) |
|---|---|---|---|---|---|---|
| 218 | OMe | morpholin-4-yl | 2R-Me | 6S-Me | 176–178 | 431 |
| 219 | Me | 4-methyl-piperazin-1-yl | 3R-Me | 5S-Me | | 428 |
| 220 | Me | H | 2R-Me | 6S-Me | 91–94 | 330 |
| 221 | OMe | OMe | 2R-Me | 6S-Me | 128–129 | 376 |
| 222 | OEt | Me | 3R-Me | 5S-Me | 141–142 | 374 |
| 223 | OiPr | Me | 3R-Me | 5S-Me | 87–91 | 388 |
| 224 | phenyl | H | 3R-Me | 5S-Me | 154–155 | 392 |
| 225 | phenyl | OMe | 3R-Me | 5S-Me | | 422 |
| 226 | phenyl | OMe | 2R-Me | 6S-Me | 135–138 | 422 |
| 227 | iPr | H | 2R-Me | 6S-Me | 122–124 | 358 |
| 228 | iPr | OMe | 3R-Me | 5S-Me | 75–80 | 388 |
| 229 | phenyl | H | H | H | 115–117 | 364 |
| 230 | OMe | Me | H | H | 173–175 | 332 |
| 231 | o-tolyl | H | 3R-Me | 5S-Me | 123–125 | 406 |
| 232 | o-tolyl | OMe | 3R-Me | 5S-Me | 143–145 | 436 |
| 233 | cyclopropyl | H | 3R-Me | 5S-Me | 134–135 | 356 |
| 234 | cyclopropyl | H | 2R-Me | 6S-Me | 133–134 | 356 |
| 235 | OMe | CH₂OMe | 3R-Me | 5S-Me | 104–105 | 390 |

EXAMPLE 236

1R-{4-[4-(4-Hydroxymethyl-6-methoxy-[1,3,5]triazin-2-yl)-3R,5S-dimethyl-piperazin-1-yl]-pyrimidin-2-yl}-ethanol.

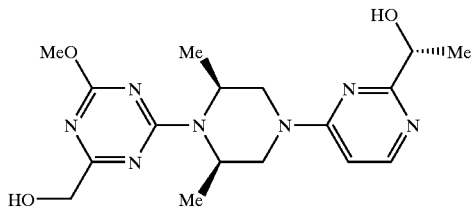

Step A: 1R-{4-[4-(4-Chloro-6-diazomethyl-[1,3,5]triazin-2-yl)-3R,5S-dimethyl-piperazin-1-yl]-pyrimidin-2-yl}-ethyl butyrate. To a solution of 1R-[4-(3R,5S-dimethyl-piperazin-1-yl)-pyrimidin-2-yl]-ethyl butyrate (prepared according to the method of Preparation Three, 3.06 g, 10.0 mmol) and sodium bicarbonate (1.68 g, 20.0 mmol) in dimethylformamide (10 mL) was added 2,4-dichloro-6-diazomethyl-[1,3,5]triazine (1.90 g, 10.0 mmol; J. Am. Chem. Soc. 1957, 79, 944) and stirred at ambient temperature for 2 h. The mixture was diluted with ethyl acetate, washed twice with water, once with saturated aqueous sodium chloride, and the organic layer was dried over sodium sulfate and filtered. The filtrate was concentrated and purified by flash chromatography (ethyl acetate) to give the title compound of Example 236, Step A as a foam, 1.84 g (41%). ¹H NMR (CDCl₃, 300 MHz) δ 0.94 (t, 3H), 1.23 (m, 6H), 1.55 (d, 3H), 1.66 (m, 2H), 2.38 (m, 2H), 3.19 (m, 2H), 4.22–4.45 (m, 2H), 4.86 (m, 2H), 5.10 (s, 1H), 5.65 (q, 1H), 6.40 (d, 1H), 8.20 (d, 1H); mp: 106–108° C.; MS (CI) 461, 463 (MH⁺).

Step B: 1R-{4-[4-(4-Hydroxymethyl-6-methoxy-[1.3,5]triazin-2-yl)-3R,5S-dimethyl-piperazin-1-yl]-pyrimidin-2-yl}-ethanol. 1R-{4-[4-(4-Chloro-6-diazomethyl-[1,3,5]triazin-2-yl)-3R,5S-dimethylpiperazin-1-yl]-pyrimidin-2-yl}-ethyl butyrate (prepared according to the method of Example 236, Step A, 1.5 g, 3.2 mmol) was dissolved in ethyl acetate (20 mL) and 10% aqueous sulfuric acid (5 mL) was added slowly at ambient temperature, stirred 5 min then basified to pH 9 with 6 N aqueous sodium hydroxide. The separated ethyl acetate layer was washed once with brine, dried over magnesium sulfate, and concentrated to a semi-solid. To a freshly prepared solution of sodium methoxide, generated by dissolving sodium metal (0.92 g, 4.0 mmol) in methanol (6 mL), was added the crude solid (0.89 g, 2.0 mmol). This mixture was stirred for 4 h at ambient temperature then evaporated to dryness. The residue was purified by flash chromatography (95:5 dichloromethane:methanol) to give the title compound as a white solid, 0.084 g (13%). ¹H NMR (CDCl₃, 300 MHz) δ 1.23 (d, 6H), 1.49 (d, 3H), 3.14–3.21 (m, 2H), 3.96 (m, 2H), 3.90 (s, 3H), 4.18–4.38 (m, 2H), 4.69 (q, 1H), 4.97 (m, 2H), 6.44 (d, 1H), 8.20 (d, 1H); mp: 170–171° C.; MS (CI) 376 (MH⁺); [α]_D +16.6 (c 1.0, MeOH).

EXAMPLE 237

1R-{4-[4-(4-Methoxymethyl-[1,3,5]triazin-2-yl)-3R,5S-dimethyl-piperazin-1-yl]-pyrimidin-2-yl}-ethanol.

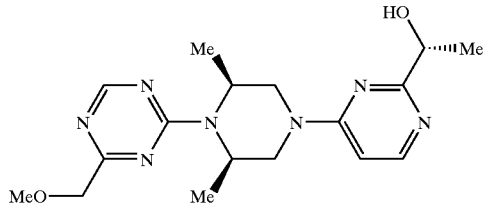

Step A: 1R-{4-[4-(4-Chloro-6-methoxymethyl-[1,3,5]triazin-2-yl)-3R,5S-dimethyl-piperazin-1-yl]-pyrimidin-2-yl}-ethyl butyrate. 1R-{4-[4-(4-Chloro-6-diazomethyl-[1,3, 5]triazin-2-yl)-3R,5S-dimethylpiperazin-1-yl]-pyrimidin-2-yl}-ethyl butyrate (prepared according to the method of Example 236, Step A, 1.5 g, 3.2 mmol) was dissolved in methanol (10 mL) and 10% aqueous sulfuric acid (3 mL) was added. This mixture was stirred at ambient temperature for 1 h then diluted with ethyl acetate. The separated ethyl acetate layer was washed once with saturated aqueous sodium chloride, dried over magnesium sulfate, and concentrated to an oil which was purified by flash chromatography (99:1 dichloromethane:methanol) to give the title compound of Example 237, Step A as an oil, 1.02 (60%). $^1$H NMR (CDCl$_3$, 300 MHz) δ 0.95 (t, 3H), 1.26 (d, 6H), 1.58 (d, 3H), 1.67 (q, 2H), 2.41 (t, 2H), 3.24 (m, 2H), 3.51 (s, 3H), 4.18–4.38 (m, 4H), 4.69 (q, 1H), 4.92 (m, 2H), 6.47 (d, 1H), 8.24 (d, 1H); MS (CI) 464, 466 (MH$^+$).

Step B: 1R-{4-[4-(4-Methoxymethyl-[1,3,5]triazin-2-yl)-3R,5S-dimethyl-piperazin-1-yl]-pyrimidin-2-yl}-ethanol. To a solution of 1R-{4-[4-(4-chloro-6-methoxymethyl-[1,3,5]triazin-2-yl)-3R,5S-dimethpiperazin-1-yl]-pyrimidin-2-yl}-ethyl butyrate (prepared according to the method of Example 237, Step A, 0.43 g, 0.92 mmol) in methanol (8 mL) and hydrochloric acid (2 M in ethyl ether, 0.7 mL, 1.37 mmol) was added ammonium formate (0.58 g, 9.2 mmol) and 10% palladium on carbon (0.085 g, 20 wt %) and heated to reflux for 3 h. The solvents were removed and concentrated hydrochloric acid (2 mL) was added and stirred at ambient temperature for 16 h, basified to pH 9 with 6 N aqueous sodium hydroxide and diluted with ethyl acetate. The separated ethyl acetate layer was washed once with saturated aqueous sodium chloride, dried over magnesium sulfate, and concentrated to an oil which was purified by flash chromatography (9:1 dichloromethane:methanol) to give the title compound as a white solid, 0.12 g (36%). $^1$H NMR (CDCl$_3$, 300 MHz) δ 1.25 (d, 6H), 1.49 (d, 3H), 3.24 (m, 2H), 3.51 (s, 3H), 4.18–4.38 (m, 4H), 4.72 (q, 1H), 4.97 (m, 2H), 6.47 (d, 1H), 8.22 (d, 1H), 8.57 (s, 1H); MS (CI) 360 (MH$^+$).

EXAMPLES 238 TO 240

Examples 238 to 240 were prepared from the appropriate starting materials in a manner analogous to the method of Example 237.

| Example | R$^{11}$ | R$^{12}$ | R$^7$ | R$^6$ | mp (° C.) | MS (MH$^+$) |
|---|---|---|---|---|---|---|
| 238 | CH$_2$OH | H | 3R-Me | 5S-Me | 173–175 | 346 |
| 239 | OMe | CH$_2$OMe | 3R-Me | 5S-Me | 143–145 | 390 |
| 240 | CH$_2$OH | phenyl | 2R-Me | 6S-Me | 173–175 | 422 |

EXAMPLE 241
1R-{4-[4-(4,6-Dimethyl-[1,3,5]triazin-2-yl)-2R,6S-dimethylpiperazin-1-yl]-pyrimidin-2-yl}-ethanol.

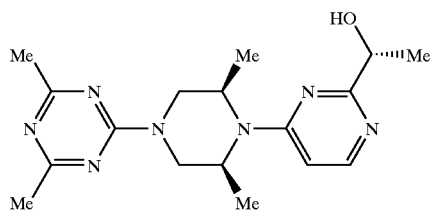

Step A: 1R-{4-[4-(4-Methyl-6-trichloromethyl-[1,3,5]triazin-2-yl)-2R,6S-dimethyl-piperazin-1-yl]-pyrimidin-2-yl}-ethyl butyrate. To a solution of 1R-[4-(2R,6S-dimethyl-piperazin-1-yl)-pyrimidin-2-yl]-ethyl butyrate dibenzoyl-L-tartrate salt (prepared according to the method of Preparation Fifteen, 1.33 g, 2.0 mmol) and sodium bicarbonate (0.34 g, 4.0 mmol) in dimethylformamide (5 mL) was added 2-methyl-4,6-bis-trichloromethyl-[1,3,5]triazine (1.00 g, 3.0 mmol; Bull. Chem. Soc., Jpn. 1969, 42, 2924) and stirred at ambient temperature for 14 h. The mixture was diluted with ethyl acetate and washed twice with water and the organic layer was dried over magnesium sulfate and concentrated. The crude oil was purified by flash chromatography (95:5 dichloromethane:methanol) to give the title compound of Example 241, Step A as a foam, 0.71 g (69%). $^1$H NMR (CDCl$_3$, 300 MHz) δ 0.95 (t, 3H), 1.22 (m, 6H), 1.56 (d, 3H), 1.66 (m, 2H), 2.37 (m, 2H), 2.55 (s, 1H), 3.27 (m, 2H), 4.484.78 (m, 2H), 4.84 (m, 2H), 5.67 (q, 1H), 6.32 (d, 1H), 8.22 (d, 1H); MS (CI) 517, 519 (MH$^+$).

Step B: 1R-{4-[4-(4,6-Dimethyl-[1,3,5]triazin-2-yl)-2R,6S-dimethylpiperazin-1-yl]-pyrimidin-2-yl}-ethanol. A suspension of 1R-{4-[4-(4-methyl-6-trichloromethyl-[1,3,5]triazin-2-yl)-2R,6S dimethyl piperazin-1-yl]-pyrimidin-2-yl}-ethyl butyrate (prepared according to the method of Example 241, Step A, 0.65 g, 1.2 mmol) and 10% palladium on carbon (0.2 g) in triethylamine (1 mL) and methanol (20 mL) was hydrogenated at 40 psi for 0.5 hours using a Parr apparatus. The catalyst was filtered and the filtrate was concentrated to a solid which was dissolved in concentrated hydrochloric acid (2 mL) and stirred for 6 hours. This mixture was diluted with water, basified to pH 9 with 6 N aqueous sodium hydroxide, and extracted into dichloromethane. The extract was washed twice with water, once with saturated aqueous sodium chloride and the organic layer was dried over sodium sulfate and filtered. The filtrate was concentrated to a clear oil which crystallized from isopropyl ether to give the title compound as a white solid, 0.25 g (58%). $^1$H NMR (CDCl$_3$, 300 MHz) δ 1.21 (d, 6H), 1.49 (d, 3H), 2.40 (s, 6H), 3.16 (m, 2H), 4.45–4.68 (m, 2H), 4.71 (q, 1H), 4.84 (m, 2H), 6.42 (d, 1H), 8.20 (d, 1H); mp: 172–173° C.; MS (CI) 344 (MH$^+$); [α]$_D$+17.2 (c 1.0, MeOH).

EXAMPLE 242
1R-{4-[4-(4,6-Dimethyl-[1,3,5]triazin-2-yl)-3R,5S-dimethyl-piperazin-1-yl]-pyrimidin-2-yl}-ethanol.

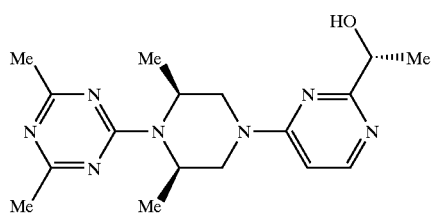

Step A: 4-Methyl-6-trichloromethyl-[1,3,5]triazin-2-yl methanesulfonate. To a solution of 2-hydroxy-4-methyl-6-trichloromethyl-[1,3,5]triazine (1.14 g, 5.0 mmol; *J. Amer. Chem. Soc.* 1956, 78, 2447) and triethylamine (0.51 g, 5.5 mmol) in dichloromethane was added methanesulfonyl chloride (0.57 g, 5.0 mmol) at 0° C. and stirred for 1 h then quenched in saturated aqueous sodium bicarbonate. The separated organic layer was washed once with saturated sodium chloride, dried over magnesium sulfate and filtered. The filtrate was evaporated to give the title compound of Example 242, Step A as an orange oil, 0.98 g (65%) which was used directly without any further purification. MS (CI) 291,293 (MH+).

Step B: 1R-{4-[3R,5S-Dimethyl-4-(4-methyl-6-trichloromethyl-[1.3.5]triazin-2-yl)-piperazin-1-yl]-pyrimidin-2-yl}-ethyl butyrate. To a solution of 1R-[4-(3R, 5S-dimethyl-piperazin-1-yl)-pyrimidin-2-yl]-ethyl butyrate (prepared according to the method of Preparation Three, 0.62 g, 2.0 mmol) and sodium bicarbonate (0.34 g, 4.0 mmol) in dimethylformamide (5 mL) was added 4-methyl-6-trichloromethyl-[1,3,5]triazin-2-yl methanesulfonate (prepared according to the method of Example 242, Step A, 1.00 g, 3.0 mmol) and stirred at ambient temperature for 14 h. The mixture was diluted with ethyl acetate and washed twice with water and the organic layer was dried over magnesium sulfate and concentrated. The crude oil was purified by flash chromatography (ethyl acetate) to give the title compound of Example 242, Step B as a clear oil, 0.41 mg (96%). $^1$H NMR (CDCl$_3$, 300 MHz) δ 0.95 (t, 3H), 1.22 (m, 6H), 1.56 (d, 3H), 1.66 (m, 2H), 2.37 (m, 2H), 2.55 (s, 3H), 3.27 (m, 2H), 4.48–4.78 (m, 2H), 4.84 (m, 2H), 5.67 (q, 1H), 6.32 (d, 1H), 8.22 (d, 1H); MS (CI) 517, 519 (MH+).

Step C: 1R-{4-[4-(4.6-Dimethyl-[1,3,5]triazin-2-yl)-3R, 5S-dimethyl-piperazin-1-yl]-pyrimidin-2-yl}-ethanol. A suspension of 1R-{4-[3R,5S-dimethyl-4-(4-methyl-6-trichloromethyl-[1,3,5]triazin-2-yl)-piperazin-1-yl]-pyrimidin-2-yl}-ethyl butyrate (prepared according to the method of Example 242, Step B, 0.65 g, 1.2 mmol) and 10% palladium on carbon (0.2 g, 30 wt %) in triethylamine (1 mL) and methanol (20 mL) was hydrogenated at 40 psi for 0.5 h using a Parr apparatus. The catalyst was filtered off and the filtrate was concentrated to a solid which was dissolved in concentrated hydrochloric acid (3 mL) and stirred for 6 h. This mixture was diluted with water, basified to pH 9 with 6 N aqueous sodium hydroxide, and extracted into dichloromethane. The extract was washed twice with water and once with saturated sodium chloride and the organic layer was dried over sodium sulfate and concentrated to a clear oil which crystallized from isopropyl ether to give the title compound as a white solid, 0.25 g (23%). $^1$H NMR (CDCl$_3$, 300 MHz) δ 1.21 (d, 6H), 1.49 (d, 3H), 2.40 (s, 6H), 3.16 (m, 2H), 4.45–4.68 (m, 2H), 4.71 (q, 1H), 6.42 (d, 1H), 8.20 (d, 1H); MS (CI) 344 (MH+); mp: 157–159° C.; [α]$_D$+17.2 (c 1.0, MeOH).

EXAMPLES 243 TO 246

Examples 243 to 246 were prepared from the appropriate starting materials in a manner analogous to the method of Example 242.

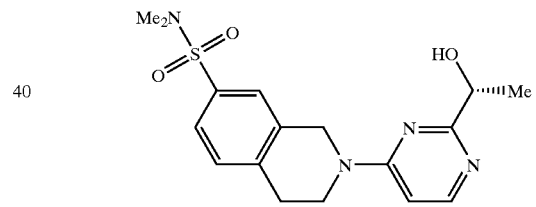

| Example | R$^{11}$ | R$^{12}$ | R$^7$ | R$^6$ | mp (° C.) | MS (MH+) |
|---|---|---|---|---|---|---|
| 243 | Me | phenyl | 2R-Me | 6S-Me | | 406 |
| 244 | Me | phenyl | 3R-Me | 5S-Me | 132–134 | 408 |
| 245 | Me | tetrahydrofuran-2-yl | 2R-Me | 6S-Me | | 428 |
| 246 | Me | o-tolyl | 2R-Me | 6S-Me | 148–150 | 436 |

EXAMPLE 247

(R)-2-[2-(1-Hydroxy-ethyl)-pyrimidin-4-yl]-1,2,3,4-tetrahydro-isoquinoline-7-sulfonic acid dimethylamide.

Step A: 2-Trifluoroacetyl-1,2,3,4-tetrahydro-isoquinoline-7-sulfonic acid dimethylamide. A mixture of 2-trifluoroacetyl-1,2,3,4-tetrahydro-isoquinoline-7-sulfonyl chloride (400 mg, 1.22 mmol, *J. Med. Chem.* 1980, 23, 837), dimethylamine hydrochloride (150 mg, 1.83 mmol), and triethylamine (0.50 mL, 3.66 mmol) in dioxane (10 mL) was refluxed with stirring for 30 min, cooled to room temperature, concentrated, and purified by flash column chromatography (10→50% ethyl acetate/hexanes) to give 337 mg (82%) of the title compound of Example 247, Step A as a yellow oil. $^1$H NMR (CDCl$_3$, 300 MHz, 9:5 mixture of rotamers) δ 7.67–7.52 (c, 2H), 7.36 (t, 1H), 4.87 (s, 1.3H), 4.81 (s, 0.7H), 3.96–3.86 (c, 2H), 3.08–3.02 (c, 2H), 2.72 (s, 6H); MS (TS) 337 (MH+).

Step B: 1,2,3,4-Tetrahydro-isoquinoline-7-sulfonic acid dimethylamide. A mixture of 2-trifluoroacetyl-1,2,3,4-tetrahydro-isoquinoline-7-sulfonic acid dimethylamide (prepared according to the method of Example 247, Step A, 337 mg, 1.0 mmol) and potassium carbonate (207 mg, 1.5 mmol) in a 3:1 mixture of methanol/water (10 mL) was stirred at room temperature for 1 h and concentrated. The remaining aqueous residue was extracted with 10% isopropanol/chloroform (7x) and the combined organic extracts were dried over sodium sulfate, filtered, and evaporated to give 214 mg (89%) of the title compound of Example 247, Step B as a white solid. $^1$H NMR (CD$_3$OD, 300 MHz) δ 7.52 (d, 1H), 7.48 (s, 1H), 7.36 (d, 1H), 4.90 (s, 2H), 3.11 (t, 2H), 2.91 (t, 2H), 2.65 (s, 6H); MS (Cl/NH$_3$) 241 (MH$^+$).

Step C: (R)-1-[4-(7-Dimethylsulfamoyl-3,4-dihydro-1H-isoquinolin-2-yl)-pyrimidin-2-yl]-ethyl acetate. To a solution of 1,2,3,4-tetrahydro-isoquinoline-7-sulfonic acid dimethylamide (prepared according to the method of Example 247, Step B, 210 mg, 0.88 mmol) in isopropanol (5 mL) was added (R)-1-(4-chloro-pyrimidin-2-yl)-ethyl acetate (prepared according to the method of Preparation Five, 175 mg, 0.88 mmol) followed by triethylamine (0.24 mL, 1.75 mmol). This mixture was stirred at room temperature for 1.75 h then heated to reflux for 1.5 h, cooled to room temperature, evaporated, and purified by flash column chromatography (1% methanol/chloroform) to give 327 mg (92%) of the title compound of Example 247, Step C as a white solid. $^1$H NMR (CDCl$_3$, 250 MHz) δ 8.28 (d, 1H), 7.68–7.58 (c, 2H), 7.47 (d, 1H), 6.44 (d, 1H), 5.72 (q, 1H), 4.86 (s, 2H), 3.92 (t, 2H), 3.05 (t, 2H), 2.73 (s, 6H), 2.19 (s, 3H), 1.62 (d, 3H); MS (TS) 431 (MH$^+$).

Step D: (R)-2-[2-(1-Hydroxy-ethyl)-pyrimidin-4-yl]-1,2,3,4-tetrahydro-isoquinoline-7-sulfonic acid dimethylamide. To a solution of (R)-1-[4-(7-dimethylsulfamoyl-3,4-dihydro-1H-isoquinolin-2-yl)-pyrimidin-2-yl]-ethyl acetate (prepared according to the method of Example 247, Step C, 326 mg, 0.81 mmol) in a 4:1 mixture of methanol/water (8 mL) was added lithium hydroxide hydrate (170 mg, 4.0 mmol). This mixture was stirred at room temperature for 50 min, concentrated, re-suspended in water, and extracted with 10% isopropanol/chloroform (3x). The combined organic extracts were dried over sodium sulfate, filtered, evaporated, and purified by flash column chromatography (1% methanol/chloroform) to give a white foam which was further purified by recrystallization from ether/methanol to give 90 mg (31%) of the title compound as a white solid. mp: 120.5–122° C.; $^1$H NMR (CDCl$_3$, 300 MHz) δ 8.24 (d, 1H), 7.62–7.59 (c, 2H), 7.35 (d, 1H), 6.44 (d, 1H), 4.83 (s, 2H), 4.73 (q, 1H), 4.34 (br s, 1H), 3.93–3.85 (c, 2H), 3.03 (t, 2H), 2.71 (s, 6H), 1.52 (d, 3H); MS (TS) 363 (MH$^+$).

EXAMPLE 248

1-[4-(6-Thiophen-3-yl-3,4-dihydro-1H-isoquinolin-2-yl)-pyrimidin-2-yl]-ethanol.

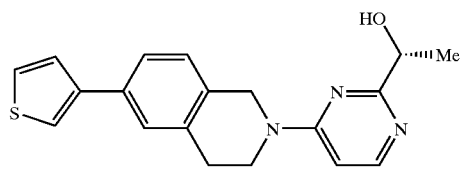

Step A: 6-Thiophen-3-yl-3,4-dihydro-1H-isoquinoline-2-carboxylic acid tert-butyl ester. A mixture of bis(benzonitrile)palladium(II) chloride (30 mg, 0.079 mmol) and 1,4-bis(diphenylphosphino)butane (33.6 mg, 0.079 mmol) in toluene (3 mL) was stirred at room temperature for 20 min. To this mixture was added 6-trifluoromethanesulfonyloxy-3,4-dihydro-1H-isoquinoline-2-carboxylic acid tert-butyl ester (300 mg, 0.79 mmol, Synth. Commun. 1995, 25, 3255), thiophene-3-boronic acid (131 mg, 1.02 mmol), 1 M aqueous sodium carbonate (1.57 mL, 1.57 mmol), and ethanol (2 mL). This dark mixture was heated to reflux with stirring under nitrogen overnight, cooled to room temperature, diluted with saturated aqueous sodium bicarbonate, and extracted with ethyl acetate (4x). The combined organic extracts were dried over sodium sulfate, filtered through Celite, evaporated, and purified by flash column chromatography (hexanes-5% ethyl acetate/hexanes) to give 252 mg (100%) of the title compound of Example 248, Step A as a pale yellow waxy solid. $^1$H NMR (CDCl$_3$, 250 MHz) δ 7.47–7.38 (c, 5H), 7.14 (d, 1H), 4.60 (s, 2H), 3.72–3.64 (c, 2H), 2.95–2.82 (c, 2H), 1.52 (s, 9H); MS (TS) 316 (MH$^+$).

Step B: 6-Thiophen-3-yl-3,4-dihydro-1H-isoquinoline hydrochloride. A mixture of 6-(thiophen-3-yl-3,4-dihydro-1H-isoquinoline-2-carboxylic acid tert-butyl ester (prepared according to the method of Example 248, Step A, 250 mg, 0.79 mmol) and hydrochloric acid (4 M in dioxane, 6 mL, 23.8 mmol) was stirred at room temperature for 1 h and concentrated to give 170 mg (86%) of the title compound of Example 248, Step B as a yellow solid that was used without purification in the next step. $^1$H NMR (CD$_3$OD, 250 MHz) δ 7.66 (m, 1H), 7.61–7.53 (c, 2H), 7.51–7.42 (c, 2H), 7.23 (d, 2H), 4.38 (s, 2H), 3.52 (t, 2H), 3.16 (t, 2H); MS (TS) 216 (MH$^+$).

Step C: (R)-1-[4-(6-Thiophen-3-yl-3.4-dihydro-1H-isoquinolin-2-yl)-pyrimidin-2-yl]-ethyl acetate. To a solution of 6-thiophen-3-yl-3,4-dihydro-1H-isoquinoline hydrochloride (prepared according to the method of Example 248, Step B, 170 mg, 0.68 mmol) in isopropanol (6 mL) was added (R)-1-(4-chloro-pyrimidin-2-yl)-ethyl acetate (prepared according to the method of Preparation Five, 136 mg, 0.68 mmol) followed by triethylamine (0.28 mL, 2.04 mmol). This mixture was stirred at reflux for 7 h, cooled to room temperature overnight, evaporated, and purified by flash column chromatography (0.5–1% methanol/chloroform) to give 253 mg (98%) of the title compound of Example 248, Step C as a yellow solid. $^1$H NMR (CDCl$_3$, 250 MHz) δ 8.26 (d, 1H), 7.52–7.36 (c, 6H), 6.43 (d, 1H), 5.73 (q, 1H), 4.76 (s, 2H), 3.96–3.82 (c, 2H), 3.02 (t, 2H), 2.21 (s, 3H), 1.63 (d, 3H); MS (TS) 380 (MH$^+$).

Step D: 1-[4-(6-Thiophen-3-yl-3.4-dihydro-1H-isoquinolin-2-yl)-pyrimidin-2-yl]-ethanol.

To a solution of (R)-1-[4-(6-thiophen-3-yl-3,4-dihydro-1H-isoquinolin-2-yl)-pyrimidin-2-yl]-ethyl acetate (prepared according to the method of Example 248, Step C, 253 mg, 0.67 mmol) in a 3:1:1 mixture of methanol/tetrahydrofuran/water (5 mL) was added lithium hydroxide hydrate (84 mg, 2.0 mmol). This mixture was stirred at room temperature for 1 h, concentrated, re-suspended in water, and extracted with chloroform (4x). The combined organic extracts were dried over sodium sulfate, filtered, evaporated, and purified by flash column chromatography (2% methanol/chloroform) to give a yellow solid which was further purified by recrystallization from ether/methanol to give 163 mg (72%) of the title compound as a white solid. mp: 125.5–127.5° C.; $^1$H NMR (CDCl$_3$, 300 MHz) δ 8.22 (d, 1H), 7.47–7.35 (c, 5H), 7.22 (d, 1H), 6.42 (d, 1H), 4.78–4.72 (c, 2H), 4.46 (br s, 1H), 3.93–3.84 (c, 2H), 2.99 (t, 2H), 1.54 (d, 3H); MS (APCI) 338 (MH$^+$).

EXAMPLES 249 TO 252

Examples 249 to 252 were prepared from the appropriate starting materials in a manner analogous to the method of Example 248.

| Example | R²⁸ | mp (° C.) | MS (MH⁺) |
|---|---|---|---|
| 249 | 6-thiophen-2-yl | 104–105 | 338 |
| 250 | 6-pyrimidin-5-yl | | 334 |
| 251 | 7-pyrimidin-5-yl | 135–137 | 334 |
| 252 | 6-hydroxy | | 272 |

EXAMPLES 253 TO 258

Examples 253 to 258 were prepared from the appropriate starting materials in a manner analogous to the method of Example 86.

| Example | R²⁸ | mp (° C.) | MS (MH⁺) |
|---|---|---|---|
| 253 | H | 79–82 | 258 |
| 254 | Me | | 272 |
| 255 | CF₃ | 130–132 | 326 |
| 256 | NH₂ | 208–210 | 273 |
| 257 | Ph | 128–131 | 334 |
| 258 | pyridin-4-yl | 144–148 | 335 |

EXAMPLE 259

(R)-1-[4-(3-Benzothiazol-2-yl-5,6-dihydro-8H-[1,2,4]triazolo[4,3-a]pyrazin-7-yl)-pyrimidin-2-yl]-ethanol.

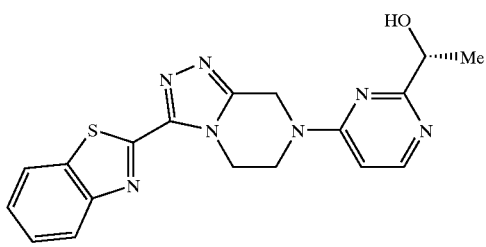

Step A: 5-Ethoxy-3,6-dihydro-2H-pyrazine-1-carboxylic acid benzyl ester. To a solution of 3-oxo-piperazine-1-carboxylic acid benzyl ester (2.0 g, 8.54 mmol, Maybridge) in dichloromethane (18 mL) at room temperature was added triethyloxonium tetrafluoroborate (4.1 g, 21.3 mmol). This mixture was allowed to stir for about 3 days then quenched by the addition of ice chips followed by saturated aqueous sodium bicarbonate until a neutral pH was obtained. The organic layer was separated and the aqueous layer was extracted with chloroform (3×). The combined organic extracts were washed with brine (1×), dried over sodium sulfate, and concentrated to give 2.11 g (95%) of the title compound of Example 259, Step A as a slightly yellow oil that was sufficiently pure to carry on to the next step. ¹H NMR (CDCl₃, 300 MHz) δ 7.43–6.97 (c, 5H), 5.17 (s, 2H), 4.10 (q, 2H), 3.98 (s, 2H), 3.60–3.40 (c, 4H), 1.27 (t, 3H); MS (APCI) 263 (MH⁺).

Step B: 3-Benzothiazol-2-yl-5,6-dihydro-8H-[1,2,4]triazolo[4,3-a]pyrazine-7-carboxylic acid benzyl ester. A mixture of 5-ethoxy-3,6-dihydro-2H-pyrazine-1-carboxylic acid benzyl ester (prepared according to the method of Example 259, Step A, 490 mg, 1.87 mmol) and benzothiazole-2-carboxylic acid hydrazide (360 mg, 1.87 mmol; *J. Org. Chem.* 1958, 23, 1344) in n-butanol (2 mL) was stirred at reflux overnight, cooled to room temperature, concentrated, and purified by flash column chromatography (1% methanol/chloroform) to give 580 mg of the title compound of Example 259, Step B (contaminated with an equimolar amount of benzothiazole-2-carboxylic acid hydrazide which was removed in the subsequent step) as a yellow solid.

Step C: 3-Benzothiazol-2-yl-5,6-dihydro-8H-[1,2,4]triazolo[4,3-a]pyrazine. To a solution of 3-benzothiazol-2-yl-5,6-dihydro-8H-[1,2,4]triazolo[4,3-a]pyrazine-7-carboxylic acid benzyl ester (prepared according to the method of Example 259, Step B, 580 mg, contaminated with benzothiazole-2-carboxylic acid hydrazide) in dichloromethane (10 mL) at 0° C. was added a solution of boron tribromide (1 M in dichloromethane, 4.45 mL, 4.45 mmol). This mixture was warmed to room temperature overnight, quenched by addition of water, and concentrated. The residual aqueous layer was washed with ether (6×), neutralized with saturated aqueous sodium bicarbonate, and extracted with 10% isopropanol/chloroform (3×). The combined organic extracts were dried over sodium sulfate, filtered, evaporated, and purified by flash column chromatography (1–10% methanol/chloroform) to give 175 mg (36%, two steps) of the title compound of Example 259, Step C as a white solid. ¹H NMR (CDCl₃, 300 MHz) δ 8.05 (d, 1H), 7.96 (d, 1H), 7.57–7.41 (c, 2H), 4.62 (t, 2H), 4.36 (s, 2H), 3.35 (t, 2H); MS (APCI) 258 (MH⁺).

Step D: (R)-1-[4-(3-Benzothiazol-2-yl-5,6-dihydro-8H-[1,2,4]triazolo[4,3-a]pyrazin-7-yl)-pyrimidin-2-yl]-ethyl butyrate. A mixture of 3-benzothiazol-2-yl-5,6-dihydro-8H-[1,2,4]triazolo[4,3-a]pyrazine (prepared according to the method of Example 259, Step C, 170 mg, 0.66 mmol), (R)-1-(4-chloro-pyrimidin-2-yl)-ethyl butyrate (prepared according to the method of Preparation Seven, 150 mg, 0.66 mmol), and triethylamine (0.28 mL, 1.98 mmol) in n-butanol (2.2 mL) was heated to reflux overnight, cooled to room temperature, evaporated, and purified by flash column chromatography (1% methanol/chloroform) to give 224 mg (76%) of the title compound of Example 259, Step D as a colorless solid. ¹H NMR (CDCl₃, 300 MHz) δ 8.37 (d, 1H), 8.08 (d, 1H), 7.97 (d, 1H), 7.57–7.43 (c, 2H), 6.53 (d, 1H), 5.71 (q, 1H), 5.09 (s, 2H), 4.82 (t, 2H), 4.33–4.26 (c, 2H), 2.42 (t, 2H), 1.78–1.64 (c, 2H), 1.61 (d, 3H), 0.99 (t, 3H); MS (APCI) 450 (MH⁺).

Step E: (R)-1-[4-(3-Benzothiazol-2-yl-5,6-dihydro-8H-[1,2,4]triazolo[4,3-a]pyrazin-7-yl)-pyrimidin-2-yl]-ethanol. To a solution of (R)-1-[4-(3-benzothiazol-2-yl-5,6-dihydro-8H-[1,2,4]triazolo[4,3-a]pyrazin-7-yl)-pyrimidin-2-yl]-ethyl butyrate (prepared according to the method of Example 259, Step D, 220 mg, 0.49 mmol) in a 3:1:1 mixture of tetrahydrofuran/methanol/water (5 mL) was added lithium hydroxide hydrate (62 mg, 1.47 mmol). This mixture was stirred at room temperature for 3 h, concentrated, and extracted with chloroform (3×). The combined organic extracts were dried over sodium sulfate, filtered, evaporated, and purified by flash column chromatography (5% methanol/chloroform) to give 192 mg (100%) of the title compound as a colorless solid. mp: 216.5–218.5° C.; $^1$H NMR (CDCl$_3$, 300 MHz) δ 8.37 (d, 1H), 8.06 (d, 1H), 7.97 (d, 1H), 7.56–7.45 (c, 2H), 6.56 (d, 1H), 5.11 (s, 2H), 4.83 (t, 2H), 4.77 (m, 1H), 4.35–4.25 (c, 2H), 4.16 (s, 1H), 1.54 (d, 3H); MS (APCI) 380 (MH$^+$), [α]$_D$+14.2 (c 1.0, CHCl$_3$).

EXAMPLES 260 TO 263

Examples 260 to 263 were prepared from the appropriate starting materials in a manner analogous to the method of Example 259.

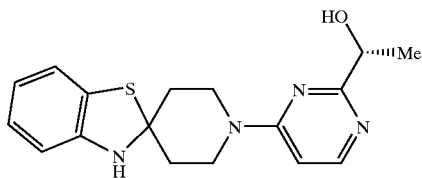

| Example | R$^{33}$ | mp (° C.) | MS (MH$^+$) |
|---|---|---|---|
| 260 | phenyl | 161–164 | 323 |
| 261 | quinoxalin-6-yl | 212–215 | 375 |
| 262 | benzothiophen-2-yl | 224–226 | 379 |
| 263 | biphen-4-yl | 123–125 | 399 |

EXAMPLE 264

(R)-1-[4-(Spiro[benzothiazoline-2,4'-piperidine])-pyrimidin-2-yl]-ethanol.

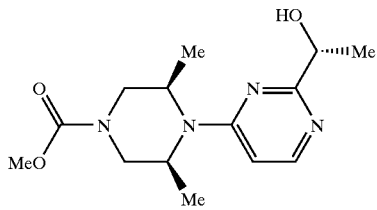

Step A: Spiro[benzothiazolin-2.4°-piperidine] hydrochloride. To a solution of 1'-benzylspiro[benzothiazoline-2,4'-piperidine] (500 mg, 1.69 mmol; Indian J. Chem. 1976, 14B, 984) in acetone (5 mL) at 0° C. was added 1-chloroethyl chloroformate (0.37 mL, 3.38 mmol). This mixture was stirred at 0° C. for 2 h, warmed to room temperature, and concentrated. The residue was purified by flash column chromatography (10→25% ethyl acetate/hexanes) to give the intermediate carbamate which was refluxed in methanol (2 mL) for 30 min. Evaporation of the reaction mixture provided 128 mg (31%) of the title compound of Example 264, Step A as a white solid. $^1$H NMR (CD$_3$OD, 400 MHz) δ 6.98 (dd, 1H), 6.88 (t, 1H), 6.68–6.64 (c, 2H), 3.48–3.34 (c, 2H), 3.25–3.11 (c, 2H), 2.39–2.20 (c, 4H); MS (APCI) 207 (MH$^+$).

Step B: (R)-1-[4-(Spiro[benzothiazoline-2.4°-piperidine])-pyrimidin-2-yl]-ethyl butyrate. To a solution of spiro[benzothiazolin-2,4'-piperidine] hydrochloride (prepared according to the method of Example 264, Step A, 147 mg, 0.60 mmol) in isopropanol (4 mL) was added (R)-1-(4-chloro-pyrimidin-2-yl)-ethyl butyrate (prepared according to the method of Preparation Seven, 140 mg, 0.60 mmol) followed by triethylamine (0.25 mL, 1.8 mmol). This mixture was stirred at reflux for 2 h, concentrated, and purified by flash column chromatography (1%→2% methanol/chloroform) to give 210 mg (88%) the title compound of Example 264, Step B as a yellow oil. $^1$H NMR (CDCl$_3$, 300 MHz) δ 8.20 (d, 1H), 7.09 (dd, 1H), 6.95 (t, 1H), 6.78 (t, 1H), 6.68 (d, 1H), 6.40 (d, 1H), 5.68 (q, 1H), 4.32–4.18 (c, 2H), 4.02 (s, 1H), 3.38–3.25 (c, 2H), 2.39 (t, 2 h), 2.36–2.25 (c, 2H), 1.99–1.83 (c, 2H), 1.75–1.64 (c, 2H), 1.57 (d, 3H), 0.96 (t, 3H); MS (APCI) 399 (MH$^+$).

Step C: (R)-1-[4-(Spiro[benzothiazoline-2,4'-piperidine])-pyrimidin-2-yl]-ethanol. A mixture of (R)-1-[4-(spiro[benzothiazoline-2,4'-piperidine])-pyrimidin-2-yl]-ethyl butyrate (prepared according to the method of Example 264, Step B, 204 mg, 0.51 mmol) and lithium hydroxide hydrate (65 mg, 1.53 mmol) in a 2:2:1 mixture of tetrahydrofuran/methanol/water (5 mL) was stirred at room temperature for 1 h. The organic solvents were evaporated and the residue was extracted with 10% isopropanol/chloroform (3×). The combined organic extracts were dried over sodium sulfate, filtered, evaporated, and purified by flash column chromatography (2% methanol/chloroform, 2×) to give a red foam which was further recyrstallized (ethyl acetate) to give 42 mg (25%) of the title compound as a yellow solid. $^1$H NMR (CDCl$_3$, 400 MHz) δ 8.18 (d, 1H), 7.07 (d, 1H), 6.93 (td, 1H), 6.78 (td, 1H), 6.69 (d, 1H), 6.42 (d, 1H), 4.69 (m, 1H), 4.35–4.16 (c, 3H), 4.02 (s, 1H), 3.41–3.28 (c, 2H), 2.37–2.24 (c, 2H), 1.99–1.85 (c, 2H), 1.49 (d, 3H); MS (APCI) 329 (MH$^+$); [α]$_D$+17.3 (c 1.0, MeOH).

EXAMPLE 265

4-[2-(1R-Hydroxy-ethyl)-pyrimidin-4-yl]-3R,5S-dimethyl-piperazine-1-carboxylic acid methyl ester.

To a solution of 1R-[4-(2R,6S-dimethyl-piperazin-1-yl)-pyrimidin-2-yl]-ethyl butyrate (prepared according to the procedure of Preparation Four, 70 mg, 23 μmol) in tetrahydrofuran (2 mL) at room temperature under nitrogen was added triethylamine (63 μL, 46 μmol) followed by methyl chloroformate (21 μL, 27 μmol). This mixture was stirred for 1 h and concentrated. The residue was dissolved in a 3:1:1 mixture of methanol/tetrahydrofuran/water (2 mL) and lithium hydroxide hydrate (29 mg, 69 μmol) was added. This mixture was stirred for 1 h, concentrated, re-suspended in water, and extracted with 10% isopropanol/chloroform (4×). The combined organic extracts were washed with saturated aqueous sodium bicarbonate (1×), dried over sodium sulfate, filtered, and evaporated to give 50 mg (74%, 2 steps) of the title compound as a colorless oil. $^1$H NMR (CDCl$_3$, 400 MHz) δ 8.21 (d, 1H), 6.33 (d, 1H), 4.70 (m, 1H), 4.63–3.92 (c, 5H), 3.76 (s, 3H), 3.20–3.02 (c, 2H), 1.50 (d, 3H), 1.25 (d, 6H); MS (APCI) 295 (MH$^+$); [α]$_D$+19.0 (c 0.9, MeOH).

EXAMPLE 266

1R-(4-{4-[2-(1R-Butyryloxy-ethyl)-pyrimidin-4-yl]-2R,6S-dimethyl-piperazin-1-yl}-pyrimidin-2-yl)-ethyl butyrate.

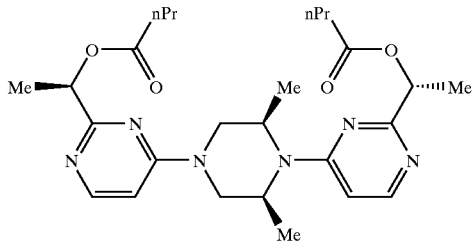

To a solution of 1R-[4-(2R,6S-dimethyl-piperazin-1-yl)-pyrimidin-2-yl]-ethyl butyrate (prepared according to the procedure of Preparation Four, 200 mg, 0.65 mmol) in isopropanol (2 mL) at room temperature was added triethylamine (0.18 mL, 1.31 mmol) followed by (R)-1-(4-chloro-pyrimidin-2-yl)-ethyl butyrate (prepared according to the procedure of Preparation Seven, 150 mg, 0.65 mmol). This mixture was heated to reflux for 18 h, cooled to room temperature, concentrated and purified by flash column chromatography (1% methanol/chloroform) to give 321 mg (99%) of the title compound as a yellow oil. $^1$H NMR (CDCl$_3$, 400 MHz) δ 8.22 (d, 2H), 6.43 (d, 1H), 6.32 (d, 1H), 5.68 (q, 2H), 4.72–4.24 (c, 4H), 3.30–3.12 (c, 2H), 2.39 (t, 4H), 1.77–1.63 (c, 4H), 1.57 (d, 6H), 1.28–1.17 (c, 6H), 0.96 (t, 6H); MS (APCI) 499 (MH$^+$).

EXAMPLE 267

4-{4-[2-(1R-Hydroxy-ethyl)-pyrimidin-4-yl]-2R,6S-dimethyl-piperazin-1-yl}-6-methyl-[1,3,5]triazin-2-ol.

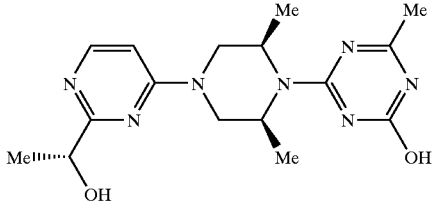

1R-{4-[4-(4-Chloro-6-methyl-[1,3,5]triazin-2-yl)-3R,5S-dimethylpiperazin-1-yl]-pyrimidin-2-yl}-ethyl butyrate (prepared according to the method of Example 213, Step A, 0.30 g, 0.70 mmol) was added to concentrated hydrochloric acid (3 mL) and heated to reflux for 12 h. The mixture was neutralized to pH 7 with solid sodium bicarbonate and extracted into chloroform. The organic extract was dried over sodium sulfate and filtered. The filtrate was concentrated to an oil which was purified by flash chromatography (92:8 chloroform:methanol) to give the title compound as a white solid, 0.15 g (64%). $^1$H NMR (CDCl$_3$, 300 MHz) δ 1.21 (d, 6H), 1.49 (d, 3H), 2.36 (s, 3H), 3.21–3.27 (m, 2H), 4.22–4.43 (m, 2H), 4.63 (m, 2H), 4.69 (q, 1H), 6.42 (d, 1H), 8.18 (d, 1H); mp: 247–248° C.; MS (CI) 346 (MH$^+$).

EXAMPLES 268 TO 275

Examples 268 to 275 were prepared from the appropriate starting materials in a manner analogous to the method of Example 267.

| Example | R$^{11}$ | R$^6$ | R$^7$ | mp (° C.) | MS (MH$^+$) |
|---|---|---|---|---|---|
| 268 | H | 3R-Me | 5S-Me | >250 | 332 |
| 269 | isopropyl | 3R-Me | 5S-Me | >250 | 374 |
| 270 | cyclohexyl | 3R-Me | 5S-Me | >250 | 414 |
| 271 | phenyl | 3R-Me | 5S-Me | >250 | 408 |
| 272 | cyclopropyl | 3R-Me | 5S-Me | >250 | 372 |
| 273 | methyl | 2R-Me | 6S-Me | >250 | 346 |
| 274 | cyclopropyl | 2R-Me | 6S-Me | >250 | 372 |
| 275 | phenyl | 2R-Me | 6S-Me | >250 | 408 |

EXAMPLE 276

(E)-[4-Oxo-3-(5-trifluoromethyl-benzothiazol-2-ylmethyl)-3,4-dihydro-phthalazin-1-yl]-acetic acid 1R-{4-[4-(3-thiophen-2-yl-acryloyl)-piperazin-1-yl]-pyrimidin-2-yl}-ethyl ester.

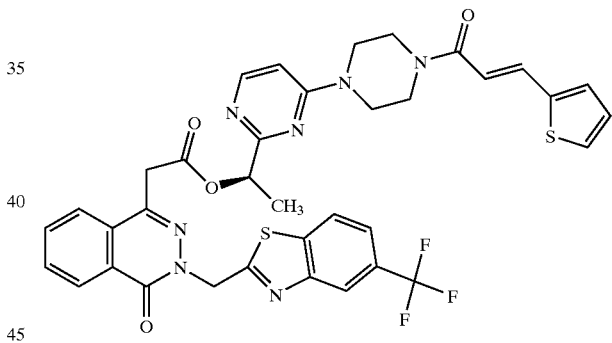

To a solution of [4-oxo-3-(5-trifluoromethyl-benzothiazol-2-ylmethyl)-3,4-dihydro-phthalazin-1-yl]-acetic acid (0.59 g, 1.41 mmol) in dichloromethane (30 mL) and 4-dimethylaminopyridine (0.18 g, 1.41 mmol) was added 1-(3-dimethylaminopropyl)-3-ethylcarbodiimide hydrochloride (0.54 g, 2.82 mmol) followed by (E)-1-{4-[2-(1R-hydroxy-ethyl)-pyrimidin-4-yl]-piperazin-1-yl}-3-thiophen-2-yl-propenone (prepared according to the method of Example 127, 0.49 g, 1.41 mmol) at ambient temperature and stirred for 20 h. The mixture was washed once with saturated aqueous sodium bicarbonate, once with saturated aqueous sodium chloride, dried over magnesium sulfate and filtered. The filtrate was concentrated to an oil which was purified by flash chromatography (ethyl acetate) to give the title compound as a white foam, 0.65 g (62%). $^1$H NMR (CDCl$_3$, 300 MHz) δ 1.51 (d, 3H), 3.41–3.77 (m, 8H), 4.28 (m, 2H), 5.18 (q, 1H), 5.79 (d, 1H), 6.35 (d, 1H), 6.68 (d, 1H), 7.05, (m, 1H), 7.32 (d, 1H), 7.68 (m, 1H), 7.71–7.90 (m, 5H), 8.18 (d, 1H), 8.27 (d, 1H), 8.46 (m, 1H); mp: 105–109° C.; MS (CI) 746 (MH$^+$); [α]$_D$+49.2 (c 1.0, MeOH).

EXAMPLE 277

(E)-[4-Oxo-3-(5-trifluoromethyl-benzothiazol-2-ylmethyl)-3,4-dihydro-phthalazin-1-yl]-acetic acid 1R-[4-(4-quinoxalin-2-yl-piperazin-1-yl)-pyrimidin-2-yl]-ethyl ester.

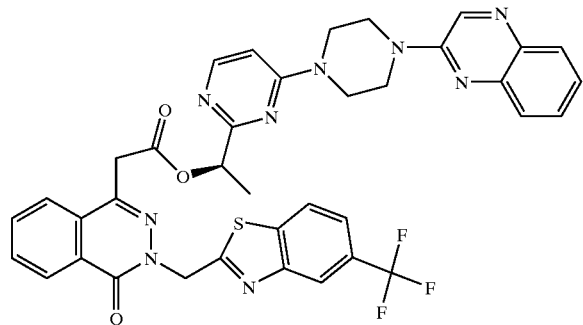

Example 277 was prepared from the appropriate starting materials in a manner analogous to the method of Example 276. $^1$H NMR (CDCl$_3$, 300 MHz) δ 1.53 (d, 3H), 3.38–3.87 (m, 8H), 4.28 (m, 2H), 5.18 (q, 1H), 6.35 (d, 1H), 7.68 (m, 1H), 7.68–7.94 (m, 8H), 8.18 (d, 1H), 8.21–8.37 (m, 2H), 8.46 (m, 1H); mp: 108–112° C.; MS (CI) 738 (MH$^+$).

2-Methoxymethyl-4-piperazin-1-yl-pyrimidine.

Step A: 2-Methoxymethyl-pyrimidin-4-yl-methanesulfonate. To an ice cold solution of 2-methoxymethyl-3H-pyrimidin-4-one (35.0 g, 250 mmol; U.S. Pat. No. 5,215,990) and triethylamine (25.6 g, 250 mmol) in dichloromethane (250 mL) was added methanesulfonyl chloride (28.6 g, 250 mmol) dropwise. This mixture was allowed to warm slowly to room temperature over 1 h then washed successively with saturated aqueous sodium bicarbonate and water. The organic layer was dried over magnesium sulfate, filtered, and evaporated to give the title compound of Preparation One, Step A as a tan solid, 49.2 g (90%). $^1$H NMR (CDCl$_3$, 300 MHz) δ 3.55 (s, 3H), 3.82 (s, 3H), 4.42 (s, 2H), 6.36 (d, 1H), 8.12 (d, 1H); mp: 39–40° C.; MS (TS) 219 (MH$^+$).

Step B: 2-Methoxymethyl-4-piperazin-1-yl-pyrimidine. To a solution of 2-methoxymethyl-pyrimidin4-yl-methanesulfonate (prepared according to the method of Preparation One, Step A, 43.6 g, 200 mmol) in tetrahydrofuran (400 mL) was added piperazine (34.4 g, 400 mmol). This mixture was heated to reflux for 0.5 h, cooled to room temperature, and filtered. The filtrate was concentrated and dried under reduced pressure to give the title compound as a semi-solid, 36.6 g (85%). $^1$H NMR (CDCl$_3$, 300 MHz) δ 2.45 (br s, 1H), 2.88 (m, 4H), 3.45 (s, 3H), 3.72 (m, 4H), 4.46 (s, 2H), 6.38 (d, 1H), 8.22 (d, 1H); MS (TS) 209 (MH$^+$).

Preparation Two (R)-1-(4-Piperazin-1-yl-pyrimidin-2-yl)-ethyl acetate. A mixture of (R)-1-(4-methanesulfonyloxy-pyrimidin-2-yl)-ethyl acetate (prepared according to the method of Preparation Six, 24.1 g, 92 mmol) and piperazine (16.0 g, 184 mmol) in tetrahydrofuran (200 mL) was heated at reflux for 1 h. This mixture was cooled, filtered, concentrated, and purified by flash column chromatography (9:1 dichloromethane/methanol) to give 24.4 g (88%) of the title compound as an oil. $^1$H NMR (CDCl$_3$, 300 MHz) δ 1.56 (d, 3H), 2.25 (s, 3H), 2.83 (m, 4H), 3.63 (m, 4H), 5.54 (q, 1H), 6.38 (d, 1H), 8.24 (d, 1H); MS (CI) 251 (MH$^+$).

Preparation Three

1R-[4-(3R,5S-Dimethyl-piperazin-1-yl)-pyrimidin-2-yl]-ethyl butyrate. A mixture of (R)-1-(4-chloro-pyrimidin-2-yl)-ethyl butyrate (prepared according to the method of Preparation Seven, 18.5 g, 80.9 mmol) and cis-2,6-dimethylpiperazine (18.6 g, 162 mmol) in tetrahydrofuran (400 mL) was stirred at room temperature overnight, diluted with ether, and washed with saturated aqueous sodium bicarbonate (1×) and water (3×). The combined aqueous extracts were back-extracted with 10% isopropanol/chloroform (6×). The combined organic extracts were dried over sodium sulfate, filtered, evaporated, and purified by flash column chromatography (1→5% methanol/chloroform) to give 20.9 g (84%) of the title compound as a waxy yellow solid. $^1$H NMR (CDCl$_3$, 400 MHz) δ 8.14 (d, 1H), 6.31 (d, 1H), 5.65 (q, 1H), 4.53–4.16 (c, 2H), 2.89–2.78 (c, 2H), 2.47–2.33 (c, 2H), 2.38 (t, 2H), 1.73–1.60 (c, 2H), 1.55 (d, 3H), 1.11 (d, 6H), 0.94 (t, 3H); MS (APCI) 307 (MH$^+$).

Preparation Four

1R-[4-(2R,6S-Dimethyl-piperazin-1-yl)-pyrimidin-2-yl]-ethyl butyrate.

Step A: 1-[4-(4-Benzyl-2R,6S-dimethyl-piperazin-1-yl)-pyrimidin-2-yl]-ethyl butyrate. A mixture of (R)-1-(4-trifluoromethanesulfonyloxy-pyrimidin-2-yl)-ethyl butyrate (prepared according to the method of Preparation Nine, 84.8 g, 248 mmol) and cis-1-benzyl-3,5-dimethyl-piperazine (101 g, 496 mmol, Org. Prep. Proceed. Int. 1976, 8, 19) in acetonitrile (310 mL) was stirred at reflux for 15 h, concentrated, and purified by flash column chromatography (15% ethyl acetate/hexanes) to give 52 g (53%) of the title compound of Preparation Four, Step A as an orange oil. $^1$H NMR(CDCl$_3$, 400 MHz) δ 8.15 (d, 1H), 7.39–7.24 (c, 5H), 6.25 (d, 1H), 5.66 (q, 1H), 4.45 (m, 1H), 4.24 (m, 1H), 3.52 (s, 2H), 2.73 (d, 2H), 2.37 (t, 2H), 2.22 (d, 2H), 1.70–1.60 (c, 2H), 1.55 (d, 3H), 1.30 (d, 3H), 1.27 (d, 3H), 0.93 (t, 3H); MS (APCI) 398 (MH$^+$).

Step B: 1R-[4-(4-Benzyl-2R,6S-dimethyl-piperazin-1-yl)-pyrimidin-2-yl]-ethyl butyrate and 1S-[4-(4-Benzyl-2R,6S-dimethyl-piperazin-1-yl)-pyrimidin-2-yl]-ethyl butyrate. 1-[4-(4-Benzyl-2R,6S-dimethyl-piperazin-1-yl)-pyrimidin-2-yl]-ethyl butyrate (prepared according to the method of Preparation Four, Step A, 131 g, 79% ee) was purified by chiral HPLC under the following conditions (column: 15 cm id×25 cm Prochrom column packed with Chiracel AD obtained from Chiral Technologies Inc., 730 Springdale Dr., Exton, Pa., 19341; mobile phase: 90:10 n-heptane/isopropanol; flow rate: about 1 L/min; loading: 4.2 g/cycle) to provide the title compounds of Preparation Four, Step B (109 g, >98% ee) and (12.6 g, 93% ee), respectively, both as yellow oils. The $^1$H NMR and MS data for the preceding compounds were in agreement with that for scalemic material of Preparation Four, Step A.

Step C: 1R-[4-(4-Benzyl-2R,6S-dimethyl-piperazin-1-yl)-pyrimidin-2-yl]-ethyl butyrate hydrochloride. To a solution of 1R-[4-(4-benzyl-2R,6S-dimethyl-piperazin-1-yl)-pyrimidin-2-yl]-ethyl butyrate (prepared according to the method of Preparation Four, Step B, 109 g, 275 mmol) in methanol (500 mL) was added hydrogen chloride (5 M in methanol, 56 mL, 278 mmol). This mixture was stirred at room temperature for 5 min and concentrated to give 118 g (99%) of the title compound of Preparation Four, Step C as a slightly yellow foam.

Step D: 1R-[4-(2R,6S-Dimethyl-piperazin-1-yl)-pyrimidin-2-yl]-ethyl butyrate. To a solution of 1R-[4-(4-benzyl-2R,6S-dimethyl-piperazin-1-yl)-pyrimidin-2-yl]-ethyl butyrate hydrochloride (prepared according to the method of Preparation Four, Step C, 54.2 g, 125 mmol) in methanol (200 mL) was added ammonium formate (79 g, 1.25 mol) followed by a slurry of 10% palladium on carbon (13.5 g, 25 wt %) in methanol (200 mL). This mixture was stirred at reflux for 1 h and filtered through Celite. The filtrate was concentrated, diluted with saturated aqueous sodium bicarbonate, and extracted with chloroform (2×). The combined organic extracts were dried over sodium sulfate, filtered, and evaporated to give 40.8 g of the title compound as a yellow oil. $^1$H NMR (CDCl$_3$, 400 MHz) 38.16 (d, 1H), 6.26 (d, 1H), 5.66 (q, 1H), 4.39 (m, 1H), 4.22 (m, 1H), 2.93 (app s, 4H), 2.38 (t, 2H), 1.71–1.62 (c, 2H), 1.56 (d, 3H), 1.27 (d, 3H), 1.24 (d, 3H), 0.94 (t, 3H); MS (APCI) 307 (MH$^+$).

Preparation Five (R)-1-(4-Chloro-pyrimidin-2-yl)-ethyl acetate. (R)-2-(1-Acetoxy-ethyl)-3H-pyrimidin-4-one (prepared according to the method of Preparation Thirteen, 3.00 g, 16.5 mmol) was added to phosphorus oxychloride (10 mL) at ambient temperature and stirred for 3 h. Excess phosphorus oxychloride was removed under vacuum and the resulting oil was partitioned between chloroform and saturated aqueous sodium carbonate. The layers were separated and the organic layer was washed twice with water, once with saturated aqueous sodium chloride and dried over magnesium sulfate and filtered. The filtrate was evaporated to give the title compound as an orange oil, 2.88 g (87%). $^1$H NMR (CDCl$_3$, 300 MHz) δ 1.56 (d, 3H), 2.18 (s, 3H), 5.68 (q, 1H), 6.32 (d, 1H), 8.21 (d, 1H); MS (CI) 201, 203 (MH$^+$); [α]$_D$+27.6 (c 1.0, MeOH).

Preparation Six (R)-1-(4-Methanesulfonyloxy-pyrimidin-2-yl)-ethyl acetate. To an ice cold solution of (R)-2-(1-acetoxy-ethyl)-3H-pyrimidin-4-one (prepared according to the method of Preparation Thirteen, 2.58 g, 14.2 mmol) and triethylamine (1.43 g, 14.2 mmol) in dichloromethane (20 mL) was added methanesulfonyl chloride (1.63 g, 14.2 mmol) dropwise and stirred for 1 h. The mixture was washed successively with saturated aqueous sodium bicarbonate and water, dried over magnesium sulfate and filtered. The filtrate was evaporated to give the title compound as an oil, 3.15 g (85%). $^1$H NMR (CDCl$_3$, 300 MHz) δ 1.56 (d, 3H), 2.18 (s, 3H), 3.82 (s, 3H), 5.56 (q, 1H), 6.38 (d, 1H), 8.24 (d, 1H); MS (CI) 261 (MH$^+$); [α]$_D$+53.8 (c 1.1, MeOH).

Preparation Seven (R)-1-(4-Chloro-pyrimidin-2-yl)-ethyl butyrate. (R)-2-(1-Butyryloxy-ethyl)-3H-pyrimidin-4-one (prepared according to the method of Preparation Fourteen, 3.00 g, 16.5 mmol) was added to phosphorus oxychloride (10 mL) at ambient temperature and stirred for 3 h. Excess phosphorus oxychloride was removed under vacuum and the resulting oil was partitioned between dichloromethane and saturated aqueous sodium carbonate. The layers were separated and the organic layer was washed once with water, once with saturated aqueous sodium chloride and dried over magnesium sulfate and filtered. The filtrate was evaporated to give the title compound as an orange oil, 3.19 g (85%). $^1$H NMR (CDCl$_3$, 300 MHz) δ 0.98 (t, 3H), 1.54 (d, 3H), 1.67 (m, 2H), 2.48 (t, 2H), 5.68 (q, 1H), 6.36 (d, 1H), 8.21 (d, 1H); [α]$_D$+27.6 (c 1.0, MeOH).

Preparation Eight (R)-1-(4-Methanesulfonyloxy-pyrimidin-2-yl)-ethyl butyrate. To an ice cold solution of (R)-2-(1-butyryloxy-ethyl)-3H-pyrimidin-4-one (prepared according to the method of Preparation Fourteen, 17.8 g, 97.8 mmol) and triethylamine (9.9 g, 97.8 mmol) in dichloromethane (100 mL) was added methanesulfonyl chloride (11.21 g, 97.8 mmol) dropwise and stirred for 1 h. The mixture was washed successively with saturated aqueous sodium bicarbonate and water, dried over magnesium sulfate and filtered. The filtrate was evaporated to give the title compound as an oil, 24.1 g (94%). $^1$H NMR (CDCl$_3$, 300 MHz) δ 0.99 (t, 3H), 1.54 (d, 3H), 1.68 (m, 2H), 2.48 (t, 2H), 3.81 (s, 3H), 5.54 (q, 1H), 6.38 (d, 1H), 8.24 (d, 1H); MS (CI) 261 (MH$^+$); [α]$_D$+28.8 (c 1.0, MeOH).

Preparation Nine (R)-1-(4-Trifluoromethanesulfonyloxy-pyrimidin-2-yl)-ethyl butyrate.

Method 1: To a solution of (R)-2-(1-butyryloxy-ethyl)-3H-pyrimidin-4-one (prepared according to the method of Preparation Fourteen, 52 g, 248 mmol) and triethylamine (36.2 mL, 260 mmol) in dichloromethane (830 mL) at 0° C. with stirring under nitrogen atmosphere was added a solution of trifluoromethanesulfonic anhydride (44 mL, 260 mmol) in dichloromethane (70 mL) dropwise via addition funnel over 30 min, maintaining an internal temperature of 4–8° C. This mixture was allowed to stir an additional 15 min at 4° C., then quenched with water. After stirring for 10 min, the layers were separated and the aqueous layer was extracted with dichloromethane (3×). The combined organic extracts were dried over sodium sulfate, filtered, and concentrated to give 47.2 g (~100%) of the title compound as a dark oil which was used immediately in the next step. $^1$H NMR (CDCl$_3$, 400 MHz) δ 8.83 (d, 1H), 7.03 (d, 1H), 5.82 (q, 1H), 2.41–2.32 (c, 2H), 1.72–1.60 (c, 2H), 1.62 (d, 3H), 0.95 (t, 3H); MS (APCI) 343 (MH$^+$).

Method 2: To a solution of (R)-2-(1-butyryloxy-ethyl)-3H-pyrimidin-4-one (prepared according to the method of Preparation Fourteen, 4.20 g, 20.0 mmol) and triethylamine (2.02 g, 20.0 mmol) in dichloromethane (20 mL) was added trifluoromethanesulfonyl chloride (3.37 g, 20.0 mmol) dropwise, maintaining an internal temperature less than −20° C., and stirred for 0.5 h. The mixture was washed successively with saturated aqueous sodium bicarbonate and water, dried over sodium sulfate and filtered. The filtrate was evaporated to give the title compound as a dark oil, 6.42 g (94%), which was used immediately in the next step. $^1$H NMR and MS data were were in agreement with that from Preparation Nine, Method 1.

Preparation Ten (R)-1-(4-Chloro-pyrimidin-2-yl)-ethanol. To a solution of (R)-1-(4-chloro-pyrimidin-2-yl)-ethyl butyrate (prepared according to the method of Preparation Seven, 250 mg, 1.1 mmol) in dioxane (0.9 mL) was added concentrated hydrochloric acid (0.9 mL). This mixture was allowed to stir at room temperature for 5 h, quenched with saturated aqueous sodium bicarbonate followed by solid sodium bicarbonate until no more gas evolution was evident. Dichloromethane was added and the layers were separated. The aqueous phase was extracted with dichloromethane (3×) and the combined organic extracts were dried over sodium sulfate, filtered, and evaporated to give 125 mg (71%) of the title compound as a pale yellow oil. $^1$H NMR (CDCl$_3$, 400 MHz) δ 8.59 (d, 1H), 7.25 (d, 1H), 4.92 (q, 1H), 3.81 (br s, 1H), 1.56 (d, 3H); MS (APCI) 159, 161 (MH$^+$).

Preparation Eleven (R)-(+)-2-(1-Hydroxy-ethyl)-3H-pyrimidin-4-one hydrochloride.

Step A: R-(+)-2-Hydroxy-propionamidine hydrochloride. To a 22L, 3-neck round bottom flask equipped with reflux condenser, mechanical stirrer, thermometer and nitrogen inlet was added tetrahydrofuran (7.3 L), R-(+)-2-hydroxy-propionamide (731 g, 8.2 mol) and triethyloxonium tetrafluoroborate (95%, 1.97 kg, 9.8 mol). The resulting yellow solution was allowed to stir at room temperature for 2 h, at which time an NMR sample indicated consumption of starting material and the presence of the desired imidate. The solution was concentrated under vacuum to provide a yellow oil which was taken up in methanol (2 L). This solution was cooled to 15° C. and anhydrous ammonia was bubbled through the solution for 5 h. The resulting suspension was allowed to stir for 2 h. concentrated to a thick mixture, diluted with ethyl acetate and filtered through Celite. The filtrate was then cooled to 10° C., anhydrous hydrogen chloride was bubbled through the solution for 2 h, warmed to room temperature, and filtered to provide 418 g (41%) of the title compound of Preparation Eleven, Step A. mp: 134–138° C.; $^1$H NMR (DMSO-$d_6$, 300 MHz) δ 1.33 (t, 3H), 4.42 (q, 1H), 6.25–6.88 (br s, 1H), 8.72–9.25 (br s, 3H).

Step B: (R)-(+)-2-(1-Hydroxy-ethyl)-3H-pyrimidin-4-one hydrochloride. To a 22 L, 3-neck round bottom flask equipped with a reflux condenser, mechanical stirrer, thermometer and nitrogen inlet was added methanol (8 L), potassium hydroxide (946 g, 14.7 mol), R-(+)-2-hydroxy-propionamidine (prepared according to the method of Preparation Eleven, Step A, 1848 g, 14.7 mol) and ethyl 3-hydroxy-acrylate sodium salt (prepared according to the method of Preparation Twelve, Step C, 2030 g, 14.7 mol). The resulting slurry was stirred at room temperature for 3 h. The pH was adjusted from 12.5 to 7 by the addition of concentrated hydrochloric acid (1.32 L). The solids were filtered off and washed with isopropanol. The filtrate was concentrated to an oil, diluted with isopropanol (4 L), cooled to 10° C. and anhydrous hydrogen chloride was bubbled through the solution for 4 h. The resulting suspension was filtered and the solids were dried to provide 2242 g (87%) of the title compound. mp: 180–184° C. (dec); $^1$H NMR (DMSO-$d_6$, 400 MHz) δ 1.46 (d, 3H), 4.84 (q, 1H), 6.52 (d, 1H), 8.00 (d, 1H).

Preparation Twelve 2-(1-Hydroxy-ethyl)-3H-pyrimidin-4-one.

Step A: 2-Hydroxy-propionimidic acid ethyl ester hydrochloride. A solution of lactonitrile (378 g, 5.32 mol) in ethyl ether (1.46 L) and ethanol (0.34 L) was saturated with hydrogen chloride gas at 0–5° C. for 0.5 h and kept at 5° C. for 60 h. The resulting precipitate was filtered off and washed twice with ethyl ether to give the title compound of Preparation Twelve, Step A as a solid, 815 g (99%). mp: 165–168° C.; $^1$H NMR (CD$_3$OD, 250 MHz) δ 1.45–1.53 (c, 6H), 4.40–4.61 (c, 3H).

Step B: 2-Hydroxy-propionamidine hydrochloride. A suspension of 2-hydroxypropionimidic acid ethyl ester hydrochloride (prepared according to the method of Preparation Twelve, Step A, 751 g, 4.87 mol) in ethanol (3.75 L) at 0° C. was saturated with ammonia gas, maintaining an internal temperature <5° C., for 1 h then stirred at ambient temperature for 18 h. The solid was filtered off and dried under vacuum at 40° C. to give an initial crop of material. The filtrate was concentrated to one-half volume and a second crop was collected and dried under vacuum. The first and second crops were combined to give the title compound of Preparation Twelve, Step B as a yellow solid, 608 g (99%). mp: 134–138° C.; $^1$H NMR (DMSO-$d_6$, 400 MHz) δ 1.30 (d, 3H), 4.38 (q, 1H), 6.23 (br s, 1H), 7.35 (br s, 1H), 8.78 (br s, 3H).

Step C: Ethyl 3-hydroxy-acrylate sodium salt. To a suspension of sodium hydride (60% dispersion in oil, 269 g, 16.7 mol) in isopropyl ether (12 L) was added slowly ethyl acetate (1280 g, 14.2 mol) at a rate which maintained an internal temperature of 45° C. This mixture was stirred for and additional 0.5 h, then ethyl formate (2232 g, 30.1 mol) was added dropwise at 42° C. and stirred at ambient temperature for 18 h. The mixture was filtered and the solids were washed twice with ethyl ether and once with hexanes and dried to give the title compound of Preparation Twelve, Step C as a white solid, 1930 g (99%). $^1$H NMR (DMSO-$d_6$, 300 MHz) δ 1.03 (t, 3H), 3.86 (q, 2H), 4.08 (d, 1H), 8.03 (d, 1H).

Step D: 2-(1-Hydroxy-ethyl)-3H-pyrimidin-4-one. To a solution of ethyl 3-hydroxy-acrylate sodium salt (prepared according to the method of Preparation Twelve, Step C, 1301 g, 9.42 mol) in water (1.3 L) was added a solution of 2-hydroxy-propionamidine hydrochloride (prepared according to the method of Preparation Twelve, Step B, 610 g, 4.9 mol) in water (1.3 L) at ambient temperature and stirred for 48 h. The solution was adjusted to pH 7.0 with acetic acid then continuously extracted with chloroform for 48 h. The extract was dried over sodium sulfate and filtered. The filtrate was concentrated to a solid, slurried in ethyl ether, filtered, and dried to give the title compound as a solid, 232 g (38%). mp: 121–124° C.; $^1$H NMR (DMSO-$d_6$, 400 MHz) δ 1.30 (d, 3H), 4.46 (q, 1H), 5.62 (br s, 1H), 6.13 (d, 1H), 7.80 (d, 1H).

Preparation Thirteen (R)-2-(1-Acetoxy-ethyl)-3H-pyrimidin-4-one. To a solution of vinyl acetate (4.3 g, 50 mmol) in dioxane (63 mL) was added 2-(1-hydroxy-ethyl)-3H-pyrimidin-4-one (prepared according to the method of Preparation Twelve, 2.1 g, 15.1 mmol), and the mixture was heated to 50° C. To the resulting solution was added lipase P30 (0.21 g, 10 wt %) and the heating was continued for 24 h. The reaction mixture was filtered and the filtrate was evaporated to obtain a thick syrupy liquid residue. The residue was purified by flash column chromatography (95:5 dichloromethane:methanol) to give the title compound as a colorless liquid, 0.97 g (92% of theory). $^1$H NMR (CDCl$_3$, 300 MHz) δ 1.61 (d, 3H), 2.20 (s, 3H), 5.65 (q, 1H), 6.35 (d, 1H), 7.97 (d, 1H), 11.94 (s, 1H); [α]$_D$+39.9 (c 1.0, MeOH).

Preparation Fourteen (R)-2-(1-Butyryloxy-ethyl)-3H-pyrimidin-4-one.

Method 1: To a solution of vinyl butyrate (17.7 g, 310 mmol) in dioxane (650 mL) was added 2-(1-hydroxy-ethyl)-3H-pyrimidin-4-one (prepared according to the method of Preparation Twelve, 21.8 g, 155 mmol), and the mixture was heated to 50° C. To the resulting solution was added lipase P30 (4.35 g, 20 wt %) and the heating was continued for 24 h. The reaction mixture was filtered and the filtrate was evaporated to obtain a thick syrupy liquid residue which was partitioned between dichloromethane and water. The layers were separated and the organic layer was dried over sodium sulfate, filtered, and evaporated to give the title compound as a colorless liquid, 9.35 g (86% of theory). $^1$H NMR (CDCl$_3$, 300 MHz) 0.95 (t, 3H), 1.65 (m, 5H), 2.40 (m, 2H), 5.65 (q, 1H), 6.45 (d, 1H), 8.00 (d, 1H); [a]$_D$+29.5 (c 1.0, MeOH).

Method 2: To a chilled (5° C.) solution of (R)-(+)-2-(1-hydroxy-ethyl)-3H-pyrimidin-4-one hydrochloride (prepared according to the method of Preparation Eleven, 750 g, 4.3 mol) in dichloromethane (8 L) was added triethylamine (1216 mL, 8.7 mol) followed by 4-dimethylaminopyridine (25.9 g, 0.21 mol). A solution of butyric anhydride (730 mL, 4.4 mol) in dichloromethane (730 mL) was then slowly added over a period of 5 h, keeping the temperature <3° C. The mixture was washed twice with half-saturated brine (4 L) and once with saturated aqueous sodium bicarbonate (4 L), dried over sodium sulfate, filtered, and concentrated under vacuum to give 869 g (96%) of the title compound as an oil. The $^1$H NMR and MS data for this compound are in agreement with that of Preparation Fourteen, Method 1.

Preparation Fifteen

1R-[4-(2R,6S-Dimethyl-piperazin-1-yl)-pyrimidin-2-yl]-ethyl butyrate dibenzoyl-L-tartrate salt.

Step A: 1R-[4-(4-Benzyl-2R,6S-dimethyl-piperazin-1-yl)-pyrimidin-2-yl]-ethyl butyrate bis dibenzoyl-L-tartrate salt. To a solution of (R)-2-(1-butyryloxy-ethyl)-3H-pyrimidin-4-one (prepared according to the method of Preparation Fourteen, 254 g, 1.25 mol) and triethylamine (176 mL, 1.3 mol) in dichloromethane (2.3 L) at 5° C. was slowly added a solution of trifluoromethanesulfonic anhydride (211 mL, 1.25 mol) in dichloromethane (355 mL) over a period of 3 h. The reaction was then quenched by the addition of cold water (1.4 L) and the layers were separated. The organic layer was washed once with saturated aqueous sodium bicarbonate (1.5 L), once with saturated aqueous sodium chloride (1 L), and the solvent was removed under vacuum. The resulting oil was dissolved in dimethylacetamide (890 mL) and added slowly to a solution of cis-1-benzyl-3,5-dimethyl-piperazine (735 g, 3.6 mol) in dimethylacetamide (1.3 L) at 80° C. over a 1 h period. Heating at 80° C. was continued for 3.5 h, at which time the reaction was judged complete by gas chromatography. After cooling to room temperature, water (2.5 L) and isopropyl ether (2.5 L) were added, the layers were separated, and the organic layer was washed once with water (2 L). The isopropyl ether layer was then mixed well with a solution of $CuSO_4$ (126 g) in water (3 L) and filtered through a layer of Celite, washing the filter cake with isopropyl ether (1 L). The aqueous layer of the filtrate was drained-off, and the remaining organic layer was washed with water (2L) and treated with a solution of dibenzoyl-L-tartaric acid (619 g, 2.4 mol) in isopropyl ether (5.3 L). The resulting thick white slurry was stirred for 16 h and the solids were filtered off, washed with isopropyl ether (2 L), and vacuum dried at 50° C. to yield 854 g (71%) of the title compound of Preparation Fifteen, Step A as a white solid. $^1$H NMR (DMSO-$d_6$, 400 MHz) δ 0.89 (t, 3H), 1.23 (d, 3H), 1.25 (d, 3H), 1.48 (d, 3H), 1.54 (dd, 2H), 2.20 (dd, 2H), 2.31 (dt, 2H), 2.77 (d, 2H), 3.57 (s, 1H), 4.45 (m, 1H), 4.24 (m, 1H), 5.51 (q, 1H), 6.60 (d, 1H), 7.30 (m, 1H), 7.39 (m, 4H), 7.64 (m, 7H), 7.77 (m, 4H), 8.05 (c, 7H), 8.17 (d, 1H).

Step B: 1R-[4-(2R,6S-Dimethyl-piperazin-1-yl)-pyrimidin-2-yl]-ethyl butyrate dibenzoyl-L-tartrate salt. To a mixture of 1R-[4-(4-benzyl-2R,6S-dimethyl-piperazin-1-yl)-pyrimidin-2-yl]-ethyl butyrate bis dibenzoyl-L-tartrate salt (prepared according to the method of Preparation Fifteen, Step A, 50 g, 0.045 mol) and 5% palladium on carbon (50% wet, 10 g, 20 wt %) in methanol (400 mL) under a nitrogen atmosphere was added cyclohexene (4.6 mL, 0.045 mol). This mixture was heated to reflux for 6 h, at which time the reaction was judged complete by TLC.

After cooling to 40° C., the mixture was filtered through Celite and washed with methanol (100 mL). The methanol was gradually displaced with isopropanol by atmospheric pressure distillation until a constant boiling point of 80–82° C. was attained, and the resulting white slurry was cooled to room temperature and stirred for 4 h. The solids were filtered off, washed with isopropanol (100 mL), and vacuum dried at 50° C. to yield 25.7 g (86%) of the title compound as a white solid. $^1$H NMR (DMSO-$d_6$, 400 MHz) δ 0.90 (t, 3H), 1.15 (d, 3H), 1.21 (d, 3H), 1.47 (d, 3H), 1.55 (q, 2H), 2.3 (m, 2H), 3.04 (m, 2H), 3.2 (m, 2H), 4.4 (br s, 1H), 4.6 (br s, 1H), 5.5 (q, 1H), 5.74 (s, 2H), 6.6 (d, 1H), 7.5 (t, 4H), 7.6 (m, 2H), 8.0 (m, 4H), 8.2 (d, 1H).

What is claimed is:

1. A compound of the formula $I^A$,

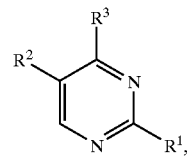

$I^A$ wherein:
$R^1$ is C—(OR$^{80}$)$R^4R^5$, where $R^{80}$ is independently ($C_1$–$C_4$)alkyl, benzyl, ($C_1$–$C_6$)alkylcarbonyl or phenylcarbonyl, where said benzyl and said phenyl are optionally substituted with up to three ($C_1$–$C_4$)alkyl, ($C_1$–$C_4$)alkoxy, halo or nitro;
$R^4$ and $R^5$ are each independently hydrogen, methyl, ethyl or hydroxy-($C_1$–$C_3$)alkyl;
$R^2$ is hydrogen, ($C_1$–$C_4$)alkyl or ($C_1$–$C_4$)alkoxy;
$R^3$ is a radical of the formula

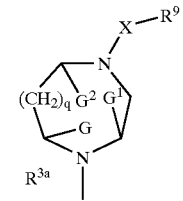

wherein said radical of formula $R^{3a}$ is substituted by $R^6$, $R^7$ and $R^8$;
G, $G^1$ and $G^2$ are taken separately and are each hydrogen and $R^6$ is hydrogen, ($C_1$–$C_4$)alkyl, ($C_1$–$C_4$)alkoxycarbonyl, ($C_1$–$C_4$)alkoxy-($C_1$–$C_4$)alkyl, hydroxy-$C_1$–$C_4$)alkyl or phenyl optionally independently substituted with up to three hydroxy, halo, hydroxy-($C_1$–$C_4$)alkyl, ($C_1$–$C_4$)alkoxy-($C_1$–$C_4$)alkyl, ($C_1$–$C_4$)alkyl or ($C_1$–$C_4$)alkoxy, wherein said ($C_1$–$C_4$) alkyl in the definition of $R^6$ and said ($C_1$–$C_4$)alkoxy in the definition of $R^6$ are optionally and independently substituted with up to five fluoro; $R^7$ and $R^8$ are each independently hydrogen or ($C_1$–$C_4$)alkyl; or
G and $G^1$ are taken together and are ($C_1$–$C_3$)alkylene and $R^6$, $R^7$, $R^8$ and $G^2$ are hydrogen; or
$G^1$ and $G^2$ are taken together and are ($C_1$–$C_3$)alkylene and $R^6$, $R^7$, $R^8$ and G are hydrogen;
q is 0 or 1;
X is a covalent bond, —(C=NR$^{10}$)—, oxycarbonyl, vinylenylcarbonyl, oxy($C_1$–$C_4$)alkylenylcarbonyl, ($C_1$–$C_4$)alkylenylcarbonyl, ($C_3$–$C_4$)alkenylcarbonyl, thio($C_1$–$C_4$)alkylenylcarbonyl, vinylenylsulfonyl, sulfinyl-($C_1$–$C_4$)alkylenylcarbonyl, sulfonyl-($C_1$–$C_4$) alkylenylcarbonyl or carbonyl($C_0$–$C_4$) alkylenylcarbonyl; wherein said oxy($C_1$–$C_4$)

alkylenylcarbonyl, $(C_1-C_4)$alkylenylcarbonyl, $(C_3-C_4)$ alkenylcarbonyl and thio$(C_1-C_4)$alkylenylcarbonyl in the definition of X are each optionally and independently substituted with up to two $(C_1-C_4)$alkyl, benzyl or Ar; said vinylenylsulfonyl and said vinylenylcarbonyl in the definition of X are optionally substituted independently on one or two vinylenyl carbons with $(C_1-C_4)$alkyl, benzyl or Ar; and said carbonyl$(C_0-C_4)$ alkylenylcarbonyl in the definition of X is optionally substituted independently with up to three $(C_1-C_4)$ alkyl, benzyl or Ar;

$R^{10}$ is hydrogen or $(C_1-C_4)$alkyl;

$R^9$ is $(C_3-C_7)$cycloalkyl, $Ar^1$—$(C_0-C_3)$alkylenyl or $(C_1-C_6)$alkyl optionally substituted with up to five fluoro; provided that when q=0 and X is a covalent bond, oxycarbonyl or $(C_1-C_4)$alkylenylcarbonyl, then $R^9$ is not $(C_1-C_6)$alkyl;

Ar and $Ar^1$ are phenyl, naphthyl, pyridyl, pymidyl, pyrazinyl, triazinyl, quinolyl, isoquinolyl, quinazolyl, quinoxalyl, phthalazinyl, cinnolinyl, naphthyridinyl, pteridinyl, pyrazinopyrazinyl, pyrazinopyridazinyl, pyrimidopyridazinyl, pyrimidopyrimidyl, pyridopyrimidyl, pyridopyrazinyl, pyridopyridazinyl, pyrrolyl, furanyl, thienyl, imidazolyl, tetrazolyl, indolyl, pyrazolyl, isoxazolyl, isothiazolyl, triazolyl, oxadiazolyl, thiadiazolyl, tetrazolyl, thiazolyl, pyrazolyl, isoxazolyl, isothiazolyl, triazolyl, oxadiazolyl, thiadiazolyl, tetrazolyl, indolyl, benzofuranyl, benzothienyl, benzimidazolyl, benzoxazolyl, benzothiazolyl, indazolyl, benzisoxazolyl, benzisothiazolyl, pyrrolopyridyl, furopyridyl, thienopyridyl, imidazolopyridyl, oxazolopyridyl, thizolopyridyl, pyrazolopyridyl, isoxazolopyridyl, isothiazolopyridyl, pyrrolopyrimidyl, furopyrimidyl, thienopyrimidyl, imidazolopyrimidyl, oxazolopyrimidyl, thiazolopyrimidyl, pyrazolopyrimidyl, isoxazolopyrimidyl, isothiazolopyrimidyl, pyrrolopyrazinyl, furopyrazinyl, thinenopyrazinyl, imidazolopyrazinyl, oxazolopyrazinyl, thiazolopyrazinyl, pyrazolopyrazinyl, isoxazolopyrazinyl, isothiazolopyrazinyl, pyrrolopyridazinyl, furopyridazinyl, thienopyridazinyl, imidazolopyridazinyl, oxazolopyridazinyl, thiazolopyridazinyl, pyrazolopyridazinyl, isoxazolopyridazinyl, or isothiazolopyridazinyl;

Ar and $Ar^1$ are optionally independently substituted on carbon or nitrogen, on one ring if the moiety is monocyclic, on one or both rings if the moiety is bicyclic, or on one, two or three rings if the moiety is tricyclic, with up to a total of four substituents independently selected from $R^{11}$, $R^{12}$, $R^{13}$ and $R^{14}$; wherein $R^{11}$, $R^{12}$, $R^{13}$ and $R^{14}$ are each taken separately and are each independently halo, formyl, $(C_1-C_6)$ alkoxycarbonyl, $(C_1-C_6)$alkylenyloxycarbonyl, $(C_1-C_4)$alkoxy-$(C_1-C_4)$alkyl, C(OH)$R^{15}R^{16}$, naphthyl, phenyl, imidazolyl, pyridyl, triazolyl, morpholinyl, $(C_0-C_4)$alkylsulfamoyl, N—$(C_0-C_4)$alkylcarbamoyl, N,N-di-$(C_1-C_4)$alkylcarbamoyl, N-phenylcarbamoyl, N—$(C_1-C_4)$alkyl-N-phenylcarbamoyl, N,N-diphenyl carbamoyl, $(C_1-C_4)$alkylcarbonylamido, $(C_3-C_7)$ cycloalkylcarbonylamido, phenylcarbonylamido, piperidinyl, pyrrolidinyl, piperazinyl, cyano, benzimidazolyl, amino, anilino, pyrimidyl, oxazolyl, isoxazolyl, tetrazolyl, thienyl, thiazolyl, benzothiazolyl, pyrrolyl, pyrazolyl, tetrahydroquinolyl, tetrahydroisoquinolyl, benzoxazolyl, pyridazinyl, pyridyloxy, pyridylsulfanyl, furanyl, 8-$(C_1-C_4)$alkyl-3, 8-diaza[3.2.1]bicyclooctyl, 3,5-dioxo-1,2,4-triazinyl, phenoxy, thiophenoxy, $(C_1-C_4)$alkylsulfanyl, $(C_1-C_4)$ alkylsulfonyl, $(C_3-C_7)$cycloalkyl, $(C_1-C_4)$alkyl optionally substituted with up to five fluoro or $(C_1-C_4)$alkoxy optionally substituted with up to five fluoro; said naphthyl, phenyl, pyridyl, piperidinyl, benzimidazolyl, pyrimidyl, thienyl, benzothiazolyl, pyrrolyl, tetrahydroquinolyl, tetrahydroisoquinolyl, benzoxazolyl, pyridazinyl, pyridyloxy, pyridylsulfanyl, furanyl, thiophenoxy, anilino and phenoxy in the definition of $R^{11}$, $R^{12}$, $R^{13}$ and $R^{14}$ are optionally substituted with up to three substituents independently selected from hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said imidazolyl, oxazolyl, isoxazolyl, thiazolyl and pyrazolyl in the definition of $R^{11}$, $R^{12}$, $R^{13}$ and $R^{14}$ are optionally substituted with up to two substituents independently selected from hydroxy, halo, hydroxy-$(C_1-C_4)$alkyl, $(C_1-C_4)$alkoxy-$(C_1-C_4)$alkyl, $(C_1-C_4)$ alkyl optionally substituted with up to five fluoro and $(C_1-C_4)$alkoxy optionally substituted with up to five fluoro; said morpholinyl in the definition of $R^{11}$, $R^{12}$, $R^{13}$ and $R^{14}$ is optionally substituted with up to two substituents independently selected from $(C_1-C_4)$alkyl; said pyrrolidinyl in the definition of $R^{11}$, $R^{12}$, $R^{13}$ and $R^{14}$ is optionally substituted with up to two substituents independently selected from hydroxy, hydroxy-$(C_1-C_3)$alkyl, $(C_1-C_4)$alkoxy-$(C_1-C_4)$alkyl, $(C_1-C_4)$ alkyl optionally substituted with up to five fluoro and $(C_1-C_4)$alkoxy optionally substituted with up to five fluoro; said piperazinyl in the definition of $R^{11}$, $R^{12}$, $R^{13}$ and $R^{14}$ is optionally substituted with up to three substituents independently selected from $(C_1-C_4)$ alkoxy-$(C_1-C_4)$alkyl, hydroxy-$(C_1-C_3)$alkyl, phenyl, pyridyl, $(C_0-C_4)$alkylsulfamoyl, $(C_1-C_4)$alkyl optionally substituted with up to five fluoro and $(C_1-C_4)$ alkoxy optionally substituted with up to five fluoro; said triazolyl in the definition of $R^{11}$, $R^{12}$, $R^{13}$ and $R^{14}$ is optionally substituted with hydroxy, halo, hydroxy-$(C_1-C_4)$alkyl, $(C_1-C_4)$alkoxy-$(C_1-C_4)$alkyl, $(C_1-C_4)$ alkyl optionally substituted with up to five fluoro and $(C_1-C_4)$alkoxy optionally substituted with up to five fluoro; said tetrazolyl in the definition of $R^{11}$, $R^{12}$, $R^{13}$ and $R^{14}$ is optionally substituted with hydroxy-$(C_2-C_3)$ alkyl or $(C_1-C_4)$alkyl optionally substituted with up to five fluoro; and said phenyl and pyridyl which are optionally substituted on piperazine in the definition of $R^{11}$, $R^{12}$, $R^{13}$ and $R^{14}$ are optionally substituted with up to three hydroxy, halo, hydroxy-$(C_1-C_4)$alkyl, $(C_1-C_4)$ alkoxy-$(C_1-C_4)$alkyl, $(C_1-C_4)$alkyl optionally substituted with up to five fluoro and $(C_1-C_4)$alkoxy optionally substituted with up to five fluoro; or $R^{11}$ and $R^{12}$ are taken together on adjacent carbon atoms and are —CH$_2$OC(CH$_3$)$_2$OCH$_2$— or —O—(CH$_2$)$_p$— O—, and $R^{13}$ and $R^{14}$ are taken separately and are each independently hydrogen or $(C_1-C_4)$alkyl;

p is 1, 2 or 3;

$R^{15}$ and $R^{16}$ are taken separately and are each independently hydrogen, $(C_1-C_4)$alkyl optionally substituted with up to five fluoro; or $R^{15}$ and $R^{16}$ are taken separately and $R^{15}$ is hydrogen and $R^{16}$ is $(C_3-C_6)$ cycloalkyl, hydroxy-$(C_1-C_3)$alkyl, phenyl, pyridyl, pyrimidyl, thienyl, furanyl, thiazolyl, oxazolyl, imidazolyl, benzothiazolyl or benzoxazolyl; or $R^{15}$ and $R^{16}$ are taken together and are $(C_3-C_6)$alkylene.

2. A compound of claim 1 selected from 1R-(4-{4-[2-(1R-butyryloxy-ethyl)-pyrimidin-4-yl]-2R,6S-dimethyl-piperazin-1-yl}-pyrimidin-2-yl)-ethyl butyrate; 1R-(4-{4-[2-(1S-butyryloxy-ethyl)-pyrimidin-4-yl]-2R,6S-dimethyl-piperazin-1-yl}-pyrimidin-2-yl)-ethyl butyrate; 1S-(4-{4-[2-(1R-butyryloxy-ethyl)-pyrimidin-4-yl]-2R,6S-dimethyl-piperazin-1-yl}-pyrimidin-2-yl)-ethyl butyrate; (E)-1R-{4-[4-(2-methyl-32-phenyl-acryloyl)-piperazin-1-yl]-pyrimidin-2-yl}-ethyl acetate; (R)-1-[4-(4-quinoxalin-2-yl-piperazin-1-yl)-pyrimidin-2-yl]-ethyl acetate; 1R-(4-{4-[2-(1RS-hydroxy-ethyl)-pyrimidin-4-yl]-2R,6S-dimethyl-piperazin-1-yl}-pyrimidin-2-yl)-ethyl butyrate; 1RS-(4-{4-[2-(1R-hydroxy-ethyl)-pyrimidin-4-yl]-3R,5S-dimethyl-piperazin-1-yl}-pyrimidin-2-yl)-ethyl butyrate; 1R-[4-(3S-methyl-4-oxazolo[5,4-b]pyridin-2-yl-piperazin-1-yl)-pyrimidin-2-yl]-ethyl butyrate; 1R-{4-[3R,5S-dimethyl-4-(4-methyl-6-phenyl-[1,3,5]triazin-2-yl)-piperazin-1-yl]-pyrimidin-2-yl}-ethyl butyrate; 1R-{4-[4-(4-cyclopropyl-[1,3,5]triazin-2-yl)-3R,5S-dimethyl-piperazin-1-yl]-pyrimidin-2-yl}-ethyl butyrate; 1R-{4-[4-(4-cyclopropyl-[1,3,5]triazin-2-yl)-2R,6S-dimethyl-piperazin-1-pyrimidin-2-yl}-ethyl butyrate; 1R-{4-[4-(4,6-dimethyl-[1,3,5]triazin-2-yl)-2R,1-yl]-pyrimidin-2-yl}-ethyl butyrate; 1R-{4-[4-(4-hydroxymethyl-6-phenyl-[1,3,5]triazin-2-yl)-2R,6S-dimethyl-piperazin-1-yl]-pyrimidin-2-yl}-ethyl butyrate; 1R-{4-[4-(4-methoxy-6-methoxymethyl-[1,3,5]triazin-2-yl)-R,6S-dimethyl-piperazin-1-yl]-pyrimidin-2-yl}-ethyl butyrate; and 1R-{4-[2R,6S-dimethyl-4-(4-methyl-[1,3,5]triazin-2-yl)-piperazin-1-yl]-pyrimidin-2-yl}-ethyl butyrate.

* * * * *